United States Patent
Pons et al.

(10) Patent No.: US 11,613,564 B2
(45) Date of Patent: Mar. 28, 2023

(54) METHODS OF TREATING CANCER

(71) Applicant: ALX Oncology Inc., South San Francisco, CA (US)

(72) Inventors: Jaume Pons, San Francisco, CA (US); Hong Wan, Foster City, CA (US); Sophia Randolph, Chico, CA (US)

(73) Assignee: ALX Oncology Inc., South San Francisco, CA (US)

( * ) Notice: Subject to any disclaimer, the term of this patent is extended or adjusted under 35 U.S.C. 154(b) by 72 days.

(21) Appl. No.: 16/886,559

(22) Filed: May 28, 2020

(65) Prior Publication Data

US 2020/0392199 A1    Dec. 17, 2020

Related U.S. Application Data

(60) Provisional application No. 63/022,187, filed on May 8, 2020, provisional application No. 62/855,821, filed on May 31, 2019.

(51) Int. Cl.
| | | |
|---|---|---|
| *C07K 14/705* | (2006.01) | |
| *A61P 35/00* | (2006.01) | |
| *C07K 16/28* | (2006.01) | |
| *C07K 16/32* | (2006.01) | |
| *A61K 39/00* | (2006.01) | |

(52) U.S. Cl.
CPC ............ *C07K 14/705* (2013.01); *A61P 35/00* (2018.01); *C07K 16/2818* (2013.01); *C07K 16/2887* (2013.01); *C07K 16/32* (2013.01); *A61K 2039/507* (2013.01); *A61K 2039/54* (2013.01); *A61K 2039/545* (2013.01); *C07K 2319/30* (2013.01)

(58) Field of Classification Search
CPC .. C07K 14/705; C07K 16/2818; C07K 16/32; A61K 2039/507
See application file for complete search history.

(56) References Cited

U.S. PATENT DOCUMENTS

| | | | |
|---|---|---|---|
| 3,773,919 A | 11/1973 | Boswell et al. | |
| 5,116,964 A | 5/1992 | Capon et al. | |
| 5,306,809 A | 4/1994 | Boon et al. | |
| 5,478,925 A | 12/1995 | Wallach et al. | |
| 5,505,931 A | 4/1996 | Pribish | |
| 5,648,237 A | 7/1997 | Carter | |
| 5,697,901 A | 12/1997 | Eriksson | |
| 5,972,707 A | 10/1999 | Roy et al. | |
| 6,174,529 B1 | 1/2001 | Michael et al. | |
| 6,261,554 B1 | 7/2001 | Valerio et al. | |
| 6,541,615 B1 | 4/2003 | Ullrich et al. | |
| 6,591,129 B1 | 7/2003 | Ben-Haim et al. | |
| 6,613,332 B1 | 9/2003 | Michael et al. | |
| 7,402,155 B2 | 7/2008 | Palasis et al. | |
| 7,514,229 B2 | 4/2009 | Jamieson et al. | |
| 7,662,367 B2 | 2/2010 | Desjarlais et al. | |
| 7,691,970 B2 | 4/2010 | Skerra et al. | |
| 7,892,558 B2 | 2/2011 | Zagury | |
| 8,216,805 B2 | 7/2012 | Carter et al. | |
| 8,377,448 B2 | 2/2013 | Smith et al. | |
| 8,399,219 B2 | 3/2013 | Stagliano et al. | |
| 8,518,404 B2 | 8/2013 | Daugherty et al. | |
| 8,518,869 B2 | 8/2013 | Hallstrom et al. | |
| 8,529,898 B2 | 9/2013 | Daugherty et al. | |
| 8,541,203 B2 | 9/2013 | Daugherty et al. | |
| 8,562,997 B2 | 10/2013 | Jaiswal et al. | |
| 8,603,778 B2 | 12/2013 | Heavner et al. | |
| 8,613,922 B2 | 12/2013 | Clemmons et al. | |
| 8,728,476 B2 | 5/2014 | Van Den Berg | |
| 8,748,399 B2 | 6/2014 | Bedzyk et al. | |
| 8,993,266 B2 | 3/2015 | Stagliano et al. | |
| 9,017,675 B2 | 4/2015 | Liu et al. | |
| 9,169,321 B2 | 10/2015 | Daugherty et al. | |
| 9,352,037 B2 | 5/2016 | Van Den Berg | |
| 9,382,320 B2 | 7/2016 | Liu et al. | |
| 9,394,365 B1 | 7/2016 | Eisenbach-Schwartz et al. | |
| 9,475,882 B2 | 10/2016 | Clemmons et al. | |
| 9,512,225 B2 | 12/2016 | Eisenbach-Schwartz et al. | |
| 9,512,227 B2 | 12/2016 | Eisenbach-Schwartz et al. | |

(Continued)

FOREIGN PATENT DOCUMENTS

| | | |
|---|---|---|
| CN | 102257001 A | 11/2011 |
| CN | 102596233 A | 7/2012 |

(Continued)

OTHER PUBLICATIONS

Zhang et al., Blocking CD47 and autophagy for the therapy of non-small cell lung cancer, Annals of Oncology, vol. 27, Supplement 9, 399P, Publication Date: Dec. 2016 (Year: 2016).*

(Continued)

*Primary Examiner* — Peter J Reddig
*Assistant Examiner* — Cheng Lu
(74) *Attorney, Agent, or Firm* — Morrison & Foerster LLP

(57) ABSTRACT

Provided are methods of treating cancer (e.g., non-small cell lung cancer (NSCLC), head and neck squamous cell carcinoma (HNSCC), HER2-positive gastric/gastroesophageal junction (GEJ) cancer, de novo or transformed diffuse large B cell lymphoma (DLBCL), or indolent lymphoma) in an individual that comprise administering to the individual (a) a polypeptide comprising a SIRPα D1 domain variant and an Fc domain variant, and (b) an anti-cancer antibody (e.g., an anti-PD1 antibody, anti-HER2 antibody, or an anti-CD20 antibody). Also provided are related kits pharmaceutical compositions.

7 Claims, 26 Drawing Sheets

Specification includes a Sequence Listing.

(56) References Cited

U.S. PATENT DOCUMENTS

| | | | |
|---|---|---|---|
| 9,534,052 | B2 | 1/2017 | Eisenbach-Schwartz et al. |
| 9,546,206 | B2 | 1/2017 | Ring et al. |
| 9,562,087 | B2 | 2/2017 | Ring et al. |
| 9,944,911 | B2 | 4/2018 | Ring et al. |
| 10,259,859 | B2 | 4/2019 | Pons et al. |
| 10,696,730 | B2 | 6/2020 | Pons et al. |
| 10,907,209 | B2 | 2/2021 | Wang et al. |
| 11,208,459 | B2 | 12/2021 | Pons et al. |
| 11,208,481 | B2 | 12/2021 | Ring et al. |
| 2004/0213792 | A1 | 10/2004 | Clemmons et al. |
| 2007/0148201 | A1 | 6/2007 | Skerra et al. |
| 2008/0160013 | A1 | 7/2008 | Clemmons et al. |
| 2009/0068195 | A1 | 3/2009 | Vugmeyster et al. |
| 2010/0189651 | A1 | 7/2010 | Stagliano et al. |
| 2010/0215640 | A1 | 8/2010 | Clemmons et al. |
| 2010/0239578 | A1 | 9/2010 | Danska et al. |
| 2010/0239579 | A1 | 9/2010 | Smith et al. |
| 2011/0081345 | A1 | 4/2011 | Moore et al. |
| 2011/0110938 | A1 | 5/2011 | Chiu et al. |
| 2011/0184145 | A1 | 7/2011 | Silence et al. |
| 2011/0237498 | A1 | 9/2011 | Raymond et al. |
| 2012/0189625 | A1 | 7/2012 | Wang et al. |
| 2012/0283408 | A1 | 11/2012 | Lee et al. |
| 2013/0011401 | A1 | 1/2013 | Huber et al. |
| 2014/0010810 | A1 | 1/2014 | West et al. |
| 2014/0023664 | A1 | 1/2014 | Lowman et al. |
| 2014/0024111 | A1 | 1/2014 | Kannan et al. |
| 2014/0051634 | A1 | 2/2014 | Hallstrom et al. |
| 2014/0113348 | A1 | 4/2014 | Williams et al. |
| 2014/0140926 | A1 | 5/2014 | Discher et al. |
| 2014/0161800 | A1 | 6/2014 | Blankenship et al. |
| 2014/0193408 | A1 | 7/2014 | Huber et al. |
| 2014/0242095 | A1 | 8/2014 | Wang et al. |
| 2015/0071905 | A1 | 3/2015 | Ring et al. |
| 2015/0203559 | A1 | 7/2015 | Stagliano et al. |
| 2015/0329616 | A1 | 11/2015 | Uger et al. |
| 2015/0353642 | A1 | 12/2015 | Tykocinski |
| 2015/0376288 | A1 | 12/2015 | Weiskopf et al. |
| 2016/0000909 | A1 | 1/2016 | Eisenbach-Schwartz et al. |
| 2016/0008429 | A1 | 1/2016 | Willingham et al. |
| 2016/0008463 | A1 | 1/2016 | Eisenbach-Schwartz et al. |
| 2016/0045532 | A1 | 2/2016 | Roberts et al. |
| 2016/0069898 | A1 | 3/2016 | Weiskopf et al. |
| 2016/0144009 | A1 | 5/2016 | Tseng et al. |
| 2016/0152715 | A1* | 6/2016 | Wong ............... A61P 15/00 424/139.1 |
| 2016/0177276 | A1 | 6/2016 | Lo et al. |
| 2016/0186150 | A1 | 6/2016 | Deming et al. |
| 2016/0193295 | A1 | 7/2016 | Kannan et al. |
| 2016/0194406 | A1 | 7/2016 | Leeper et al. |
| 2016/0244522 | A1 | 8/2016 | Van Den Berg |
| 2016/0297866 | A1 | 10/2016 | Clemmons et al. |
| 2016/0304609 | A1 | 10/2016 | Liu et al. |
| 2017/0029508 | A1 | 2/2017 | Eisenbach-Schwartz et al. |
| 2017/0044258 | A1 | 2/2017 | Van Den Berg |
| 2017/0107270 | A1 | 4/2017 | Pons et al. |
| 2017/0285037 | A1* | 10/2017 | Kulangara ....... G01N 33/57492 |
| 2018/0141986 | A1 | 5/2018 | Tian et al. |
| 2018/0195054 | A1 | 7/2018 | Ring et al. |
| 2018/0371435 | A1 | 12/2018 | Deming et al. |
| 2019/0093174 | A1 | 3/2019 | Wang et al. |
| 2019/0169266 | A1 | 6/2019 | Pons et al. |
| 2020/0239543 | A1 | 7/2020 | Pons et al. |
| 2020/0263154 | A1 | 8/2020 | Deming et al. |
| 2020/0400662 | A1 | 12/2020 | Wan et al. |
| 2021/0070838 | A1 | 3/2021 | Pons et al. |
| 2021/0154269 | A1 | 5/2021 | Wan et al. |
| 2021/0388329 | A1 | 12/2021 | Deming et al. |
| 2022/0064293 | A1 | 3/2022 | Ring et al. |
| 2022/0196651 | A1 | 6/2022 | Pons et al. |
| 2022/0213166 | A1 | 7/2022 | Pons et al. |
| 2022/0242928 | A1 | 8/2022 | Pons et al. |

FOREIGN PATENT DOCUMENTS

| | | |
|---|---|---|
| CN | 102939303 A | 2/2013 |
| CN | 103635490 A | 3/2014 |
| CN | 104812413 A | 7/2015 |
| CN | 107252476 A | 10/2017 |
| CO | 2018/0002471 A2 | 5/2018 |
| EA | 15538 B1 | 8/2011 |
| EP | 2429574 B1 | 5/2015 |
| JP | 2011-500005 A | 1/2011 |
| JP | 2012-533631 A | 12/2012 |
| JP | 2013-541542 A | 11/2013 |
| JP | 2015-504899 A | 2/2015 |
| WO | WO-1993/000077 A1 | 1/1993 |
| WO | WO-1999/040940 A1 | 8/1999 |
| WO | WO-2000/077026 A1 | 12/2000 |
| WO | WO-2001/048020 A1 | 7/2001 |
| WO | WO-2003/031650 A2 | 4/2003 |
| WO | WO-2003/095618 A2 | 11/2003 |
| WO | WO-2004/011618 A2 | 2/2004 |
| WO | WO-2004/096133 A2 | 11/2004 |
| WO | WO-2005/108415 A2 | 11/2005 |
| WO | WO-2007/084344 A2 | 7/2007 |
| WO | WO-2009/046541 A1 | 4/2009 |
| WO | WO-2009/091601 A1 | 7/2009 |
| WO | WO-2009/131453 A1 | 10/2009 |
| WO | WO-2010/070047 A2 | 6/2010 |
| WO | WO-2010/096838 A2 | 8/2010 |
| WO | WO-2010/130053 A1 | 11/2010 |
| WO | WO-2011/011315 A1 | 1/2011 |
| WO | WO-2011/066501 A1 | 6/2011 |
| WO | WO-2011/076781 A1 | 6/2011 |
| WO | WO-2011/143624 A2 | 11/2011 |
| WO | WO-2012/048332 A2 | 4/2012 |
| WO | WO-2012/130831 A1 | 10/2012 |
| WO | WO-2012/142515 A2 | 10/2012 |
| WO | WO-2012/172521 A1 | 12/2012 |
| WO | WO-2013/032948 A1 | 3/2013 |
| WO | WO-2013/063076 A1 | 5/2013 |
| WO | WO-2013/109752 A1 | 7/2013 |
| WO | WO-2014/045022 A2 | 3/2014 |
| WO | WO-2014/094122 A1 | 6/2014 |
| WO | WO-2014/121093 A1 | 8/2014 |
| WO | WO-2014/124028 A1 | 8/2014 |
| WO | WO-2014/149477 A1 | 9/2014 |
| WO | WO-2014/160183 A1 | 10/2014 |
| WO | WO-2014/179132 A1 | 11/2014 |
| WO | WO-2014/186761 A2 | 11/2014 |
| WO | WO-2015/041987 A1 | 3/2015 |
| WO | WO-2015/042557 A1 | 3/2015 |
| WO | WO-2015/048329 A2 | 4/2015 |
| WO | WO-2015/057834 A1 | 4/2015 |
| WO | WO-2015/116933 A2 | 8/2015 |
| WO | WO-2015/136541 A2 | 9/2015 |
| WO | WO-2016/022971 A1 | 2/2016 |
| WO | WO-2016/022994 A2 | 2/2016 |
| WO | WO-2016/023001 A1 | 2/2016 |
| WO | WO-2016/023040 A1 | 2/2016 |
| WO | WO-2016/024021 A1 | 2/2016 |
| WO | WO-2016/033201 A1 | 3/2016 |
| WO | WO-2016/044021 A1 | 3/2016 |
| WO | WO-2016/057980 A1 | 4/2016 |
| WO | WO-2016/063233 A1 | 4/2016 |
| WO | WO-2016/065329 A1 | 4/2016 |
| WO | WO-2016/081423 A1 | 5/2016 |
| WO | WO-2016/138306 A1 | 9/2016 |
| WO | WO-2016/169261 A1 | 10/2016 |
| WO | WO-2017/009829 A1 | 1/2017 |
| WO | WO-2017/027422 A1 | 2/2017 |
| WO | WO-2017/178653 A2 | 10/2017 |
| WO | WO-2018/057669 A1 | 3/2018 |
| WO | WO-2020/243338 A1 | 12/2020 |
| WO | WO-2020/247820 A1 | 12/2020 |
| WO | WO-2021/108693 A1 | 6/2021 |
| WO | WO-2021/247430 A1 | 12/2021 |

(56) References Cited

FOREIGN PATENT DOCUMENTS

| WO | WO-2022/010806 A1 | 1/2022 |
|---|---|---|
| WO | WO-2022/120286 A1 | 6/2022 |

OTHER PUBLICATIONS

Keytruda, reference ID: 4003165, Publication Date: 2016/10 (Year: 2016).*
Kim et al., Association of CD47 with Natural Killer Cell-Mediated Cytotoxicity of Head-and-Neck Squamous Cell Carcinoma Lines, Tumor Biology, 29:28-34, Publication Date: May 23, 2008 (Year: 2008).*
History of Changes for Study: NCT02358031: A Study of Pembrolizumab (MK-3475) for First Line Treatment of Recurrent or Metastatic Squamous Cell Cancer of the Head and Neck (MK-3475-048/KEYNOTE-048), retrieved from https://clinicaltrials.gov/ct2/show/NCT02358031 (Year: 2019).*
Lala et al., Clinical outcomes with therapies for previously treated recurrent/metastatic head-and-neck squamous cell carcinoma (R/M HNSCC): A systematic literature review, Oral Oncology, 84: 108-120, Publication Date: Aug. 1, 2018 (Year: 2018).*
Weiskopf, Cancer immunotherapy targeting the CD47/SIRPa axis, European Journal of Cancer, 76:100-109, Publication Date: Mar. 10, 2017 (Year: 2017).*
Abrahao-Machado et al. (2016). "HER2 testing in gastric cancer: An update," World J. Gastroenterol. 22(19):4619-4625.
Ayyappan et al. (2018) "Marginal Zone Lymphoma: Clinicopathologic Variations and Approaches to Therapy," Curr Oncol Rep. 20(4):687, 11 pages.
Balsas et al. (2017) "SOX11 promotes tumor protective microenvironment interactions through CXCR4 and FAK regulation in mantle cell lymphoma," Blood, 130(4):501-513.
Barclay et al. (Jun. 2006). "The SIRP family of receptors and immune regulation," Nat. Rev. Immunol. 6(6):457-464.
Borrok et al. (epub Jul. 10, 2012). "Revisiting the role of glycosylation in the structure of human IgG Fc." ACS Chemical Biology 7(9):1596-1602.
CDC (2020). "United States Cancer Statistics (USCS)," retrieved Sep. 8, 2020 from <https://www.cdc.gov/cancer/uscs/>, 2 pages.
Cheson et al. (2014) "Recommendations for Initial Evaluation, Staging and Response Assessment of Hodgkin and Non-Hodgkin Lymphoma: The Lugano Classification." J. Clin Oncol. 32:3059-3067.
Ciobanu et al. (2013) "Indolent Lymphoma: Diagnosis and Prognosis in Medical Practice." Maedica (Buchar), 8(4):338-342.
Dreyling et al. (2013). "ESMO Consensus Guidelines: Marginal Cell Lymphoma, Mantle Cell Lymphoma, Peripheral T-cell Lymphoma," Ann Oncol. 24(4):857-877.
Dreyling et al. (2014). "Mantle Cell Lymphoma: Biology, Clinical Presentation, and Therapeutic Approaches," Am Soc Clin Oncol Educ Book, pp. 191-198.
Eisenhauer et al. (2009). "New response evaluation criteria in solid tumours: revised RECIST guideline (version 1.1)," Eur J. Cancer. 45:228-247.
European Medicines Agency "Herceptin, Annex I, Summary of Product Characteristics," retrieved Sep. 8, 2020 from <https://www.ema.europa.eu/en/documents/product-information/herceptin-epar-product-information_en.pdf>, 91 pages.
European Medicines Agency "KEYTRUDA, Annex I, Summary of Product Characteristics," retrieved Sep. 8, 2020 from <https://www.ema.europa.eu/en/documents/product-information/keytruda-epar-product-information_en.pdf>, 156 pages.
European Medicines Agency "MabThera, Annex I, Summary of Product Characteristics," retrieved Sep. 8, 2020 from <https://www.ema.europa.eu/en/documents/product-information/mabthera-epar-product-information_en.pdf>, 149 pages.
European Search Report dated Nov. 7, 2016 for European Application No. 16183261.3, filed on Aug. 8, 2016, 14 pages.
European Search Report dated Oct. 23, 2015 for European Application No. 13738232.1, filed on Jan. 17, 2013, seven pages.
FDA "Summary of Safety and Effectiveness Data," PD-L1 IHC 22C3 pharmDx, retrieved Sep. 8, 2020 from <www.accessdata.fda.gov/cdrh_docs/pdf15/p150013b.pdf>, 22 p.
FDA (2012). "RITUXAN (rituximab) Label," Highlights of Prescribing Information, retrieved Sep. 8, 2020 from <https://www.accessdata.fda.gov/drugsatfda_docs/label/2012/103705s5367s5388lbl.pdf> , 40 pages.
FDA (2016). "KEYTRUDA® (pembrolizumab) Label," Highlights of Prescribing Information, retrieved Sep. 8, 2020 from <https://www.accessdata.fda.gov/drugsatfda_docs/label/2016/125514s012lbl.pdf>, 26 pages.
FDA (2017). "HERCEPTIN® (trastuzumab) Label," Highlights of Prescribing Information, retrieved Sep. 8, 2020 from <https://www.accessdata.fda.gov/drugsatfda_docs/label/2017/103792s5337lbl.pdf>, 38 pages.
Fehrenbacher et al. (2016). "Atezolizumab versus docetaxel for patients with previously treated non-small-cell lung cancer (POPLAR): a multicentre, open-label, phase 2 randomised controlled trial," Lancet, 387(10030):1837-46.
Gabrilovich et al. (2012). "Coordinated regulation of myeloid cells by tumours," Nat Rev Immunol.12(4):253-68.
Garon et al. (2015). "Pembrolizumab for the Treatment of Non-Small-Cell Lung Cancer," New Engl J Med. 372:2018-28.
GenBank Accession No. NP_037148.2, (ROD Sep. 1, 2016, last updated Apr. 16, 2017), "tyrosine-protein phosphatase non-receptor type substrate 1 precursor [Rattus norvegicus]," located at <http://www.ncbi.nlm.nih.gov/protein/NP_037148.2>, last visited on Jun. 9, 2017, four pages.
Gunasekaran et al. (epub Apr. 16, 2010). "Enhancing antibody Fc heterodimer formation through electrostatic steering effects: applications to bispecific molecules and monovalent IgG," J Biol Chem. 285(25):19637-19646.
Hatherley et al. (epub Jul. 23, 2009). "Structure of signal-regulatory protein alpha: a link to antigen receptor evolution," J Biol Chem. 284(39):26613-26619.
Hatherley et al. (epub Mar. 16, 2007). "The structure of the macrophage signal regulatory protein alpha (SIRPalpha) inhibitory receptor reveals a binding face reminiscent of that used by T cell receptors." J Biol Chem. 282(19):14567-14575.
Hatherley et al. (Jul. 25, 2008). "Paired receptor specificity explained by structures of signal regulatory proteins alone and complexed with CD47," Mol. Cell. 31(2):266-277.
Herbst et al. (2016). "Pembrolizumab versus docetaxel for previously treated, PD-L1-positive, advanced non-small-cell lung cancer (KEYNOTE-010): a randomised controlled trial," The Lancet, 387:1540-50.
Hezareh et al. (2001) "Effector function activities of a panel of mutants of a broadly neutralizing antibody against human immunodeficiency virus type 1," J Virol., 75(24):12161-8.
Ho et al. (2015). "'Velcro' Engineering of High Affinity CD47 Ectodomain as Signal Regulatory Protein a (SIRPα) Antagonists That Enhance Antibody-Dependent Cellular Phagocytosis," J Biol Chem, 290(20):12650-63.
Hwang et al. (2017). "Response Evaluation of Chemotherapy for Lung Cancer." Tuberc Respir Dis (Seoul). 80(2):136-142.
International Preliminary Report on Patentability dated Feb. 23, 2017 for PCT Application No. PCT/US2015/044528, filed on Aug. 10, 2015, 11 pages.
International Preliminary Report on Patentability dated Jan. 24, 2017, for PCT Application No. PCT/US2016/045914, filed on Aug. 5, 2016, 20 pages.
International Preliminary Report on Patentability dated Jul. 31, 2014 for PCT Application No. PCT/US2013/021937, filed on Jan. 17, 2013, 7 pages.
International Search Report dated Dec. 22, 2015 for PCT Application No. PCT/US2015/044528, filed on Aug. 10, 2015, four pages.
International Search Report dated Jan. 24, 2017, for PCT Application No. PCT/US2016/045914, filed on Aug. 5, 2016, six pages.
International Search Report dated May 21, 2013, for PCT Application No. PCT/US2013/021937, filed on Jan. 17, 2013, five pages.

(56) References Cited

OTHER PUBLICATIONS

Jang et al. (2013). "Comparison of RECIST version 1.0 and 1.1 in assessment of tumor response by computed tomography in advanced gastric cancer," Chin J. Cancer Res. 25(6):689-694.

Jawa et al. (epub Sep. 25, 2013). "T-cell dependent immunogenicity of protein therapeutics: Preclinical assessment and mitigation," Clin Immunol. 149(3):534-555.

Jin et al. (2018) "Pharmacokinetic and pharmacodynamic characterization of ALX148, a CD47 blocker, in patients with advanced malignancy and non-Hodgkin lymphoma," Soc Immunotherpay of Cancer Conference, #P340.

Kabat et al. (1991). Sequences of proteins of immunological interest, 5th ed. U.S. Dept. of Health and Human Services, Public Health Service, National Institutes of Health Bethesda, MD.

Kim et al. (2015). "Single-Lesion Measurement per Organ for Assessing Tumor Response in Advanced Gastric Cancer," Oncology. 88:69-75.

Kim et al. (2019). "A Phase 1 Study of ALX148, a CD47 Blocker, in Combination with Rituximab in Patients with Non-Hodgkin Lymphoma," Blood, 134, Supplement_1, Abstract #1953.

Kurokawa et al. (2013) "Which is the optimal response criteria for evaluating preoperative treatment in esophageal cancer: RECIST or histology?" Ann Surg Oncol. 20(9):3009-3014.

Kwon et al. (Dec. 21, 1999). "Elimination of residual metastatic prostate cancer after surgery and adjunctive cytotoxic T lymphocyte-associated antigen 4 (CTLA-4) blockade immunotherapy," Proc. Natl. Acad. Sci. USA. 96(26):15074-15079.

Larouche et al. (2010). "Lymphoma recurrence 5 years or later following diffuse large B-cell lymphoma: clinical characteristics and outcome," J Clin Oncol, 28(12):2094-100.

Lee et al. (Dec. 1, 2007). "Novel structural determinants on SIRP alpha that mediate binding to CD47," The Journal of Immunology 179(11):7741-7750.

Lee et al. (epub Sep. 7, 2010). "The role of cis dimerization of signal regulatory protein alpha (SIRPalpha) in binding to CD47," J Biol Chem. 285(49):37953-37963.

Lin et al. (epub Jul. 17, 2012). "Soluble extracellular domains of human SIRPa and CD47 expressed in *Escherichia coli* enhances the phagocytosis of leukemia cells by macrophages in vitro," Protein Expr Purif. 85(1):109-116.

Liu et al. (2007, epub Oct. 3, 2006). "Functional elements on SIRPalpha IgV domain mediate cell surface binding to CD47," Journal of Molecular Biology 365(3):680-693.

Liu et al. (Feb. 15, 2004). "Peptide-mediated inhibition of neutrophil transmigration by blocking CD47 interactions with signal regulatory protein alpha," J Immunol.172 (4) 2578-2585.

Lordick et al. (2016). "Oesophageal cancer: ESMO Clinical Practice Guidelines for diagnosis, treatment and follow-up," Ann Oncol. 27(suppl 5): v50-v57.

Miller et al. (1981). Reporting results of cancer treatment, Cancer. 47:207-214.

Montoto et al. (2007). "Risk and clinical implications of transformation of follicular Tymphoma to diffuse large B-cell lymphoma," J Clin Oncol (2007) 25(17):2426-33.

Nakaishi et al. (2008, epub Nov. 7, 2007). "Structural insight into the specific interaction between murine SHPS-1/SIRP alpha and its ligand CD47," J Mol Biol. 375(3):650-660.

NICE (Jul. 2016). "Non-Hodgkin's Lymphoma: Diagnosis and Management," London, National Institute for Health and Care Excellence (NICE), Guideline No. 52, 26 pages.

Nishino et al. (2013). "Developing a Common Language for Tumor Response to Immunotherapy: Immune-Related Response Criteria Using Unidimensional Measurements," Clinical Cancer Research, 19(14):3936-43.

Oken et al. (1982). "ECOG Performance Status," as published in "Toxicity and Response Criteria of the Eastern Cooperative Oncology Group," Am J Clin Oncol, 5:649-655, retrieved Sep. 8, 2020 from <http://www.npcrc.org/files/news/ECOG_performance_status.pdf>, 1 page.

Oldenborg (2013). "CD47: A Cell Surface Glycoprotein Which Regulates Multiple Functions of Hematopoietic Cells in Health and Disease," ISRN Hematol, Article ID 614619, 19 pages.

Oldenborg et al. (Jun. 16, 2000). "Role of CD47 as a marker of self on red blood cells," Science 288(5473):2051-2054.

Reck et al. (2016) "Pembrolizumab versus Chemotherapy for PD-L1-Positive Non-Small-Cell Lung Cancer." NEJM. 375: 1823-1833.

Ridgway et al. (Jul. 1996). "'Knobs-into-holes' engineering of antibody CH3 domains for heavy chain heterodimerization," Protein Eng. 9(7):617-621.

Sim et al. (2019). "Discovery of high affinity, pan-allelic, and pan-mammalian reactive antibodies against the myeloid checkpoint receptor SIRPa," mAbs, 11(6): 1-17.

Subramanian et al. (2007, epub Nov. 10, 2006). "Phylogenetic divergence of CD47 interactions with human signal regulatory protein alpha reveals locus of species specificity. Implications for the binding site," J Biol Chem. 282(3):1805-1818.

Takenaka et al. (epub Nov. 4, 2007). "Polymorphism in SIRPα modulates engraftment of human hematopoietic stem cells," Nat Immunol. 8(12):1313-1323.

Therasse et al. (2000). "New Guidelines to Evaluate the Response to Treatment in Solid Tumors," J. Natl Cancer Inst. 92:205-216.

Tsai et al. (epub Mar. 17, 2010). "Self inhibition of phagocytosis: the affinity of 'marker of self' CD47 for SIRPalpha dictates potency of inhibition but only at low expression Tevels," Blood Cells Mol Dis. 45(1):67-74.

U.S. Appl. No. 16/825,850, filed Mar. 20, 2020 for Pons et al. (Copy not submitted herewith pursuant to the waiver of 37 C.F.R. § 1,98(a)(2)(iii) issued by the Office Sep. 21, 2004).

Vose (2017). "Mantle cell lymphoma: 2017 update on diagnosis, risk-stratification, and clinical management," Am J. Hematol. 92(8):806-813.

Wan et al. (2019). "Pharmacodynamic Biomarker Characterization of ALX148, a CD47 Blocker, in Combination with Established Anticancer Antibodies in Patients with Advanced Malignancy," Society for Immunotherapy of Cancer (SITC), Abstract #P449.

Weiskopf et al. (epub May 30, 2013). "Engineered SIRPα variants as immunotherapeutic adjuvants to anticancer antibodies," Science 341(6141):88-91.

WHO (1979) Handbook for Reporting Results of Cancer Treatment. Geneva: World Health Organization Offset Publication, No. 48, 46 pages.

WHO Cancer Fact Sheets (2018), "All Cancers," the Global Cancer Observatory, retrieved Sep. 8, 2020 from <https://gco.iarc.fr/today/data/factsheets/cancers/39-All-cancers-fact-sheet.pdf>, 2 pages.

Wray et al. (2016) "Therapy Response Assessment and Patient Outcomes in Head and Neck Squamous Cell Carcinoma: FDG PET Hopkins Criteria Versus Residual Neck Node Size and Morphologic Features." Am J. Roentgenology, 207:641-647.

Written Opinion dated Dec. 22, 2015 for PCT Application No. PCT/US2015/044528, filed on Aug. 10, 2015, nine pages.

Written Opinion dated Jan. 24, 2017 for PCT Application No. PCT/US2016/045914, filed on Aug. 5, 2016, 19 pages.

Written Opinion of the International Searching Authority dated May 21, 2013 for PCT Application No. PCT/US2013/021937, filed on Jan. 17, 2013, five pages.

Yamao et al. (Feb. 3, 1997). "Mouse and human SHPS-1: molecular cloning of cDNAs and chromosomal localization of genes," Biochem Biophys Res Commun. 231(1):61-67.

Yanagawa et al. (2012) "Evaluation of response to neoadjuvant chemotherapy for esophageal cancer: PET response criteria in solid tumors versus response evaluation criteria in solid tumors," J Nucl Med. 53(6):872-880.

Zhao et al. (epub Oct. 31, 2011). "CD47-signal regulatory protein-α (SIRPα) interactions form a barrier for antibody-mediated tumor cell destruction," Proc Natl Acad Sci USA. 108(45):18342-18347.

Anonymous (2019). "A Phase 1 Dose Escalation Trial of Intratumoral Injections of TTI-621 in Subjects With Relapsed and Refractory Percutaneously-Accessible Solid Tumors and Mycosis Fungoide," clinical trials.gov, pp. 1-5, Retrieved Jan. 25, 2021 <https://clinicaltrials.gov/ct2/history/NCT02890368?V_13=View#StudyPageTop>.

(56) References Cited

OTHER PUBLICATIONS

Anonymous (2019). "A Phase 1a/1b Dose Escalation and Expansion Trial of TTI-621, a Novel Biologic Targeting CD47, in Subjects With Relapsed or Refractory Hematologic Malignancies and Selected Solid Tumors," clinical trials.gov, pp. 1-7, Retrieved Jan. 25, 2021 <https://clinicaltrials.gov/ct2/history/NCT02663518?V_21=View#StudyPageTop>.

Anonymous (2019). "A Phase 1a/1b Dose Escalation and Expansion Trial of TTI-622 in Patients With Advanced Relapsed or Refractory Lymphoma or Myeloma," clinical trials.gov, pp. 1-4, Retrieved Jan. 25, 2021 Khttps://clinicaltrials.gov/ct2/history/NCT035306837V_10=View#StudyPageTop>.

Ansell et al. (2017). "TTI-621 (SIRPαFc), an Immune Checkpoint Inhibitor Blocking the CD47 "Do Not Eat" Signal, Induces Objective Responses in Patients with Advanced, Relapsed/Refractory Diffuse Large B-Cell Lymphoma (DLBCL)," Blood, 130 (Supplement 1): 4116, Abstract.

Icard, P. et al. (epub Jul. 25, 2012). "A global view of the biochemical pathways involved in the regulation of the metabolism of cancer cells," Biochim Biophys Acta. 1826(2):423-433.

Kharitonenkov et al., "A family of proteins that inhibit signalling through tyrosine kinase receptors," Nature (Mar. 13, 1997), 386(6621):181-186.

Petrova et al. (2016.) "TTI-621 (SIRPαFc): A CD47-Blocking Innate Immune Checkpoint Inhibitor with Broad Antitumor Activity and Minimal Erythrocyte Binding," Clin Cancer Res, 23(4):1068-1079.

Rudikoff et al. (1982). "Single amino acid substitution altering antigen-binding specificity," Immunology, vol. 79, pp. 1979-1983.

Sazinsky et al. (2008). "Aglycosylated immunoglobulin G1 variants productively engage activating Fc receptors," Proc Natl Acad Sci U S A, 105(51): 20167-20172.

U.S. Appl. No. 17/334,151, filed May 28, 2021 for Pons et al. (Copy not submitted herewith pursuant to the waiver of 37 C.F.R. § 1.98(a)(2)(iii) issued by the Office Sep. 21, 2004).

U.S. Appl. No. 17/530,287, filed Nov. 18, 2021 for Ring et al. (Copy not submitted herewith pursuant to the waiver of 37 C.F.R. § 1.98(a)(2)(iii) issued by the Office Sep. 21, 2004).

U.S. Appl. No. 17/543,569, filed Dec. 6, 2021 for Pons et al. (Copy not submitted herewith pursuant to the waiver of 37 C.F.R. § 1.98(a)(2)(iii) issued by the Office Sep. 21, 2004).

Weiskopf et al. (2017.) "Cancer immunotherapy targeting the CD47/SIRPα axis," European Journal of Cancer, vol. 76, pp. 100-109.

Wilson et al. (Jul. 1984). "The structure of an antigenic determinant in a protein," Cell 37(3)767-778.

U.S. Appl. No. 17/743,350, filed May 12, 2022 for Wan et al., titled "Combination Therapies for Treating Cancer," (Copy not submitted herewith pursuant to the waiver of 37 C.F.R. § 1.98(a)(2)(iii) issued by the Office Sep. 21, 2004).

* cited by examiner

METHODS OF TREATING CANCER

CROSS-REFERENCE TO RELATED APPLICATIONS

This application claims the priority benefit of U.S. Provisional Application No. 62/855,821, filed May 31, 2019 and U.S. Provisional Application No. 63/022,187, filed May 8, 2020, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 757972001000SEQLIST.TXT, date recorded: May 26, 2020, size: 333 KB).

FIELD OF THE INVENTION

The present invention relates to methods of treating cancer that comprise administering a polypeptide (e.g. a fusion polypeptide) that comprises a SIRPα D1 domain variant and an Fc domain variant in conjunction with a therapeutic antibody.

BACKGROUND

Many cancers have a poor prognosis, even when treated with available therapeutics. For example, non-small cell lung cancer (NSCLC) patients with metastatic disease receiving PD-1 and PD-L1 checkpoint inhibitors who have failed prior platinum based therapies have a median overall survival rate of approximately one year (Garon et al., New Engl J Med (2015) 372:2018-28; Herbst et al., Lancet (2016) 387:1540-50; Fehrenbacher et al., Lancet (2016) 387 (10030):1837-46), and over half NSCLC patients with advanced stage disease have an overall 5-year survival rate of 17.7% (U.S. Cancer Statistics Working Group, available at the web site www(dot)cdc(dot)gov/uscs). Similarly, the overall 5-year survival rate for gastric cancer patients in the United States is 30.4% (U.S. Cancer Statistics Working Group). In patients with relapsed indolent lymphomas, subsequent relapses usually occur with increasingly aggressive histologies and a transformation risk of 30% by 10 years in one series (Montoto et al., J Clin Oncol (2007) 25(17):2426-33). Further, for patients with recurrent aggressive histologies, cure is rare, and novel salvage regimens are needed (Larouche et al., J Clin Oncol (2010) 28(12):2094-100). CD20-positive non-Hodgkin lymphoma (NHL) as the 10th most common cancer globally, is also the 10th leading cause of cancer death, accounting for 199,670 deaths per year, worldwide (World Health Organization 2016(a), available at the website globocan(dot)iarc(dot)fr/Pages/fact_sheets_cancer(dot)aspx). There are estimated to be over 35,000 people living in the US with metastatic HNSCC, with over 50,000 newly incident cases at all stages diagnosed in 2019. Five-year survival is 84% for patients diagnosed with localized disease but decreases to only 39% for those diagnosed with metastatic disease. There is a need in the art for new treatments to provide additional therapeutic options and improve outcomes for such patients.

Tumor cells manipulate the myeloid compartment to evade the anti-tumor host immune response (Gabrilovich et al., Nat Rev Immunol (2012) 12(4):253-68). For example, while CD47 expressed on the surface of normal cells binds SIRPα on macrophages and provides a "don't eat me" signal, tumor cells have also been found to overexpress CD47 to evade the macrophage component of immune surveillance (Oldenborg, ISRN Hematol (2013) 614619).

Macrophage-mediated destruction of cancer cells requires both the disruption of "don't eat me" signals (e.g., CD47-SIRPα) and the activation of "eat me" signals. Neither component alone is sufficient to trigger maximal phagocytic reaction against tumor cells. As described above, CD47 provides a fundamental "don't eat me" signal through its interaction with SIRPα on macrophages. The pro-phagocytic "eat me" signal can be provided to the same macrophages by binding to their activating Fc gamma receptors. For example, the pro-phagocytic "eat me" signal can be provided by binding of anti-tumor antibodies to Fc receptors on macrophages.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY OF THE INVENTION

Provided is a method of treating non-small cell lung cancer (NSCLC) in an individual, comprising administering to the individual an effective amount of (a) a polypeptide comprising a SIRPα D1 domain variant and an Fc domain variant, and (b) an anti-PD-1 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the individual is a human. In some embodiments, the NSCLC in the individual has progressed on a prior immune checkpoint inhibitor (CPI) therapy and/or has a PD-L1 tumor proportion score (TPS) of less than 50%, Also provided is a polypeptide comprising a SIRPα D1 domain variant and an Fc domain variant for use in the manufacture of a medicament for treating NSCLC in an individual, wherein the medicament is for use (such as formulated for use) in combination with an anti-PD1 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat; and wherein the individual is a human. In some embodiments, the NSCLC in the individual has progressed on a prior immune checkpoint inhibitor (CPI) therapy and/or has a PD-L1 tumor proportion score (TPS) of less than 50%.

Also provided is a composition (such a pharmaceutical composition) comprising a polypeptide comprising a SIRPα D1 domain variant and an Fc domain variant for use in combination with an anti-PD1 antibody for treating NSCLC in an individual (e.g., for use in a method of treating NSCLC in an individual), wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the individual is a human. In some embodiments, the NSCLC in the individual has progressed on a prior immune checkpoint inhibitor (CPI) therapy and/or has a PD-L1 tumor proportion score (TPS) of less than 50%.

In some embodiments, the prior CPI (immune checkpoint inhibitor therapy) comprised one or more agents selected from the group consisting of: nivolumab, pembrolizumab, atezolizumab, avelumab, durvalumab, and cemiplimab. In some embodiments, the anti-PD-1 antibody blocks the interaction between PD-1 and PD-L1. In some embodiments, the anti-PD-1 antibody is pembrolizumab. In some embodiments, the pembrolizumab is administered to the individual at a dose of 200 mg every 3 weeks (Q3W) by intravenous (IV) infusion.

Also provided is a method of treating head and neck squamous cell carcinoma (HNSCC) in an individual, comprising administering to the individual an effective amount of (a) a polypeptide comprising a SIRPα D1 domain variant and an Fc domain variant, and (b) an anti-PD-1 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat; wherein the HNSCC in the individual has progressed while on a prior platinum therapy or after the platinum therapy, and wherein the individual is a human.

Also provided is a polypeptide comprising a SIRPα D1 domain variant and an Fc domain variant for use in the manufacture of a medicament for treating HNSCC in an individual, wherein the medicament is for use (such as formulated for use) in combination with an anti-PD1 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat; wherein the HNSCC in the individual has progressed while on a prior platinum therapy or after the platinum therapy, and wherein the individual is a human.

Also provided is a composition (such a pharmaceutical composition) comprising a polypeptide comprising a SIRPα D1 domain variant and an Fc domain variant for use in combination with an anti-PD1 antibody for treating HNSCC in an individual (e.g., for use in a method of treating HNSCC in an individual), wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the HNSCC in the individual has progressed while on a prior platinum therapy or after the platinum therapy, and wherein the individual is a human.

In some embodiments, the individual with HNSCC received prior therapy with an immune checkpoint inhibitor (e.g., an immune checkpoint inhibitor described herein). In some embodiments, such individual is considered to be/referred to as "checkpoint inhibitor experienced." In some embodiments, the individual with HNSCC has not received prior therapy with an immune checkpoint inhibitor. In some embodiments, such individual is considered to be/referred to as "checkpoint inhibitor naïve." In some embodiments, the prior platinum therapy comprised one or more therapeutic agents selected from the group consisting of: cisplatin, carboplatin, and oxaliplatin. In some embodiments, the anti-PD-1 antibody blocks the interaction between PD-1 and PD-L1. In some embodiments, the anti-PD-1 antibody is pembrolizumab. In some embodiments, the pembrolizumab is administered (such as formulated for administration) to the individual at a dose of 200 mg every 3 weeks (Q3W) by intravenous (IV) infusion.

Provided is a method of treating HER2-positive gastric/gastroesophageal junction (GEJ) cancer in an individual, comprising administering to the individual an effective amount of (a) a polypeptide comprising a SIRPα D1 domain variant and an Fc domain variant, and (b) an anti-HER2 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the gastric/GEJ cancer in the individual has progressed following a prior treatment with a fluoropyrimidine-based therapy and/or a prior treatment with an anti-HER2 antibody, and wherein the individual is a human.

Also provided is a polypeptide comprising a SIRPα D1 domain variant and an Fc domain variant for use in the manufacture of a medicament for treating HER2-positive gastric/gastroesophageal junction (GEJ) cancer in an individual, wherein the medicament is for use (such as formulated for use) in combination with an anti-HER2 antibody, wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the gastric/GEJ cancer in the individual has progressed following a prior treatment with a fluoropyrimidine-based therapy and/or a prior treatment with an anti-HER2 antibody, and wherein the individual is a human.

Also provided is a composition (such a pharmaceutical composition) comprising a polypeptide comprising a SIRPα D1 domain variant and an Fc domain variant for use in combination with an anti-HER2 antibody for treating HER2-positive gastric/gastroesophageal junction (GEJ) cancer in an individual (e.g., for use in a method of treating HER2-positive gastric/gastroesophageal junction (GEJ) cancer in an individual), wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the gastric/GEJ cancer in the individual has progressed following a prior treatment with a fluoropyrimidine-based therapy and/or a prior treatment with an anti-HER2 antibody, and wherein the individual is a human.

In some embodiments, the prior treatment with the fluoropyrimidine-based therapy or the prior treatment with the anti-HER2 antibody comprised one or more therapeutic agents selected from the group consisting of: trastuzumab, pertuzumab, 5-fluorouracil, capecitabine, margetuximab, and FOLFOX. In some embodiments, the anti-HER2 antibody is trastuzumab. In some embodiments, trastuzumab is administered (such as formulated for administration) to the individual at an initial dose of 8 mg/kg and at a dose of 6 mg/kg for each subsequent dose, and wherein trastuzumab is administered to the individual by IV infusion every 3 weeks (Q3W).

Provided is a method of treating aggressive non-Hodgkin lymphoma (NHL) in an individual, comprising administering to the individual an effective amount of (a) a polypeptide comprising a SIRPα D1 domain variant and an Fc domain variant, and (b) an anti-CD20 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat; wherein the aggressive NHL in the individual is relapsed and/or refractory to a prior treatment for aggressive NHL and there is no available curative therapy, and wherein the individual is a human.

Also provided is a polypeptide comprising a SIRPα D1 domain variant and an Fc domain variant for use in the manufacture of a medicament for treating aggressive non-Hodgkin lymphoma (NHL) in an individual, wherein the medicament is for use (such as formulated for use) in combination with an anti-CD20 antibody, wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and deG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the aggressive NHL in the individual is relapsed and/or refractory to a prior treatment for aggressive NHL and there is no available curative therapy, and wherein the individual is a human.

Also provided is a composition (such a pharmaceutical composition) comprising a polypeptide comprising a SIRPα D1 domain variant and an Fc domain variant for use in combination with an anti-CD20 antibody for treating aggressive non-Hodgkin lymphoma (NHL) in an individual (e.g., for use in a method of treating aggressive NHL), wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and deG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the aggressive NHL in the individual is relapsed and/or refractory to a prior treatment for aggressive NHL and there is no available curative therapy, and wherein the individual is a human.

In some embodiments, the aggressive NHL is diffuse large B-cell lymphoma (DLBCL), e.g., de novo DLBCL or transformed DLBCL. In some embodiments, the prior treatment(s) for aggressive NHL comprised rituximab, cyclophosphamide, doxorubicin, vincristine, gemcitabine, lenalidomide, prednisone, prednisolone, etoposide, procarbazine, epirubicin, bendamustine, cisplatin, oxaliplatin, cytarabine, ifosfaide, carboplatin, dexamethasone, mesna, carmustine nielphalan, solumedrol, methyl-glyoxal-bis (guanylhydrazone), thiotepa, methotrexate, ibrutinib, obinituzumab, tisagenlecleucel, axicabtagene, brentuximab vedotin, and combinations thereof. In some embodiments, the anti-CD20 antibody is rituximab. In some embodiments, the rituximab is administered (such as formulated for administration) to the individual at a dose of 375 mg/m$^2$ by IV infusion, wherein rituximab is administered (such as formulated for administration) to the individual once per week for four weeks and once per month thereafter.

Provided is a method of treating indolent lymphoma in an individual, comprising administering to the individual an effective amount of (a) a polypeptide comprising a SIRPα D1 domain variant and an Fc domain variant, and (b) an anti-CD20 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the indolent lymphoma in the individual is relapsed and/or refractory to a prior treatment for indolent lymphoma, and wherein the individual is a human.

Also provided is a polypeptide comprising a SIRPα D1 domain variant and an Fc domain variant for use in the manufacture of a medicament for treating indolent lymphoma in an individual, wherein the medicament is for use (such as formulated for use) in combination with an anti-CD20 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat; wherein the indolent lymphoma in the individual is relapsed and/or refractory to a prior treatment for indolent lymphoma, and wherein the individual is a human.

Also provided is a composition (such a pharmaceutical composition) comprising a polypeptide comprising a SIRPα D1 domain variant and an Fc domain variant for use in combination with an anti-CD20 antibody for treating indolent lymphoma in an individual (e.g., for use in a method of treating indolent lymphoma in an individual), wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; wherein the indolent lymphoma in the individual is relapsed and/or refractory to a prior treatment for indolent lymphoma, and wherein the individual is a human.

In some embodiments, the indolent lymphoma is an indolent non-Hodgkin lymphoma (NHL). In some embodiments, the indolent NHL is a marginal zone lymphoma or a follicular lymphoma. In some embodiments, the prior treatment for indolent lymphoma comprised rituximab, cyclophosphamide, doxorubicin, vincristine, gemcitabine, lenalidomide, prednisone, prednisolone, etoposide, procarbazine, epirubicin, bendamustine, cisplatin, oxaliplatin, cytarabine, ifosfamide, carboplatin, dexamethasone, mesna, carmustine, melphalan, solumedrol, methyl-glyoxal-bis (guanylhydrazone), thiotepa, methotrexate, ibrutinib, obinituzumab, tisagenlecleucel, axicabtagene, brentuximab vedotin, fludarabine mitoxantrone, everolimus, bortezomib, navitoclax, and combinations thereof. In some embodiments, the anti-CD20 antibody is rituximab. In some embodiments, the rituximab is administered (such as formulated for administration) to the individual at a dose of 375 mg/m$^2$ by IV infusion, wherein rituximab is administered (such as formulated for administration) to the individual once per week for four weeks and once per month thereafter. In some embodiments, the polypeptide comprising a SIRPα D1 domain variant and an Fc domain variant (such as the medicament manufactured using such polypeptide or a pharmaceutical composition comprising such polypeptide) is administered (such as formulated for administration) to the individual at a dose of 10 mg/kg or 15 mg/kg once per week (QW), e.g., by IV infusion.

In some embodiments of any of the methods herein, the SIRPα D1 domain variant comprises the amino acid sequence of SEQ ID NO: 85. In some embodiments, the SIRPα D1 domain variant comprises the amino acid sequence of SEQ ID NOL: 81. In some embodiments, the Fc domain variant is a human IgG1 Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the polypeptide comprising a SIRPα D1 domain variant and an Fc domain variant comprises the amino acid sequence of SEQ ID NO: 136. In some embodiments, the polypeptide comprising a SIRPα D domain variant and an Fc domain variant comprises the amino acid sequence of SEQ ID NO: 135. In some embodiments, the polypeptide comprising a SIRPα D1 domain variant and an Fc domain variant forms a homodimer.

In some embodiments, the polypeptide comprising a SIRPα D1 domain variant and an Fc domain variant (such as the medicament manufactured using such polypeptide or a pharmaceutical composition comprising such polypeptide) is administered (such as formulated for administration) to the individual at a dose of 10 mg/kg once per week (QW).

In some embodiments, the polypeptide comprising a SIRPα D1 domain variant and an Fc domain variant (or the medicament manufactured therefrom or the pharmaceutical composition comprising such polypeptide) is administered (such as formulated for administration) to the individual by IV infusion.

Also provided is a kit comprising a polypeptide comprising a SIRPα D1 domain variant and an Fc domain variant (such as the medicament manufactured using such polypeptide or a pharmaceutical composition comprising such polypeptide), for use in combination with pembrolizumab for treating non-small cell lung cancer (NSCLC) in an individual (e.g., human individual) in need thereof, according to a method described herein. In some embodiments, the SIRPα D1 domain variant comprises the amino acid sequence of SEQ ID NO: 81 or SEQ ID NO: 85; the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and deG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the NSCLC in the individual has progressed on a prior immune checkpoint inhibitor (CPI) therapy and/or has a PD-L1 tumor proportion score (TPS) of less than 50%. In some embodiments, the kit further comprises instructions for administering pembrolizumab at a dose of 200 mg every 3 weeks (Q3W) by IV infusion. In some embodiments, the kit further comprises instructions for administering the polypeptide (e.g. fusion polypeptide) at a dose of 10 mg/kg once a week, e.g., by IV infusion.

Also provided is a kit comprising a polypeptide comprising a SIRPα D1 domain variant and an Fc domain variant (such as the medicament manufactured using such polypeptide or a pharmaceutical composition comprising such polypeptide) for use in combination with pembrolizumab for treating head and neck squamous cell carcinoma (HNSCC) in an individual (e.g., a human individual) in need thereof, according to a method described herein. In some embodiments, the SIRPα D1 domain variant comprises the amino acid sequence of SEQ ID NO: 81 or SEQ ID NO: 85; the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and the HNSCC in the individual has progressed while on a prior platinum therapy or after the platinum therapy. In some embodiments, the individual received prior therapy with an immune checkpoint inhibitor. In some embodiments, the individual has not received prior therapy with an immune checkpoint inhibitor. In some embodiments, the kit further comprises instructions for administering pembrolizumab at a dose of 200 mg every 3 weeks (Q3W) by IV infusion. In some embodiments, the kit further comprises instructions for administering the polypeptide (e.g. fusion polypeptide) at a dose of 10 mg/kg once a week, e.g., by IV infusion.

Also provided herein is a kit comprising a polypeptide comprising a SIRPα D1 domain variant and an Fc domain variant in a pharmaceutically acceptable carrier for use in combination with trastuzumab for treating HER2-positive gastric/gastroesophageal junction (GEJ) cancer in an individual (e.g., a human individual) in need thereof, according to a method described herein. In some embodiments, the SIRPα D1 domain variant comprises the amino acid sequence of SEQ ID NO: 81 or SEQ ID NO: 85; the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat; and the HER2-positive gastric/GEJ cancer in the individual has progressed following a prior fluoropyrimidine-based therapy or a prior treatment with an anti-HER2 antibody. In some embodiments, the kit further comprises instructions for administering trastuzumab at an initial dose of 8 mg/kg and at a dose of 6 mg/kg for each subsequent dose, and wherein trastuzumab is administered to the individual by IV infusion every 3 weeks (Q3W). In some embodiments, the kit further comprises instructions for administering the polypeptide (e.g. fusion polypeptide) at a dose of 10 mg/kg once a week, e.g., by IV infusion.

Provided is a kit comprising a polypeptide comprising a SIRPα D1 domain variant and an Fc domain variant in a pharmaceutically acceptable carrier for use in combination with rituximab for treating aggressive non-Hodgkin lymphoma (NHL) in an individual (e.g., a human individual) in need thereof, according to a method described herein. In some embodiments, the SIRPα D1 domain variant comprises the amino acid sequence of SEQ ID NO: 81 or SEQ ID NO: 85; the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and deG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and the aggressive NHL in the individual is relapsed and/or refractory to a prior treatment for aggressive NHL and there is no available curative therapy. In some embodiments, the aggressive NHL is a diffuse large B-cell lymphoma (DLBCL), e.g., a de novo DLBCL or a transformed DLBCL. In some embodiments, the aggressive NHL is a mantle cell lymphoma. In some embodiments, the kit further comprises instructions for administering rituximab at a dose of 375 mg/m$^2$ by IV infusion, wherein rituximab is administered to the individual once per week for four weeks and once per month thereafter. In some embodiments, the kit further comprises instructions for administering the polypeptide (e.g. fusion polypeptide) at a dose of 10 mg/kg or 15 mg/kg once a week, e.g., by IV infusion.

Also provided is a kit comprising a polypeptide comprising a SIRPα D1 domain variant and an Fc domain variant in a pharmaceutically acceptable carrier, for use in combination with rituximab for treating indolent lymphoma in an individual (e.g., a human individual) in need thereof, according to a method described herein. In some embodiments, the SIRPα D1 domain variant comprises the amino acid sequence of SEQ ID NO: 81 or SEQ ID NO: 85; the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and deG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and the indolent lymphoma in the individual is relapsed or refractory to a prior treatment for indolent lymphoma. In some embodiments, the indolent lymphoma is an indolent non-Hodgkin lymphoma (NHL). In some embodiments, the indolent NHL is a Marginal zone lymphoma or a follicular lymphoma. In some embodiments, the kit further comprises instructions for administering rituximab at a dose of 375 mg/m² by IV infusion, wherein rituximab is administered to the individual once per week for four weeks and once per month thereafter. In some embodiments, the kit further comprises instructions for administering the polypeptide (e.g. fusion polypeptide) at a dose of 10 mg/kg or 15 mg/kg once a week, e.g., by IV infusion.

In some embodiments of any of the kits, the SIRPα D1 domain variant comprises the amino acid sequence of SEQ ID NO: 85. In some embodiments, the SIRPα D1 domain variant comprises the amino acid sequence of SEQ ID NOL: 81. In some embodiments, the Fc domain variant is a human IgG Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the polypeptide comprising a SIRPα D1 domain variant and an Fc domain variant comprises the amino acid sequence of SEQ ID NO: 136. In some embodiments, the polypeptide comprising a SIRPα D1 domain variant and an Fc domain variant comprises the amino acid sequence of SEQ ID NO: 135. In some embodiments, the polypeptide comprising a SIRPα D1 domain variant and an Fc domain variant forms a homodimer. In some embodiments, further comprising instructions for administering the polypeptide comprising a SIRPα D1 domain variant and an Fc domain variant (or the medicament manufactured therefrom or the pharmaceutical composition comprising such polypeptide) to the individual at a dose of 10 mg/kg once per week (QW). In some embodiments, the kit comprises instructions for administering the polypeptide comprising a SIRPα D1 domain variant and an Fc domain variant (or the medicament manufactured therefrom or the pharmaceutical composition comprising such polypeptide) to the individual by IV infusion.

BRIEF DESCRIPTION OF THE DRAWINGS

FIG. 3A provides the change in tumor size, shown as percent from baseline. ORR=overall response rate; DCR=disease control rate; mPFS=median progression-free; CI=confidence interval. The changes in tumor sizes shown as percent from baseline for each patient over the course of the study are provided in FIG. 3B. For FIGS. 3A-3B: patients who received at least one dose of Drug A in the expansion phase, had a baseline assessment, and at least one post-baseline disease assessment are included; the top dashed line indicates the threshold for objective progression; the bottom dashed line indicates the threshold for overall response. The duration of treatment for each enrolled patient who received at least one dose of Drug A in the expansion phase is provided in FIG. 3C. Tumors were assessed according to the Response Evaluation Criteria in Solid Tumors (RECIST) version 1.1 (E. A. Eisenhauer, et al., European Journal of Cancer 45 (2009) 228-247.)

FIG. 4A provides the change in tumor size, shown as percent from baseline. ORR=overall response rate; DCR=disease control rate; mPFS=median progression-free survival; CI=confidence interval; CP=immune checkpoint therapy; CPS=combination positive score for PD-L1 staining. The changes in tumor sizes shown as percent from baseline for each patient over the course of the study are provided in FIG. 4B. For FIGS. 4A-4B: patients who received at least one dose of Drug A in the expansion phase, had a baseline assessment, and at least one post-baseline disease assessment are included; the top dashed line indicates the threshold for objective progression; the bottom dashed line indicates the threshold for overall response. The duration of treatment for each enrolled patient who received at least one dose of Drug A in the expansion phase is provided in FIG. 4C. Tumors were assessed according to the Response Evaluation Criteria in Solid Tumors (RECIST) version 1.1 (E. A. Eisenhauer, et al., European Journal of Cancer 45 (2009) 228-247.)

FIG. 5A provides the change in tumor size, shown as percent from baseline. DCR=disease control rate; mPFS=median progression-free survival; CI=confidence interval; TPS=tumor proportion score for PD-L1 staining. The changes in tumor sizes shown as percent from baseline for each patient over the course of the study are provided in FIG. 5B. For FIGS. 5A-5B: patients who received at least one dose of Drug A in the expansion phase, had a baseline assessment, and at least one post-baseline disease assessment are included; the top dashed line indicates the threshold for objective progression; the bottom dashed line indicates the threshold for partial response. The duration of treatment for each enrolled patient who received at least one dose of Drug A in the expansion phase is provided in FIG. 5C. Tumors were assessed according to the Response Evaluation Criteria in Solid Tumors (RECIST) version 1.1 (E. A. Eisenhauer, et al., European Journal of Cancer 45 (2009) 228-247.)

As shown in FIG. 6A, Drug A PK (Drug A serum concentration) were within predicted 95% intervals based on an established population PK model. The steady-state half-life of Drug A (10 mg/kg QW) was predicted to be approximately 16 days. Drug A PK time points included intensive sampling in cycles 1 and 3, and pre-dose and end-of-infusion only in every cycle thereafter. FIG. 6B shows that near complete CD47 target occupancy is maintained in CD4+ T cells that express CD47 throughout the Drug A dosing interval when Drug A was administered in combination with pembrolizumab or trastuzumab. TO=target occupancy.

In FIGS. 7B-7C: the graph to the right shows the changes in tumor sizes as percent from baseline for each patient over the course of the study; the top dashed line indicates the threshold for objective progression; the bottom dashed line indicates the threshold for partial response. CD68 and CD163 markers indicate macrophages; the CD8 marker indicates T lymphocytes.

DETAILED DESCRIPTION OF THE INVENTION

Definitions

Figure 1:
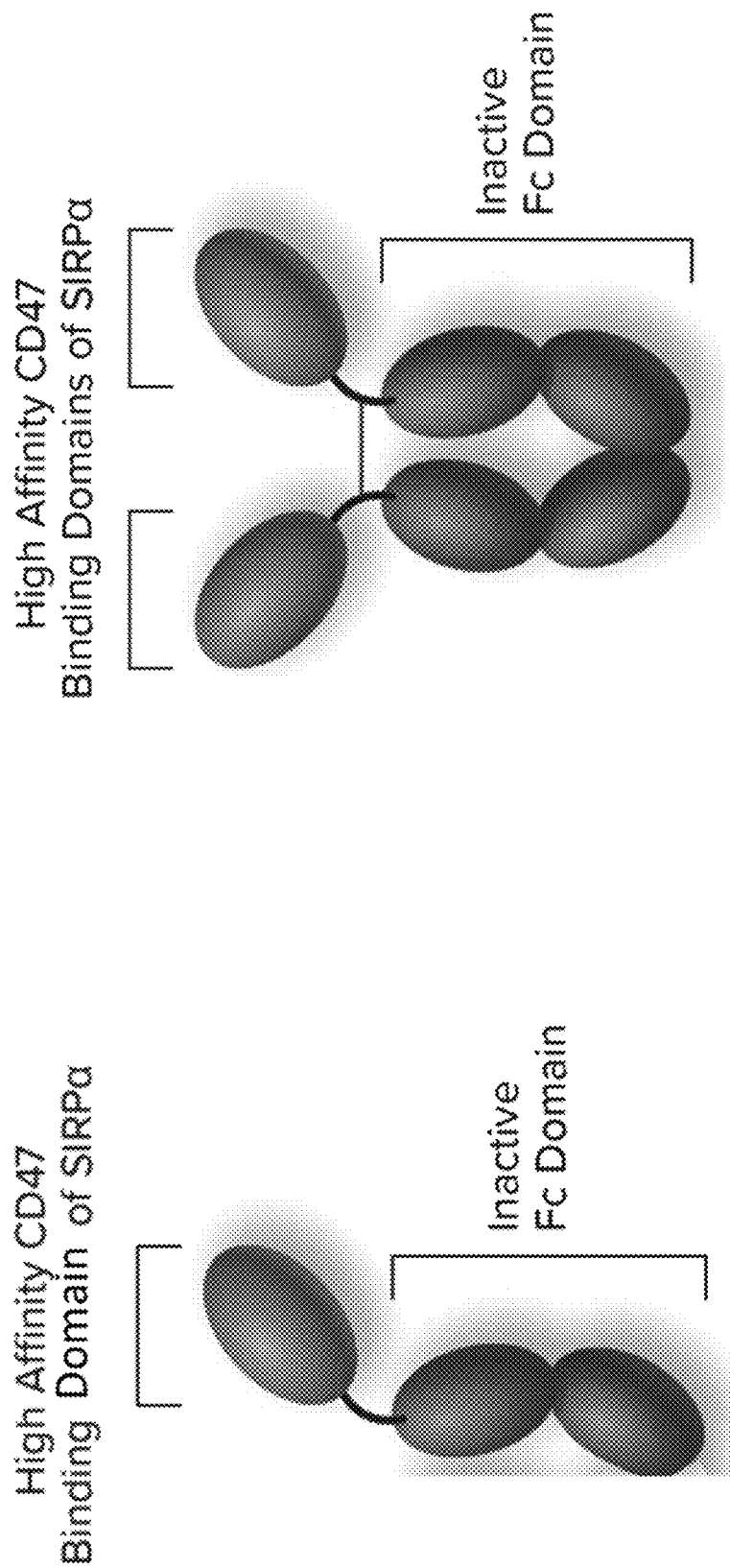
FIGS. 1A-1B depicts Drug A is a monomer (FIG. 1A), and as a homodimer (FIG. 1B). The SIRPα D1 domain variant selectively binds CD47 with picomolar binding affinity to block its interactions with SIRPα. The molecular weight of Drug A is half the size of a typical antibody, allowing twice the molar concentration to be delivered to tumors. The Fc domain is modified to eliminate binding to Fc gamma receptors to minimize toxicity. Drug A exhibits antibody-like pharmacokinetics.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description or the claims, such terms are intended to be inclusive in a manner similar to the term "comprising."

As used herein, the terms "treatment", "treating", and the like, refer to administering an agent, or carrying out a procedure, for the purposes of obtaining an effect. In some embodiments, the effect is prophylactic in terms of completely or partially preventing a disease or symptom thereof. In some embodiments, the effect is therapeutic in terms of affecting a partial or complete cure for a disease or symptoms of the disease.

As used herein, the term "antibody" refers to intact antibodies; antibody fragments, provided that they exhibit the desired biological activity (e.g. epitope binding); monoclonal antibodies; polyclonal antibodies; monospecific antibodies; multi-specific antibodies (e.g., bispecific antibodies); and antibody-like proteins.

As used herein, the term "antibody variable domain" refers to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs).

As used herein, the term "linker" refers to a linkage between two elements, e.g., protein domains. In some embodiments, a linker can be a covalent bond or a spacer. The term "spacer" refers to a moiety (e.g., a polyethylene glycol (PEG) polymer) or an amino acid sequence (e.g., a 1-200 amino acid sequence) occurring between two polypeptides or polypeptide domains to provide space or flexibility (or both space and flexibility) between the two polypeptides or polypeptide domains. In some embodiments, an amino acid spacer is part of the primary sequence of a polypeptide (e.g., joined to the spaced polypeptides or polypeptide domains via the polypeptide backbone).

As used herein, the term "effective amount" refers to an amount of a polypeptide or a pharmaceutical composition containing a polypeptide described herein, e.g., a polypeptide having a SIRPα D1 domain or variant thereof, that is sufficient and effective in achieving a desired therapeutic effect in treating a patient having a disease, such as a cancer, e.g., solid tumor or hematological cancer. In some embodiments, an effective amount of polypeptide will avoid adverse side effects.

As used herein, the term "pharmaceutical composition" refers to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with the polypeptide. In some embodiments, the pharmaceutical composition is in tablet or capsule form for oral administration or in aqueous form for intravenous or subcutaneous administration, for example by injection.

As used herein, the terms "subject," "individual," and "patient" are used interchangeably to refer to a vertebrate, for example, a mammal. Mammals include, but are not limited to, murines, simians, humans, farm animals, sport animals, and pets. Tissues, cells, and their progeny of a biological entity obtained in vivo or cultured in vitro are also encompassed. None of the terms entail supervision of a medical professional.

As used herein, the term "affinity" or "binding affinity" refers to the strength of the binding interaction between two molecules. Generally, binding affinity refers to the strength of the sum total of non-covalent interactions between a molecule and its binding partner, such as a SIRPα D1 domain variant and CD47. Unless indicated otherwise, binding affinity refers to intrinsic binding affinity, which reflects a 1:1 interaction between members of a binding pair. The binding affinity between two molecules is commonly described by the dissociation constant (KD) or the association constant (KA). Two molecules that have low binding affinity for each other generally bind slowly, tend to dissociate easily, and exhibit a large KD. Two molecules that have high affinity for each other generally bind readily, tend to remain bound longer, and exhibit a small KD. In some embodiments, the KD of two interacting molecules is determined using known methods and techniques, e.g., surface plasmon resonance (SPR). KD can be calculated as the ratio of koff/kon.

As used herein, the term "$K_D$ less than" refers to a numerically smaller $K_D$ value and an increasing binding affinity relative to the recited KD value. As used herein, the term "KD greater than" refers to a numerically larger KD value and a decreasing binding affinity relative to the recited KD value.

As used herein, "in conjunction with" refers to administration of one treatment modality in addition to another treatment modality. As such, "in conjunction with" refers to administration of one treatment modality before, during, or after administration of the other treatment modality to the individual.

Overview

Provided herein are methods of treating cancer in an individual (e.g., a human individual) that comprise administering to the individual (a) a polypeptide (e.g., a fusion polypeptide) that comprises a SIRPα D1 domain variant and an Fc domain variant and (b) a therapeutic antibody. In some embodiments, the polypeptide comprises any one of the SIRPα D1 domain variants described herein (unless otherwise specified).

In some embodiments, provided is a method of treating non-small cell lung cancer (NSCLC) in an individual, comprising administering to the individual an effective amount of (a) a polypeptide comprising a SIRPα D1 domain variant and an Fc domain variant, and (b) an anti-PD-1 antibody, wherein the SIRPα D1 domain variant comprises the amino acid sequence of SEQ ID NO: 81 or SEQ ID NO: 85, wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the individual is a human. In some embodiments, the NSCLC in the individual has progressed on a prior immune checkpoint inhibitor (CPI) therapy and/or has a PD-L1 tumor proportion score (TPS) of less than 50%. In some embodiments, the individual has not received prior CPI therapy. In some embodiments, the individual is PD-L1 negative. In some embodiments, the individual is PD-L1 positive.

In some embodiments, provided is a method of treating head and neck squamous cell carcinoma (HNSCC) in an individual, comprising administering to the individual an effective amount of (a) a polypeptide comprising a SIRPα D1 domain variant and an Fc domain variant, and (b) an anti-PD-1 antibody, wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat; and wherein the HNSCC in the individual has progressed while on a prior platinum therapy or after the platinum therapy, and wherein the individual is a human. In some embodiments, the individual received prior immune checkpoint inhibitor (CPI) therapy (e.g., treatment with an immune checkpoint inhibitor described herein). In some embodiments, the individual has not received prior CPI therapy. In some embodiments, the individual is PD-L1 negative. In some embodiments, the individual is PD-L1 positive.

In some embodiments an individual is "PD-L1 negative" if the individual has a cancer that does not express PD-L1 biomarker or expresses very low levels of PD-L1. In some embodiments, the individual is "PD-L1 negative" or has a "PD-L1 negative cancer" if PD-L1 expression (e.g., protein expression) is not detected on (or in) tumor cells (TC) in a sample from the individual, if PD-L1 expression (e.g., protein expression) is not detected on (or in) tumor-infiltrating immune cells (IC) in a sample from the individual, or if PD-L1 expression (e.g., protein expression) is detected at very low levels on (or in) TC and/or IC in a sample from the individual. In some embodiments, the individual is PD-L1 negative if, e.g., 0%, less than about 1%, less than about 5%, or less than about 10% of the tumor cells (TC) and/or tumor-infiltrating immune cells (IC) in a sample obtained from the individual express PD-L1, as determined using an assay (e.g., an assay described herein) for determining the PD-L1 status of an individual. In some embodiments, an individual or tumor may be considered PD-L1 negative because it has no T-cell infiltrates. Such assays are known and routinely used by medical professionals.

In some embodiments, an individual is "PD-L1 positive" if the individual has a cancer that expresses (has been shown to express e.g., in a diagnostic test) PD-L1 biomarker. In some embodiments, such individual is "PD-L1 positive" or has cancer that is a "PD-L1 positive cancer." In some embodiments, the individual is "PD-L1 positive" or has a "PD-L1 positive cancer" if PD-L1 expression (e.g., protein expression) is detected on (or in) tumor cells (TC) in a sample from the individual, or if PD-L1 expression (e.g., protein expression) is detected on (or in) tumor-infiltrating immune cells (IC) in a sample from the individual. In some embodiments, the individual's TC and/or IC express low levels of PD-L1 biomarker. In some embodiments, the individual's TC and/or IC express high levels PD-L1 biomarker. In some embodiments, the individual is "PD-L1 positive" or has cancer that is a "PD-L1 positive cancer" if the PD-L1 biomarker is present (e.g., detected) in more than 0% of a sample, in at least 1% of a sample, in at least 5% of a sample, or in at least 10% of a sample from the individual (e.g., a sample from the individual that contains the individual's TC and/or IC), as determined using an assay (e.g., an assay described herein) for determining the PD-L1 status of an individual. Such assays are known and routinely used by medical professionals. In some embodiments, an individual is "PD-L" positive or has a "PD-L1 positive cancer" if the individual's tumor proportion score (TPS) is ≥50% (i.e., if ≥50% of the viable tumor cells in a sample from the individual express PD-L1, e.g., at any level).

In some embodiments, provided is a method of treating HER2-positive gastric/gastroesophageal junction (GEJ) cancer in an individual, comprising administering to the individual an effective amount of (a) a polypeptide comprising a SIRPα D1 domain variant and an Fc domain variant, and (b) an anti-HER2 antibody, wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the gastric/GEJ cancer in the individual has progressed following a prior treatment with a fluoropyrimidine-based therapy and/or a prior treatment with an anti-HER2 antibody, and wherein the individual is a human.

In some embodiments, provided is a method of treating aggressive non-Hodgkin lymphoma or "NHL" (e.g., de novo or transformed diffuse large B cell lymphoma (DLBCL) or mantle cell lymphoma) in an individual, comprising administering to the individual an effective amount of (a) a polypeptide comprising a SIRPα D1 domain variant and an Fc domain variant, and (b) an anti-CD20 antibody, wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and deG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the aggressive NHL in the individual is relapsed and/or refractory to a prior treatment for aggressive NHL and there is no available curative therapy, and wherein the individual is a human. In some embodiments, the relapsed/refractory aggressive NHL is relapsed/refractory DLBCL (e.g., de novo or transformed DLBCL). In some embodiments, the a relapsed/refractory aggressive NHL is relapsed/refractory mantle cell lymphoma (MCL).

In some embodiments, provided is a method of treating indolent lymphoma in an individual, comprising administering to the individual an effective amount of (a) a polypeptide comprising a SIRPα D1 domain variant and an Fc domain variant, and (b) an anti-CD20 antibody, wherein the SIRPα D1 domain variant comprises the amino acid sequence of SEQ ID NO: 81 or SEQ ID NO: 85; wherein the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the indolent lymphoma in the individual is relapsed and/or refractory to a prior treatment for indolent lymphoma, and wherein the individual is a human. In some embodiments, the indolent lymphoma (such as a relapsed/refractory indolent lymphoma) is a non-Hodgkin lymphoma (NHL), e.g., a relapsed/refractory indolent NHL. In some embodiments, the indolent NHL (e.g., relapsed/refractory NHL) is a follicular lymphoma (e.g., a relapsed/refractory follicular lymphoma). In some embodiments, the indolent NHL (e.g., relapsed/refractory NHL) is a marginal zone lymphoma (e.g., a relapsed/refractory marginal zone lymphoma).

Further details regarding the methods of treatment and polypeptides comprising a SIRP D1 domain variant and an Fc domain variant are described below. See also U.S. Pat. No. 10,259,859, the contents of which are incorporated by reference herein in their entirety.

Signal-Regulatory Protein α (SIRP-α) D1 Domain and Variants Thereof

Disclosed herein, in some embodiments, are polypeptides comprising a signal-regulatory protein α (SIRP-α) D1 variant comprising a SIRPα D1 domain, or a fragment thereof, that comprises an amino acid mutation at residue 80 relative to a wild-type SIRPα D1 domain; and at least one additional amino acid mutation relative to a wild-type SIRPα D1 domain at a residue selected from the group consisting of residue 6, residue 27, residue 31, residue 47, residue 53, residue 54, residue 56, residue 66, and residue 92.

Also disclosed herein, in some embodiments, are polypeptides comprising an Fc domain variants, wherein an Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Signal-regulatory protein α ("SIRP-α" or "SIRP-alpha") is a transmembrane glycoprotein belonging to the Ig superfamily that is widely expressed on the membrane of myeloid cells. SIRPα interacts with CD47, a protein broadly expressed on many cell types in the body. The interaction of SIRPα with CD47 prevents engulfment of "self" cells, which can otherwise be recognized by the immune system. It has been observed that high CD47 expression on tumor cells can act, in acute myeloid leukemia and several solid tumor cancers, as a negative prognostic factor for survival.

Native SIRPα comprises 3 highly homologous immunoglobulin (Ig)-like extracellular domains—D1, D2, and D3. The SIRPα D1 domain ("D1 domain") refers to the membrane distal, extracellular domain of SIRPα and mediates binding of SIRPα to CD47. As used herein, the term "SIRPα polypeptide" refers to any SIRPα polypeptide or fragment thereof that is capable of binding to CD47. There are at least ten variants of wild-type human SIRPα. Table 1 shows the amino acid sequences of the D1 domains of the ten naturally occurring wild-type human SIRPα D1 domain variants (SEQ ID NOs: 1-10). In some embodiments, a SIRPα polypeptide comprises a SIRPα D1 domain. In some embodiments, a SIRPα polypeptide comprises a wild-type D1 domain, such as those provided in SEQ ID NOs: 1-10. In some embodiments, a SIRPα polypeptide includes a D2 or D3 domain (or both a D2 and a D3 domain) (see Table 3) of a wild-type human SIRPα.

TABLE 1

Sequences of Wild-Type SIRPα D1 Domains

| SEQ ID NO: | Description | Amino Acid Sequence |
|---|---|---|
| 1 | Wild-type D1 domain variant 1 | EEELQVIQPDKSVLVAAGETATLRCTATSLIPVGPIQWFRGAGPGRELIYNQKEGHFPRVTTVSDLTKRNNMDFSIRIGNITPADAGTYYCVKFRKGSPDDVEFKSGAGTELSVRAKPS |
| 2 | Wild-type D1 domain variant 2 | EEELQVIQPDKSVSVAAGESAILHCTVTSLIPVGPIQWFRGAGPARELIYNQKEGHFPRVTTVSESTKRENMDFSISISNITPADAGTYYCVKFRKGSPDTEFKSGAGTELSVRAKPS |
| 3 | Wild-type D1 domain variant 3 | EEELQVIQPDKSVSVAAGESAILLCTVTSLIPVGPIQWFRGAGPARELIYNQKEGHFPRVTTVSESTKRENMDFSISISNITPADAGTYYCVKFRKGSPDTEFKSGAGTELSVRAKPS |
| 4 | Wild-type D1 domain variant 4 | EEGLQVIQPDKSVSVAAGESAILHCTATSLIPVGPIQWFRGAGPGRELIYNQKEGHFPRVTTVSDLTKRNNMDFSIRIGNITPADAGTYYCVKFRKGSPDDVEFKSGAGTELSVRAKPS |
| 5 | Wild-type D1 domain variant 5 | EEELQVIQPDKFVLVAAGETATLRCTATSLIPVGPIQWFRGAGPGRELIYNQKEGHFPRVTTVSDLTKRNNMDFSIRIGNITPADAGTYYCVKFRKGSPDDVEFKSGAGTELSVRAKPS |
| 6 | Wild-type D1 domain variant 6 | EEELQVIQPDKSVLVAAGETATLRCTATSLIPVGPIQWFRGAGPGRELIYNQKEGHFPRVTTVSDLTKRNNMDFPIRIGNITPADAGTYYCVKFRKGSPDDVEFKSGAGTELSVRAKPS |
| 7 | Wild-type D1 domain variant 7 | EEELQVIQPDKSVSVAAGESAILHCTVTSLIPVGPIQWFRGAGPARELIYNQKEGHFPRVTTVSESTKRENMDFSISISNITPADAGTYYCVKFRKGSPDTEFKSGAGTELSVRGKPS |
| 8 | Wild-type D1 domain variant 8 | EEELQVIQPDKSVLVAAGETATLRCTATSLIPVGPIQWFRGAGPARELIYNQKEGHFPRVTTVSESTKRENMDFSISISNITPADAGTYYCVKFRKGSPDTEFKSGAGTELSVRAKPS |

TABLE 1-continued

Sequences of Wild-Type SIRPα D1 Domains

| SEQ ID NO: | Description | Amino Acid Sequence |
|---|---|---|
| 9 | domain variant 9 Wild-type D1 | EEELQVIQPDKSVLVAAGETATLRCTATSLIPVGPIQ WFRGAGPGRELIYNQKEGHFPRVTTVSDLTKRNNM DFSIRISNITPADAGTYYCVKFRKGSPDDVEFKSGAG TELSVRAKPS |
| 10 | Wild-type D1 domain variant 10 | EEELQVIQPDKSVSVAAGESAILHCTVTSLIPVGPIQW FRGAGPARELIYNQKEGHFPRVTTVSESTKRENMDF SISISNITPADAGTYYCVKFRKGSPDTEFKSGAGTELS VRAKPS |
| 11 | Wild-type pan-D1 domain | EEX$_1$LQVIQPDKX$_2$VX$_3$VAAGEX$_4$AX$_5$LX$_6$CTX$_7$TSLIP VGPIQWFRGAGPX$_8$RELIYNQKEGHFPRVTTVSX$_9$X$_{10}$ TKRX$_{11}$NMDFX$_{12}$IX$_{13}$IX$_{14}$NITPADAGTYYCVKFRKGS X$_{15}$X$_{16}$DX$_{17}$EFKSGAGTELSVRX$_{18}$KPS |
|  | Amino acid substitutions relative to SEQ ID NO: 11 | X$_1$ is E or G; X$_2$ is S or F; X$_3$ is L or S; X$_4$ is T or S; X$_5$ is T or I; X$_6$ is R, H, or L; X$_7$ is A or V; X$_8$ is G or A; X$_9$ is D or E; X$_{10}$ is L or S; X$_{11}$ is N or E or D; X$_{12}$ is S or P; X$_{13}$ is R or S; X$_{14}$ is G or S; X$_{15}$ is P or absent; X$_{16}$ is D or P; X$_{17}$ is V or T; and X$_{18}$ is A or G |

As used herein, the term "SIRPα D1 domain variant" refers to a polypeptide comprising a SIRPα D1 domain or a CD47-binding portion of a SIRPα polypeptide that has a higher affinity to CD47 than wild-type SIRPα. A SIRPα D1 domain variant comprises at least one amino acid substitution, deletion, or insertion (or a combination thereof) relative to a wild-type SIRPα.

In some embodiments, SIRPα D1 domain variants disclosed herein comprise a SIRPα D1 domain or variant thereof. In some embodiments, a SIRPα D1 domain variant comprises one or more amino acid substitutions, insertions, additions, or deletions relative to a wild-type D1 domain shown in SEQ ID NOs: 1-10. Table 2 lists exemplary amino acid substitutions in each SIRPα D1 domain variant (SEQ ID NOs: 13-22). In some embodiments, the SIRPα D1 domain polypeptide or SIRPα D1 domain variant comprises a fragment of the D1 domain. In some embodiments, the SIRPα polypeptide fragment or SIRPα D1 domain variant fragment comprises an amino acid sequence of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. In some embodiments, the SIRPα D1 domain fragments retain the ability to bind to CD47.

In some embodiments, a polypeptide of the disclosure comprising a SIRPα D1 domain variant binds with higher binding affinity to CD47 than a wild-type human SIRPα D1 domain. In some embodiments, the SIRPα D1 domain variant binds to human CD47 with at least 1-fold (e.g., at least 1.5-fold, 2-fold, 2.5-fold, 3-fold, 3.5-fold, 4-fold, 5-fold or greater than 5-fold) affinity than the affinity of a naturally occurring D1 domain. In some embodiments, the SIRPα D1 domain variant binds to human CD47 with at least 1-fold (e.g., at least 10-fold, 100-fold, 1000-fold or greater than 1000-fold) affinity than the affinity of a naturally occurring D1 domain.

As used herein, the term "optimized affinity" or "optimized binding affinity" refers to an optimized strength of the binding interaction between a polypeptide disclosed herein, including a SIRPα D1 domain variant, and CD47. For example, in some embodiments, the polypeptide binds primarily or with higher affinity to CD47 on cancer cells and does not substantially bind or binds with lower affinity to CD47 on non-cancer cells. In some embodiments, the binding affinity between the polypeptide and CD47 is optimized such that the interaction does not cause clinically relevant toxicity or decreases toxicity compared to a variant which binds with maximal affinity. In some embodiments, in order to achieve an optimized binding affinity between a polypeptide provided herein and CD47, the polypeptide including a SIRPα D1 domain variant is developed to have a lower binding affinity to CD47 than which is maximally achievable. In some embodiments, the SIRPα D domain variants disclosed herein cross react with rodent, non-human primate (NHP), and human CD47.

As used herein, the term "immunogenicity" refers to the property of a protein (e.g., a therapeutic protein) which causes an immune response in the host as though it is a foreign antigen. The immunogenicity of a protein can be assayed in vitro in a variety of different ways, such as through in vitro T-cell proliferation assays.

As used herein, the term "minimal immunogenicity" refers to an immunogenicity of a protein (e.g., a therapeutic protein) that has been modified, e.g., through amino acid substitutions, to be lower (e.g., at least 10%, 25%, 50%, or 100% lower) than the immunogenicity before the amino acid substitutions are introduced (e.g., an unmodified protein). In some embodiments, a protein (e.g., a therapeutic protein) is modified to have minimal immunogenicity and causes no or very little host immune response even though it is a foreign antigen.

In some embodiments, the SIRPα D1 domain variant demonstrates minimal immunogenicity. In some embodiments, a SIRPα polypeptide of the disclosure administered to a subject has the same amino acid sequence as that of the SIRPα polypeptide in a biological sample of the subject, except for amino acid changes which increase affinity of the SIRPα D1 domain variant. In some embodiments, the polypeptide variants disclosed herein lower the risk of side effects compared to anti-CD47 antibodies or wild-type SIRPα. In some embodiments, the polypeptide variants disclosed herein lower the risk of anemia compared to anti-CD47 antibodies or wild-type SIRPα. In some embodiments, the polypeptide variants disclosed herein do not cause acute anemia in rodent or non-human primates (NHP) studies.

Table 2 lists specific amino acid substitutions in a SIRPα D1 domain variant relative to each D1 domain sequence. In some embodiments, a SIRPα D1 domain variant includes one or more (e.g., two, three, four, five, six, seven, eight, nine, ten, eleven, twelve, thirteen, fourteen or more) of the substitutions listed in Table 2. In some embodiments, a SIRPα D1 domain variant includes at most fourteen amino acid substitutions relative to a wild-type D1 domain. In some embodiments, a SIRPα D1 domain variant includes at most ten amino acid substitutions relative to a wild-type D1 domain. In some embodiments, a SIRPα D1 domain variant includes at most seven amino acid substitutions relative to a wild-type D1 domain. In some embodiments, a SIRPα D1 domain variant of the disclosure has at least 90% (e.g., at least 92%, 95%, 97% or greater than 97%) amino acid sequence identity to a sequence of a wild-type D1 domain.

In some embodiments, a SIRPα D1 domain variant is a chimeric SIRPα D1 domain variant that includes a portion of two or more wild-type D1 domains or variants thereof (e.g., a portion of one wild-type D1 domain or variant thereof and a portion of another wild-type D1 domain or variant thereof). In some embodiments, a chimeric SIRPα D1 domain variant includes at least two portions (e.g., three, four, five or more portions) of wild-type D1 domains or variants thereof, wherein each of the portions is from a different wild-type D1 domain. In some embodiments, a chimeric SIRPα D1 domain variant further includes one or more amino acid substitutions listed in Table 2.

TABLE 2

Amino Acid Substitutions in a SIRPα D1 domain variant

| SEQ ID NO: | Description | Amino Acid Sequence |
|---|---|---|
| 13 | D1 domain v1 | EEEX$_1$QX$_2$IQPDKSVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFSIRIGNITPADAGTYYCX$_{12}$KX$_{13}$RKGSPDDVE X$_{14}$KSGAGTELSVRAKPS |
| — | Amino acid substitutions relative to SEQ ID NO: 13 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = V, I; X$_{13}$ = F, L, V; X$_{14}$ = F, V |
| 14 | D1 domain v2 | EEEX$_1$QX$_2$IQPDKSVSVAAGESX$_3$ILHCTX$_4$TSLX$_5$PVGPI QWFRGAGPARX$_6$LIYNQX$_7$X$_8$GX$_9$FPRVTTVSEX$_{10}$TX$_{11}$R ENMDFSISISNITPADAGTYYCX$_{12}$KX$_{13}$RKGSPDTEX$_{14}$K SGAGTELSVRAKPS |
| — | Amino acid substitutions relative to SEQ ID NO: 14 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = V, I; X$_{13}$ = F, L, V; X$_{14}$ = F, V |
| 15 | D1 domain v3 | EEEX$_1$QX$_2$IQPDKSVSVAAGESX$_3$ILLCTX$_4$TSLX$_5$PVGPI QWFRGAGPARX$_6$LIYNQX$_7$X$_8$GX$_9$FPRVTTVSEX$_{10}$TX$_{11}$R ENMDFSISISNITPADAGTYYCX$_{12}$KX$_{13}$RKGSPDTEX$_{14}$K SGAGTELSVRAKPS |
| — | Amino acid substitutions relative to SEQ ID NO: 15 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = V, I; X$_{13}$ = F, L, V; X$_{14}$ = F, V |
| 16 | D1 domain v4 | EEGX$_1$QX$_2$IQPDKSVSVAAGESX$_3$ILHCTX$_4$TSLX$_5$PVGPI QWFRGAGPGRX$_6$LIYNQX$_7$X$_8$GX$_9$FPRVTTVSDX$_{10}$TX$_{11}$ RNNMDFSIRIGNITPADAGTYYCX$_{12}$KX$_{13}$RKGSPDDVE X$_{14}$KSGAGTELSVRAKPS |
| — | Amino acid substitutions relative to SEQ ID NO: 16 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = V, I; X$_{13}$ = F, L, V; X$_{14}$ = F, V |
| 17 | D1 domain v5 | EEEX$_1$QX$_2$IQPDKFVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFSIRIGNITPADAGTYYCX$_{12}$KX$_{13}$RKGSPDDVE X$_{14}$KSGAGTELSVRAKPS |
| — | Amino acid substitutions relative to SEQ ID NO: 17 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = V, I; X$_{13}$ = F, L, V; X$_{14}$ = F, V |
| 18 | D1 domain v6 | EEEX$_1$QX$_2$IQPDKSVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFPIRIGNITPADAGTYYCX$_{12}$KX$_{13}$RKGSPDDVE X$_{14}$KSGAGTELSVRAKPS |

TABLE 2-continued

Amino Acid Substitutions in a SIRPα D1 domain variant

| SEQ ID NO | Description | Amino Acid Sequence |
|---|---|---|
| — | Amino acid substitutions relative to SEQ ID NO: 18 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = V, I; $X_{13}$ = F, L, V; $X_{14}$ = F, V |
| 19 | D1 domain v7 | EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRGKPS |
| — | Amino acid substitutions relative to SEQ ID NO: 19 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = V, I; $X_{13}$ = F, L, V; $X_{14}$ = F, V |
| 20 | D1 domain v8 | EEEX$_1$QX$_2$IQPDKSVLVAAGETX$_3$TLRCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRAKPS |
| — | Amino acid substitutions relative to SEQ ID NO: 20 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = V, I; $X_{13}$ = F, L, V; $X_{14}$ = F, V |
| 21 | D1 domain v9 | EEEX$_1$QX$_2$IQPDKSVLVAAGETX$_3$TLRCTX$_4$TSLX$_5$PVGPIQWFRGAGPGRX$_6$LIYNQX$_7$X$_8$GX$_9$FPRVTTVSDX$_{10}$TX$_{11}$RNNMDFSIRISNITPADAGTYYCX$_{12}$KX$_{13}$RKGSPDDVEX$_{14}$KSGAGTELSVRAKPS |
| — | Amino acid substitutions relative to SEQ ID NO: 21 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = V, I; $X_{13}$ = F, L, V; $X_{14}$ = F, V |
| 22 | D1 domain v10 | EEEX$_1$QX$_2$IQPDKSVSVAAGESX$_3$ILHCTX$_4$TSLX$_5$PVGPIQWFRGAGPARX$_6$LIYNQX$_7$X$_8$GX$_9$FPRVTTVSEX$_{10}$TX$_{11}$RENMDFSISISNITPADAGTYYCX$_{12}$KX$_{13}$RKGSPDTEX$_{14}$KSGAGTELSVRAKPS |
| — | Amino acid substitutions relative to SEQ ID NO: 22 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = V, I; $X_{13}$ = F, L, V; $X_{14}$ = F, V |
| 23 | Pan D1 domain | EEX$_1$X$_2$QX$_3$IQPDKX$_4$VX$_5$VAAGEX$_6$X$_7$X$_8$LX$_9$CTX$_{10}$TSLX$_{11}$PVGPIQWFRGAGPX$_{12}$RX$_{13}$LIYNQX$_{14}$X$_{15}$GX$_{16}$FPRVTTVSX$_{17}$X$_{18}$TX$_{19}$RX$_{20}$NMDFX$_{21}$IX$_{22}$IX$_{23}$NITPADAGTYYCX$_{24}$KX$_{25}$RKGSPDX$_{26}$X$_{27}$EX$_{28}$KSGAGTELSVRX$_{29}$KPS |
| — | Amino acid substitutions relative to SEQ ID NO: 23 | $X_1$ = E, G; $X_2$ = L, I, V; $X_3$ = V, L, I; $X_4$ = S, F; $X_5$ = L, S; $X_6$ = S, T; $X_7$ = A, V; $X_8$ = I, T; $X_9$ = H, R; $X_{10}$ = A, V, I, L; $X_{11}$ = I, T, S, F; $X_{12}$ A, G; $X_{13}$ = E, V, L; $X_{14}$ = K, R; $X_{15}$ = E, Q; $X_{16}$ = H, P, R; $X_{17}$ = D, E; $X_{18}$ = S, L, T, G; $X_{19}$ = K, R; $X_{20}$ = E, D; $X_{21}$ = S, P; $X_{22}$ = S, R; $X_{23}$ = S, G; $X_{24}$ = V, I; $X_{25}$ = F, L, V; $X_{26}$ = D or absent; $X_{27}$ = T, V; $X_{28}$ = F, V; and $X_{29}$ = A, G |

In some embodiments, a polypeptide comprises a SIRPα D1 domain variant that comprises a sequence of: EEEX$_1$QX$_2$IQPDKSVLVAAGETX$_3$TLRCTX$_4$TSLX$_5$PVG PIQWFRGAGPGRX$_6$LIYNQX$_7$X$_8$GX$_9$F PRVTTVSDX$_{10}$TX$_{11}$RNNMDFSIRIGNITPADAGTYYC X$_{12}$KX$_{13}$RKGSPDDVEX$_{14}$KSGAGTELSV RAKPS (SEQ ID NO: 13), wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is L, T, or G; $X_{11}$ is K or R; $X_{12}$ is V or I; $X_{13}$ is F, L, or V; and $X_{14}$ is F or V; and wherein the variant comprises at least one amino acid substitution relative to a wild-type SIRPα D1 domain that comprises the sequence of SEQ ID NO: 1.

In some embodiments, a polypeptide comprises a SIRPα D1 domain variant that comprises a sequence of: EEGX$_1$QX$_2$IQPDKSVSVAAGESX$_3$ILHCTX$_4$TSLX$_5$PVG PIQWFRGAGPGRX$_6$LIYNQX$_7$X$_8$GX$_9$FP RVTTVSDX$_{10}$TX$_{11}$RNNMDFSIRIGNITPADAGTYYC X$_{12}$KX$_{13}$RKGSPDDVEX$_{14}$KSGAGTELSV RAKPS (SEQ ID NO: 16), wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is L, T, or G; $X_{11}$ is K or R; $X_{12}$ is V or I; $X_{13}$ is F, L, or V; and $X_{14}$ is F or V; and wherein the variant comprises at least one amino acid substitution relative to a wild-type SIRPα D1 domain that comprises the sequence of SEQ ID NO: 4.

In some embodiments, a polypeptide comprises a SIRPα D1 domain variant that comprises a sequence of: EEEX$_1$QX$_2$IQPDKFVLVAAGETX$_3$TLRCTX$_4$TSLX$_5$PVG PIQWFRGAGPGRX$_6$LIYNQX$_7$X$_8$GX$_9$F PRVTTVSDX$_{10}$TX$_{11}$RNNMDFSIRIGNITPADAGTYYC X$_{12}$KX$_{13}$RKGSPDDVEX$_{14}$KSGAGTELSV RAKPS (SEQ ID NO: 17), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 5.

In some embodiments, a polypeptide comprises a SIRPα D1 domain variant that comprises a sequence of: EEEX$_1$QX$_2$IQPDKSVLVAAGETX$_3$TLRCTX$_4$TSLX$_5$PVG PIQWFRGAGPGRX$_6$LIYNQX$_7$X$_8$GX$_9$F PRVTTVSDX$_{10}$TX$_{11}$RNNMDFPIRIGNITPADAGTYYC X$_{12}$KX$_{13}$RKGSPDDVEX$_{14}$KSGAGTELSV RAKPS (SEQ ID NO: 18), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 6.

In some embodiments, a polypeptide comprises a SIRPα D1 domain variant that comprises a sequence of: EEEX$_1$QX$_2$IQPDKSVLVAAGETX$_3$TLRCTX$_4$TSLX$_5$PVG PIQWFRGAGPGRX$_6$LIYNQX$_7$X$_8$GX$_9$F PRVTTVSDX$_{10}$TX$_{11}$RNNMDFSIRISNITPADAGTYYC X$_{12}$KX$_{13}$RKGSPDDVEX$_{14}$KSGAGTELSV RAKPS (SEQ ID NO: 21), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 9.

In any of the aforementioned embodiments, a polypeptide comprises a SIRPα D1 domain variant that comprises the sequence of any one of SEQ ID NOs: 13, 16-18, and 21, wherein X$_1$ is L, I, or V. In any of the aforementioned embodiments, X$_2$ is V, L, or, I. In any of the aforementioned embodiments, X$_3$ is A or V. In any of the aforementioned embodiments, X$_4$ is A, I, or L. In any of the aforementioned embodiments, X$_5$ is I, T, S, or F. In any of the aforementioned embodiments, X$_6$ is E, V, or L. In any of the aforementioned embodiments, X$_7$ is K or R. In any of the aforementioned embodiments, X$_8$ is E or Q. In any of the aforementioned embodiments, X$_9$ is H, P, or R. In any of the aforementioned embodiments, X$_{10}$ is L, T, or G. In any of the aforementioned embodiments, X$_{11}$ is K or R. In any of the aforementioned embodiments, X$_{12}$ is V or I. In any of the aforementioned embodiments, X$_{13}$ is F, L, V. In any of the aforementioned embodiments, X$_{14}$ is F or V. In some embodiments, the polypeptide of this aspect of the disclosure includes no more than six amino acid substitutions relative to the wild-type SIRPα D1 domain that comprises the sequence of any one of SEQ ID NOs: 1, 4-6, and 9.

In some embodiments, the polypeptide binds CD47 with at least 10-fold greater binding affinity than the wild-type SIRPα D1 domain that comprises the sequence of any one of SEQ ID NOs: 1, 4-6, and 9. In some embodiments, the polypeptide binds CD47 with at least 100-fold greater binding affinity than the wild-type SIRPα D1 domain that comprises the sequence of any one of SEQ ID NOs: 1, 4-6, and 9. In some embodiments, the polypeptide binds CD47 with at least 1000-fold greater binding affinity than the wild-type SIRPα D1 domain that comprises the sequence of any one of SEQ ID NOs: 1, 4-6, and 9. In some embodiments, a SIRPα D1 domain variant polypeptide or fragment thereof binds to CD47 with a K$_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a KD between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant that comprises a sequence of: EEEX$_1$QX$_2$IQPDKSVSVAAGESX$_3$ILHCTX$_4$TSLX$_5$PVG PIQWFRGAGPARX$_6$LIYNQX$_7$X$_8$GX$_9$FP RVTTVSEX$_{10}$TX$_{11}$RENMDFSISISNITPADAGTYYCX$_{12}$ KX$_{13}$RKGSPDTEX$_{14}$KSGAGTELSVRA KPS (SEQ ID NO: 14), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 2.

In some embodiments, a polypeptide includes a SIRPα D1 domain variant that comprises a sequence of: EEEX$_1$QX$_2$IQPDKSVSVAAGESX$_3$ILLCTX$_4$TSLX$_5$PVG PIQWFRGAGPARX$_6$LIYNQX$_7$X$_8$GX$_9$FP RVTTVSEX$_{10}$TX$_{11}$RENMDFSISISNITPADAGTYYCX$_{12}$ KX$_{13}$RKGSPDTEX$_{14}$KSGAGTELSVRA KPS (SEQ ID NO: 15), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 3.

In some embodiments, a polypeptide includes a SIRPα D1 domain variant that comprises a sequence of: EEEX$_1$QX$_2$IQPDKSVSVAAGESX$_3$ILHCTX$_4$TSLX$_5$PVG PIQWFRGAGPARX$_6$LIYNQX$_7$X$_8$GX$_9$FP RVTTVSEX$_{10}$TX$_{11}$RENMDFSISISNITPADAGTYYCX$_{12}$ KX$_{13}$RKGSPDTEX$_{14}$KSGAGTELSVRG KPS (SEQ ID NO: 19), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 7.

In some embodiments, a polypeptide includes a SIRPα D1 domain variant that comprises a sequence of: EEEX$_1$QX$_2$IQPDKSVSVAAGESX$_3$ILHCTX$_4$TSLX$_5$PVG PIQWFRGAGPARX$_6$LIYNQX$_7$X$_8$GX$_9$FP RVTTVSEX$_{10}$TX$_{11}$RENMDFSISISNITPADAGTYYCX$_{12}$ KX$_{13}$RKGSPDTEX$_{14}$KSGAGTELSVRA KPS (SEQ ID NO: 22), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 10.

In any of the aforementioned embodiments in this aspect of the disclosure, the polypeptide comprises the sequence of any one of SEQ ID NOs: 14, 15, 19, and 22, wherein X$_1$ is L, I, or V. In any of the aforementioned embodiments, X$_2$ is V, L, or, I. In any of the aforementioned embodiments, $X_3$ is A or V. In any of the aforementioned embodiments, $X_4$ is V, I, or L. In any of the aforementioned embodiments, $X_5$ is I, T, S, or F. In any of the aforementioned embodiments, $X_6$ is E, V, or L. In any of the aforementioned embodiments, $X_7$ is K or R. In any of the aforementioned embodiments, $X_8$ is E or Q. In any of the aforementioned embodiments, $X_9$ is H, P, or R. In any of the aforementioned embodiments, $X_{10}$ is S, T, or G. In any of the aforementioned embodiments, $X_{11}$ is K or R. In any of the aforementioned embodiments, $X_{12}$ is V or I. In any of the aforementioned embodiments, $X_{13}$ is F, L, or V. In any of the aforementioned embodiments, $X_{14}$ is F or V. In some embodiments, the polypeptide of this aspect of the disclosure includes no more than six amino acid substitutions relative to the wild-type SIRPα D1 domain that comprises the sequence of any one of SEQ ID NOs: 2, 3, 7, and 10.

In some embodiments, the polypeptide binds CD47 with at least 10-fold greater binding affinity than the wild-type SIRPα D1 domain having the sequence of any one of SEQ ID NOs: 2, 3, 7, and 10. In some embodiments, the polypeptide binds CD47 with at least 100-fold greater binding affinity than the wild-type SIRPα D1 domain having the sequence of any one of SEQ ID NOs: 2, 3, 7, and 10. In some embodiments, the polypeptide binds CD47 with at least 1000-fold greater binding affinity than the wild-type SIRPα D1 domain having the sequence of any one of SEQ ID NOs: 2, 3, 7, and 10. In some embodiments, a SIRPα D1 domain variant polypeptide or fragment thereof binds to CD47 with a $K_D$ less than $1\times10^{-8}$M, less than $5\times10^{-9}$M, less than $1\times10^{-9}$M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEEX$_1$QX$_2$IQPDKSVLVAAGETX$_3$TLRCTX$_4$TSLX$_5$PVG PIQWFRGAGPARX$_6$LIYNQX$_7$X$_8$GX$_9$F PRVTTVSEX$_{10}$TX$_{11}$RENMDFSISISNITPADAGTYYC X$_{12}$KX$_{13}$RKGSPDTEX$_{14}$KSGAGTELSVR AKPS (SEQ ID NO: 20), wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is V or I; $X_{13}$ is F, L, or V; and $X_{14}$ is F or V; and wherein the variant comprises at least one amino acid substitution relative to a wild-type SIRPα D1 domain having the sequence of SEQ ID NO: 8.

In some embodiments, the polypeptide comprises the sequence of SEQ ID NO: 20, wherein $X_1$ is L, I, or V. In any of the aforementioned embodiments in this aspect of the disclosure, $X_2$ is V, L, or, I. In any of the aforementioned embodiments, $X_3$ is A or V. In any of the aforementioned embodiments, $X_4$ is A, I, or L. In any of the aforementioned embodiments, $X_5$ is I, T, S, or F. In any of the aforementioned embodiments, $X_6$ is E, V, or L. In any of the aforementioned embodiments, $X_7$ is K or R. In any of the aforementioned embodiments, $X_8$ is E or Q. In any of the aforementioned embodiments, $X_9$ is H, P, or R. In any of the aforementioned embodiments, $X_{10}$ is S, T, or G. In any of the aforementioned embodiments, $X_{11}$ is K or R. In any of the aforementioned embodiments, $X_{12}$ is V or I. In any of the aforementioned embodiments, $X_{13}$ is F, L, or V. In any of the aforementioned embodiments, $X_{14}$ is F or V. In some embodiments, the polypeptide of this aspect of the disclosure includes no more than six amino acid substitutions relative to the wild-type SIRPα D1 domain having the sequence of SEQ ID NO: 8.

In some embodiments, the polypeptide binds CD47 with at least 10-fold greater binding affinity than the wild-type SIRPα D1 domain having the sequence of SEQ ID NO: 8. In some embodiments, the polypeptide binds CD47 with at least 100-fold greater binding affinity than the wild-type SIRPα D1 domain having the sequence of SEQ ID NO: 8. In some embodiments, the polypeptide binds CD47 with at least 1000-fold greater binding affinity than the wild-type SIRPα D1 domain having the sequence of SEQ ID NO: 8. In some embodiments, a SIRPα D1 domain variant polypeptide or fragment thereof binds to CD47 with a $K_D$ less than $1\times10^{-8}$M, less than $5\times10^{-9}$ M, less than $1\times10^{-9}$M, less $5\times10^{-10}$ M, less than $1\times10^{10}$M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEX$_1$X$_2$QX$_3$IQPDKX$_4$VX$_5$VAAGEX$_6$X$_7$X$_8$LX$_9$CTX$_{10}$TS LX$_{11}$PVGPIQWFRGAGPX$_{12}$RX$_{13}$LIYNQ X$_{14}$X$_{15}$GX$_{16}$FPRVTTVSX$_{17}$X$_{18}$TX$_{19}$RX$_{20}$NMDFX$_{21}$IX$_{22}$ IX$_{23}$NITPADAGTYYCX$_{24}$KX$_{25}$RKGSPDX$_{26}$X$_{27}$EX$_{28}$KS GAGTELSVRX$_{29}$KPS (SEQ ID NO: 23), wherein $X_1$ is E or G; $X_2$ is L, I, or V; $X_3$ is V, L, or, I; $X_4$ is S or F; $X_5$ is L or S; $X_6$ is S or T; $X_7$ is A or V; $X_8$ is I or T; $X_9$ is H or R; $X_{10}$ is A, V, I, or L; $X_{11}$ is I, T, S, or F; $X_{12}$ is A or G; $X_{13}$ is E, V, or L; $X_{14}$ is K or R; $X_{15}$ is E or Q; $X_{16}$ is H, P, or R; $X_{17}$ is D or E; $X_{18}$ is S, L, T, or G; $X_{19}$ is K or R; $X_{20}$ is E or D; $X_{21}$ is S or P; $X_{22}$ is S or R; $X_{23}$ is S or G; $X_{24}$ is V or I; $X_{25}$ is F, L, V; $X_{26}$ is D or absent; $X_{27}$ is T or V; $X_{28}$ is F or V; and $X_{29}$ is A or G; and wherein the variant comprises at least one amino acid substitution relative to a wild-type SIRPα D1 domain having the sequence of any one of SEQ ID NOs: 1-10.

In any of the aforementioned embodiments in this aspect of the disclosure, $X_2$ is L, I, or V. In any of the aforementioned embodiments, $X_3$ is V, L, or, I. In any of the aforementioned embodiments, $X_4$ is S or F. In any of the aforementioned embodiments, $X_5$ is L or S. In any of the aforementioned embodiments, $X_6$ is S or T. In any of the aforementioned embodiments, $X_7$ is A or V. In any of the aforementioned embodiments, $X_8$ is I or T. In any of the aforementioned embodiments, $X_9$ is H or R. In any of the aforementioned embodiments, $X_{10}$ is A, V, I, or L. In any of the aforementioned embodiments, $X_{11}$ is I, T, S, or F. In any of the aforementioned embodiments, $X_{12}$ is A or G. In any of the aforementioned embodiments, $X_{13}$ is E, V, or L. In any of the aforementioned embodiments, $X_{14}$ is K or R. In any of the aforementioned embodiments, $X_5$ is E or Q. In any of the aforementioned embodiments, $X_{16}$ is H, P, or R. In any of the aforementioned embodiments, $X_{17}$ is D or E. In any of the aforementioned embodiments, $X_{18}$ is S, L, T, or G. In any of the aforementioned embodiments, $X_{19}$ is K or R. In any of the aforementioned embodiments, $X_{20}$ is E or D. In any of the aforementioned embodiments, $X_{21}$ is S or P. In any of the aforementioned embodiments, $X_{22}$ is S or R. In any of the aforementioned embodiments, $X_{23}$ is S or G. In any of the aforementioned embodiments, $X_{24}$ is V or I. In any of the aforementioned embodiments, $X_{25}$ is F, L, V. In any of the aforementioned embodiments, $X_{26}$ is D or absent. In any of the aforementioned embodiments, $X_{27}$ is T or V. In any of the aforementioned embodiments, $X_{28}$ is F or V. In any of the aforementioned embodiments, $X_{29}$ is A or G. In some embodiments, the polypeptide of this aspect of the disclosure includes no more than six amino acid substitutions relative to the wild-type SIRPα D1 domain having the sequence of any one of SEQ ID NOs: 1-10.

In some embodiments, the polypeptide binds CD47 with at least 10-fold greater binding affinity than the wild-type SIRPα D1 domain having the sequence of any one of SEQ ID NOs: 1-10. In some embodiments, the polypeptide binds CD47 with at least 100-fold greater binding affinity than the wild-type SIRPα D1 domain having the sequence of any one of SEQ ID NOs: 1-10. In some embodiments, the polypeptide binds CD47 with at least 1000-fold greater binding affinity than the wild-type SIRPα D1 domain having the sequence of any one of SEQ ID NOs: 1-10. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide of the disclosure including a SIRPα D1 domain variant further comprises a D2 domain having the sequence of SEQ ID NO: 24, a D3 domain having the sequence of SEQ ID NO: 25, or a D2 domain having the sequence of SEQ ID NO: 24 and a D3 domain having the sequence of SEQ ID NO: 25 of a wild-type human SIRPα as shown in Table 3. In some embodiments, the SIRPα D1 domain variant further comprises a fragment or variant of a D2 domain or a fragment or variant of a D3 domain. In some embodiments, the SIRPα D1 domain variant further comprises a fragment or variant of a D2 domain and a fragment or variant of a D3 domain. In some embodiments, a SIRPα D1 domain variant is joined to a D2 or D3 domain by way of a linker. In some embodiments, a SIRPα D1 domain variant is joined to a D2 and D3 domain by way of a linker.

TABLE 3

Amino Acid Sequences of SIRPα D2 and D3 Domains

| SEQ ID NO: | Description | Amino Acid Sequence |
| --- | --- | --- |
| 24 | SIRPα D2 domain | APVVSGPAARATPQHTVSFTCESHGF SPRDITLKWFKNGNELSDFQTNVDPV GESVSYSIHSTAKVVLTREDVHSQVI CEVAHVTLQGDPLRGTANLSETIR |
| 25 | SIRPα D3 domain | VPPTLEVTQQPVRAENQVNVTCQVR KFYPQRLQLTWLENGNVSRTETAST VTENKDGTYNWMSWLLVNVSAHRDD VKLTCQVEHDGQPAVSKSHDLKVS |

In some embodiments, a polypeptide of the disclosure including a SIRPα D1 domain variant is attached to an Fc domain variant in order to improve the pharmacokinetic properties of the polypeptide, e.g., increase serum half-life.

In some embodiments, a SIRPα D1 domain variant is attached to an Fc domain variant that is unable to dimerize. In some embodiments, Fc domain variants serve to increase the serum half-life of the polypeptides described herein. In some embodiments, a polypeptide of the disclosure including a SIRPα D1 domain variant does not include the sequence of any one of SEQ ID NOs: 26-36 shown in Table 4.

TABLE 4

| SEQ ID NO: | Amino Acid Sequence |
| --- | --- |
| 26 | EEELQVIQPDKSVSVAAGESAILHCTITSLIPVGPIQWFRGAGPAR ELIYNQREGHFPRVTTVSETTRRENMDFSISISNITPADAGTYYCV KFRKGSPDTEVKSGAGTELSVRAKPS |
| 27 | EEEVQVIQPDKSVSVAAGESAILHCTLTSLIPVGPIQWFRGAGPAR VLIYNQRQGHFPRVTTVSEGTRRENMDFSISISNITPADAGTYYCI KFRKGSPDTEFKSGAGTELSVRAKPS |
| 28 | EEEVQIIQPDKSVSVAAGESVILHCTITSLTPVGPIQWFRGAGPAR LLIYNQREGPFPRVTTVSETTRRENMDFSISISNITPADAGTYYCV KLRKGSPDTEFKSGAGTELSVRAKPS |
| 29 | EEELQIIQPDKSVSVAAGESAILHCTITSLSPVGPIQWFRGAGPAR VLIYNQRQGPFPRVTTVSEGTKRENMDFSISISNITPADAGTYYCI KLRKGSPDTEFKSGAGTELSVRAKPS |
| 30 | EEEIQVIQPDKSVSVAAGESVIIHCTVTSLFPVGPIQWFRGAGPAR VLIYNQRQGRFPRVTTVSEGTKRENMDFSISISNITPADAGTYYCV KVRKGSPDTEVKSGAGTELSVRAKPS |
| 31 | EEEVQIIQPDKSVSVAAGESIILHCTVTSLFPVGPIQWFRGAGPAR VLIYNQREGRFPRVTTVSEGTRRENMDFSISISNITPADAGTYYCI KLRKGSPDTEFKSGAGTELSVRAKPS |
| 32 | EEEVQLIQPDKSVSVAAGESAILHCTVTSLFPVGPIQWFRGAGPAR VLIYNQREGPFPRVTTVSEGTKRENMDFSISISNITPADAGTYYCI KFRKGSPDTEVKSGAGTELSVRAKPS |
| 33 | EEELQIIQPDKSVLVAAGETATLRCTITSLFPVGPIQWFRGAGPG RVLIYNQRQGPFPRVTTVSDTTKRNNMDFSIRIGNITPADAGTYY CIKFRKGSPDDVEFKSGAGTELSVRAKPS |
| 34 | EEELQIIQPDKSVSVAAGESAILHCTITSLFPVGPIQWFRGAGPA RLLIYNQRQGPFPRVTTVSETTKRENMDFSISISNITPADAGTYY CVKFRKGSPDTEFKSGAGTELSVRAKPS |
| 35 | EEEVQIIQPDKSVSVAAGESAILHCTITSLFPVGPIQWFRGAGPA RVLIYNQKQGPFPRVTTISETTRRENMDFSISISNITPADAGTYY CIKFRKGSPDTEFKSGAGTELSVRAKPS |
| 36 | EEELQIIQPDKSVSVAAGESAILHCTITSLTPVGPIQWFRGAGPA RVLIYNQRQGPFPRVTTVSEGTRRENMDFSISISNITPADAGTYY CIKFRKGSPDTEVKSGAGTELSVRAKPS |

In some embodiments, the polypeptides and polypeptide constructs described herein are utilized in vitro for binding assays, such as immune assays. For example, in some embodiments, the polypeptides and polypeptide constructs described herein are utilized in liquid phase or bound to a solid phase carrier. In some embodiments, polypeptides utilized for immunoassays are detectably labeled in various ways.

In some embodiments, polypeptides and polypeptide constructs described herein are bound to various carriers and used to detect the presence of specific antigen expressing cells. Examples of carriers include glass, polystyrene, polypropylene, polyethylene, dextran, nylon, amylases, natural and modified celluloses, polyacrylamides, agaroses, and magnetite. The nature of the carrier can be either soluble or insoluble.

Various different labels and methods of labeling are known. Examples of labels include enzymes, radioisotopes, fluorescent compounds, colloidal metals, chemiluminescent compounds, and bio-luminescent compounds. Various techniques for binding labels to polypeptides disclosed herein are available.

In some embodiments, the polypeptides are coupled to low molecular weight haptens. These haptens are then specifically detected by means of a second reaction. For example, in some embodiments, the hapten biotin is used with avidin or the haptens dinitrophenol, pyridoxal, or fluorescein are detected with specific anti-hapten antibodies (e.g., anti-dinitrophenol antibodies, anti-pyridoxal antibodies, and anti-fluorescein antibodies respectively).

SIRPα D1 Domain Variants with Altered Glycosylation Patterns

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc domain variant, wherein an Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, a polypeptide in a composition disclosed herein comprises a SIRPα D1 domain variant that has reduced or minimal glycosylation. The D1 domain of each of the ten wild-type human SIRPα proteins (SEQ ID NOs: 1-10 in Table 1) contains a single potential N-linked glycosylation site at amino acid N80 in the sequence N80ITP. Expression of a SIRPα D1 domain in Chinese Hamster Ovary (CHO) cells results in a major band of 16 kDa (non-glycosylated) and a minor band of higher molecular weight that was removed by Endo Hf. Endo Hf is a recombinant protein fusion of Endoglycosidase H and maltose binding protein. Endo Hf cleaves within the chitobiose core of high mannose and some hybrid oligosaccharides from N-linked glycoproteins. This implies that a proline at amino acid position 83 can reduce the efficiency of glycosylation, leading to a protein with different degrees of glycosylation and therefore heterogeneity. For drug development, heterogeneity can give rise to challenges in process development. Therefore, to investigate the possibility of generating homogenous, non-glycosylated forms of SIRPα D1 domain variants, in some embodiments, amino acid N80 of a SIRPα D1 variant is mutated to Ala. In some embodiments, to make a non-glycosylated, SIRPα D1 domain variant, amino acid N80 in a SIRPα D1 domain variant is replaced by any amino acid, including any naturally and non-naturally occurring amino acid, e.g., N80A and N80Q. In some embodiments, a SIRPα D1 domain variant comprises an N80A mutation and at least 1 additional mutation (e.g., at least 2, 3, 4, 5, 6, 7, 8, 9, or 10 additional mutations or more). In some embodiments, the additional mutation is in the CD47 binding site. In some embodiments, the additional mutation is in the hydrophobic core of the D1 domain.

In some embodiments, a polypeptide in a composition disclosed herein includes a SIRPα D1 domain variant that has increased glycosylation relative to a wild-type SIRPα D1 domain. Another option to increase homogeneity of the final product is to enhance the efficiency of glycosylation at amino acid N80 and generate SIRPα D1 domain variants with increased glycosylation relative to a wild-type. In some embodiments, the amino acid P83 in the sequence NITP83 affects the degree of glycosylation at amino acid N80. In some embodiments, changing P83 to any amino acid increases the efficiency of glycosylation at N80. In some embodiments, amino acid P83 in a SIRPα D1 domain variant is replaced by any amino acid, including naturally and non-naturally amino acids, e.g., P83V, P83A, P83I, and P83L. In some embodiments, a polypeptide of the disclosure is expressed in a cell that is optimized not to glycosylate proteins that are expressed by such cell, for example by genetic engineering of the cell line (e.g., genetically engineered yeast or mammalian host) or modifications of cell culture conditions such as addition of kifunensine or by using a naturally non-glycosylating host such as a prokaryote (*E. coli*, etc.).

Table 5 lists specific amino acid substitutions in a SIRPα D1 domain variant relative to each D1 domain variant sequence. In some embodiments, a SIRPα D1 domain variant includes one or more (e.g., two, three, four, five, six, seven, eight, nine, ten, eleven, twelve, thirteen, fourteen or more) of the substitutions listed in Table 5. In some embodiments, the SIRPα D1 domain variants are not glycosylated or are minimally glycosylated. In some embodiments, the SIRPα D1 domain variants are fully glycosylated or almost fully glycosylated. In some embodiments, a SIRPα D1 domain variant includes at most fourteen amino acid substitutions relative to a wild-type D1 domain. In some embodiments, a SIRPα D1 domain variant includes at most ten amino acid substitutions relative to a wild-type D1 domain. In some embodiments, a SIRPα D1 domain variant includes at most seven amino acid substitutions relative to a wild-type D1 domain. In some embodiments, a SIRPα D1 domain variant of the disclosure has at least 90% (e.g., at least 92%, 95%, 97% or greater than 97%) amino acid sequence identity to a sequence of a wild-type D1 domain.

In some embodiments, a SIRPα D1 domain variant is a chimeric SIRPα D1 domain variant that includes a portion of two or more wild-type D1 domains or variants thereof (e.g., a portion of one wild-type D1 domain or variant thereof and a portion of another wild-type D1 domain or variant thereof). In some embodiments, a chimeric SIRPα D1 domain variant includes at least two portions (e.g., three, four, five or more portions) of wild-type D1 domains or variants thereof, wherein each of the portions is from a different wild-type D1 domain. In some embodiments, a chimeric SIRPα D1 domain variant further includes one or more amino acid substitutions listed in Table 5.

TABLE 5

Amino Acid Substitutions in a SIRPα D1 domain variant

| SEQ ID NO: | Description | Amino Acid Sequence |
|---|---|---|
| 37 | D1 domain v1 | EEEX$_1$QX$_2$IQPDKSVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFSIRIGX$_{12}$ITX$_{13}$ADAGTYYCX$_{14}$KX$_{15}$RKGSPDD VEX$_{16}$KSGAGTELSVRAKPS |
| — | Amino acid substitutions relative to SEQ ID NO: 37 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 38 | D1 domain v2 | EEEX$_1$QX$_2$IQPDKSVSVAAGESX$_3$ILHCTX$_4$TSLX$_5$PVGPI QWFRGAGPARX$_6$LIYNQX$_7$X$_8$GX$_9$FPRVTTVSEX$_{10}$TX$_{11}$R ENMDFSISISX$_{12}$ITX$_{13}$ADAGTYYCX$_{14}$KX$_{15}$RKGSPDTEX$_{16}$ KSGAGTELSVRAKPS |
| — | Amino acid substitutions relative to SEQ ID NO: 38 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 39 | D1 domain v3 | EEEX$_1$QX$_2$IQPDKSVSVAAGESX$_3$ILLCTX$_4$TSLX$_5$PVGPI QWFRGAGPARX$_6$LIYNQX$_7$X$_8$GX$_9$FPRVTTVSEX$_{10}$TX$_{11}$R ENMDFSISISX$_{12}$ITX$_{13}$ADAGTYYCX$_{14}$KX$_{15}$RKGSPDTEX$_{16}$ KSGAGTELSVRAKPS |
| — | Amino acid substitutions relative to SEQ ID NO: 39 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 40 | D1 domain v4 | EEGX$_1$QX$_2$IQPDKSVSVAAGESX$_3$ILHCTX$_4$TSLX$_5$PVGPI QWFRGAGPGRX$_6$LIYNQX$_7$X$_8$GX$_9$FPRVTTVSDX$_{10}$TX$_{11}$ RNNMDFSIRIGX$_{12}$ITX$_{13}$ADAGTYYCX$_{14}$KX$_{15}$RKGSPDD VEX$_{16}$KSGAGTELSVRAKPS |
| — | Amino acid substitutions relative to SEQ ID NO: 40 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 41 | D1 domain v5 | EEEX$_1$QX$_2$IQPDKFVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFSIRIGX$_{12}$ITX$_{13}$ADAGTYYCX$_{14}$KX$_{15}$RKGSPDD VEX$_{16}$KSGAGTELSVRAKPS |
| — | Amino acid substitutions relative to SEQ ID NO: 41 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 42 | D1 domain v6 | EEEX$_1$QX$_2$IQPDKSVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFPIRIGX$_{12}$ITX$_{13}$ADAGTYYCX$_{14}$KX$_{15}$RKGSPDD VEX$_{16}$KSGAGTELSVRAKPS |
| — | Amino acid substitutions relative to SEQ ID NO: 42 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 43 | D1 domain v7 | EEEX$_1$QX$_2$IQPDKSVSVAAGESX$_3$ILHCTX$_4$TSLX$_5$PVGPI QWFRGAGPARX$_6$LIYNQX$_7$X$_8$GX$_9$FPRVTTVSEX$_{10}$TX$_{11}$R ENMDFSISISX$_{12}$ITX$_{13}$ADAGTYYCX$_{14}$KX$_{15}$RKGSPDTEX$_{16}$ KSGAGTELSVRGKPS |

TABLE 5-continued

Amino Acid Substitutions in a SIRPα D1 domain variant

| SEQ ID NO | Description | Amino Acid Sequence |
|---|---|---|
| — | Amino acid substitutions relative to SEQ ID NO: 43 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 44 | D1 domain v8 | EEEX$_1$QX$_2$IQPDKSVLVAAGETX$_3$TLRCTX$_4$TSLX$_5$PVGP IQWFRGAGPARX$_6$LIYNQX$_7$X$_8$GX$_9$FPRVTTVSEX$_{10}$TX$_{11}$ RENMDFSISISX$_{12}$ITX$_{13}$ADAGTYYCX$_{14}$KX$_{15}$RKGSPDTE X$_{16}$KSGAGTELSVRAKPS |
| — | Amino acid substitutions relative to SEQ ID NO: 44 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 45 | D1 domain v9 | EEEX$_1$QX$_2$IQPDKSVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFSIRISX$_{12}$ITX$_{13}$ADAGTYYCX$_{14}$KX$_{15}$RKGSPDD VEX$_{16}$KSGAGTELSVRAKPS |
| — | Amino acid substitutions relative to SEQ ID NO: 45 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 46 | D1 domain v10 | EEEX$_1$QX$_2$IQPDKSVSVAAGESX$_3$ILHCTX$_4$TSLX$_5$PVGPI QWFRGAGPARX$_6$LIYNQX$_7$X$_8$GX$_9$FPRVTTVSEX$_{10}$TX$_{11}$R ENMDFSISISX$_{12}$ITX$_{13}$ADAGTYYCX$_{14}$KX$_{15}$RKGSPDTEX$_{16}$ KSGAGTELSVRAKPS |
| — | Amino acid substitutions relative to SEQ ID NO: 46 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 47 | Pan D1 domain | EEX$_1$X$_2$QX$_3$IQPDKX$_4$VX$_5$VAAGEX$_6$X$_7$X$_8$LX$_9$CTX$_{10}$TSLX$_{11}$ PVGPIQWFRGAGPX$_{12}$RX$_{13}$LIYNQX$_{14}$X$_{15}$GX$_{16}$FPRVTT VSX$_{17}$X$_{18}$TX$_{19}$RX$_{20}$NMDFX$_{21}$IX$_{22}$X$_{23}$X$_{24}$ITX$_{25}$ADAGTYY CX$_{26}$KX$_{27}$RKGSPDX$_{28}$X$_{29}$EX$_{30}$KSGAGTELSVRX$_{31}$KPS |
| — | Amino acid substitutions relative to SEQ ID NO: 47 | $X_1$ = E, G; $X_2$ = L, I, V; $X_3$ = V, L, I; $X_4$ = S, F; $X_5$ = L, S; $X_6$ = S, T; $X_7$ = A, V; $X_8$ = I, T; $X_9$ = H, R, L; $X_{10}$ = A, V, I, L; $X_{11}$ = I, T, S, F; $X_{12}$ = A, G; $X_{13}$ = E, V, L; $X_{14}$ = K, R; $X_{15}$ = E, Q; $X_{16}$ = H, P, R; $X_{17}$ = D, E; $X_{18}$ = S, L, T, G; $X_{19}$ = K, R; $X_{20}$ = E, N; $X_{21}$ = S, P; $X_{22}$ = S, R; $X_{23}$ = S, G; $X_{24}$ = any amino acid; $X_{25}$ = any amino acid; $X_{26}$ = V, I; $X_{27}$ = F, L, V; $X_{28}$ = D or absent; $X_{29}$ = T, V; $X_{30}$ = F, V; and $X_{31}$ = A, G |
| 48 | Pan D1 domain | EEELQX$_1$IQPDKSVX$_2$VAAGEX$_3$AX$_4$LX$_5$CTX$_6$TSLX$_7$PV GPIQWFRGAGPX$_8$RX$_9$LIYNQX$_{10}$X$_{11}$GX$_{12}$FPRVTTVSX$_{13}$ X$_{14}$TKRX$_{15}$NMDFSIX$_{16}$IX$_{17}$X$_{18}$ITPADAGTYYCX$_{19}$KFRK GX$_{20}$X$_{21}$X$_{22}$DX$_{23}$EFKSGAGTELSVRAKPS |
| — | Amino acid substitutions relative to SEQ ID NO: 48 | $X_1$ = V, I; $X_2$ = L, S; $X_3$ = T, S; $X_4$ = T, I; $X_5$ = R, H; $X_6$ = A, V, I; $X_7$ = I, R, Y, K, F; $X_8$ = G, A; $X_9$ = E, V; $X_{10}$ = K, R; $X_{11}$ = E, D, Q; $X_{12}$ = H, P; $X_{13}$ = D, E; $X_{14}$ = S, L, T; $X_{15}$ = N, E; $X_{16}$ = R, S; $X_{17}$ = G, S; $X_{18}$ = N, A; $X_{19}$ = V, I; $X_{20}$ = S, I, M; $X_{21}$ = P or absent; $X_{22}$ = D, P; and $X_{23}$ = V, T |
| 49 | Pan D1 domain | EEELQX$_1$IQPDKSVLVAAGETATLRCTX$_2$TSLX$_3$PVGPIQ WFRGAGPGRX$_4$LIYNQX$_5$X$_6$GX$_7$FPRVTTVSDX$_8$TKRNN MDFSIRIGX$_9$ITPADAGTYYCX$_{10}$KFRKGSPDDVEFKSG AGTELSVRAKPS |
| — | Amino acid substitutions relative to SEQ ID NO: 49 | $X_1$ = V, I, L; $X_2$ = A, I, V, L; $X_3$ = I, F, S, T; $X_4$ = E, V, L; $X_5$ = K, R; $X_6$ = E, Q; $X_7$ = H, P, R; $X_8$ = L, T, S, G; $X_9$ = A; and $X_{10}$ = V, I |

TABLE 5-continued

Amino Acid Substitutions in a SIRPα D1 domain variant

| SEQ ID NO | Description | Amino Acid Sequence |
|---|---|---|
| 50 | Pan D1 domain | EEELQX$_1$IQPDKSVSVAAGESAILHCTX$_2$TSLX$_3$PVGPIQ WFRGAGPARX$_4$LIYNQX$_5$X$_6$GX$_7$FPRVTTVSEX$_8$TKREN MDFSISISX$_9$ITPADAGTYYCX$_{10}$KFRKGSPDTEFKSGAG TELSVRAKPS |
| — | Amino acid substitutions relative to SEQ ID NO: 50 | X$_1$ = V, I; X$_2$ = V, I; X$_3$ = I, F; X$_4$ = E, V; X$_5$ = K, R; X$_6$ = E, Q; X$_7$ = H, P; X$_8$ = S, T; X$_9$ = N, A; and X$_{10}$ = V, I |
| 51 | Pan D1 domain | EEELQX$_1$IQPDKSVLVAAGETATLRCTX$_2$TSLX$_3$PVGPIQ WFRGAGPGRX$_4$LIYNQX$_5$EGX$_6$FPRVTTVSDX$_7$TKRNN MDFSIRIGX$_8$ITPADAGTYYCX$_9$KFRKGSPDDVEFKSGA GTELSVRAKPS |
| — | Amino acid substitutions relative to SEQ ID NO: 51 | X$_1$ = V, I; X$_2$ = A, I; X$_3$ = I, F; X$_4$ = E, V; X$_5$ = K, R; X$_6$ = H, P; X$_7$ = L, T; X$_8$ = N, A; and X$_9$ = V, I |
| 52 | Pan D1 domain | EEELQX$_1$IQPDKSVLVAAGETATLRCTX$_2$TSLX$_3$PVGPIQ WFRGAGPRELIYNQX$_4$EGX$_5$FPRVTTVSDX$_6$TKRNNM DFSIRIGX$_7$ITPADAGTYYCVKFRKGSPDDVEFKSGAGT ELSVRAKPS |
| — | Amino acid substitutions relative to SEQ ID NO: 52 | X$_1$ = V, L, I; X$_2$ = A, I, L; X$_3$ = I, T, S, F; X$_4$ = K, R; X$_5$ = H, P, R; X$_6$ = L, T, G; and X$_7$ = N, A |
| 212 | Pan D1 domain | EEELQX$_1$IQPDKSVSVAAGESAILHCTX$_2$TSLX$_3$PVGPIQ WFRGAGPARELIYNQX$_4$EGX$_5$FPRVTTVSEX$_6$TKRENM DFSISISX$_7$ITPADAGTYYCVKFRKGSPDTEFKSGAGTE LSVRAKPS |
| — | Amino acid substitutions relative to SEQ ID NO: 212 | X$_1$ = V, L, I; X$_2$ = V, I, L; X$_3$ = I, T, S, F; X$_4$ = K, R; X$_5$ = H, P, R; X$_6$ = S, T, G; and X$_7$ = N, A |
| 218 | Pan D1 domain | EEELQX$_1$IQPDKSVLVAAGETATLRCTX$_2$TSLX$_3$PVGPIQ WFRGAGPGRX$_4$LIYNQX$_5$X$_6$GX$_7$FPRVTTVSDX$_8$TKRNN MDFSIRIGX$_9$X$_{10}$X$_{11}$X$_{12}$ADAGTYYCX$_{13}$KFRKGSPDDVE FKSGAGTELSVRAKPS |
| — | Amino acid substitutions relative to SEQ ID NO: 218 | X$_1$ = V, L, or I; X$_2$ = A, V, L, or I; X$_3$ = I, S, T, or F; X$_4$ = E, L, or V; X$_5$ = K or R; X$_6$ = E or Q; X$_7$ = H, R or P; X$_8$ = S, G, L or T; X$_9$ = any amino acid; X$_{10}$ = any amino acid; X$_{11}$ = any amino acid; X$_{12}$ = any amino acid; and X$_{13}$ = V or I |
| 219 | Pan D1 domain | EEELQX$_1$IQPDKSVLVAAGETATLRCTX$_2$TSLX$_3$PVGPIQ WFRGAGPGRX$_4$LIYNQX$_5$X$_6$GX$_7$FPRVTTVSDX$_8$TKRNN MDFSIRIGX$_9$ITX$_{10}$ADAGTYYCX$_{11}$KFRKGSPDDVEFKS GAGTELSVRAKPS |
| — | Amino acid substitutions relative to SEQ ID NO: 219 | X$_1$ = V, L or I; X$_2$ = A, V, L, or I; X$_3$ = I, S, T or F; X$_4$ = E, L, or V; X$_5$ = K or R; X$_6$ = E or Q; X$_7$ = H, R or P; X$_8$ = S, G, L, or T; X$_9$ = N; X$_{10}$ = any amino acid other than P; and X$_{11}$ = V or I |

In some embodiments, a polypeptide includes a SIRPα D1 domain variant having a sequence of:
EEEX$_1$QX$_2$IQPDKSVLVAAGETX$_3$TLRCTX$_4$TSLX$_5$PVG PIQWFRGAGPGRX$_6$LIYNQX$_7$X$_8$GX$_9$F PRVTTVSDX$_{10}$TX$_{11}$RNNMDFSIRIGX$_{12}$ITX$_{13}$ADAGTY YCX$_{14}$KX$_{15}$RKGSPDDVEX$_{16}$KSGAGTE LSVRAKPS (SEQ ID NO: 37), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant comprises at least one amino acid substitution relative to a wild-type SIRPα D1 domain having the sequence of SEQ ID NO: 1.

In some embodiments, a polypeptide includes a SIRPα D1 domain variant having a sequence of:
EEGX$_1$QX$_2$IQPDKSVSVAAGESX$_3$ILHCTX$_4$TSLX$_5$PVG PIQWFRGAGPGRX$_6$LIYNQX$_7$X$_8$GX$_9$FP RVTTVSDX$_{10}$TX$_{11}$RNNMDFSIRIGX$_{12}$ITX$_{13}$ADAGTYY CX$_{14}$KX$_{15}$RKGSPDDVEX$_{16}$KSGAGTEL SVRAKPS (SEQ ID NO: 40), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I;

$X_{15}$ is F, L, or V; and $X_{16}$ is F or V; and wherein the variant comprises at least one amino acid substitution relative to a wild-type SIRPα D1 domain having the sequence of SEQ ID NO: 4.

In some embodiments, a polypeptide includes a SIRPα D1 domain variant having a sequence of:
EEEX$_1$QX$_2$IQPDKFVLVAAGETX$_3$TLRCTX$_4$TSLX$_5$PVG
PIQWFRGAGPGRX$_6$LIYNQX$_7$X$_8$GX$_9$F
PRVTTVSDX$_{10}$TX$_{11}$RNNMDFSIRIGX$_{12}$ITX$_{13}$ADAGTY
YCX$_{14}$KX$_{15}$RKGSPDDVEX$_{16}$KSGAGTE LSVRAKPS (SEQ ID NO: 41), wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is L, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant comprises at least one amino acid substitution relative to a wild-type SIRPα D1 domain having the sequence of SEQ ID NO: 5.

In some embodiments, a polypeptide includes a SIRPα D1 domain variant having a sequence of:
EEEX$_1$QX$_2$IQPDKSVLVAAGETX$_3$TLRCTX$_4$TSLX$_5$PVG
PIQWFRGAGPGRX$_6$LIYNQX$_7$X$_8$GX$_9$F
PRVTTVSDX$_{10}$TX$_{11}$RNNMDFPIRIGX$_{12}$ITX$_{13}$ADAGTY
YCX$_{14}$KX$_{15}$RKGSPDDVEX$_{16}$KSGAGTE LSVRAKPS (SEQ ID NO: 42), and wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is L, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant comprises at least one amino acid substitution relative to a wild-type SIRPα D1 domain having the sequence of SEQ ID NO: 6.

In some embodiments, a polypeptide includes a SIRPα D1 domain variant having a sequence of:
EEEX$_1$QX$_2$IQPDKSVLVAAGETX$_3$TLRCTX$_4$TSLX$_5$PVG
PIQWFRGAGPGRX$_6$LIYNQX$_7$X$_8$GX$_9$F
PRVTTVSDX$_{10}$TX$_{11}$RNNMDFSIRISX$_{12}$ITX$_{13}$ADAGTY
YCX$_{14}$KX$_{15}$RKGSPDDVEX$_{16}$KSGAGTEL SVRAKPS (SEQ ID NO: 45), and wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is L, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant comprises at least one amino acid substitution relative to a wild-type SIRPα D1 domain having the sequence of SEQ ID NO: 9.

In any of the aforementioned embodiments in this aspect of the disclosure, a polypeptide includes a SIRPα D1 domain variant having a sequence of any one of SEQ ID NOs: 37, 40-42, and 45, wherein $X_1$ is L, I, or V. In any of the aforementioned embodiments, $X_2$ is V, L, or, I. In any of the aforementioned embodiments, $X_3$ is A or V. In any of the aforementioned embodiments, $X_4$ is A, I, or L. In any of the aforementioned embodiments, $X_5$ is I, T, S, or F. In any of the aforementioned embodiments, $X_6$ is E, V, or L. In any of the aforementioned embodiments, $X_7$ is K or R. In any of the aforementioned embodiments, $X_8$ is E or Q. In any of the aforementioned embodiments, $X_9$ is H, P, or R. In any of the aforementioned embodiments, $X_{10}$ is L, T, or G. In any of the aforementioned embodiments, $X_{11}$ is K or R. In any of the aforementioned embodiments, $X_{12}$ is N, A, C, D, E, F, G, H, I, K, L, M, P, Q, R, S, T, V, W, or Y. In any of the aforementioned embodiments, $X_{13}$ is P, A, C, D, E, F, G, H, I, K, L, M, N, Q, R, S, T, V, W, or Y. In any of the aforementioned embodiments, $X_{14}$ is V or I. In any of the aforementioned embodiments, $X_{15}$ is F, L, V. In any of the aforementioned embodiments, $X_{16}$ is F or V.

In some embodiments, a polypeptide provided herein includes no more than ten amino acid substitutions relative to the wild-type SIRPα D1 domain having the sequence of any one of SEQ ID NOs: 1, 4-6, and 9. In some embodiments, the polypeptide provided herein includes no more than seven amino acid substitutions relative to the wild-type SIRPα D1 domain having the sequence of any one of SEQ ID NOs: 1, 4-6, and 9.

In some embodiments, the polypeptide binds CD47 with at least 10-fold greater binding affinity than the wild-type SIRPα D1 domain having the sequence of any one of SEQ ID NOs: 1, 4-6, and 9. In some embodiments, the polypeptide binds CD47 with at least 100-fold greater binding affinity than the wild-type SIRPα D1 domain having the sequence of any one of SEQ ID NOs: 1, 4-6, and 9. In some embodiments, the polypeptide binds CD47 with at least 1000-fold greater binding affinity than the wild-type SIRPα D1 domain having the sequence of any one of SEQ ID NOs: 1, 4-6, and 9. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-1}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of:
EEEX$_1$QX$_2$IQPDKSVSVAAGESX$_3$ILHCTX$_4$TSLX$_5$PVG
PIQWFRGAGPARX$_6$LIYNQX$_7$X$_8$GX$_9$FP
RVTTVSEX$_{10}$TX$_{11}$RENMDFSISISX$_{12}$ITX$_{13}$ADAGTYY
CX$_{14}$KX$_{15}$RKGSPDTEX$_{16}$KSGAGTELSV RAKPS (SEQ ID NO: 38), wherein $X_1$ is L, I, or V; $X_2$ is V, L, or, I; $X_3$ is A or V; $X_4$ is V, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant comprises at least one amino acid substitution relative to a wild-type SIRPα D1 domain having the sequence of SEQ ID NO: 2.

In some embodiments, a polypeptide includes a SIRPα D1 domain variant having a sequence of:
EEEX$_1$QX$_2$IQPDKSVSVAAGESX$_3$ILLCTX$_4$TSLX$_5$PVG
PIQWFRGAGPARX$_6$LIYNQX$_7$X$_8$GX$_9$FP
RVTTVSEX$_{10}$TX$_{11}$RENMDFSISISX$_{12}$ITX$_{13}$ADAGTYYC
X$_{14}$KX$_{15}$RKGSPDTEX$_{16}$KSGAGTELSV RAKPS (SEQ ID NO: 39), wherein $X_1$ is L, I, or V; $X_2$ is V, L, or, I; $X_3$ is A or V; $X_4$ is V, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant comprises at least one amino acid substitution relative to a wild-type SIRPα D domain having the sequence of SEQ ID NO: 3.

In some embodiments, a polypeptide includes a SIRPα D1 domain variant having a sequence of:
EEEX$_1$QX$_2$IQPDKSVSVAAGESX$_3$ILHCTX$_4$TSLX$_5$PVG PIQWFRGAGPARX$_6$LIYNQX$_7$X$_8$GX$_9$FP RVTTVSEX$_{10}$TX$_{11}$RENMDFSISISX$_{12}$ITX$_{13}$ADAGTYYC X$_{14}$KX$_{15}$RKGSPDTEX$_{16}$KSGAGTELSV RGKPS (SEQ ID NO: 43), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant comprises at least one amino acid substitution relative to a wild-type SIRPα D domain having the sequence of SEQ ID NO: 7.

In some embodiments, a polypeptide includes a SIRPα D1 domain variant having a sequence of:
EEEX$_1$QX$_2$IQPDKSVSVAAGESX$_3$ILHCTX$_4$TSLX$_5$PVG PIQWFRGAGPARX$_6$LIYNQX$_7$X$_8$GX$_9$FP RVTTVSEX$_{10}$TX$_{11}$RENMDFSISISX$_{12}$ITX$_{13}$ADAGTYYC X$_{14}$KX$_{15}$RKGSPDTEX$_{16}$KSGAGTELSV RAKPS (SEQ ID NO: 46), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant comprises at least one amino acid substitution relative to a wild-type SIRPα D1 domain having the sequence of SEQ ID NO: 10.

In any of the aforementioned embodiments in this aspect of the disclosure, a polypeptide includes a SIRPα D1 domain variant having a sequence of any one of SEQ ID NOs: 38, 39, 43, and 46, wherein X$_1$ is L, I, or V. In any of the aforementioned embodiments, X$_2$ is V, L, or, I. In any of the aforementioned embodiments, X$_3$ is A or V. In any of the aforementioned embodiments, X$_4$ is V, I, or L. In any of the aforementioned embodiments, X$_5$ is I, T, S, or F. In any of the aforementioned embodiments, X$_6$ is E, V, or L. In any of the aforementioned embodiments, X$_7$ is K or R. In any of the aforementioned embodiments, X$_8$ is E or Q. In any of the aforementioned embodiments, X$_9$ is H, P, or R. In any of the aforementioned embodiments, X$_{10}$ is S, T, or G. In any of the aforementioned embodiments, X$_{11}$ is K or R. In any of the aforementioned embodiments, X$_{12}$ is N, A, C, D, E, F, G, H, I, K, L, M, P, Q, R, S, T, V, W, or Y. In any of the aforementioned embodiments, X$_{13}$ is P, A, C, D, E, F, G, H, I, K, L, M, N, Q, R, S, T, V, W, or Y. In any of the aforementioned embodiments, X$_{14}$ is V or I. In any of the aforementioned embodiments, X$_{18}$ is F, L, or V. In any of the aforementioned embodiments, X$_{16}$ is F or V.

In some embodiments, a polypeptide includes a SIRPα D1 domain variant having no more than ten amino acid substitutions relative to the wild-type SIRPα D1 domain having the sequence of any one of SEQ ID NOs: 2, 3, 7, and 10. In some embodiments, a polypeptide includes a SIRPα D1 domain variant having no more than seven amino acid substitutions relative to the wild-type SIRPα D1 domain having the sequence of any one of SEQ ID NOs: 2, 3, 7, and 10.

In some embodiments, the polypeptide binds CD47 with at least 10-fold greater binding affinity than the wild-type SIRPα D1 domain having the sequence of any one of SEQ ID NOs: 2, 3, 7, and 10. In some embodiments, the polypeptide binds CD47 with at least 100-fold greater binding affinity than the wild-type SIRPα D1 domain having the sequence of any one of SEQ ID NOs: 2, 3, 7, and 10. In some embodiments, the polypeptide binds CD47 with at least 1000-fold greater binding affinity than the wild-type SIRPα D1 domain having the sequence of any one of SEQ ID NOs: 2, 3, 7, and 10. In some embodiments, a SIRPα D1 domain variant polypeptide or fragment thereof binds to CD47 with a $K_D$ less than $1\times10^{-8}$M, less than $5\times10^{-9}$M, less than $1\times10^{-9}$M, less $5\times10^{-10}$M, less than $1\times10^{-10}$M or less than $1\times10^{-11}$M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of:
EEEX$_1$QX$_2$IQPDKSVLVAAGETX$_3$TLRCTX$_4$TSLX$_5$PVG PIQWFRGAGPARX$_6$LIYNQX$_7$X$_8$GX$_9$F PRVTTVSEX$_{10}$TX$_{11}$RENMDFSISISX$_{12}$ITX$_{13}$ADAGTYY CX$_{14}$KX$_{15}$RKGSPDTEX$_{16}$KSGAGTELS VRAKPS (SEQ ID NO: 44), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant comprises at least one amino acid substitution relative to a wild-type SIRPα D domain having the sequence of SEQ ID NO: 8.

In some embodiments, the polypeptide comprises the sequence of SEQ ID NO: 44, wherein X$_1$ is L, I, or V. In any of the aforementioned embodiments in this aspect of the disclosure, X$_2$ is V, L, or, I. In any of the aforementioned embodiments, X$_3$ is A or V. In any of the aforementioned embodiments, X$_4$ is A, I, or L. In any of the aforementioned embodiments, X$_5$ is I, T, S, or F. In any of the aforementioned embodiments, X$_6$ is E, V, or L. In any of the aforementioned embodiments, X$_7$ is K or R. In any of the aforementioned embodiments, X$_8$ is E or Q. In any of the aforementioned embodiments, X$_9$ is H, P, or R. In any of the aforementioned embodiments, X$_{10}$ is S, T, or G. In any of the aforementioned embodiments, X$_{11}$ is K or R. In any of the aforementioned embodiments, X$_{12}$ is N, A, C, D, E, F, G, H, I, K, L, M, P, Q, R, S, T, V, W, or Y. In any of the aforementioned embodiments, X$_{13}$ is P, A, C, D, E, F, G, H, I, K, L, M, N, Q, R, S, T, V, W, or Y. In any of the aforementioned embodiments, X$_{14}$ is V or I. In any of the aforementioned embodiments, X$_{18}$ is F, L, or V. In any of the aforementioned embodiments, X$_{16}$ is F or V.

In some embodiments, a polypeptide includes a SIRPα D1 domain variant having no more than ten amino acid substitutions relative to the wild-type SIRPα D1 domain having the sequence of SEQ ID NO: 8. In some embodiments, a polypeptide includes a SIRPα D1 domain variant having no more than seven amino acid substitutions relative to the wild-type SIRPα D1 domain having the sequence of SEQ ID NO: 8.

In some embodiments, the polypeptide binds CD47 with at least 10-fold greater binding affinity than the wild-type SIRPα D1 domain having the sequence of SEQ ID NO: 8. In some embodiments, the polypeptide binds CD47 with at least 100-fold greater binding affinity than the wild-type SIRPα D1 domain having the sequence of SEQ ID NO: 8. In some embodiments, the polypeptide binds CD47 with at least 1000-fold greater binding affinity than the wild-type SIRPα D1 domain having the sequence of SEQ ID NO: 8. In some embodiments, a SIRPα D1 domain variant polypeptide or fragment thereof binds to CD47 with a $K_D$ less than $1×10^{-8}$ M, less than $5×10^{-9}$ M, less than $1×10^{-9}$ M, less $5×10^{-10}$ M, less than $1×10^{10}$ M or less than $1×10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEX$_1$X$_2$QX$_3$IQPDKX$_4$VX$_5$VAAGEX$_6$X$_7$X$_8$LX$_9$CTX$_{10}$SL X$_{11}$PVGPIQWFRGAGPX$_{12}$RX$_{13}$LIYNQ X$_{14}$X$_{15}$GX$_{16}$FPRVTTVSX$_{17}$X$_{18}$TX$_{19}$RX$_{20}$NMDFX$_{21}$IX$_{22}$I X$_{23}$X$_{24}$ITX$_{25}$ADAGTYYCX$_{26}$KX$_{27}$RKGSP DX$_{28}$X$_{29}$EX$_{30}$KSGAGTELSVRX$_{31}$KPS (SEQ ID NO: 47), wherein X$_1$ is E or G; X$_2$ is L, I, or V; X$_3$ is V, L, or, I; X$_4$ is S or F; X$_5$ is L or S; X$_6$ is S or T; X$_7$ is A or V; X$_8$ is I or T; X$_9$ is H, R, or L; X$_{10}$ is A, V, I, or L; X$_{11}$ is I, T, S, or F; X$_{12}$ is A or G; X$_{13}$ is E, V, or L; X$_{14}$ is K or R; X$_{15}$ is E or Q; X$_{16}$ is H, P, or R; X$_{17}$ is D or E; X$_{18}$ is S, L, T, or G; X$_{19}$ is K or R; X$_{20}$ is E or N; X$_{21}$ is S or P; X$_{22}$ is S or R; X$_{23}$ is S or G; X$_{24}$ is any amino acid; X$_{25}$ is any amino acid; X$_{26}$ is V or I; X$_{27}$ is F, L, V; X$_{28}$ is D or absent; X$_{29}$ is T or V; X$_{30}$ is F or V; and X$_{31}$ is A or G; and wherein the variant comprises at least one amino acid substitution relative to a wild-type SIRPα D1 domain having the sequence of any one of SEQ ID NOs: 1-10.

In some embodiments, the polypeptide comprises the sequence of SEQ ID NO: 47, wherein X$_1$ is E or G. In any of the aforementioned embodiments in this aspect of the disclosure, X$_2$ is L, I, or V. In any of the aforementioned embodiments, X$_3$ is V, L, or, I. In any of the aforementioned embodiments, X$_4$ is S or F. In any of the aforementioned embodiments, X$_5$ is L or S. In any of the aforementioned embodiments, X$_6$ is S or T. In any of the aforementioned embodiments, X$_7$ is A or V. In any of the aforementioned embodiments, X$_8$ is I or T. In any of the aforementioned embodiments, X$_9$ is H or R. In any of the aforementioned embodiments, X$_{10}$ is A, V, I, or L. In any of the aforementioned embodiments, X$_{11}$ is I, T, S, or F. In any of the aforementioned embodiments, X$_{12}$ is A or G. In any of the aforementioned embodiments, X$_{13}$ is E, V, or L. In any of the aforementioned embodiments, X$_{14}$ is K or R. In any of the aforementioned embodiments, X$_{15}$ is E or Q. In any of the aforementioned embodiments, X$_{16}$ is H, P, or R. In any of the aforementioned embodiments, X$_{17}$ is D or E. In any of the aforementioned embodiments, X$_{18}$ is S, L, T, or G. In any of the aforementioned embodiments, X$_{19}$ is K or R. In any of the aforementioned embodiments, X$_2$ is E or N. In any of the aforementioned embodiments, X$_{21}$ is S or P. In any of the aforementioned embodiments, X$_{22}$ is S or R. In any of the aforementioned embodiments, X$_{23}$ is S or G. In any of the aforementioned embodiments, X$_{24}$ is N, A, C, D, E, F, G, H, I, K, L, M, P, Q, R, S, T, V, W, or Y. In any of the aforementioned embodiments, X$_{25}$ is P, A, C, D, E, F, G, H, I, K, L, M, N, Q, R, S, T, V, W, or Y. In any of the aforementioned embodiments, X$_{26}$ is V or I. In any of the aforementioned embodiments, X$_{27}$ is F, L, V. In any of the aforementioned embodiments, X$_{28}$ is D or absent. In any of the aforementioned embodiments, X$_{29}$ is T or V. In any of the aforementioned embodiments, X$_{30}$ is F or V. In any of the aforementioned embodiments, X$_{31}$ is A or G.

In some embodiments, the polypeptide of this aspect of the disclosure includes no more than ten amino acid substitutions relative to the wild-type SIRPα D1 domain having the sequence of any one of SEQ ID NOs: 1-10. In some embodiments, the polypeptide of this aspect of the disclosure includes no more than seven amino acid substitutions relative to the wild-type SIRPα D1 domain having the sequence of any one of SEQ ID NOs: 1-10.

In some embodiments, the polypeptide binds CD47 with at least 10-fold greater binding affinity than the wild-type SIRPα D1 domain having the sequence of any one of SEQ ID NOs: 1-10. In some embodiments, the polypeptide binds CD47 with at least 100-fold greater binding affinity than the wild-type SIRPα D1 domain having the sequence of any one of SEQ ID NOs: 1-10. In some embodiments, the polypeptide binds CD47 with at least 1000-fold greater binding affinity than the wild-type SIRPα D1 domain having the sequence of any one of SEQ ID NOs: 1-10. In some embodiments, a SIRPα D1 domain variant polypeptide or fragment thereof binds to CD47 with a $K_D$ less than $1×10^{-8}$ M, less than $5×10^{-9}$ M, less than $1×10^{-9}$ M, less $5×10^{-10}$ M, less than $1×10^{- identity (e.g., at least 86%, 87%, 88%, 89%, 90%, 91%, 92%, 93%, 94%, 95%, 96%, 97%, 98%, 99%, or 100% sequence identity) to SEQ ID NO: 49, wherein each of $X_1$, $X_2$, $X_3$, $X_4$, $X_5$, $X_6$, $X_7$, $X_8$, $X_9$, and $X_{10}$ are not a wild-type amino acid.

In some embodiments, the polypeptide of this aspect of the disclosure includes no more than ten amino acid substitutions relative to the wild-type SIRPα D1 domain having the sequence of any one of SEQ ID NO: 1. In some embodiments, the polypeptide of this aspect of the disclosure includes no more than seven amino acid substitutions relative to the wild-type SIRPα D1 domain having the sequence of any one of SEQ ID NO: 1.

In some embodiments, the polypeptide binds CD47 with at least 10-fold greater binding affinity than the wild-type SIRPα D1 domain having the sequence of any one of SEQ ID NO: 1. In some embodiments, the polypeptide binds CD47 with at least 100-fold greater binding affinity than the wild-type SIRPα D1 domain having the sequence of any one of SEQ ID NO: 1. In some embodiments, the polypeptide binds CD47 with at least 1000-fold greater binding affinity than the wild-type SIRPα D1 domain having the sequence of any one of SEQ ID NO: 1. In some embodiments, a SIRPα D1 domain variant polypeptide or fragment thereof binds to CD47 with a $K_D$ less than $1 \times 10^{-8}$ M, less than $5 \times 10^{-9}$ M, less than $1 \times 10^{-9}$ M, less $5 \times 10^{-1}$ M, less than $1 \times 10^{-10}$ M or less than $1 \times 10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVSVAAGESAILHCTX$_2$TSLX$_3$PVGPI QWFRGAGPARX$_4$LIYNQX$_5$X$_6$GX$_7$FPR VTTVSEX$_8$TKRENMDFSISISX$_9$ITPADAGTYYCX$_{10}$KF RKGSPDTEFKSGAGTELSVRAKPS, (SEQ ID NO: 50), wherein $X_1$ is V or I; $X_2$ is V or I; $X_3$ is I or F; $X_4$ is E or V; $X_5$ is K or R; $X_6$ is E or Q; $X_7$ is H or P; $X_8$ is S or T; $X_9$ is N or A; and $X_{10}$ V or I; and wherein the variant comprises at least one amino acid substitution relative to a wild-type SIRPα D1 domain having the sequence of any one of SEQ ID NO: 2.

In some embodiments, the polypeptide comprises the sequence of SEQ ID NO: 50, wherein $X_1$ is V or I. In any of the aforementioned embodiments in this aspect of the disclosure, $X_2$ is V or I. In any of the aforementioned embodiments, $X_3$ is I or F. In any of the aforementioned embodiments, $X_4$ is E or V. In any of the aforementioned embodiments, $X_5$ is K or R. In any of the aforementioned embodiments, $X_6$ is E or Q. In any of the aforementioned embodiments, $X_7$ is H or P. In any of the aforementioned embodiments, $X_8$ is S or R. In any of the aforementioned embodiments, $X_9$ is N or A. In any of the aforementioned embodiments, $X_{10}$ is V or I.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 50, wherein each of $X_1$, $X_2$, $X_3$, $X_4$, $X_5$, $X_6$, $X_7$, $X_8$, $X_9$, and $X_{10}$ is not a wild-type amino acid.

In some embodiments, the polypeptide of this aspect of the disclosure includes no more than ten amino acid substitutions relative to the wild-type SIRPα D1 domain having the sequence of any one of SEQ ID NO: 2. In some embodiments, the polypeptide of this aspect of the disclosure includes no more than seven amino acid substitutions relative to the wild-type SIRPα D1 domain having the sequence of any one of SEQ ID NO: 2.

In some embodiments, the polypeptide binds CD47 with at least 10-fold greater binding affinity than the wild-type SIRPα D1 domain having the sequence of any one of SEQ ID NO: 2. In some embodiments, the polypeptide binds CD47 with at least 100-fold greater binding affinity than the wild-type SIRPα D1 domain having the sequence of any one of SEQ ID NO: 2. In some embodiments, the polypeptide binds CD47 with at least 1000-fold greater binding affinity than the wild-type SIRPα D1 domain having the sequence of any one of SEQ ID NO: 2. In some embodiments, a SIRPα D1 domain variant polypeptide or fragment thereof binds to CD47 with a $K_D$ less than $1 \times 10^{-8}$ M, less than $5 \times 10^{-9}$ M, less than $1 \times 10^{-9}$ M, less $5 \times 10^{-1}$ M, less than $1 \times 10^{-10}$ M or less than $1 \times 10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVLVAAGETATLRCTX$_2$TSLX$_3$PVGPI QWFRGAGPGRX$_4$LIYNQX$_5$EGX$_6$FPR VTTVSDX$_7$TKRNNMDFSIRIGX$_8$ITPADAGTYYCX$_9$KF RKGSPDDVEFKSGAGTELSVRAKPS (SEQ ID NO: 221), wherein $X_1$ is V or I; $X_2$ is A or I; $X_3$ is I or F; $X_4$ is E or V; $X_5$ is K or R; $X_6$ is H or P; $X_7$ is L or T; $X_8$ is N or A; and $X_9$ is V or I; and wherein the variant comprises at least one amino acid substitution relative to a wild-type SIRPα D1 domain having the sequence of any one of SEQ ID NO: 1.

In some embodiments, the polypeptide comprises the sequence of SEQ ID NO: 51, wherein $X_1$ is V or I. In any of the aforementioned embodiments in this aspect of the disclosure, $X_2$ is A or I. In any of the aforementioned embodiments, $X_3$ is I or F. In any of the aforementioned embodiments, $X_4$ is E or V. In any of the aforementioned embodiments, $X_5$ is K or R. In any of the aforementioned embodiments, $X_6$ is H or P. In any of the aforementioned embodiments, $X_7$ is L or T. In any of the aforementioned embodiments, $X_8$ is N or A. In any of the aforementioned embodiments, $X_9$ is V or I. In some embodiments, $X_4$ is not V.

In some embodiments, the polypeptide comprises the sequence of SEQ ID NO: 51, wherein $X_8$ is A. In any of the aforementioned embodiments in this aspect of the disclosure, $X_8$ is A and $X_1$ is V or I. In any of the aforementioned embodiments in this aspect of the disclosure, $X_8$ is A and $X_2$ is A or I. In any of the aforementioned embodiments, $X_8$ is A and $X_3$ is I or F. In any of the aforementioned embodiments, $X_8$ is A and $X_4$ is E or V. In some embodiments, $X_4$ is not V. In any of the aforementioned embodiments, $X_8$ is A and $X_5$ is K or R. In any of the aforementioned embodiments, $X_8$ is A and $X_6$ is H or P. In any of the aforementioned embodiments, $X_8$ is A and $X_7$ is A or V. In any of the aforementioned embodiments, $X_8$ is A and $X_9$ is V or I.

In some embodiments, the polypeptide comprises the sequence of SEQ ID NO: 51, wherein $X_8$ is A. In any of the aforementioned embodiments in this aspect of the disclosure, $X_8$ is A and $X_1$ is I. In any of the aforementioned embodiments in this aspect of the disclosure, $X_8$ is A and $X_2$ is I. In any of the aforementioned embodiments, $X_8$ is A and $X_3$ is F. In any of the aforementioned embodiments, $X_8$ is A and $X_4$ is V. In any of the aforementioned embodiments, $X_8$ is A and $X_5$ is R. In any of the aforementioned embodiments, $X_8$ is A and $X_6$ is P. In any of the aforementioned embodiments, $X_8$ is A and $X_7$ is T. In any of the aforementioned embodiments, $X_8$ is A and $X_9$ is I.

In some embodiments, the polypeptide comprises a SIRPα D1 domain variant that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 51, wherein each of $X_1$, $X_2$, $X_3$, $X_4$, $X_5$, $X_6$, $X_7$, $X_8$, and $X_9$ is not a wild-type amino acid.

In some embodiments, the polypeptide of this aspect of the disclosure comprises no more than ten amino acid substitutions relative to the wild-type SIRPα D1 domain having the sequence of any one of SEQ ID NO: 1. In some embodiments, the polypeptide of this aspect of the disclosure comprises no more than seven amino acid substitutions relative to the wild-type SIRPα D1 domain having the sequence of any one of SEQ ID NO: 1.

In some embodiments, the polypeptide binds CD47 with at least 10-fold greater binding affinity than the wild-type SIRPα D1 domain having the sequence of any one of SEQ ID NO: 1. In some embodiments, the polypeptide binds CD47 with at least 100-fold greater binding affinity than the wild-type SIRPα D1 domain having the sequence of any one of SEQ ID NOs: 1. In some embodiments, the polypeptide binds CD47 with at least 1000-fold greater binding affinity than the wild-type SIRPα D1 domain having the sequence of any one of SEQ ID NO: 1. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQ$X_1$IQPDKSVLVAAGETATLRCT$X_2$TSL$X_3$PVGPI QWFRGAGPGRELIYNQ$X_4$EG$X_5$FPRV TTVSD$X_6$TKRNNMDFSIRIG$X_7$ITPADAGTYYCVKFRK GSPDDVEFKSGAGTELSVRAKPS (SEQ ID NO: 222), wherein $X_1$ is V, L, or I; $X_2$ is A, I, or L; $X_3$ is I, T, S, or F; $X_4$ is K or R; $X_5$ is H or P; $X_6$ is L, T, or G; $X_7$ is N or A; and wherein the variant comprises at least one amino acid substitution relative to a wild-type SIRPα D1 domain having a sequence according to SEQ ID NO: 1.

In some embodiments, the polypeptide comprises the sequence of SEQ ID NO: 222, wherein $X_1$ is V, L, or I. In any of the aforementioned embodiments in this aspect of the disclosure, $X_2$ is A, I, or L. In any of the aforementioned embodiments, $X_3$ is I, T, S, or F. In any of the aforementioned embodiments, $X_4$ is K or R. In any of the aforementioned embodiments, $X_5$ is H or P. In any of the aforementioned embodiments, $X_6$ is L, T, or G. In any of the aforementioned embodiments, $X_7$ is N or A.

In some embodiments, the polypeptide comprises the sequence of SEQ ID NO: 222, wherein $X_1$ is V or I. In any of the aforementioned embodiments in this aspect of the disclosure, $X_2$ is A or I. In any of the aforementioned embodiments, $X_3$ is I or F. In any of the aforementioned embodiments, $X_4$ is K or R. In any of the aforementioned embodiments, $X_5$ is H or P. In any of the aforementioned embodiments, $X_6$ is L or T. In any of the aforementioned embodiments, $X_7$ is N or A.

In some embodiments, the polypeptide comprises the sequence of SEQ ID NO: 222, wherein $X_7$ is A. In any of the aforementioned embodiments in this aspect of the disclosure, $X_7$ is A and $X_1$ is V or I. In any of the aforementioned embodiments in this aspect of the disclosure, $X_7$ is A and $X_2$ is A or I. In any of the aforementioned embodiments, $X_7$ is A and $X_3$ is I or F. In any of the aforementioned embodiments, $X_7$ is A and $X_4$ is K or R. In any of the aforementioned embodiments, $X_7$ is A and $X_5$ is H or P. In any of the aforementioned embodiments, $X_7$ is A and $X_6$ is L or T.

In some embodiments, the polypeptide comprises the sequence of SEQ ID NO: 222, wherein $X_7$ is A. In any of the aforementioned embodiments in this aspect of the disclosure, $X_7$ is A and $X_1$ is I. In any of the aforementioned embodiments in this aspect of the disclosure, $X_7$ is A and $X_2$ is I. In any of the aforementioned embodiments, $X_7$ is A and $X_3$ is F. In any of the aforementioned embodiments, $X_7$ is A and $X_4$ is R. In any of the aforementioned embodiments, $X_7$ is A and $X_5$ is P. In any of the aforementioned embodiments, $X_7$ is A and $X_6$ is T.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 222, wherein each of $X_1$, $X_2$, $X_3$, $X_4$, $X_5$, $X_6$, and $X_7$ is not a wild-type amino acid.

In some embodiments, the polypeptide of this aspect of the disclosure includes no more than ten amino acid substitutions relative to the wild-type SIRPα D1 domain having the sequence of any one of SEQ ID NO: 1. In some embodiments, the polypeptide of this aspect of the disclosure includes no more than seven amino acid substitutions relative to the wild-type SIRPα D1 domain having the sequence of any one of SEQ ID NO: 1.

In some embodiments, the polypeptide binds CD47 with at least 10-fold greater binding affinity than the wild-type SIRPα D1 domain having the sequence of any one of SEQ ID NO: 1. In some embodiments, the polypeptide binds CD47 with at least 100-fold greater binding affinity than the wild-type SIRPα D1 domain having the sequence of any one of SEQ ID NO: 1. In some embodiments, the polypeptide binds CD47 with at least 1000-fold greater binding affinity than the wild-type SIRPα D1 domain having the sequence of any one of SEQ ID NO: 1. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRPα D1 domain variant polypeptides and fragments thereof bind to CD47 with a higher affinity than a SIRPα polypeptide binds to CD47. For example, in some embodiments, a SIRPα D1 domain variant polypeptide or fragment thereof binds to CD47 with a $K_D$ less than $1\times10^{-8}$ M, less than $5\times10^{-9}$M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVSVAAGESAILHCTX$_2$TSLX$_3$PVGPI QWFRGAGPARELIYNQX$_4$EGX$_5$FPRV TTVSEX$_6$TKRENMDFSISISX$_7$ITPADAGTYYCVKFRK GSPDTEFKSGAGTELSVRAKPS (SEQ ID NO: 212), wherein X$_1$ is V, L, or I; X$_2$ is V, I, or L; X$_3$ is I, T, S, or F; X$_4$ is K or R; X$_5$ is H, P, or R; X$_6$ is S, T, of G; X$_7$ is N or A; and wherein the variant comprises at least one amino acid substitution relative to a wild-type SIRPα D1 domain having the sequence of any one of SEQ ID NO: 2.

In some embodiments, the polypeptide comprises the sequence of SEQ ID NO: 212, wherein X$_1$ is V, L, or I. In any of the aforementioned embodiments in this aspect of the disclosure, X$_2$ is V, I, or L. In any of the aforementioned embodiments, X$_3$ is I, T, S, or F. In any of the aforementioned embodiments, X$_4$ is K or R. In any of the aforementioned embodiments, X$_5$ is H or P. In any of the aforementioned embodiments, X$_6$ is S, T, or G. In any of the aforementioned embodiments, X$_7$ is N or A.

In some embodiments, the polypeptide comprises the sequence of SEQ ID NO: 212, wherein X$_1$ is V or I. In any of the aforementioned embodiments in this aspect of the disclosure, X$_2$ is V or I. In any of the aforementioned embodiments, X$_3$ is I or F. In any of the aforementioned embodiments, X$_4$ is K or R. In any of the aforementioned embodiments, X$_5$ is H or P. In any of the aforementioned embodiments, X$_6$ is S or T. In any of the aforementioned embodiments, X$_7$ is N or A.

In some embodiments, the polypeptide comprises the sequence of SEQ ID NO: 212, wherein X$_7$ is A. In any of the aforementioned embodiments in this aspect of the disclosure, X$_7$ is A and X$_1$ is V or I. In any of the aforementioned embodiments in this aspect of the disclosure, X$_7$ is A and X$_2$ is V or I. In any of the aforementioned embodiments, X$_7$ is A and X$_3$ is I or F. In any of the aforementioned embodiments, X$_7$ is A and X$_4$ is K or R. In any of the aforementioned embodiments, X$_7$ is A and X$_5$ is H or P. In any of the aforementioned embodiments, X$_7$ is A and X$_6$ is S or T.

In some embodiments, the polypeptide comprises the sequence of SEQ ID NO: 212, wherein X$_7$ is A. In any of the aforementioned embodiments in this aspect of the disclosure, X$_7$ is A and X$_1$ is I. In any of the aforementioned embodiments in this aspect of the disclosure, X$_7$ is A and X$_2$ is I. In any of the aforementioned embodiments, X$_7$ is A and X$_3$ is F. In any of the aforementioned embodiments, X$_7$ is A and X$_4$ is R. In any of the aforementioned embodiments, X$_7$ is A and X$_5$ is P. In any of the aforementioned embodiments, X$_7$ is A and X$_6$ is T.

In some embodiments, the polypeptide comprises a SIRPα D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 212, wherein each of X$_1$, X$_2$, X$_3$, X$_4$, X$_5$, X$_6$, and X$_7$ is not a wild-type amino acid.

In some embodiments, the polypeptide of this aspect of the disclosure includes no more than ten amino acid substitutions relative to the wild-type SIRPα D1 domain having the sequence of any one of SEQ ID NO: 2. In some embodiments, the polypeptide of this aspect of the disclosure includes no more than seven amino acid substitutions relative to the wild-type SIRPα D1 domain having the sequence of any one of SEQ ID NO: 2.

In some embodiments, the polypeptide binds CD47 with at least 10-fold greater binding affinity than the wild-type SIRPα D1 domain having the sequence of any one of SEQ ID NO: 2. In some embodiments, the polypeptide binds CD47 with at least 100-fold greater binding affinity than the wild-type SIRPα D1 domain having the sequence of any one of SEQ ID NO: 2. In some embodiments, the polypeptide binds CD47 with at least 1000-fold greater binding affinity than the wild-type SIRPα D1 domain having the sequence of any one of SEQ ID NO: 2. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRPα D1 domain variant polypeptides and fragments thereof bind to CD47 with a higher affinity than a SIRPα polypeptide binds to CD47. For example, in some embodiments, a SIRPα D1 domain variant polypeptide or fragment thereof binds to CD47 with a K$_D$ less than $1\times10^{-8}$ M, less than $5\times10^{-9}$M, less than $1\times10^{-9}$ M, less $5\times10^{-10}$M, less than $1\times10^{-10}$ M or less than $1\times10^{-11}$ M. In some embodiments, a SIRPα D1 domain variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

Described herein, in some embodiments, is a polypeptide comprising a SIRPα D1 domain variant having a sequence according to: EEELQX$_1$IQPDKSVLVAAGETATLRCTX$_2$TSLX$_3$PVGPI QWFRGAGPGRX$_4$LIYNQX$_5$X$_6$GX$_7$FP RVTTVSDX$_8$TKRNNMDFSIRIGX$_9$X$_{10}$X$_{11}$X$_{12}$ADAGTY YCX$_{13}$KFRKGSPDDVEFKSGAGTELSV RAKPS (SEQ ID NO: 218), wherein X$_1$ is V, L, or I; X$_2$ is A, V, L, or I; X$_3$ is I, S, T, or F; X$_4$ is E, L, or V; X$_5$ is K or R; X$_6$ is E or Q; X$_7$ is H, R, or P; X$_8$ is S, G, L, or T; X$_9$ is any amino acid; X$_{10}$ is any amino acid; X$_{11}$ is any amino acid; X$_{12}$ is any amino acid; and X$_{13}$ is V or I; and wherein the SIRPα D1 domain variant comprises at least two amino acid substitutions relative to a wild-type SIRPα D1 domain having a sequence according to SEQ ID NO: 1.

In some embodiments, the polypeptide comprises the sequence of SEQ ID NO: 212, wherein X$_1$, wherein X$_9$ is A. In any of the aforementioned embodiments in this aspect of the disclosure, X$_9$ is N. In any of the aforementioned embodiments in this aspect of the disclosure X$_{10}$ is I. In any of the aforementioned embodiments in this aspect of the disclosure X$_9$ is N and X$_{10}$ is P. In any of the aforementioned embodiments in this aspect of the disclosure X$_9$ is N and X$_{11}$ is any amino acid other than S, T, or C. In any of the aforementioned embodiments in this aspect of the disclosure X$_{11}$ is T. In any of the aforementioned embodiments in this aspect of the disclosure X$_{11}$ is an amino acid other than T. In any of the aforementioned embodiments in this aspect of the disclosure X$_{12}$ is P. In any of the aforementioned embodiments in this aspect of the disclosure X$_9$ is N and X$_{12}$ is any amino acid other than P.

Described herein, in some embodiments, is a polypeptide comprising a SIRPα D1 domain variant having a sequence according to: EEELQX$_1$IQPDKSVLVAAGETATLRCTX$_2$ TSLX$_3$PVGPIQWFRGAGPGRX$_4$LIYNQX$_5$X$_6$GX$_7$FP RVTTVSDX$_8$TKRNNMDFSIRIGX$_9$ITX$_{10}$ADAGTYYC X$_{11}$KFRKGSPDDVEFKSGAGTELSVRA KPS (SEQ ID NO: 219), wherein X$_1$ is V, L, or I; X$_2$ is A, V, L, or I; X$_3$ is I, S, T, or F; X$_4$ is E, L, or V; X$_5$ is K or R; X$_6$ is E or Q; X$_7$ is H, R, or P; X$_8$ is S, G, L, or T; X$_9$ is N; X$_{10}$ is any amino acid other than P; and X$_{11}$ is V or I; and wherein the SIRPαD1 domain variant comprises at least two amino acid substitutions relative to a wild-type SIRPα D1 domain having a sequence according to SEQ ID NO: 1.

In another aspect of the disclosure, compositions are disclosed herein which include a SIRPα D1 domain variant polypeptide having the amino acid sequence of SEQ ID NO: 48, or a fragment thereof. In some embodiments, the SIRPα D1 domain variant polypeptide or fragment thereof binds to CD47 with a higher affinity compared to the affinity that a SIRPα polypeptide binds to the CD47. In some embodiments, the SIRPα D1 domain variant polypeptide binds to CD47 with a K$_D$ less than $1\times10^{-8}$M, or less than $1\times10^{-9}$M, less than $1\times10^{-10}$ M or less than $1\times10^{-11}$M. In some embodiments, the above-mentioned SIRPα D1 domain variant polypeptides are attached or fused to a second polypeptide. In some embodiments, the second polypeptide includes, without limitation, an Fc polypeptide, an Fc variant or a fragment of the foregoing.

Without limiting the foregoing, in some embodiments, a SIRPα D1 domain variant polypeptide is selected from any one of SEQ ID NOs: 53-87 and 213 shown in Table 6.

TABLE 6

SIRPα Variant Polypeptides

| SEQ ID NO: | Amino Acid Sequence |
| --- | --- |
| 53 | EEELQIIQPDKSVSVAAGESAILHCTITSLFPVGPIQWFRGAGPARVLIYNQRQGPFPRVTTVSETTKRENMDFSISISNITPADAGTYYCIKFRKGSPDTEFKSGAGTELSVRAKPS |
| 54 | EEELQVIQPDKSVSVAAGESAILHCTVTSLFPVGPIQWFRGAGPARELIYNQRQGPFPRVTTVSESTKRENMDFSISISNITPADAGTYYCVKFRKGSPDTEFKSGAGTELSVRAKPS |
| 55 | EEELQVIQPDKSVSVAAGESAILHCTITSLFPVGPIQWFRGAGPARVLIYNQRQGPFPRVTTVSETTKRENMDFSISISNITPADAGTYYCIKFRKGSPDTEFKSGAGTELSVRAKPS |
| 56 | EEELQIIQPDKSVSVAAGESAILHCTVTSLFPVGPIQWFRGAGPARVLIYNQRQGPFPRVTTVSETTKRENMDFSISISNITPADAGTYYCIKFRKGSPDTEFKSGAGTELSVRAKPS |
| 57 | EEELQIIQPDKSVSVAAGESAILHCTITSLIPVGPIQWFRGAGPARVLIYNQRQGPFPRVTTVSETTKRENMDFSISISNITPADAGTYYCIKFRKGSPDTEFKSGAGTELSVRAKPS |
| 58 | EEELQIIQPDKSVSVAAGESAILHCTITSLFPVGPIQWFRGAGPARELIYNQRQGPFPRVTTVSETTKRENMDFSISISNITPADAGTYYCIKFRKGSPDTEFKSGAGTELSVRAKPS |
| 59 | EEELQIIQPDKSVSVAAGESAILHCTITSLFPVGPIQWFRGAGPARVLIYNQKQGPFPRVTTVSETTKRENMDFSISISNITPADAGTYYCIKFRKGSPDTEFKSGAGTELSVRAKPS |
| 60 | EEELQIIQPDKSVSVAAGESAILHCTITSLFPVGPIQWFRGAGPARVLIYNQREGPFPRVTTVSETTKRENMDFSISISNITPADAGTYYCIKFRKGSPDTEFKSGAGTELSVRAKPS |
| 61 | EEELQIIQPDKSVSVAAGESAILHCTITSLFPVGPIQWFRGAGPARVLIYNQRQGHPFPRVTTVSETTKRENMDFSISISNITPADAGTYYCIKFRKGSPDTEFKSGAGTELSVRAKPS |
| 62 | EEELQIIQPDKSVSVAAGESAILHCTITSLFPVGPIQWFRGAGPARVLIYNQRQGPFPRVTTVSESTKRENMDFSISISNITPADAGTYYCIKFRKGSPDTEFKSGAGTELSVRAKPS |
| 63 | EEELQIIQPDKSVSVAAGESAILHCTITSLFPVGPIQWFRGAGPARVLIYNQRQGPFPRVTTVSETTKRENMDFSISISNITPADAGTYYCVKFRKGSPDTEFKSGAGTELSVRAKPS |
| 64 | EEELQVIQPDKSVSVAAGESAILHCTVTSLIPVGPIQWFRGAGPARELIYNQREGPFPRVTTVSESTKRENMDFSISISNITPADAGTYYCVKFRKGSPDTEFKSGAGTELSVRAKPS |
| 65 | EEELQVIQPDKSVSVAAGESAILHCTVTSLFPVGPIQWFRGAGPARELIYNQREGPFPRVTTVSESTKRENMDFSISISNITPADAGTYYCVKFRKGSPDTEFKSGAGTELSVRAKPS |
| 66 | EEELQVIQPDKSVSVAAGESAILHCTITSLFPVGPIQWFRGAGPARELIYNQREGPFPRVTTVSESTKRENMDFSISISNITPADAGTYYCVKFRKGSPDTEFKSGAGTELSVRAKPS |

TABLE 6-continued

SIRPα Variant Polypeptides

| SEQ ID NO: | Amino Acid Sequence |
|---|---|
| 67 | EEELQVIQPDKSVSVAAGESAILHCTITSLFPVGPIQWFRGAGPARELIYNQRE<br>GPFPRVTTVSETTKRENMDFSISISNITPADAGTYYCVKFRKGSPDTEFKSGAG<br>TELSVRAKPS |
| 68 | EEELQIIQPDKSVSVAAGESAILHCTITSLFPVGPIQWFRGAGPARELIYNQREG<br>PFPRVTTVSESTKRENMDFSISISNITPADAGTYYCVKFRKGSPDTEFKSGAGT<br>ELSVRAKPS |
| 69 | EEELQVIQPDKSVSVAAGESAILHCTITSLIPVGPIQWFRGAGPARELIYNQRE<br>GPFPRVTTVSESTKRENMDFSISISNITPADAGTYYCVKFRKGSPDTEFKSGAG<br>TELSVRAKPS |
| 70 | EEELQIIQPDKSVSVAAGESAILHCTITSLFPVGPIQWFRGAGPARELIYNQREG<br>PFPRVTTVSETTKRENMDFSISISNITPADAGTYYCVKFRKGSPDTEFKSGAGT<br>ELSVRAKPS |
| 71 | EEELQVIQPDKSVLVAAGETATLRCTATSLFPVGPIQWFRGAGPGRELIYNQR<br>QGPFPRVTTVSDLTKRNNMDFSIRIGNITPADAGTYYCVKFRKGSPDDVEFKS<br>GAGTELSVRAKPS |
| 72 | EEELQIIQPDKSVLVAAGETATLRCTITSLFPVGPIQWFRGAGPGRELIYNQRE<br>GPFPRVTTVSDLTKRNNMDFSIRIGNITPADAGTYYCVKFRKGSPDDVEFKSG<br>AGTELSVRAKPS |
| 73 | EEELQVIQPDKSVLVAAGETATLRCTITSLFPVGPIQWFRGAGPGRELIYNQRE<br>GPFPRVTTVSDTTKRNNMDFSIRIGNITPADAGTYYCVKFRKGSPDDVEFKSG<br>AGTELSVRAKPS |
| 74 | EEELQIIQPDKSVLVAAGETATLRCTITSLFPVGPIQWFRGAGPGRELIYNQRE<br>GPFPRVTTVSDTTKRNNMDFSIRIGNITPADAGTYYCVKFRKGSPDDVEFKSG<br>AGTELSVRAKPS |
| 75 | EEELQVIQPDKSVLVAAGETATLRCTITSLFPVGPIQWFRGAGPGRELIYNQRE<br>GPFPRVTTVSDLTKRNNMDFSIRIGNITPADAGTYYCVKFRKGSPDDVEFKSG<br>AGTELSVRAKPS |
| 76 | EEELQVIQPDKSVLVAAGETATLRCTATSLFPVGPIQWFRGAGPGRELIYNQR<br>EGPFPRVTTVSDLTKRNNMDFSIRIGNITPADAGTYYCVKFRKGSPDDVEFKS<br>GAGTELSVRAKPS |
| 77 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPS |
| 78 | EEELQIIQPDKSVLVAAGETATLRCTITSLFPVGPIQWFRGAGPGRVLIYNQRQ<br>GPFPRVTTVSDTTKRNNMDFSIRIGAITPADAGTYYCIKFRKGSPDDVEFKSG<br>AGTELSVRAKPS |
| 79 | EEELQVIQPDKSVLVAAGETATLRCTATSLFPVGPIQWFRGAGPGRELIYNQR<br>QGPFPRVTTVSDLTKRNNMDFSIRIGAITPADAGTYYCVKFRKGSPDDVEFKS<br>GAGTELSVRAKPS |
| 80 | EEELQIIQPDKSVLVAAGETATLRCTITSLFPVGPIQWFRGAGPGRVLIYNQRE<br>GPFPRVTTVSDTTKRNNMDFSIRIGAITPADAGTYYCIKFRKGSPDDVEFKSG<br>AGTELSVRAKPS |
| 81 | EEELQVIQPDKSVLVAAGETATLRCTATSLFPVGPIQWFRGAGPGRELIYNQR<br>EGPFPRVTTVSDLTKRNNMDFSIRIGAITPADAGTYYCVKFRKGSPDDVEFKS<br>GAGTELSVRAKPS |
| 82 | EEELQVIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPS |
| 83 | EEELQIIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPS |
| 84 | EEELQVIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPS |
| 85 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPS |

TABLE 6-continued

SIRPα Variant Polypeptides

| SEQ ID NO: | Amino Acid Sequence |
|---|---|
| 86 | EEELQIIQPDKSVLVAAGETATLRCTITSLFPVGPIQWFRGAGPGRVLIYNQRQ GPFPRVTTVSDTTKRNNMDFSIRIGNITPADAGTYYCIKFRKGSPDDVEFKSG AGTELSVRAKPS |
| 87 | EEELQVIQPDKSVLVAAGETATLRCTATSLIPVGPIQWFRGAGPGRELIYNQK EGEIFPRVTTVSDLTKRNNMDFSIRIGNITPADAGTYYCVKFRKGSPDDVEFKS GAGTELSVRAKPS |
| 195 | EEELQIIQPDKSVLVAAGETATLRCTMTSLFPVGPIQWFRGAGPGRELIYNQR EGPFPRVTTVSDTTKRNNMDFSIRIGAITPADAGTYYCVKFRKGSPDDVEFKS GAGTELSVRAKPS |
| 196 | EEELQIIQPDKSVLVAAGETATLRCTITSLKPVGPIQWFRGAGPGRELIYNQRE GPFPRVTTVSDTTKRNNMDFSIRIGAITPADAGTYYCVKFRKGSPDDVEFKSG AGTELSVRAKPS |
| 197 | EEELQIIQPDKSVLVAAGETATLRCTITSLRPVGPIQWFRGAGPGRELIYNQRE GPFPRVTTVSDTTKRNNMDFSIRIGAITPADAGTYYCVKFRKGSPDDVEFKSG AGTELSVRAKPS |
| 198 | EEELQIIQPDKSVLVAAGETATLRCTITSLYPVGPIQWFRGAGPGRELIYNQRE GPFPRVTTVSDTTKRNNMDFSIRIGAITPADAGTYYCVKFRKGSPDDVEFKSG AGTELSVRAKPS |
| 199 | EEELQIIQPDKSVLVAAGETATLRCTITSLFPVGPIQWFRGAGPGRELIYNQRD GPFPRVTTVSDTTKRNNMDFSIRIGAITPADAGTYYCVKFRKGSPDDVEFKSG AGTELSVRAKPS |
| 200 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGIPDDVEFKSG AGTELSVRAKPS |
| 201 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGMPDDVEFKS GAGTELSVRAKPS |
| 202 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDVEFKSGA GTELSVRAKPS |
| 203 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSSEPDVEFKS GAGTELSVRAKPS |
| 204 | EEELQIIQPDKSVLVAAGETATLRCTITSLRPVGPIQWFRGAGPGRELIYNQRD GPFPRVTTVSDTTKRNNMDFSIRIGAITPADAGTYYCVKFRKGSPDDVEFKSG AGTELSVRAKPS |
| 205 | EEELQIIQPDKSVLVAAGETATLRCTITSLRPVGPIQWFRGAGPGRELIYNQRE GPFPRVTTVSDTTKRNNMDFSIRIGAITPADAGTYYCVKFRKGIPDDVEFKSG AGTELSVRAKPS |
| 206 | EEELQIIQPDKSVLVAAGETATLRCTITSLRPVGPIQWFRGAGPGRELIYNQRD GPFPRVTTVSDTTKRNNMDFSIRIGAITPADAGTYYCVKFRKGIPDDVEFKSG AGTELSVRAKPS |
| 207 | EEELQIIQPDKSVLVAAGETATLRCTITSLYPVGPIQWFRGAGPGRELIYNQRD GPFPRVTTVSDTTKRNNMDFSIRIGAITPADAGTYYCVKFRKGSPDDVEFKSG AGTELSVRAKPS |
| 208 | EEELQIIQPDKSVLVAAGETATLRCTITSLYPVGPIQWFRGAGPGRELIYNQRE GPFPRVTTVSDTTKRNNMDFSIRIGAITPADAGTYYCVKFRKGIPDDVEFKSG AGTELSVRAKPS |
| 209 | EEELQIIQPDKSVLVAAGETATLRCTITSLYPVGPIQWFRGAGPGRELIYNQRD GPFPRVTTVSDTTKRNNMDFSIRIGAITPADAGTYYCVKFRKGIPDDVEFKSG AGTELSVRAKPS |
| 210 | EEELQIIQPDKSVLVAAGETATLRCTITSLFPVGPIQWFRGAGPGRELIYNQRD GPFPRVTTVSDTTKRNNMDFSIRIGAITPADAGTYYCVKFRKGIPDDVEFKSG AGTELSVRAKPS |

TABLE 6-continued

SIRPα Variant Polypeptides

SEQ ID NO:   Amino Acid Sequence

213          EEELQVIQPDKSVLVAAGETATLRCTATSLFPVGPIQWFRGAGPGRELIYNQR
             QGPFPRVTTVSDLTKRNNMDFSIRIGNITVADAGTYYCVKFRKGSPDDVEFKS
             GAGTELSVRAKPS

In some embodiments, the polypeptide comprises a SIRPα D1 domain variant that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 6.

In some embodiments, the polypeptide comprises a SIRPα D1 domain that has at least 85% sequence identity (e.g., at least 86%, 87%, 88%, 89%, 90%, 91%, 92%, 93%, 94%, 95%, 96%, 97%, 98%, 99 (SEQ ID NO: 223)%, or 100% sequence identity) to SEQ ID NOs: 80, 81, or 85 in Table 6.

Fc Domain Variants and Fusion Polypeptides Comprising Same

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of: residue 6, residue 27, residue 31, residue 47, residue 53, residue 54, residue 56, residue 66, and residue 92.

Also disclosed herein, in some embodiments, are Fc domain variant dimers, wherein the Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Antibodies that target cell surface antigens can trigger immunostimulatory and effector functions that are associated with Fc receptor (FcR) engagement on immune cells. There are a number of Fc receptors that are specific for particular classes of antibodies, including IgG (gamma receptors), IgE (eta receptors), IgA (alpha receptors) and IgM (mu receptors). Binding of the Fc region to Fc receptors on cell surfaces can trigger a number of biological responses including phagocytosis of antibody-coated particles (antibody-dependent cell-mediated phagocytosis, or ADCP), clearance of immune complexes, lysis of antibody-coated cells by killer cells (antibody-dependent cell-mediated cytotoxicity, or ADCC) and, release of inflammatory mediators, placental transfer, and control of immunoglobulin production. Additionally, binding of the C1 component of complement to antibodies can activate the complement system. Activation of complement can be important for the lysis of cellular pathogens. However, the activation of complement can also stimulate the inflammatory response and can also be involved in autoimmune hypersensitivity or other immunological disorders. Variant Fc regions with reduced or ablated ability to bind certain Fc receptors are useful for developing therapeutic antibodies and Fc-fusion polypeptide constructs which act by targeting, activating, or neutralizing ligand functions while not damaging or destroying local cells or tissues.

In some embodiments, a SIRPα D1 polypeptide construct comprises a non-naturally occurring SIRPα D1 domain variant linked to an Fc domain variant which forms an Fc domain having ablated or reduced effector function.

In some embodiments, a Fc domain variant refers to a polypeptide chain that includes second and third antibody constant domains (e.g., CH2 and CH3). In some embodiments, an Fc domain variant also includes a hinge domain. In some embodiments, the Fc domain variant is of any immunoglobulin antibody isotype, including IgG, IgE, IgM, IgA, and IgD. Additionally, in some embodiments, an Fc domain variant is of any IgG subtype (e.g., IgG, IgG2, IgG2a, IgG2b, IgG2c, IgG3, and IgG4). In some embodiments, an Fc domain variant comprises as many as ten amino acid modifications (e.g., insertions, deletions and/or substitutions) relative to a wild-type Fc domain monomer sequence (e.g., 1-10, 1-8, 1-6, 1-4 amino acid substitutions, additions or insertions, deletions, or combinations thereof) that alter the interaction between an Fc domain and an Fc receptor.

As used herein, the term "Fc domain dimer" refers to a dimer of two Fc domains. In a wild-type Fc domain dimer, two wild-type Fc domains dimerize by the interaction between the two CH3 antibody constant domains, as well as one or more disulfide bonds that form between the hinge domains of the two dimerized Fc domains.

As used herein, the term "Fc domain dimer variant" comprises at least one Fc domain variant. In some embodiments, an Fc domain dimer variant comprises Fc domain variants that are mutated to lack effector functions, for example a "dead Fc domain dimer variant." In some embodiments, each of the Fc domains in an Fc domain dimer variant includes amino acid substitutions in the CH2 antibody constant domain to reduce the interaction or binding between the Fc domain dimer variant and an Fc receptor, such as an Fcγ receptor (FcγR), an Fcα receptor (FcαR), or an Fcε (FcεR).

In some embodiments, a SIRPα D1 domain variant (e.g., any of the variants described in Tables 2, 5, and 6) is fused to an Fc domain variant of an immunoglobulin or a fragment of an Fc domain variant. In some embodiments, an Fc domain variant of an immunoglobulin or a fragment of an Fc domain variant is capable of forming an Fc domain dimer with another Fc domain variant. In some embodiments, an Fc domain variant of an immunoglobulin or a fragment of an Fc domain variant is not capable of forming an Fc domain dimer with another Fc domain variant. In some embodiments, an Fc domain variant or a fragment of an Fc domain variant is fused to a polypeptide of the disclosure to increase serum half-life of the polypeptide. In some embodiments, an Fc domain variant or a fragment of an Fc domain variant fused to a polypeptide of the disclosure dimerizes with a second Fc domain variant to form an Fc domain dimer variant which binds an Fc receptor, or alternatively, an Fc domain variant binds to an Fc receptor. In some embodiments, an Fc domain variant or a fragment of the Fc domain variant fused to a polypeptide to increase serum half-life of the polypeptide does not induce any immune system-related response.

In some embodiments, a SIRPα polypeptide or construct provided herein includes a SIRPα D1 domain or variant thereof joined to a first Fc domain variant and an antibody variable domain joined to a second Fc domain variant, in which the first and second Fc domain variants combine to form an Fc domain dimer variant (e.g., a heterodimeric Fc domain dimer variant). An Fc domain dimer is the protein structure that is found at the C-terminus of an immunoglobulin. An Fc domain dimer includes two Fc domains that are dimerized by the interaction between the CH3 antibody constant domains. A wild-type Fc domain dimer forms the minimum structure that binds to an Fc receptor, e.g., FcγRI, FcγRIIa, FcγRIIb, FcγRIIIa, FcγRIIIb, and FcγRIV.

The Fc domain dimer is not involved directly in binding an antibody to its target, but can be involved in various effector functions, such as participation of the antibody in antibody-dependent cellular toxicity. In some embodiments, the Fc domain in a SIRPα polypeptide or construct of the disclosure comprises amino acid substitutions, additions or insertions, deletions, or any combinations thereof that lead to decreased effector function such as decreased antibody-dependent cell-mediated cytotoxicity (ADCC), decreased complement-dependent cytolysis (CDC), decreased antibody-dependent cell-mediated phagocytosis (ADCP), or any combinations thereof. In some embodiments, the SIRPα polypeptides or constructs of the disclosure are characterized by decreased binding (e.g., minimal binding or absence of binding) to a human Fc receptor and decreased binding (e.g., minimal binding or absence of binding) to complement protein C1q. In some embodiments, the SIRPα constructs of the disclosure are characterized by decreased binding (e.g., minimal binding or absence of binding) to human FcγRI, FcγRIIA, FcγRIIB, FcγRIIIB, or any combinations thereof, and C1q. To alter or reduce an antibody-dependent effector function, such as ADCC, CDC, ADCP, or any combinations thereof, in some embodiments, the Fc domains in SIRPα constructs of the disclosure are of the IgG class and comprise one or more amino acid substitutions at E233, L234, L235, G236, G237, D265, D270, N297, E318, K320, K322, A327, A330, P331, or P329 (numbering according to the EU index of Kabat (Sequences of Proteins of Immunological Interest, 5th Ed. Public Health Service, National Institutes of Health, Bethesda, Md. (1991))).

In some embodiments, polypeptide constructs comprising a non-native Fc region described herein exhibit reduced or ablated binding to at least one of Fcγ receptors CD16a, CD32a, CD32b, CD32c, and CD64 as compared to a polypeptide construct comprising a native Fc region. In some cases, the polypeptide constructs described herein exhibit reduced or ablated binding to CD16a, CD32a, CD32b, CD32c, and CD64 Fcγ receptors.

CDC refers to a form of cytotoxicity in which the complement cascade is activated by the complement component C1q binding to antibody Fc domains. In some embodiments, polypeptide constructs comprising a non-native Fc region described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising a non-native Fc region as described herein exhibit reduced CDC as compared to a polypeptide construct comprising a wild-type Fc region. In some embodiments, polypeptide constructs comprising a non-native Fc region as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising a non-natural Fc domain variants or Fc domain dimer variants as described herein exhibit negligible CDC as compared to a polypeptide construct comprising a wild-type Fc region.

In some embodiments, the Fc domain variants or Fc domain dimer variants described herein are minimally glycosylated or have reduced glycosylation relative to a wild-type sequence. In some embodiments, deglycosylation is accomplished with a mutation of N297A, or by mutating N297 to any amino acid which is not N. In some embodiments, deglycosylation is accomplished by disrupting the motif N-Xaa1-Xaa2-Xaa3, wherein N=asparagine; Xaa1=any amino acid except P (proline); Xaa2=T (threonine), S (serine) or C (cysteine); and Xaa3=any amino acid except P (proline). In one embodiment, the N-Xaa1-Xaa2-Xaa3 motif refers to residues 297-300 as designated according to Kabat et al., 1991. In some embodiments, a mutation to any one or more of N, Xaa1, Xaa2, or Xaa3 results in deglycosylation of the Fc domain variant or Fc domain dimer variant.

In some embodiments, variants of antibody IgG constant regions (e.g., Fc domain variants or Fc domain dimer variants) possess a reduced capacity to specifically bind Fcγ receptors or have a reduced capacity to induce phagocytosis. In some embodiments, variants of antibody IgG constant regions (e.g., Fc domain variants or Fc domain dimer variants) possess a reduced capacity to specifically bind Fcγ receptors and have a reduced capacity to induce phagocytosis. For example, in some embodiments, an Fc domain variant is mutated to lack effector functions, typical of a "dead" Fc domain variant. For example, in some embodiments, an Fc domain variant includes specific amino acid substitutions that are known to minimize the interaction between the Fc domain dimer and an Fcγ receptor. In some embodiments, an Fc domain variant is from an IgG1 antibody and includes one or more of amino acid substitutions L234A, L235A, G237A, and N297A (as designated according to the EU numbering system per Kabat et al., 1991). In some embodiments, one or more additional mutations are included in such IgG1 Fc domain variant. Non-limiting examples of such additional mutations for human IgG1 Fc domain variants include E318A and K322A. In some instances, a human IgG1 Fc domain variant has up to 12, 11, 10, 9, 8, 7, 6, 5 or 4 or fewer mutations in total as compared to wild-type human IgG1 sequence. In some embodiments, one or more additional deletions are included in such IgG1 Fc domain variant. For example, in some embodiments, the C-terminal lysine of the Fc domain IgG1 heavy chain constant region provided in SEQ ID NO: 88 in Table 7 is deleted, for example to increase the homogeneity of the polypeptide when the polypeptide is produced in bacterial or mammalian cells. In some instances, a human IgG1 Fc domain variant has up to 12, 11, 10, 9, 8, 7, 6, 5 or 4 or fewer deletions in total as compared to wild-type human IgG1 sequence (see, e.g., SEQ ID NO: 161 below). In some embodiments, a IgG1 Fc domain variant has a sequence according to any one of SEQ ID NO: 135, SEQ ID NO: 136 or SEQ ID NO: 137.

SEQ ID NO: 161:
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPG

In some embodiments, an Fc domain variant is from an IgG2 or IgG4 antibody and includes amino acid substitutions A330S, P331S, or both A330S and P331S. The aforementioned amino acid positions are defined according to Kabat, et al. (1991). The Kabat numbering of amino acid residues can be determined for a given antibody by alignment at regions of homology of the sequence of the antibody with a "standard" Kabat numbered sequence. In some embodiments, the Fc domain variant comprises a human IgG2 Fc domain sequence comprising one or more of A330S, P331S and N297A amino acid substitutions (as designated according to the EU numbering system per Kabat, et al. (1991). In some embodiments, one or more additional mutations are included in such IgG2 Fc domain variants. Non-limiting examples of such additional mutations for human IgG2 Fc domain variant include V234A, G237A, P238S, V309L and H268A (as designated according to the EU numbering system per Kabat et al. (1991)). In some instances, a human IgG2 Fc domain variant has up to 12, 11, 10, 9, 8, 7, 6, 5, 4, 3 or fewer mutations in total as compared to wild-type human IgG2 sequence. In some embodiments, one or more additional deletions are included in such IgG2 Fc domain variant. For example, in some embodiments, the C-terminal lysine of the Fc domain IgG2 heavy chain constant region provided in SEQ ID NO: 89 in Table 7 is deleted, for example to increase the homogeneity of the polypeptide when the polypeptide is produced in bacterial or mammalian cells. In some instances, a human IgG2 Fc domain variant has up to 12, 11, 10, 9, 8, 7, 6, 5 or 4 or fewer deletions in total as compared to wild-type human IgG2 sequence (see, e.g., SEQ ID NO: 162 below).

SEQ ID NO: 162:
ERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEY

-continued
KCKVSNKGLPAPIEKTISKTKGQPREPQVYTLPPSREEMTKNQVSLTCLV

KGFYPSDIAVEWESNGQPENNYKTTPPMLDSDGSFFLYSKLTVDKSMVQQ

GNVFSCSVMHEALHNHYTQKSLSLSPG

When the Fc domain variant is an IgG4 Fc domain variant, in some embodiments, such Fc domain variant comprises a S228P mutation (as designated according to Kabat, et al. (1991)). In some instances, a human IgG4 Fc domain variant has up to 12, 11, 10, 9, 8, 7, 6, 5, 4, 3, 2 or 1 mutation(s) in total as compared to wild-type human IgG4 sequence. In some embodiments, the Fc domain variant comprises a human IgG4 Fc sequence comprising one or more of S228P, E233P, F234V, L235A, and delG236 amino acid substitutions (as designated according to the EU numbering system per Kabat, et al. (1991). In some embodiments, the Fc domain variant comprises a human IgG4 Fc sequence comprising one or more of S228P, E233P, F234V, L235A, deG236, and N297A amino acid substitutions (as designated according to the EU numbering system per Kabat, et al. (1991).

In some embodiments, the Fc domain variant includes at least one of the mutations L234A, L235A, G237A or N297A of an IgG1 Fc region or at least one of the mutations A330S, P331S or N297A of an IgG2 Fc region. In some embodiments, the Fc domain variant includes at least two of the mutations L234A, L235A, G237A or N297A of an IgG1 Fc region or at least two of the mutations A330S, P331S or N297A of an IgG2 Fc region. In some embodiments, the Fc domain variant includes at least three of the mutations L234A, L235A, G237A or N297A of an IgG1 Fc region or consists of the mutations A330S, P331S and N297A of an IgG2 Fc region. In some embodiments, the Fc domain variant consists of the mutations L234A, L235A, G237A and N297A.

In some embodiments, the Fc domain variant exhibits reduced binding to an Fc receptor of the subject compared to the wild-type human IgG Fc region. In some embodiments, the Fc domain variant exhibits ablated binding to an Fc receptor of the subject compared to the wild-type human IgG Fc region. In some embodiments, the Fc domain variant exhibits a reduction of phagocytosis compared to the wild-type human IgG Fc region. In some embodiments, the Fc domain variant exhibits ablated phagocytosis compared to the wild-type human IgG Fc region. SEQ ID NO: 88 and SEQ ID NO: 89 provide amino acid sequences of Fc domain IgG1 and IgG2 heavy chain constant regions. In some embodiments, an Fc domain variant is any variant of SEQ ID NOs: 90-95 as shown in Table 7.

TABLE 7

Amino Acid Sequences of Fc Domain Variants

| SEQ ID NO: | Amino Acid Sequence |
| --- | --- |
| 88 | EPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQG NVFSCSVMHEALHNHYTQKSLSLSPGK |
| 89 | STKGPSVFPLAPCSRSTSESTAALGCLVKDYFPEPVTVSWNSGALTSGVHTFP AVLQSSGLYSLSSVVTVPSSSLGTQTYTCNVDEIKPSNTKVDKTVERKCCVE CPPCPAPPVAGPSVFLFPPKPKDTLMISRTPEVTCVVVDVSHEDPEVQFNWY VDGVEVHNAKTKPREEQFNSTFRVVSVLTVVHQDWLNGKEYKCKVSNKGL PAPIEKTISKTKGQPREPQVYTLPPSREEMTKNQVSLTCLVKGFYPSDIAVEW ESNGQPENNYKTTPPMLDSDGSFFLYSKLTVDKSRWQQGNVFSCSVMHEAL HNHYTQKSLSLSPGK |

TABLE 7-continued

Amino Acid Sequences of Fc Domain Variants

| SEQ ID NO: | Amino Acid Sequence |
|---|---|
| 90 | DKTHTCPPCPAPEAAGAPSVFLFPPKPKDTLMISRTPEVTCVVVDVSHEDPE<br>VKFNWYVDGVEVHNAKTKPREEQYASTYRVVSVLTVLHQDWLNGKEYKC<br>KVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFS<br>CSVMHEALHNHYTQKSLSLSPGK |
| 91 | DKTHTCPPCPAPEAAGAPSVFLFPPKPKDTLMISRTPEVTCVVVDVSHEDPE<br>VKFNWYVDGVEVHNAKTKPREEQYASTYRVVSVLTVLHQDWLNGKEYKC<br>KVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFS<br>CSVMHEALHNHYTQKSLSLSPG |
| 92 | VECPPCPAPPVAGPSVFLFPPKPKDTLMISRTPEVTCVVVDVSHEDPEVQFN<br>WYVDGVEVHNAKTKPREEQFASTFRVVSVLTVVHQDWLNGKEYKCKVSN<br>KGLPSSIEKTISKTKGQPREPQVYTLPPSREEMTKNQVSLTCLVKGFYPSDIA<br>VEWESNGQPENNYKTTPPMLDSDGSFFLYSKLTVDKSRWQQGNVFSCSVM<br>HEALHNHYTQKSLSLSPGK |
| 93 | VECPPCPAPPVAGPSVFLFPPKPKDTLMISRTPEVTCVVVDVSHEDPEVQFN<br>WYVDGVEVHNAKTKPREEQFASTFRVVSVLTVVHQDWLNGKEYKCKVSN<br>KGLPSSIEKTISKTKGQPREPQVYTLPPSREEMTKNQVSLTCLVKGFYPSDIA<br>VEWESNGQPENNYKTTPPMLDSDGSFFLYSKLTVDKSRWQQGNVFSCSVM<br>HEALHNHYTQKSLSLSPG |
| 94 | ERKSSVECPPCPAPPVAGPSVFLFPPKPKDTLMISRTPEVTCVVVDVSHEDPE<br>VQFNWYVDGVEVHNAKTKPREEQFASTFRVVSVLTVVHQDWLNGKEYKC<br>KVSNKGLPSSIEKTISKTKGQPREPQVYTLPPSREEMTKNQVSLTCLVKGFYP<br>SDIAVEWESNGQPENNYKTTPPMLDSDGSFFLYSKLTVDKSRWQQGNVFSC<br>SVMHEALHNHYTQKSLSLSPGK |
| 95 | ERKSSVECPPCPAPPVAGPSVFLFPPKPKDTLMISRTPEVTCVVVDVSEIEDPE<br>VQFNWYVDGVEVEINAKTKPREEQFASTFRVVSVLTVVHQDWLNGKEYKC<br>KVSNKGLPSSIEKTISKTKGQPREPQVYTLPPSREEMTKNQVSLTCLVKGFYP<br>SDIAVEWESNGQPENNYKTTPPMLDSDGSFFLYSKLTVDKSRWQQGNVFSC<br>SVMHEALHNHYTQKSLSLSPG |

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc domain variant or Fc domain dimer variant as described herein exhibit reduced ADCC or ADCP as compared to a polypeptide construct comprising a wild-type Fc region. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in ADCC or ADCP compared to a polypeptide construct comprising a wild-type Fc region. In some embodiments, polypeptide constructs comprising an Fc domain variant or Fc domain dimer variant as described herein exhibit ablated ADCC or ADCP as compared to a polypeptide construct comprising a wild-type Fc region.

Complement-directed cytotoxicity, which is also referred to herein as CDC, refers to a form of cytotoxicity in which the complement cascade is activated by the complement component C1q binding to antibody Fc domains. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising an Fc domain variant or Fc domain dimer variant as described herein exhibit reduced CDC as compared to a polypeptide construct comprising a wild-type Fc region. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising an Fc domain variant or Fc domain dimer variant as described herein exhibit negligible CDC as compared to a polypeptide construct comprising a wild-type Fc region.

Fc domain variants or Fc domain dimer variants herein include those that exhibit reduced binding to an Fcγ receptor compared to the wild-type human IgG Fc region. For example, in some embodiments, an Fc domain variant or Fc domain dimer variant exhibits binding to an Fcγ receptor that is less than the binding exhibited by a wild-type human IgG Fc region to an Fcγ receptor, as described in the Examples. In some instances, an Fc domain variant or Fc domain dimer variant has reduced binding to an Fcγ receptor by a factor of 10%, 20% 30%, 40%, 50%, 60%, 70%, 80%, 90%, 95%, 96%, 97%, 98%, 99% or 100% (fully ablated effector function). In some embodiments, the reduced binding is for any one or more Fcγ receptor, e.g., CD16a, CD32a, CD32b, CD32c, or CD64.

In some instances, the Fc domain variants or Fc domain dimer variants disclosed herein exhibit a reduction of phagocytosis compared to its wild-type human IgG Fc region. Such Fc domain variants or Fc domain dimer variants exhibit a reduction in phagocytosis compared to its wild-type human IgG Fc region, wherein the reduction of phagocytosis activity is e.g., by a factor of 10%, 20%, 30%, 40%, 50%, 60%, 70%, 80%, 90%, 95%, 96%, 97%, 98%, 99% or 100%. In some instances, an Fc domain variant or Fc domain dimer variant exhibits ablated phagocytosis compared to its wild-type human IgG Fc region.

In some embodiments, the Fc domain variants or Fc domain dimer variants disclosed herein are coupled to one or more fusion partners. In some cases the fusion partner is a therapeutic moiety. In some cases, the fusion partner is selected to enable targeting of an expressed protein, purification, screening, display, and the like. In some embodiments, the fusion partner also affects the degree of binding to Fc receptors or the degree of phagocytosis reduction. As described herein, in some embodiments, when an Fc domain variant or Fc domain dimer variant is coupled to a fusion partner, it forms a polypeptide construct as described below.

In some embodiments, fusion partners are linked to the Fc domain variant or Fc domain dimer variant sequence via a linker sequence. In some embodiments, the linker sequence generally comprises a small number of amino acids, such as less than ten amino acids, although longer linkers are also utilized. In some cases, the linker has a length less than 10, 9, 8, 7, 6, or 5 amino acids or shorter. In some cases, the linker has a length of at least 10, 11, 12, 13, 14, 15, 20, 25, 30, or 35 amino acids or longer. Optionally, in some embodiments, a cleavable linker is employed.

In some embodiments, a fusion partner is a targeting or signal sequence that directs an Fc domain variant or Fc domain dimer variant protein and any associated fusion partners to a desired cellular location or to the extracellular media. In some embodiments, certain signaling sequences target a protein to be either secreted into the growth media, or into the periplasmic space, located between the inner and outer membrane of the cell. In some embodiments, a fusion partner is a sequence that encodes a peptide or protein that enables purification or screening. Such fusion partners include, but are not limited to, polyhistidine tags (His-tags) (for example His6 (SEQ ID NO: 223) and His10 (SEQ ID NO: 224)) or other tags for use with Immobilized Metal Affinity Chromatography (IMAC) systems (e.g., Ni+2 affinity columns), GST fusions, MBP fusions, Strep-tag, the BSP biotinylation target sequence of the bacterial enzyme BirA, and epitope tags which are targeted by antibodies (for example c-myc tags, flag-tags, and the like).

In some embodiments, such tags are useful for purification, for screening, or both. For example, in some embodiments, an Fc domain variant or Fc domain dimer variant is purified using a His-tag by immobilizing it to a Ni+2 affinity column, and then after purification the same His-tag is used to immobilize the antibody to a Ni+2 coated plate to perform an ELISA or other binding assay as described elsewhere herein. In some embodiments, a fusion partner enables the use of a selection method to screen Fc domain variants or Fc domain dimer variants as described herein.

Various fusion partners that enable a variety of selection methods are available. For example, by fusing the members of an Fc domain variant or Fc domain dimer variant library to the gene III protein, phage display can be employed. In some embodiments, fusion partners Fc domain variants or Fc domain dimer variants to be labeled. Alternatively, in some embodiments, a fusion partner binds to a specific sequence on the expression vector, enabling the fusion partner and associated Fc domain variant or Fc domain dimer variant to be linked covalently or noncovalently with the nucleic acid that encodes them.

In some embodiments, when a fusion partner is a therapeutic moiety, the therapeutic moiety is, e.g., a peptide, a protein, an antibody, a siRNA, or a small molecule. Non-limiting examples of therapeutic antibodies that are coupled to the Fc domain variants or Fc domain dimer variants of the present disclosure include, but are not limited to antibodies that recognize CD47. Non-limiting examples of therapeutic polypeptides that are coupled to the Fc domain variants or Fc domain dimer variants of the present disclosure include, but are not limited to, CD47 binding polypeptides, including SIRPα polypeptides. In such instances, the CD47 binding polypeptide is attached or fused to an Fc domain variant or Fc domain dimer variant of the disclosure. Examples of CD47 binding polypeptides include, but are not limited to, anti-CD47 antibodies or fragments thereof, and ligands of CD47 such as SIRPα or a fragment thereof. Additional examples of CD47 binding polypeptides include, but are not limited to naturally-occurring forms of SIRPα as well as mutants thereof.

In some embodiments, disclosed herein is a polypeptide comprising an Fc domain dimer variant, wherein the Fc domain dimer variant comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain variants are identical (i.e., homodimer). In some embodiments, the Fc domain variants are different (i.e., heterodimer). In some embodiments, at least one of the Fc domain variant in an Fc domain dimer is a human IgG1 Fc region consisting of mutations L234A, L235A, G237A, and N297A. In some embodiments, at least one of the Fc domain variants in an Fc domain dimer is a human IgG2 Fc region consisting of mutations A330S, P331S and N297A. In some embodiments, the Fc domain dimer variant exhibits ablated or reduced binding to an Fcγ receptor compared to the wild-type version of the human IgG Fc region. In some embodiments, the Fc domain dimer variant exhibits ablated or reduced binding to CD16a, CD32a, CD32b, CD32c, and CD64 Fcγ receptors compared to the wild-type version of the human IgG Fc region. In some embodiments, the Fc domain dimer variant exhibits ablated or reduced binding to C1q compared to the wild-type version of the human IgG Fc fusion. In some embodiments, at least one of the Fc domain variants in an Fc domain dimer variant is a human IgG4 Fc region comprising mutations S228P, E233P, F234V, L235A, delG236, and N297A. In some embodiments, the Fc domain dimer variant exhibits ablated or reduced binding to an Fcγ receptor compared to the wild-type human IgG4 Fc region. In some embodiments, the Fc domain dimer variant exhibits ablated or reduced binding to CD16a and CD32b Fcγ receptors compared to the wild-type version of its human IgG4 Fc region. In some embodiments, the Fc domain dimer variant binds to an Fcγ receptor with a $K_D$ greater than about $5 \times 10^{-6}$ M.

In some embodiments, the Fc domain dimer variant further comprises a CD47 binding polypeptide. In some embodiments, the Fc domain dimer variant exhibits ablated or reduced binding to an Fcγ receptor compared to a wild-type version of a human IgG Fc region. In some embodiments, the CD47 binding polypeptide does not cause acute anemia in rodents and non-human primates. In some embodiments, the CD47 binding polypeptide does not cause acute anemia in humans.

In some embodiments, the CD47 binding polypeptide is a signal-regulatory protein α (SIRP-α) polypeptide or a fragment thereof. In some embodiments, the SIRPα polypeptide comprises a SIRPα D1 domain variant comprising the amino acid sequence, EEELQX$_1$IQPDKSVLVAA GETATLRCTX$_2$TSLX$_3$PVGPIQWFRGAGPGRX$_4$LIYNQ X$_5$EGX$_6$FPR VTTVSDX$_7$TKRNNMDFSIRIGX$_8$ ITPADAGTYYCX$_9$KFRKGSPDDVEFKSGAGTELSVRA KPS (SEQ ID NO: 221), wherein X$_1$ is V or I; X$_2$ is A or I; X$_3$ is I or F; X$_4$ is E or V; X$_5$ is K or R; X$_6$ is H or P; X$_7$ is L or T; X$_8$ is any amino acid other than N; and X$_9$ is V or I. In some embodiments, the SIRPα polypeptide comprises a SIRPα D1 domain variant wherein X$_1$ is V or I; X$_2$ is A or I; X$_3$ is I or F; X$_4$ is E; X$_5$ is K or R; X$_6$ is H or P; X$_7$ is L or T; X$_8$ is not N; and X$_9$ is V.

In some embodiments, disclosed herein, is a polypeptide comprising: a SIRPα D1 domain variant, wherein the SIRPα D1 domain variant is a non-naturally occurring high affinity SIRPα D1 domain, wherein the SIRPα D1 domain variant binds to human CD47 with an affinity that is at least 10-fold greater than the affinity of a naturally occurring D1 domain; and an Fc domain variant, wherein the Fc domain variant is linked to a second polypeptide comprising a second Fc domain variant to form an Fc domain dimer variant, wherein the Fc domain dimer variant has ablated or reduced effector function. In some embodiments, the non-naturally occurring high affinity SIRPα D1 domain comprises an amino acid mutation at residue 80.

In some embodiments, disclosed herein, is a SIRPα D1 domain variant, wherein the SIRPα D1 domain variant binds CD47 from a first species with a KD less than 250 nM; and wherein the SIRPα D1 domain variant binds CD47 from a second species with a KD less than 250 nM; and the KD for CD47 from the first species and the KD for CD47 from the second species are within 100 fold of each other; wherein the first species and the second species are selected from the group consisting of human, rodent, and non-human primate. In some embodiments, the SIRPα D1 domain variant binds CD47 from at least 3 different species. In some embodiments, the non-human primate is cynomolgus monkey.

In some embodiments, disclosed herein, is a polypeptide comprising (a) a SIRPα D1 domain that binds human CD47 with a $K_D$ less than 250 nM; and (b) an Fc domain or variant thereof linked to the N-terminus or the C-terminus of the SIRPα D1 domain, wherein the polypeptide does not cause acute anemia in rodents and non-human primates. In some embodiments, the polypeptide is a non-naturally occurring variant of a human SIRP-α. In some embodiments, administration of the polypeptide in vivo results in hemoglobin reduction by less than 50% during the first week after administration. In some embodiments, administration of the polypeptide in humans results in hemoglobin reduction by less than 50% during the first week after administration. In some embodiments, the polypeptide further comprises at least one Fc domain dimer variant, wherein the Fc domain dimer variant comprises an Fc domain variant selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain variant is a human IgG1 Fc region consisting of mutations L234A, L235A, G237A, and N297A. In some embodiments, the Fc domain variant is a human IgG2 Fc region consisting of mutations A330S, P331S and N297A.

The SIRPα constructs of the disclosure include a SIRPα domain or variant thereof that has its C-terminus joined to the N-terminus of an Fc domain or variant thereof by way of a linker using conventional genetic or chemical means, e.g., chemical conjugation. In some embodiments, a linker (e.g., a spacer) is inserted between the polypeptide and the Fc domain or variant thereof. In some embodiments, a polypeptide of the disclosure including a SIRPα D1 domain variant is fused to an Fc domain variant that is incapable of forming a dimer. In some embodiments, a polypeptide of the disclosure is fused to an Fc domain or variant thereof that is capable of forming a dimer, e.g., a heterodimer, with another Fc domain or variant thereof. In some embodiments, a polypeptide of the invention is fused to an Fc domain or variant thereof and this fusion protein forms a homodimer. In some embodiments, a polypeptide of the disclosure is fused to a first Fc domain or variant thereof and a different protein or peptide (e.g., an antibody variable region) is fused to a second Fc domain or variant thereof. In some embodiments, a SIRPα D1 domain or variant thereof is joined to a first Fe domain or variant thereof and a therapeutic protein (e.g., a cytokine, an interleukin, an antigen, a steroid, an anti-inflammatory agent, or an immunomodulatory agent) is joined to a second Fc domain or variant thereof. In some embodiments, the first and second Fc domains or variants thereof form a heterodimer.

Without the limiting the foregoing, in some embodiments, a SIRPα D1 domain variant polypeptide (e.g., any of the variants described in Tables 2, 5, and 6) is fused to an Fc polypeptide or Fc variant polypeptide, such as an Fc domain or variant thereof. Examples of polypeptides comprising a SIRPα D1 domain variant polypeptide and a fused Fc domain variant polypeptide include, but are not limited to, SEQ ID NOS: 96-137, 214, and 216 shown in Table 8.

TABLE 8

Polypeptides Comprising SIRPα D1 Domain Variants Fused to Fc Domain Variants

| SEQ ID NO: | Amino Acid Sequence |
|---|---|
| 96 | EEELQIIQPDKSVLVAAGETATLRCTITSLFPVGPIQWFRGAGPGRVLIYNQRQ GPFPRVTTVSDTTKRNNMDFSIRIGNITPADAGTYYCIKFRKGSPDDVEFKSG AGTELSVRAKPSDKTHTCPPCPAPEAAGAPSVFLFPPKPKDTLMISRTPEVTC VVVDVSHEDPEVKFNWYVDGVEVHNAKTKPREEQYASTYRVVSVLTVLHQ DWLNGKEYKCKVSNKALPAPIEKTISKAKGQPREPQVYTLPPSREEMTKNQV |

TABLE 8-continued

Polypeptides Comprising SIRPα D1 Domain Variants Fused to Fc Domain Variants

| SEQ ID NO: | Amino Acid Sequence |
|---|---|
| | SLTCLVKGFYPSDIAVEWESNGQPENNYKTTPPVLDSDGSFFLYSKLTVDKSR<br>WQQGNVFSCSVMHEALHNHYTQKSLSLSPGK |
| 97 | EEELQVIQPDKSVLVAAGETATLRCTATSLFPVGPIQWFRGAGPGRELIYNQR<br>QGPFPRVTTVSDLTKRNNMDFSIRIGNITPADAGTYYCVKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVLH<br>QDWLNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLTVDKS<br>RWQQGNVFSCSVMHEALHNHYTQKSLSLSPGK |
| 98 | EEELQIIQPDKSVLVAAGETATLRCTITSLFPVGPIQWFRGAGPGRVLIYNQRQ<br>GPFPRVTTVSDTTKRNNMDFSIRIGAITPADAGTYYCIKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALHNHYTQKSLSLSPGK |
| 99 | EEELQVIQPDKSVLVAAGETATLRCTATSLFPVGPIQWFRGAGPGRELIYNQR<br>QGPFPRVTTVSDLTKRNNMDFSIRIGAITPADAGTYYCVKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVLH<br>QDWLNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLTVDKS<br>RWQQGNVFSCSVMHEALHNHYTQKSLSLSPGK |
| 100 | EEELQVIQPDKSVLVAAGETATLRCTATSLFPVGPIQWFRGAGPGRELIYNQR<br>EGPFPRVTTVSDLTKRNNMDFSIRIGAITPADAGTYYCVKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVLH<br>QDWLNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLTVDKS<br>RWQQGNVFSCSVMHEALHNHYTQKSLSLSPGK |
| 101 | EEELQVIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALEINHYTQKSLSLSPGK |
| 102 | EEELQIIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALEINHYTQKSLSLSPGK |
| 103 | EEELQVIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALEINHYTQKSLSLSPGK |
| 104 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALEINHYTQKSLSLSPGK |
| 105 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSVECPPCPAPPVAGPSVFLFPPKPKDTLMISRTPEVTCVVVD<br>VSHEDPEVQFNWYVDGVEVHNAKTKPREEQFASTFRVVSVLTVVHQDWLN<br>GKEYKCKVSNKGLPSSIEKTISKTKGQPREPQVYTLPPSREEMTKNQVSLTCL<br>VKGFYPSDIAVEWESNGQPENNYKTTPPMLDSDGSFFLYSKLTVDKSRWQQ<br>GNVFSCSVMHEALEINHYTQKSLSLSPGK |

TABLE 8-continued

Polypeptides Comprising SIRPα D1 Domain Variants Fused to Fc Domain Variants

| SEQ ID NO: | Amino Acid Sequence |
|---|---|
| 106 | EEELQVIQPDKSVLVAAGETATLRCTATSLFPVGPIQWFRGAGPGRELIYNQR QGPFPRVTTVSDLTKRNNMDFSIRIGNITPADAGTYYCVKFRKGSPDDVEFKS GAGTELSVRAKPSVECPPCPAPPVAGPSVFLFPPKPKDTLMISRTPEVTCVVV DVSHEDPEVQFNWYVDGVEVEINAKTKPREEQFASTFRVVSVLTVVHQDWL NGKEYKCKVSNKGLPSSIEKTISKTKGQPREPQVYTLPPSREEMTKNQVSLTC LVKGFYPSDIAVEWESNGQPENNYKTTPPMLDSDGSFFLYSKLTVDKSRWQ QGNVFSCSVMHEALHNHYTQKSLSLSPGK |
| 107 | EEELQIIQPDKSVLVAAGETATLRCTITSLFPVGPIQWFRGAGPGRVLIYNQRQ GPFPRVTTVSDTTKRNNMDFSIRIGAITPADAGTYYCIKFRKGSPDDVEFKSG AGTELSVRAKPSVECPPCPAPPVAGPSVFLFPPKPKDTLMISRTPEVTCVVVD VSHEDPEVQFNWYVDGVEVHNAKTKPREEQFASTFRVVSVLTVVHQDWLN GKEYKCKVSNKGLPSSIEKTISKTKGQPREPQVYTLPPSREEMTKNQVSLTCL VKGFYPSDIAVEWESNGQPENNYKTTPPMLDSDGSFFLYSKLTVDKSRWQQ GNVFSCSVMHEALEINHYTQKSLSLSPGK |
| 108 | EEELQVIQPDKSVLVAAGETATLRCTATSLFPVGPIQWFRGAGPGRELIYNQR QGPFPRVTTVSDLTKRNNMDFSIRIGAITPADAGTYYCVKFRKGSPDDVEFKS GAGTELSVRAKPSVECPPCPAPPVAGPSVFLFPPKPKDTLMISRTPEVTCVVV DVSHEDPEVQFNWYVDGVEVEINAKTKPREEQFASTFRVVSVLTVVHQDWL NGKEYKCKVSNKGLPSSIEKTISKTKGQPREPQVYTLPPSREEMTKNQVSLTC LVKGFYPSDIAVEWESNGQPENNYKTTPPMLDSDGSFFLYSKLTVDKSRWQ QGNVFSCSVMHEALHNHYTQKSLSLSPGK |
| 109 | EEELQVIQPDKSVLVAAGETATLRCTATSLFPVGPIQWFRGAGPGRELIYNQR EGPFPRVTTVSDLTKRNNMDFSIRIGAITPADAGTYYCVKFRKGSPDDVEFKS GAGTELSVRAKPSVECPPCPAPPVAGPSVFLFPPKPKDTLMISRTPEVTCVVV DVSHEDPEVQFNWYVDGVEVEINAKTKPREEQFASTFRVVSVLTVVHQDWL NGKEYKCKVSNKGLPSSIEKTISKTKGQPREPQVYTLPPSREEMTKNQVSLTC LVKGFYPSDIAVEWESNGQPENNYKTTPPMLDSDGSFFLYSKLTVDKSRWQ QGNVFSCSVMHEALHNHYTQKSLSLSPGK |
| 110 | EEELQVIQPDKSVLVAAGETATLRCTITSLFPVGPIQWFRGAGPGRELIYNQRE GPFPRVTTVSDLTKRNNMDFSIRIGAITPADAGTYYCVKFRKGSPDDVEFKSG AGTELSVRAKPSVECPPCPAPPVAGPSVFLFPPKPKDTLMISRTPEVTCVVVD VSHEDPEVQFNWYVDGVEVHNAKTKPREEQFASTFRVVSVLTVVHQDWLN GKEYKCKVSNKGLPSSIEKTISKTKGQPREPQVYTLPPSREEMTKNQVSLTCL VKGFYPSDIAVEWESNGQPENNYKTTPPMLDSDGSFFLYSKLTVDKSRWQQ GNVFSCSVMHEALEINHYTQKSLSLSPGK |
| 111 | EEELQIIQPDKSVLVAAGETATLRCTITSLFPVGPIQWFRGAGPGRELIYNQRE GPFPRVTTVSDLTKRNNMDFSIRIGAITPADAGTYYCVKFRKGSPDDVEFKSG AGTELSVRAKPSVECPPCPAPPVAGPSVFLFPPKPKDTLMISRTPEVTCVVVD VSHEDPEVQFNWYVDGVEVHNAKTKPREEQFASTFRVVSVLTVVHQDWLN GKEYKCKVSNKGLPSSIEKTISKTKGQPREPQVYTLPPSREEMTKNQVSLTCL VKGFYPSDIAVEWESNGQPENNYKTTPPMLDSDGSFFLYSKLTVDKSRWQQ GNVFSCSVMHEALEINHYTQKSLSLSPGK |
| 112 | EEELQVIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKSG AGTELSVRAKPSVECPPCPAPPVAGPSVFLFPPKPKDTLMISRTPEVTCVVVD VSHEDPEVQFNWYVDGVEVHNAKTKPREEQFASTFRVVSVLTVVHQDWLN GKEYKCKVSNKGLPSSIEKTISKTKGQPREPQVYTLPPSREEMTKNQVSLTCL VKGFYPSDIAVEWESNGQPENNYKTTPPMLDSDGSFFLYSKLTVDKSRWQQ GNVFSCSVMHEALEINHYTQKSLSLSPGK |
| 113 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKSG AGTELSVRAKPSVECPPCPAPPVAGPSVFLFPPKPKDTLMISRTPEVTCVVVD VSHEDPEVQFNWYVDGVEVHNAKTKPREEQFASTFRVVSVLTVVHQDWLN GKEYKCKVSNKGLPSSIEKTISKTKGQPREPQVYTLPPSREEMTKNQVSLTCL VKGFYPSDIAVEWESNGQPENNYKTTPPMLDSDGSFFLYSKLTVDKSRWQQ GNVFSCSVMHEALEINHYTQKSLSLSPGK |
| 114 | EEELQIIQPDKSVLVAAGETATLRCTITSLFPVGPIQWFRGAGPGRVLIYNQRQ GPFPRVTTVSDTTKRNNMDFSIRIGNITPADAGTYYCIKFRKGSPDDVEFKSG AGTELSVRAKPSERKSSVECPPCPAPPVAGPSVFLFPPKPKDTLMISRTPEVTC VVVDVSHEDPEVQFNWYVDGVEVHNAKTKPREEQFASTFRVVSVLTVVHQ DWLNGKEYKCKVSNKGLPSSIEKTISKTKGQPREPQVYTLPPSREEMTKNQV SLTCLVKGFYPSDIAVEWESNGQPENNYKTTPPMLDSDGSFFLYSKLTVDKS RWQQGNVFSCSVMHEALHNHYTQKSLSLSPGK |
| 115 | EEELQVIQPDKSVLVAAGETATLRCTATSLFPVGPIQWFRGAGPGRELIYNQR QGPFPRVTTVSDLTKRNNMDFSIRIGNITPADAGTYYCVKFRKGSPDDVEFKS GAGTELSVRAKPSERKSSVECPPCPAPPVAGPSVFLFPPKPKDTLMISRTPEVT |

TABLE 8-continued

Polypeptides Comprising SIRPα D1 Domain Variants Fused to Fc Domain Variants

| SEQ ID NO: | Amino Acid Sequence |
|---|---|
| | CVVVDVSHEDPEVQFNWYVDGVEVHNAKTKPREEQFASTFRVVSVLTVVH<br>QDWLNGKEYKCKVSNKGLPSSIEKTISKTKGQPREPQVYTLPPSREEMTKNQ<br>VSLTCLVKGFYPSDIAVEWESNGQPENNYKTTPPMLDSDGSFFLYSKLTVDK<br>SRWQQGNVFSCSVMHEALEINHYTQKSLSLSPGK |
| 116 | EEELQIIQPDKSVLVAAGETATLRCTITSLFPVGPIQWFRGAGPGRVLIYNQRQ<br>GPFPRVTTVSDTTKRNNMDFSIRIGAITPADAGTYYCIKFRKGSPDDVEFKSG<br>AGTELSVRAKPSERKSSVECPPCPAPPVAGPSVFLFPPKPKDTLMISRTPEVTC<br>VVVDVSHEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 117 | EEELQVIQPDKSVLVAAGETATLRCTATSLFPVGPIQWFRGAGPGRELIYNQR<br>QGPFPRVTTVSDLTKRNNMDFSIRIGAITPADAGTYYCVKFRKGSPDDVEFKS<br>GAGTELSVRAKPSERKSSVECPPCPAPPVAGPSVFLFPPKPKDTLMISRTPEVT<br>CVVVDVSHEDPEVQFNWYVDGVEVHNAKTKPREEQFASTFRVVSVLTVVH<br>QDWLNGKEYKCKVSNKGLPSSIEKTISKTKGQPREPQVYTLPPSREEMTKNQ<br>VSLTCLVKGFYPSDIAVEWESNGQPENNYKTTPPMLDSDGSFFLYSKLTVDK<br>SRWQQGNVFSCSVMHEALEINHYTQKSLSLSPGK |
| 118 | EEELQVIQPDKSVLVAAGETATLRCTATSLFPVGPIQWFRGAGPGRELIYNQR<br>EGPFPRVTTVSDLTKRNNMDFSIRIGAITPADAGTYYCVKFRKGSPDDVEFKS<br>GAGTELSVRAKPSERKSSVECPPCPAPPVAGPSVFLFPPKPKDTLMISRTPEVT<br>CVVVDVSEIEDPEVQFNWYVDGVEVHNAKTKPREEQFASTFRVVSVLTVVH<br>QDWLNGKEYKCKVSNKGLPSSIEKTISKTKGQPREPQVYTLPPSREEMTKNQ<br>VSLTCLVKGFYPSDIAVEWESNGQPENNYKTTPPMLDSDGSFFLYSKLTVDK<br>SRWQQGNVFSCSVMHEALEINHYTQKSLSLSPGK |
| 119 | EEELQVIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPSERKSSVECPPCPAPPVAGPSVFLFPPKPKDTLMISRTPEVTC<br>VVVDVSEIEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 120 | EEELQIIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPSERKSSVECPPCPAPPVAGPSVFLFPPKPKDTLMISRTPEVTC<br>VVVDVSEIEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 121 | EEELQVIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSERKSSVECPPCPAPPVAGPSVFLFPPKPKDTLMISRTPEVTC<br>VVVDVSEIEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 122 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSERKSSVECPPCPAPPVAGPSVFLFPPKPKDTLMISRTPEVTC<br>VVVDVSEIEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 123 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSDKTHTCPPCPAPELLGGPSVFLFPPKPKDTLMISRTPEVTCV<br>VVDVSEIEDPEVKFNWYVDGVEVINAKTKPREEQYNSTYRVVSVLTVLHQD<br>WLNGKEYKCKVSNKALPAPIEKTISKAKGQPREPQVYTLPPSREEMTKNQVS<br>LTCLVKGFYPSDIAVEWESNGQPENNYKTTPPVLDSDGSFFLYSKLTVDKSR<br>WQQGNVFSCSVMHEALEINHYTQKSLSLSPGK |
| 124 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYNSTYRVVSVLTVLHQ |

TABLE 8-continued

Polypeptides Comprising SIRPα D1 Domain Variants Fused to Fc Domain Variants

| SEQ ID NO: | Amino Acid Sequence |
|---|---|
| | DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALEINHYTQKSLSLSPGK |
| 125 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSDKTHTCPPCPAPELLGGPSVFLFPPKPKDTLMISRTPEVTCV<br>VVDVSHEDPEVKFNWYVDGVEVEINAKTKPREEQYASTYRVVSVLTVLHQD<br>WLNGKEYKCKVSNKALPAPIEKTISKAKGQPREPQVYTLPPSREEMTKNQVS<br>LTCLVKGFYPSDIAVEWESNGQPENNYKTTPPVLDSDGSFFLYSKLTVDKSR<br>WQQGNVFSCSVMHEALEINHYTQKSLSLSPGK |
| 126 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQFNWYVDGVEVHNAKTKPREEQFNSTFRVVSVLTVVHQ<br>DWLNGKEYKCKVSNKGLPAPIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 127 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQFNWYVDGVEVHNAKTKPREEQFNSTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 128 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQFNWYVDGVEVHNAKTKPREEQFASTFRVVSVLTVVHQ<br>DWLNGKEYKCKVSNKGLPAPIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 129 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 130 | EEELQVIQPDKSVSVAAGESAILHCTVTSLIPVGPIQWFRGAGPARELIYNQKE<br>GHFPRVTTVSESTKRENMDFSISISNITPADAGTYYCVKFRKGSPDTEFKSGA<br>GTELSVRAKPSESKYGPPCPSCPAPEFLGGPSVFLFPPKPKDTLMISRTPEVTC<br>VVVDVSQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEEMTKNQV<br>SLTCLVKGFYPSDIAVEWESNGQPENNYKTTPPVLDSDGSFFLYSRLTVDKSR<br>WQEGNVFSCSVMHEALEINHYTQKSLSLSLGK |
| 131 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSESKYGPPCPPCPAPEFLGGPSVFLFPPKPKDTLMISRTPEVT<br>CVVVDVSQEDPEVQFNWYVDGVEVEINAKTKPREEQFNSTYRVVSVLTVLH<br>QDWLNGKEYKCKVSNKGLPSSIEKTISKAKGQPREPQVYTLPPSQEEMTKNQ<br>VSLTCLVKGFYPSDIAVEWESNGQPENNYKTTPPVLDSDGSFFLYSRLTVDKS<br>RWQEGNVFSCSVMHEALEINHYTQKSLSLSLGK |
| 132 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSESKYGPPCPPCPAPEFEGGPSVFLFPPKPKDTLMISRTPEVT<br>CVVVDVSQEDPEVQFNWYVDGVEVEINAKTKPREEQFNSTYRVVSVLTVLH<br>QDWLNGKEYKCKVSNKGLPSSIEKTISKAKGQPREPQVYTLPPSQEEMTKNQ<br>VSLTCLVKGFYPSDIAVEWESNGQPENNYKTTPPVLDSDGSFFLYSRLTVDKS<br>RWQEGNVFSCSVMHEALEINHYTQKSLSLSLGK |
| 133 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSESKYGPPCPPCPAPPVAGPSVFLFPPKPKDTLMISRTPEVTC<br>VVVDVSQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEEMTKNQV<br>SLTCLVKGFYPSDIAVEWESNGQPENNYKTTPPVLDSDGSFFLYSRLTVDKSR<br>WQEGNVFSCSVMHEALEINHYTQKSLSLSLGK |

TABLE 8-continued

Polypeptides Comprising SIRPα D1 Domain Variants Fused to Fc Domain Variants

| SEQ ID NO: | Amino Acid Sequence |
|---|---|
| 134 | EEELQIIQPDKSVLVAAGETATLRCTITSLFPVGPIQWFRGAGPGRVLIYNQRQGPFPRVTTVSDTTKRNNMDFSIRIGNITPADAGTYYCIKFRKGSPDDVEFKSGAGTELSVRAKPSAAAPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALEINHYTQKSLSLSPGK |
| 135 | EEELQVIQPDKSVLVAAGETATLRCTATSLFPVGPIQWFRGAGPGRELIYNQREGPFPRVTTVSDLTKRNNMDFSIRIGAITPADAGTYYCVKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 136 | EEELQIIQPDKSVLVAAGETATLRCTITSLFPVGPIQWFRGAGPGRELIYNQREGPFPRVTTVSDTTKRNNMDFSIRIGAITPADAGTYYCVKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALEINHYTQKSLSLSPG |
| 137 | EEELQIIQPDKSVLVAAGETATLRCTITSLFPVGPIQWFRGAGPGRVLIYNQREGPFPRVTTVSDTTKRNNMDFSIRIGAITPADAGTYYCIKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALEINHYTQKSLSLSPG |
| 211 | EEELQIIQPDKSVLVAAGETATLRCTITSLRPVGPIQWFRGAGPGRELIYNQRDGPFPRVTTVSDTTKRNNMDFSIRIGAITPADAGTYYCVKFRKGIPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALEINHYTQKSLSLSPG |
| 214 | EEELQVIQPDKSVLVAAGETATLRCTATSLFPVGPIQWFRGAGPGRELIYNQREGPFPRVTTVSDLTKRNNMDFSIRIGAITPADAGTYYCVKFRKGSPDDVEFKSGAGTELSVRAKPSERKSSVECPPCPAPPVAGPSVFLFPPKPKDTLMISRTPEVTCVVVDVSHEDPEVQFNWYVDGVEVHNAKTKPREEQFASTFRVVSVLTVVHQDWLNGKEYKCKVSNKGLPSSIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALEINHYTQKSLSLSPG |
| 216 | EEELQIIQPDKSVLVAAGETATLRCTITSLFPVGPIQWFRGAGPGRVLIYNQRQGPFPRVTTVSDTTKRNNMDFSIRIGNITPADAGTYYCIKFRKGSPDDVEFKSGAGTELSVRAKPSDKTHTCPPCPAPELLGGPSVFLFPPKPKDTLMISRTPEVTCVVVDVSHEDPEVKFNWYVDGVEVEINAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALEINHYTQKSLSLSPGK |
| 217 | EEELQIIQPDKSVLVAAGETATLRCTITSLFPVGPIQWFRGAGPGRELIYNQREGPFPRVTTVSDTTKRNNMDFSIRIGAITPADAGTYYCVKFRKGSPDDVEFKSGAGTELSVRAKPSEKTHTCPECPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCEVKGFYPSDIAVEWESNGQPENNYKTTPPVLDSDGSFFLYSKLTVDKSRWQQGNVFSCSVMHEALIINHYTQKSLSLSPGK |

In some embodiments, the polypeptide comprises a SIRPα D1 variant domain that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 8.

In some embodiments, the polypeptide comprises a SIRPα D1 domain variant that has at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NOs: 98-104, 107-113, 116-122, or 135-137 in Table 8.

In some embodiments, the polypeptide comprises (a) a signal-regulatory protein α (SIRP-α) D1 variant, wherein the SIRPα D1 domain variant comprises the amino acid sequence, EEX$_1$X$_2$QX$_3$IQPDKX$_4$VX$_5$VAAGEX$_6$X$_7$X$_8$LX$_9$CTX$_{10}$TSLX$_{11}$PVGPIQWFRGAGPX$_{12}$RX$_{13}$LIYNQ X$_{14}$X$_{15}$GX$_{16}$FPRVTTVSX$_{17}$X$_{18}$TX$_{19}$RX$_{20}$NMDFX$_{21}$IX$_{22}$ IX$_{23}$X$_{24}$ITX$_{25}$ADAGTYYCX$_{26}$KX$_{27}$RKGSP DX$_{28}$X$_{29}$EX$_{30}$KSGAGTELSVRX$_{31}$KPS (SEQ ID NO: 47), wherein X$_1$ is E, or G; X$_2$ is L, I, or V; X$_3$ is V, L, or I; X$_4$ is S, or F; X$_5$ is L, or S; X$_6$ is S, or T; X$_7$ is A, or V; X$_8$ is I, or T; X$_9$ is H, R, or L; X$_{10}$ is A, V, I, or L; X$_{11}$ is I, T, S, or F; X$_{12}$ is A, or G; X$_{13}$ is E, V, or L; X$_{14}$ is K, or R; X$_{15}$ is E, or Q; X$_{16}$ is H, P, or R; X$_{17}$ is D, or E; X$_{18}$ is S, L, T, or G; X$_{19}$ is K, or R; X$_{20}$ is E, or N; X$_{21}$ is S, or P; X$_{22}$ is S, or R; X$_{23}$ is S, or G; X$_{24}$ is any amino acid; X$_{25}$ is any amino acid; X$_{26}$ is V, or I; X$_{27}$ is F, L, or V; X$_{28}$ is D or absent; X$_{29}$ is T, or V; X$_{30}$ is F, or V; and X$_{31}$ is A, or G; and wherein the SIRPα D1 domain variant comprises at least two amino acid substitutions relative to a wild-type SIRPα D domain having a sequence according to any one of SEQ ID NOs: 1 to 10; and (b) an Fc domain dimer variant having two Fc domain variants, wherein each Fc domain variant independently is (i) a human IgG1 Fc region comprising a N297A mutation; (ii) a human IgG1 Fc region comprising L234A, L235A, and G237A mutations; (iii) a human IgG1 Fc region comprising L234A, L235A, G237A, and N297A mutations; (iv) a human IgG2 Fc region comprising a N297A mutation; (v) a human IgG2 Fc region comprising A330S and P331S mutations; (vi) a human IgG2 Fc region comprising A330S, P331S, and N297A mutations; (vii) a human IgG4 Fc region comprising S228P, E233P, F234V, L235A, and delG236 mutations; or (viii) a human IgG4 Fc region comprising S228P, E233P, F234V, L235A, delG236, and N297A mutations.

In some embodiments, the polypeptide comprises a SIRPα D1 domain variant wherein the SIRPα D1 domain variant comprises an amino acid sequence according to SEQ ID NO: 47; an Fc domain dimer having two Fc domains, wherein one of the Fc domains is an Fc domain variant comprising a human IgG1 Fc region comprising L234A, L235A, G237A, and N297A mutations.

Dimerization of Fc Domains

In some embodiments, a SIRPα D1 domain variant polypeptide (e.g., any of the variants described in Tables 2, 5, and 6) is fused to a first Fc domain (e.g., an Fc domain variant) either at the N-terminus or at the C-terminus. In some embodiments, the first Fc domain is a variant that is incapable of forming an dimer. In some embodiments, the first Fc domain forms a dimer with a second Fc domain. In some embodiments, the first and second Fc domains comprise amino acid substitutions that promote heterodimerization between the first and second domain Fc domains.

In some embodiments, each of the two Fc domains in an Fc domain dimer includes amino acid substitutions that promote the heterodimerization of the two monomers. In some embodiments, a SIRPα construct is formed, for example, from a first subunit including a SIRPα D1 domain variant polypeptide fused to a first Fc domain and a second subunit including a second Fc domain (e.g., without a SIRPα D1 domain variant polypeptide or any other polypeptide). In some embodiments, a construct has a single SIRPα D1 domain variant polypeptide linked to an Fc domain dimer (e.g., single arm). In some embodiments, a construct has two SIRPα D1 domain variant polypeptides linked to an Fc domain dimer (e.g., double arm). In some embodiments, a SIRPα D1 domain variant having a K$_D$ of about 500 nM is particularly useful in a double arm construct. In some embodiments, a SIRPα D1 domain variant having a K$_D$ of about 50 nM is particularly useful in a double arm construct. In some embodiments, a SIRPα D1 domain variant having a K$_D$ of about 5 nM is useful in a double arm construct and a single arm construct. In some embodiments, a SIRPα D1 domain variant having a K$_D$ of about 500 pM is useful in a double arm construct and a single arm construct. In some embodiments, a SIRPα D1 domain variant having a K$_D$ of about 100 pM is useful in a double arm construct and a single arm construct. In some embodiments, a SIRPα D1 domain variant having a K$_D$ of about 50 pM is useful in a double arm construct and a single arm construct. In some embodiments, a SIRPα D1 domain variant having a K$_D$ of about 10 pM is useful in a double arm construct and a single arm construct.

In some embodiments, heterodimerization of Fc domains is promoted by introducing different, but compatible, substitutions in the two Fc domains, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain and involved in the dimerization of two Fc domains. In some embodiments, a hole in one CH3 antibody constant domain is created to accommodate a knob in another CH3 antibody constant domain, such that the knob and hole amino acids act to promote or favor the heterodimerization of the two Fc domains. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain includes the knob mutation T366W and the other Fc domain includes hole mutations T366S, L358A, and Y407V. In some embodiments, a polypeptide of the disclosure including a SIRPα D1 domain variant is fused to an Fc domain including the knob mutation T366W to limit unwanted knob-knob homodimer formation. Examples of knob-into-hole amino acid pairs are included, without limitation, in Table 9 and examples of knob-into-hole Fc domain variants and SIRPα-Fc fusions are provided in Table 10.

TABLE 9

Knob-into-Hole Amino Acid Pairs

| First Fc Domain | Y407T | Y407A | F405A | T394S | T366S L358A Y407V | T394W Y407T | T394W Y407A | T366W T394S |
|---|---|---|---|---|---|---|---|---|
| Second Fc Domain | T366Y | T366W | T394W | F405W | T366W | T366Y F405A | T366W F405W | F405W Y407A |

TABLE 10

Exemplary Fc Domain Variants and SIRPα D1 Domain Variant-Fc Domain Variant Fusion Polypeptides

| SEQ ID NO: | Amino Acid Sequence |
|---|---|
| 138 | EEELQIIQPDKSVLVAAGETATLRCTITSLFPVGPIQWFRGAGPGRVLIYNQR QGPFPRVTTVSDTTKRNNMDFSIRIGAITPADAGTYYCIKFRKGSPDDVEFKS GAGTELSVRAKPSDKTHTCPPCPAPEAAGAPSVFLFPPKPKDTLMISRTPEVT CVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKN QVSLWCLVKGFYPSDIAVEWESNGQPENNYKTTPPVLDSDGSFFLYSKLTV DKSRWQQGNVFSCSVMHEALHNHYTQKSLSLSPGK |
| 139 | DKTHTCPPCPAPEAAGAPSVFLFPPKPKDTLMISRTPEVTCVVVDVSHEDPEV KFNWYVDGVEVHNAKTKPREEQYASTYRVVSVLTVLHQDWLNGKEYKCK VSNKALPAPIEKTISKAKGQPREPQVYTLPPSREEMTKNQVSLSCAVKGFYPS DIAVEWESNGQPENNYKTTPPVLDSDGSFFLVSKLTVDKSRWQQGNVFSCS VMHEALHNHYTQKSLSLSPGK |
| 140 | EEELQIIQPDKSVLVAAGETATLRCTITSLFPVGPIQWFRGAGPGRVLIYNQR QGPFPRVTTVSDTTKRNNMDFSIRIGAITPADAGTYYCIKFRKGSPDDVEFKS GAGTELSVRAKPSDKTHTCPPCPAPEAAGAPSVFLFPPKPKDTLMISRTPEVT CVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKN QVSLSCAVKGFYPSDIAVEWESNGQPENNYKTTPPVLDSDGSFFLVSKLTVD KSRWQQGNVFSCSVMHEALHNHYTQKSLSLSPGK |
| 141 | DKTHTCPPCPAPEAAGAPSVFLFPPKPKDTLMISRTPEVTCVVVDVSHEDPEV KFNWYVDGVEVHNAKTKPREEQYASTYRVVSVLTVLHQDWLNGKEYKCK VSNKALPAPIEKTISKAKGQPREPQVYTLPPSREEMTKNQVSLWCLVKGFYP SDIAVEWESNGQPENNYKTTPPVLDSDGSFFLYSKLTVDKSRWQQGNVFSC SVMHEALHNHYTQKSLSLSPGK |
| 142 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKS GAGTELSVRAKPSDKTHTCPPCPAPEAAGAPSVFLFPPKPKDTLMISRTPEVT CVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKN QVSLWCLVKGFYPSDIAVEWESNGQPENNYKTTPPVLDSDGSFFLYSKLTV DKSRWQQGNVFSCSVMHEALHNHYTQKSLSLSPGK |
| 143 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKS GAGTELSVRAKPSDKTHTCPPCPAPEAAGAPSVFLFPPKPKDTLMISRTPEVT CVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKN QVSLSCAVKGFYPSDIAVEWESNGQPENNYKTTPPVLDSDGSFFLVSKLTVD KSRWQQGNVFSCSVMHEALHNHYTQKSLSLSPGK |
| 144 | QVQLKQSGPGLVQPSQSLSITCTVSGFSLTNYGVHWVRQSPGKGLEWLGVI WSGGNTDYNTPFTSRLSINKDNSKSQVFFKMNSLQSNDTAIYYCARALTYY DYEFAYWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCRKTHTCPRCPAPELLGGPSVFLFPPKPKDTLMISRTP EVTCVVVDVSHEDPEVKFNWYVDGVEVHNAKTKPREEQYASTYRVVSVLT VLHQDWLNGKEYKCKVSNKALPAPIEKTISKAKGQPREPQVYTLPPSREEM TKNQVSLTCLVKGFYPSDIAVEWESNGQPENNYKTTPPVLDSDGSFFLYSRL TVDKSRWQQGNVFSCSVMHEALHNHYTQKSLSLSPGK |
| 145 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKS GAGTELSVRAKPSEKTHTCPECPAPEAAGAPSVFLFPPKPKDTLMISRTPEVT CVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKN QVSLTCEVKGFYPSDIAVEWESNGQPENNYKTTPPVLDSDGSFFLYSKLTVD KSRWQQGNVFSCSVMHEALHNHYTQKSLSLSPGK |

TABLE 10-continued

Exemplary Fc Domain Variants and SIRPα D1 Domain Variant-Fc Domain Variant Fusion Polypeptides

| SEQ ID NO: | Amino Acid Sequence |
|---|---|
| 146 | EEELQVIQPDKSVLVAAGETATLRCTATSLFPVGPIQWFRGAGPGRELIYNQ RQGPFPRVTTVSDLTKRNNMDFSIRIGNITPADAGTYYCVKFRKGSPDDVEF KSGAGTELSVRAKPSDKTHTCPPCPAPEAAGAPSVFLFPPKPKDTLMISRTPE VTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSREEMT KNQVSLWCLVKGFYPSDIAVEWESNGQPENNYKTTPPVLDSDGSFFLYSKL TVDKSRWQQGNVFSCSVMHEALHNHYTQKSLSLSPGK |
| 147 | DKTHTCPPCPAPEAAGAPSVFLFPPKPKDTLMISRTPEVTCVVVDVSHEDPEV KFNWYVDGVEVEINAKTKPREEQYNSTYRVVSVLTVLHQDWLNGKEYKCK VSNKALPAPIEKTISKAKGQPREPQVYTLPPSREEMTKNQVSLSCAVKGFYPS DIAVEWESNGQPENNYKTTPPVLDSDGSFFLVSKLTVDKSRWQQGNVFSCS VMHEALHNHYTQKSLSLSPGK |
| 148 | EEELQVIQPDKSVLVAAGETATLRCTATSLFPVGPIQWFRGAGPGRELIYNQ RQGPFPRVTTVSDLTKRNNMDFSIRIGNITPADAGTYYCVKFRKGSPDDVEF KSGAGTELSVRAKPSDKTHTCPPCPAPEAAGAPSVFLFPPKPKDTLMISRTPE VTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSREEMT KNQVSLSCAVKGFYPSDIAVEWESNGQPENNYKTTPPVLDSDGSFFLVSKLT VDKSRWQQGNVFSCSVMHEALHNHYTQKSLSLSPGK |
| 149 | DKTHTCPPCPAPEAAGAPSVFLFPPKPKDTLMISRTPEVTCVVVDVSHEDPEV KFNWYVDGVEVEINAKTKPREEQYNSTYRVVSVLTVLHQDWLNGKEYKCK VSNKALPAPIEKTISKAKGQPREPQVYTLPPSREEMTKNQVSLWCLVKGFYP SDIAVEWESNGQPENNYKTTPPVLDSDGSFFLYSKLTVDKSRWQQGNVFSC SVMHEALHNHYTQKSLSLSPGK |

In addition to the knob-into-hole strategy, in some embodiments, electrostatic steering is also used to control the dimerization of Fc domains. Electrostatic steering refers to the utilization of favorable electrostatic interactions between oppositely charged amino acids in peptides, protein domains, and proteins to control the formation of higher ordered protein molecules. In particular, to control the dimerization of Fc domains using electrostatic steering, one or more amino acid residues that make up the CH3-CH3 interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In some embodiments, a negatively-charged amino acid in the interface is replaced with a positively-charged amino acid. In some embodiments, the charged amino acids are introduced to one of the interacting CH3 antibody constant domains, or both. In some embodiments, introducing charged amino acids to the interacting CH3 antibody constant domains of the two Fc domains promotes the selective formation of heterodimers of Fc domains as controlled by the electrostatic steering effects resulting from the interaction between charged amino acids. Examples of electrostatic steering amino acid pairs are included, without limitation, in Table 11.

TABLE 11

| Electrostatic Steering Amino Acid Pairs | | | | | | | | | |
|---|---|---|---|---|---|---|---|---|---|
| Fc domain monomer 1 | K409D | K409D | K409E | K409E | K392D | K392D | K392E | K392E | K409D K392D | K370E K409D K439E |
| Fc domain monomer 2 | D399K | D399R | D399K | D399R | D399K | D399R | D399K | D399R | D399K D356K | D356K E357K D399K |

Other methods used to control the heterodimerization of Fc domains, especially in the context of constructing a bispecific antibody, are available.

In some embodiments, a first Fc domain and a second Fc domain each includes one or more of the following amino acid substitutions: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1.

In some embodiments an Fc domain comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; or (b) (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and deG236 mutation relative to a human IgG4 Fc region; or (viii) a S228P, E233P, F234V, L235A, deG236, and N297A mutation relative to a human IgG4 Fc region. In some embodiments an Fc domain variant comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; and (b) further comprises (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region.

In some embodiments, the first and second Fc domains include different amino acid substitutions. In some embodiments, the first Fc domain includes T366W. In some embodiments, the second Fc domain includes T366S, L368A, and Y407V. In some embodiments, the first Fc domain includes D399K. In some embodiments, the second Fc domain includes K409D.

Linkers

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer comprising two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In the present disclosure, a linker is used to describe a linkage or connection between polypeptides or protein domains or associated non-protein moieties. In some embodiments, a linker is a linkage or connection between an Fc domain (or variant thereof) and a SIRPα D1 domain variant. In some embodiments, the linker connects the C-terminus of the SIRPα D1 domain variant and the N-terminus of the Fc domain variant, such that the two polypeptides are joined to each other in tandem series.

In some embodiments, a linker is a simple covalent bond, e.g., a peptide bond, a synthetic polymer, or any kind of bond created from a chemical reaction, e.g. chemical conjugation. When a linker is a peptide bond, in some embodiments, the carboxylic acid group at the C-terminus of one protein domain reacts with the amino group at the N-terminus of another protein domain in a condensation reaction to form a peptide bond. In some embodiments, the peptide bond is formed from synthetic means through a conventional organic chemistry reaction, or by natural production from a host cell, wherein a nucleic acid molecule encoding the DNA sequences of both proteins (e.g., an Fc domain variant and a SIRPα D1 domain variant) in tandem series can be directly transcribed and translated into a contiguous polypeptide encoding both proteins by the necessary molecular machineries (e.g., DNA polymerase and ribosome) in the host cell.

When a linker is a synthetic polymer, in some embodiments, the polymer is functionalized with reactive chemical functional groups at each end to react with the terminal amino acids at the connecting ends of two proteins.

When a linker (except peptide bond mentioned above) is made from a chemical reaction, in some embodiments, chemical functional groups (e.g., amine, carboxylic acid, ester, azide, or other functional groups), are attached synthetically to the C-terminus of one protein and the N-terminus of another protein, respectively. In some embodiments, the two functional groups then react through synthetic chemistry means to form a chemical bond, thus connecting the two proteins together.

Spacers

In the present disclosure, in some embodiments, a linker between an Fc domain monomer and a SIRPα D1 variant polypeptide of the disclosure, is an amino acid spacer including about 1-200 amino acids. Suitable peptide spacers include peptide linkers containing flexible amino acid residues such as glycine and serine. Examples of linker sequences are provided in Table 12. In some embodiments, a spacer contains motifs, e.g., multiple or repeating motifs, of GS, GG, GGS, GGG, GGGGS (SEQ ID NO: 163), GGSG (SEQ ID NO: 164), or SGGG (SEQ ID NO: 165). In some embodiments, a spacer contains 2 to 12 amino acids including motifs of GS, e.g., GS, GSGS (SEQ ID NO: 166), GSGSGS (SEQ ID NO: 167), GSGSGSGS (SEQ ID NO: 168), GSGSGSGSGS (SEQ ID NO: 169), or GSGSGSGSGSGS (SEQ ID NO: 170). In some embodiments, a spacer contains 3 to 12 amino acids including motifs of GGS, e.g., GGS, GGSGGS (SEQ ID NO: 171), GGSGGSGGS (SEQ ID NO: 172), and GGSGGSGGSGGS (SEQ ID NO: 173). In some embodiments, a spacer contains 4 to 12 amino acids including motifs of GGSG (SEQ ID NO: 164), e.g., GGSG (SEQ ID NO: 164), GGSGGGSG (SEQ ID NO: 174), or GGSGGGSGGGSG (SEQ ID NO: 175). In some embodiments, a spacer contains motifs of GGGGS (SEQ ID NO: 163), e.g., GGGGSGGGGSGGGGS (SEQ ID NO: 176). In some embodiments, a spacer contains amino acids other than glycine and serine, e.g., AAS (SEQ ID NO: 177), AAAL (SEQ ID NO: 178), AAAK (SEQ ID NO: 179), AAAR (SEQ ID NO: 180), EGKSSGSGSESKST (SEQ ID NO: 181), GSAGSAAGSGEF (SEQ ID NO: 182), AEAAAKEAAAKA (SEQ ID NO: 183), KESGSVSSEQLAQFRSLD (SEQ ID NO: 184), GGGGAGGGG (SEQ ID NO: 185), GENLYFQSGG (SEQ ID NO: 186), SACYCELS (SEQ ID NO: 187), RSIAT (SEQ ID NO: 188), RPACKIPNDLKQKVMNH (SEQ ID NO: 189), GGSAGGSGSGSSGGSSGASGTGTAGGTGSGSGTGSG (SEQ ID NO: 190), AAANSSIDLISVPVDSR (SEQ ID NO: 191), or GGSGGGSEGGGSEGGGSEGGGSEGGGSEGGGSGGGS (SEQ ID NO: 192).

In some embodiments, a spacer contains motifs, e.g., multiple or repeating motifs, of EAAAK (SEQ ID NO: 193). In some embodiments, a spacer contains motifs, e.g., multiple or repeating motifs, of proline-rich sequences such as (XP)n, in which X is any amino acid (e.g., A, K, or E) and n is from 1-5, and PAPAP(SEQ ID NO: 194).

TABLE 12

Linker Sequences

| SEQ ID NO: | AminoAcidSequence |
|---|---|
| 163 | GGGGS |
| 164 | GGSG |
| 165 | SGGG |
| 166 | GSGS |
| 167 | GSGSGS |
| 168 | GSGSGSGS |
| 169 | GSGSGSGSGS |
| 170 | GSGSGSGSGSGS |
| 171 | GGSGGS |
| 172 | GGSGGSGGS |
| 173 | GGSGGSGGSGGS |
| 174 | GGSGGGSG |
| 175 | GGSGGGSGGGSG |
| 176 | GGGGSGGGGSGGGGS |
| 177 | AAS |
| 178 | AAAL |
| 179 | AAAK |
| 180 | AAAR |
| 181 | EGKSSGSGSESKST |
| 182 | GSAGSAAGSGEF |
| 183 | AEAAAKEAAAKA |
| 184 | KESGSVSSEQLAQFRSLD |
| 185 | GGGGAGGG |
| 186 | GENLYFQSGG |
| 187 | SACYCELS |
| 188 | RSIAT |
| 189 | RPACKIPNDLKQKVMNH |
| 190 | GGSAGGSGSGSSGGSSGASGTGTAGGTGSGSGTGSG |
| 191 | AAANSSIDLISVPVDSR |
| 192 | GGSGGGSEGGGSEGGGSEGGGSEGGGSGGGS |

TABLE 12-continued

Linker Sequences

| SEQ ID NO: | AminoAcidSequence |
|---|---|
| 193 | EAAAK |
| 194 | PAPAP |

In some embodiments, the length of the peptide spacer and the amino acids used is adjusted depending on the two proteins involved and the degree of flexibility desired in the final protein fusion polypeptide. In some embodiments, the length of the spacer is adjusted to ensure proper protein folding and avoid aggregate formation. In some embodiments, a spacer is A or AAAL (SEQ ID NO: 178).

Vectors, Host Cells, and Protein Production

Disclosed herein, in some embodiments, are polypeptides comprising a signal-regulatory protein α (SRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, the polypeptides of the disclosure are produced from a host cell. A host cell refers to a vehicle that includes the necessary cellular components, e.g., organelles, needed to express the polypeptides and fusion polypeptides described herein from their corresponding nucleic acids. In some embodiments, the nucleic acids are included in nucleic acid vectors introduced into the host cell by transformation, transfection, electroporation, calcium phosphate precipitation, direct microinjection, infection, etc. In some embodiments, the choice of nucleic acid vector depends on the host cell to be used. In some embodiments, host cells are of either prokaryotic (e.g., bacterial) or eukaryotic (e.g., mammalian) origin.

In some embodiments, a polypeptide, for example a polypeptide construct comprising a SIRPα D1 domain variant (e.g., any variant provided in Tables 2, 5, and 6) and a fusion partner such as an Fc variant are produced by culturing a host cell transformed with a nucleic acid, preferably an expression vector, containing a nucleic acid encoding the polypeptide construct (e.g., Fc variant, linker, and fusion partner) under the appropriate conditions to induce or cause expression of the polypeptide construct. In some embodiments, the conditions appropriate for expression varies with the expression vector and the host cell chosen. In some embodiments, a wide variety of appropriate host cells are used, including, but not limited to, mammalian cells, bacteria, insect cells, and yeast. For example, a variety of cell lines that find use in the present disclosure are described in the ATCC® cell line catalog, available from the American Type Culture Collection. In some embodiments, Fc domain variants of this disclosure are expressed in a cell that is optimized not to glycosylate proteins that are expressed by such cell, either by genetic engineering of the cell line or modifications of cell culture conditions such as addition of kifunensine or by using a naturally non-glycosylating host such as a prokaryote (*E. coli*, etc.), and in some cases, modification of the glycosylation sequence in the Fc is not be needed.

Nucleic Acid Vector Construction and Host Cells

A nucleic acid sequence encoding the amino acid sequence of a polypeptide of the disclosure can be prepared by a variety of methods. These methods include, but are not limited to, oligonucleotide-mediated (or site-directed) mutagenesis and PCR mutagenesis. In some embodiments, a nucleic acid molecule encoding a polypeptide of the disclosure is obtained using standard techniques, e.g., gene synthesis. Alternatively, a nucleic acid molecule encoding a wild-type SIRPα D1 domain is mutated to include specific amino acid substitutions using standard techniques, e.g., QuikChange™ mutagenesis. In some cases, nucleic acid molecules are synthesized using a nucleotide synthesizer or PCR techniques.

In some embodiments, the nucleic acids that encode a polypeptide construct, for example a polypeptide construct comprising a SIRPα D1 domain variant (e.g., any variant provided in Tables 2, 5, and 6) and a fusion partner such as an Fc variant are incorporated into an expression vector in order to express the protein. A variety of expression vectors can be utilized for protein expression. Expression vectors can comprise self-replicating, extra-chromosomal vectors or vectors which integrate into a host genome. A vector can also include various components or elements. For example, in some embodiments, the vector components include, but are not limited to, transcriptional and translational regulatory sequences such as a promoter sequence, a ribosomal binding site, a signal sequence, transcriptional start and stop sequences, translational start and stop sequences, 3' and 5' untranslated regions (UTRs), and enhancer or activator sequences; an origin of replication; a selection marker gene; and the nucleic acid sequence encoding the polypeptide of interest, and a transcription termination sequence. In some embodiments, expression vectors comprise a protein operably linked with control or regulatory sequences, selectable markers, any fusion partners, additional elements, or any combinations thereof. The term "operably linked" means that the nucleic acid is placed into a functional relationship with another nucleic acid sequence. Generally, these expression vectors include transcriptional and translational regulatory nucleic acid operably linked to the nucleic acid encoding the Fc variant, and are typically appropriate to the host cell used to express the protein. A selection gene or marker, such as, but not limited to, an antibiotic resistance gene or fluorescent protein gene, can be used to select for host cells containing the expression vector, for example by antibiotic or fluorescence expression. Various selection genes are available.

In some embodiments, the components or elements of a vector are optimized such that expression vectors are compatible with the host cell type. Expression vectors which find use in the present disclosure include, but are not limited to, those which enable protein expression in mammalian cells, bacteria, insect cells, yeast, and in in vitro systems.

In some embodiments, mammalian cells are used as host cells to produce polypeptides of the disclosure. Examples of mammalian cell types include, but are not limited to, human embryonic kidney (HEK) (e.g., HEK293, HEK 293F), Chinese hamster ovary (CHO), HeLa, COS, PC3, Vero, MC3T3, NSO, Sp2/0, VERY, BHK, MDCK, W138, BT483, Hs578T, HTB2, BT20, T47D, NSO (a murine myeloma cell line that does not endogenously produce any immunoglobulin chains), CRL7030, and HsS78Bst cells. In some embodiments, *E. coli* cells are used as host cells to produce polypeptides of the disclosure. Examples of *E. coli* strains include, but are not limited to, *E. coli* 294 (ATCC®31,446), *E. coli* λ 1776 (ATCC® 31,537, *E. coli* BL21 (DE3) (ATCC® BAA-1025), and *E. coli* RV308 (ATCC® 31,608).

Different host cells have characteristic and specific mechanisms for the posttranslational processing and modification of protein products (e.g., glycosylation). In some embodiments, appropriate cell lines or host systems are chosen to ensure the correct modification and processing of the polypeptide expressed. Once the vectors are introduced into host cells for protein production, host cells are cultured in conventional nutrient media modified as appropriate for inducing promoters, selecting transformants, or amplifying the genes encoding the desired sequences.

In some embodiments, a polypeptide construct, for example a polypeptide construct comprising a SIRPα D1 domain variant (e.g., any variant provided in Tables 2, 5, and 6) and a fusion partner such as an Fc variant are expressed in mammalian expression systems, including systems in which the expression constructs are introduced into the mammalian cells using virus such as retrovirus or adenovirus. In some embodiments, human, mouse, rat, hamster, or primate cells are utilized. Suitable cells also include known research cells, including but not limited to Jurkat T cells, NIH3T3, CHO, COS, and 293 cells. Alternately, in some embodiments, proteins are expressed in bacterial cells. Bacterial expression systems are well known in the art, and include *Escherichia coli* (*E. coli*), *Bacillus subtilis*, *Streptococcus cremoris*, and *Streptococcus lividans*. In some cases, polypeptide constructs comprising Fc domain variants are produced in insect cells such as but not limited to Sf9 and Sf21 cells or yeast cells such as but not limited to organisms from the genera *Saccharomyces, Pichia, Kluyveromyces, Hansenula* and *Yarrowia*. In some cases, polypeptide constructs comprising Fc domain variants are expressed in vitro using cell free translation systems. In vitro translation systems derived from both prokaryotic (e.g., *E. coli*) and eukaryotic (e.g., wheat germ, rabbit reticulocytes) cells are available and, in some embodiments, chosen based on the expression levels and functional properties of the protein of interest. For example, as appreciated by those skilled in the art, in vitro translation is required for some display technologies, for example ribosome display. In addition, in some embodiments, the Fc domain variants are produced by chemical synthesis methods such as, but not limited to, liquid-phase peptide synthesis and solid-phase peptide synthesis. In the case of in vitro transcription using a non-glycosylating system such as bacterial extracts, the Fc will not be glycosylated even in presence of the natural glycosylation site and therefore inactivation of the Fc will be equivalently obtained.

In some embodiments, a polypeptide construct includes non-natural amino acids, amino acid analogues, amino acid mimetics, or any combinations thereof that function in a manner similar to the naturally occurring amino acids. Naturally encoded amino acids generally refer to the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, e.g., a carbon that is bound to a hydrogen, a carboxyl group, an amino group, and an R group, such as, homoserine, norleucine, methionine sulfoxide, methionine methyl sulfonium. In some embodiments, such analogs have modified R groups (such as, norleucine) or modified peptide backbones, but generally retain the same basic chemical structure as a naturally occurring amino acid.

Protein Production, Recovery, and Purification

In some embodiments, host cells used to produce polypeptides of the disclosure are grown in media suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. In some embodiments, host cells are cultured at suitable temperatures, such as from about 20° C. to about 39° C., e.g., from about 25° C. to about 37° C., preferably 37° C., and $CO_2$ levels, such as about 5% to 10%. In some embodiments, the pH of the medium is from about pH 6.8 to pH 7.4, e.g., pH 7.0, depending mainly on the host organism. If an inducible promoter is used in the expression vector, protein expression can be induced under conditions suitable for the activation of the promoter.

In some embodiments, protein recovery involves disrupting the host cell, for example by osmotic shock, sonication, or lysis. Once the cells are disrupted, cell debris is removed by centrifugation or filtration. The proteins can then be further purified. In some embodiments, a polypeptide of the disclosure is purified by various methods of protein purification, for example, by chromatography (e.g., ion exchange chromatography, affinity chromatography, and size-exclusion column chromatography), centrifugation, differential solubility, or by any other standard technique for the purification of proteins. For example, in some embodiments, the protein is isolated and purified by appropriately selecting and combining affinity columns such as Protein A column (e.g., POROS Protein A chromatography) with chromatography columns (e.g., POROS HS-50 cation exchange chromatography), filtration, ultra-filtration, de-salting and dialysis procedures. In some embodiments, a polypeptide is conjugated to marker sequences, such as a peptide to facilitate purification. An example of a marker amino acid sequence is a hexa-histidine peptide (His6-tag (SEQ ID NO: 223)), which can bind to a nickel-functionalized agarose affinity column with micromolar affinity. As an alternative, a hemagglutinin "HA" tag, which corresponds to an epitope derived from the influenza hemagglutinin protein can be used.

In some embodiments, polypeptides of the disclosure, for example a polypeptide construct comprising a SIRPα D1 domain variant (e.g., any variant provided in Tables 2, 5, and 6) and a fusion partner such as an Fc variant are produced by the cells of a subject (e.g., a human), e.g., in the context of gene therapy, by administrating a vector such as a viral vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding a polypeptide of the disclosure. The vector, once inside a cell of the subject (e.g., by transformation, transfection, electroporation, calcium phosphate precipitation, direct microinjection, infection, etc.) can be used for the expression of a polypeptide disclosed herein. In some cases, the polypeptide is secreted from the cell. In some embodiments, if treatment of a disease or disorder is the desired outcome, no further action is required. In some embodiments, if collection of the protein is desired, blood is collected from the subject and the protein purified from the blood by various methods.

Methods of Treating Cancer

Provided herein is a method of treating cancer in an individual (e.g., a human individual) that comprises administering to the individual an effective amount of (a) a polypeptide comprising a SIRPα D1 domain variant (e.g., a SIRPα D1 domain variant described herein) and an Fc domain variant (e.g., an Fc domain variant described herein) and (b) a therapeutic antibody.

Lung Cancer

In some embodiments, provided is a method of treating lung cancer (e.g., non-small cell lung cancer or "NSCLC"), in an individual (e.g., a human individual) that comprises administering to the individual an effective amount of (a) a polypeptide (e.g., fusion polypeptide) comprising a SIRPα D1 domain variant (e.g., a SIRPα D1 domain variant described herein) and an Fc domain variant (e.g., an Fc domain variant described herein) and (b) a therapeutic antibody that disrupts the interaction between PD-1 and PD-L1, wherein the individual progressed (e.g., demonstrated disease progression) while on (or following) a prior therapy for lung cancer (e.g., NSCLC). In some embodiments, the prior therapy was immune checkpoint inhibitor (CPI) therapy. Additionally or alternatively, in some embodiments, the individual has a PD-L1 tumor proportion score (TPS) of less than 50%. In some embodiments, the individual has not received prior CPI therapy. In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and deG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments the polypeptide (e.g., fusion polypeptide) administered to the individual comprises a SIRPα D1 domain variant that comprises the amino acid sequence of SEQ ID NO: 81 or SEQ ID NO: 85. In some embodiments the polypeptide (e.g., fusion polypeptide) administered to the individual comprises an Fc domain variant that is a human IgG Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the polypeptide (e.g., fusion polypeptide) administered to the individual comprises the amino acid sequence of SEQ ID NO: 136 or SEQ ID NO: 135. In some embodiments the polypeptide (e.g., fusion polypeptide) forms a homodimer. In some embodiments, the therapeutic antibody that blocks the interaction between PD-1 and PD-L1 is an anti-PD-1 antibody. In some embodiments, the anti-PD-1 antibody is pembrolizumab.

In some embodiments, the pembrolizumab is administered subcutaneously. In some embodiments, the pembrolizumab is administered via intravenous infusion. In some embodiments, the pembrolizumab is administered according to its label instructions. In some embodiments, the pembrolizumab is administered to the individual (e.g., via IV infusion) at a dose of about 200 mg every three weeks (Q3W). In some embodiments, the pembrolizumab is administered to the individual for up to 24 months. In some embodiments, the pembrolizumab is administered to the individual for at least 24 months. In some embodiments, dose modifications of pembrolizumab are made according to the local package insert. Complete information about pembrolizumab preparation, dispensing, dosage, and administration schedule can be found in the local package insert (for the United States, see, e.g., www(dot)accessdata(dot)fda(dot)gov/drugsatfda_docs/label/2016/125514s0121bl(dot)pdf, for Europe, see, e.g., www(dot)ema(dot)europa(dot)eu/en/documents/product-information/keytruda-epar-product-information_en(dot)pdf). In some embodiments, the polypeptide (e.g., fusion polypeptide) is administered (e.g., via intravenous infusion) to the individual weekly (i.e., once every 7 days or "qw"), e.g., at a dose of 10.0 mg/kg.

In some embodiments, the lung cancer is NSCLC. In some embodiments, the NSCLC is locally advanced NSCLC. In some embodiments, the NSCLC is metastatic NSCLC. In some embodiments, the individual has metastatic NSCLC and has not demonstrated disease progression within 8 weeks of the start of a prior therapy with a PD-1 or PD-L1 inhibitor. In some embodiments, the individual has a PD-L1 tumor proportion score (TPS) score of ≥1%. In some embodiments, the individual has locally advanced or metastatic NSCLC with a TPS score <50%. In some embodiments, the individual progressed following systemic therapy for their metastatic disease. In some embodiments, the individual has locally advanced or metastatic NSCLC with a TPS score ≥1%, and the individual progressed on prior checkpoint inhibitor (CPI) therapy for NSCLC.

In some embodiments, the prior CPI therapy for lung cancer (e.g., NSCLC) on which the individual progressed was a therapy that comprised treatment with nivolumab, pembrolizumab, atezolizumab, avelumab, durvalumab, cemiplimab, tislelizumab (also known as BGB-A317), toripalimab, sintilimab, camrelizumab (also known as SHR-1210 or INCSHR-1210), spartalizumab (also known as PDR001), TSR-042, and/or FAZ053. In some embodiments, the individual is considered to have progressed on the prior CPI therapy for lung cancer (e.g., NSCLC) if the individual demonstrated progressive disease (PD), e.g., as assessed by Response Evaluation In Solid Tumor (RECIST) criteria (e.g., version 1.0 or 1.1) or modified RECIST criteria (see, e.g., Therasse et al. (2000) *J Natl Cancer Inst.* 92: 205-216; Eisenhauer et al. (2009) *Eur J Cancer.* 45: 229-247; and Jang et al. (2013) *Chin J Cancer Res.* 25(6): 689-694), World Health Organization (WHO) criteria (see, e.g., WHO. Handbook for Reporting Results of Cancer Treatment. Geneva: World Health Organization Offset Publication; 1979. p. 48; and Miller et al. (1981) *Cancer.* 47: 207-214), or any set of response criteria described in Hwang et al. (2017) "Response Evaluation of Chemotherapy for Lung Cancer." *Tuberc Respir Dis* (Seoul). 80(2): 136-142 and references cited therein. In some embodiments, the individual is resistant to standard therapy (e.g., curative therapy) for lung cancer (e.g., NSCLC). In some embodiments, there is no standard therapy (e.g., curative therapy) available to treat the lung cancer (e.g., NSCLC).

In some embodiments, the individual's PD-L1 tumor proportion score (TPS) is assessed using an in vitro diagnostic immunohistochemistry (IHC) assay for detection of PD-L1 in formalin-fixed, paraffin-embedded (FFPE) human tissue sections. In some embodiments, the IHC assay is PD-L1 IHC 22C3 Pharm Dx. PD-L1 IHC 22C3 Pharm Dx is a qualitative immunohistochemical assay in which a murine monoclonal anti-PD-L1 antibody (clone 22C3) is used to detect PD-L1 (i.e., human PD-L1) in formalin-fixed, paraffin-embedded (FFPE) lung cancer tissue (e.g., NSCLC tissue) obtained from an individual (e.g., patient) on the DAKO™ AUTOSTAINER LINK 48 automated staining system using the ENVISION™ FLEX visualization system. In some embodiments, TPS is a measure of PD-L1 protein expression in the lung cancer (e.g., NSCLC) tissue sample from the individual (e.g., patient). In some embodiments, TPS is the percentage of viable tumor cells showing partial or complete membrane staining at any intensity. The specimen should be considered PD-L1 positive if TPS ≥50% of the viable tumor cells exhibit membrane staining at any intensity. In some embodiments, tumor-associated immune cells (such as infiltrating lymphocytes or macrophages) are not included in the scoring for the determination of TPS. In some embodiments the labeling of the lung cancer (e.g., NSCLC) sample is performed by a pathologist. In some embodiments, the staining is assessed via light microscope at 10×-40× magnification. Further details regarding the PD-L1 IHC 22C3 Pharm Dx assay, reagents and equipment to perform the assay, interpretation of assay results, and TPS scoring are provided at www(dot)accessdata(dot)fda(dot)gov/cdrh_docs/pdf15/p150013b(dot)pdf and Reck et al. (2016) "Pembrolizumab versus Chemotherapy for PD-L1-Positive Non-Small-Cell Lung Cancer." NEJM. 375: 1823-1833.

Head and Neck Cancer

In some embodiments, provided is a method of treating head and neck cancer (e.g., head and neck squamous cell carcinoma or "HNSSC") in an individual (e.g., a human individual) that comprises administering to the individual an effective amount of (a) a polypeptide (e.g., fusion polypeptide) comprising a SIRPα D1 domain variant (e.g., a SIRPα D1 domain variant described herein) and an Fc domain variant (e.g., an Fc domain variant described herein) and (b) a therapeutic antibody that disrupts the interaction between PD-1 and PD-L1, wherein the individual progressed (e.g., demonstrated disease progression) while on a prior therapy or following a prior therapy for head and neck cancer (e.g., HNSCC). In some embodiments, the prior therapy was a platinum-containing therapy. In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat. In some embodiments the polypeptide (e.g., fusion polypeptide) administered to the individual comprises a SIRPα D1 domain variant that comprises the amino acid sequence of SEQ ID NO: 81 or SEQ ID NO: 85. In some embodiments the polypeptide (e.g., fusion polypeptide) administered to the individual comprises an Fc domain variant that is a human IgG Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the polypeptide (e.g., fusion polypeptide) administered to the individual comprises the amino acid sequence of SEQ ID NO: 136 or SEQ ID NO: 135. In some embodiments the polypeptide (e.g., fusion polypeptide) forms a homodimer. In some embodiments, the therapeutic antibody that blocks the interaction between PD-1 and PD-L1 is an anti-PD-1 antibody. In some embodiments, the anti-PD-1 antibody is pembrolizumab. In some embodiments, the HNSCC is PD-L1 negative. In some embodiments, the HNSCC is PD-L1 positive. Further details regarding "PD-L1 negative" and "PD-L1 positive" are provided elsewhere herein In some embodiments, the pembrolizumab is administered subcutaneously. In some embodiments, the pembrolizumab is administered via intravenous infusion. In some embodiments, the pembrolizumab is administered according to its label instructions. In some embodiments, the pembrolizumab is administered to the individual (e.g., via IV infusion) at a dose of about 200 mg every three weeks (Q3W). In some embodiments, the pembrolizumab is administered to the individual for up to 24 months. In some embodiments, the pembrolizumab is administered to the individual for at least 24 months. In some embodiments, dose modifications of pembrolizumab are made according to the local package insert. Complete information about pembrolizumab preparation, dispensing, dosage, and administration schedule can be found in the local package insert (for the United States, see, e.g., www(dot)accessdata(dot)fda(dot)gov/drugsatfda_docs/label/2016/125514s021bl(dot)pdf, for Europe, see, e.g., www(dot)ema(dot)europa(dot)eu/en/documents/product-information/keytruda-epar-product-information_en(dot)pdf). In some embodiments, the polypeptide (e.g., fusion polypeptide) is administered (e.g., via intravenous infusion) to the individual weekly (i.e., once every 7 days or "qw"), e.g., at a dose of 10.0 mg/kg.

In some embodiments, the individual has recurrent HNSCC. In some embodiments, the HNSCC is metastatic HNSCC. In some embodiments, the individual received prior therapy with an immune checkpoint inhibitor ("CPI"), i.e., the individual is a "CPI experienced" individual. In some embodiments, the individual has recurrent or metastatic HNSCC and has not demonstrated with disease progression within 8 weeks of the start of a prior therapy with a CPI. In some embodiments, the prior CPI therapy was or comprised a PD-1 or PD-L1 inhibitor. In some embodiments, the prior CPI was or comprised treatment with nivolumab, pembrolizumab, atezolizumab, avelumab, durvalumab, cemiplimab, tislelizumab (also known as BGB-A317), toripalimab, sintilimab, camrelizumab (also known as SHR-1210 or INCSHR-1210), spartalizumab (also known as PDR001), TSR-042, and/or FAZ053. In some embodiments, the individual has not received prior therapy with an CPI (e.g., the individual is "immune checkpoint inhibitor naïve" or "CPI naïve").

In some embodiments, the prior platinum-containing therapy on which the individual progressed or following which the individual progressed was a therapy that comprised treatment with carboplatin, cisplatin, oxaliplatin, nedaplatin, triplatin tetranitrate, phenanthriplatin, picoplatin, and/or satraplatin. In some embodiments, the individual is considered to have progressed on or following the prior platinum-containing therapy for head and neck cancer (e.g., HNSCC) if the individual demonstrated progressive disease (PD), e.g., as assessed by Response Evaluation In Solid Tumor (RECIST) criteria (e.g., version 1.0 or 1.1) or modified RECIST criteria (see, e.g., Therasse et al. (2000) *J Natl Cancer Inst.* 92: 205-216; Eisenhauer et al. (2009) *Eur J Cancer.* 45: 229-247; and Jang et al. (2013) *Chin J Cancer Res.* 25(6): 689-694), World Health Organization (WHO) criteria (see, e.g., WHO. Handbook for Reporting Results of Cancer Treatment. Geneva: World Health Organization Offset Publication; 1979. p. 48; and Miller et al. (1981) *Cancer.* 47: 207-214), or a set of response criteria described in Wray et al. (2016) "Therapy Response Assessment and Patient Outcomes in Head and Neck Squamous Cell Carcinoma: FDG PET Hopkins Criteria Versus Residual Neck Node Size and Morphologic Features." *Am J Roentgenology.* 207:641-647. In some embodiments, the individual is resistant to standard therapy (e.g., curative therapy) for head and neck cancer (e.g., HNSCC). In some embodiments, there is no standard therapy (e.g., curative therapy) available to treat the head and neck cancer (e.g., HNSCC).

Gastric/Gastroesophageal (GEJ) Cancer

In some embodiments, provided is a method of treating gastric/gastroesophageal (GEJ) cancer (e.g., HER2-positive gastric or GEJ adenocarcinoma) in an individual (e.g., a human individual) that comprises administering to the individual an effective amount of (a) a polypeptide (e.g., fusion polypeptide) comprising a SIRPα D1 domain variant (e.g., a SIRPα D1 domain variant described herein) and an Fc domain variant (e.g., an Fc domain variant described herein) and (b) a therapeutic anti-HER2 antibody, wherein the individual progressed (e.g., demonstrated disease progression) during a prior therapy or following a prior therapy for gastric/GEJ cancer (e.g., gastric/GEJ adenocarcinoma), and wherein the prior therapy was an anti-HER2 antibody therapy and/or a fluoropyrimidine-based therapy. In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises a SIRPα D1 domain variant that comprises the amino acid sequence of SEQ ID NO: 81 or SEQ ID NO: 85. In some embodiments the polypeptide (e.g., fusion polypeptide) administered to the individual comprises an Fc domain variant that is a human IgG1 Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the polypeptide (e.g., fusion polypeptide) administered to the individual comprises the amino acid sequence of SEQ ID NO: 136 or SEQ ID NO: 135. In some embodiments the polypeptide (e.g., fusion polypeptide) forms a homodimer. In some embodiments, the therapeutic anti-HER2 antibody that administered to the individual in combination with the fusion polypeptide is trastuzumab.

In some embodiments, the trastuzumab is administered subcutaneously. In some embodiments, the trastuzumab is administered via intravenous infusion. In some embodiments, the trastuzumab is administered according to its label instructions. In some embodiments, the trastuzumab is administered to the individual (e.g., via intravenous infusion) every three weeks (Q3W). In some embodiments, the initial (i.e., first) dose of trastuzumab is about 8 mg/kg, and every subsequent dose (i.e., following the first dose) is about 6 mg/kg. In some embodiments, dose modifications of trastuzumab are made according to the local package insert. Complete information about trastuzumab preparation, dispensing, dosage, and administration schedule can be found in the local package insert (for the United States, see, e.g., www.accessdata(dot)fda(dot)gov/drugsatfda_docs/label/2017/103792s53371bl(dot) pdf; for Europe, see, e.g., www(dot)ema(dot)Europa(dot)eu/en/documents/product-information/herceptin-epar-product-information_en(dot)pdf). In some embodiments, the polypeptide (e.g., fusion polypeptide) is administered (e.g., via intravenous infusion) to the individual weekly (i.e., once every 7 days or "qw"), e.g., at a dose of 10.0 mg/kg.

In some embodiments HER2 status (i.e., HER2-positive status or HER2-negative status) of the gastric or GEJ cancer is assessed via immunohistochemistry (IHC) or in situ hybridization (ISH, e.g., fluorescent ISH or "FISH"). In some embodiments, the HER2 status of the gastric or GEJ cancer is evaluated according to criteria described in Abrahao-Machado et al. (2016) World J Gastroenterol. 22(19): 4619-4625 and references cited therein. In some embodiments, the HER2-positive gastric or HER2-positive GEJ cancer is HER2-positive gastric/HER2-positive GEJ adenocarcinoma. In some embodiments, the HER2-positive gastric/HER2-positive GEJ cancer (e.g., adenocarcinoma) is metastatic gastric/GEJ cancer (e.g., metastatic adenocarcinoma). In some embodiments, the individual has metastatic gastric/GEJ cancer (e.g., adenocarcinoma) and has demonstrated a response of at least stable disease (SD) (i.e., a response better than progressive disease (PD)) as the best response to a prior therapy.

In some embodiments, the individual progressed (e.g., demonstrated disease progression) during prior therapy or following prior therapy with an anti-HER2 antibody. In some embodiments, the prior anti-HER2 antibody therapy comprised treatment with trastuzumab, pertuzumab, and/or margetuximab. Additionally or alternatively, in some embodiments, the individual progressed (e.g., demonstrated disease progression) during prior therapy or following prior therapy with a fluoropyrimidine-based therapy. In some embodiments the prior fluoropyrimidine-based therapy comprised treatment with, e.g., capecitabine, floxuridine, 4-fluorouracil, 5-fluorouracil, carmofur, doxifluridine, ftorafur (Tegafur), UFT (i.e., a 1:4 molar combination of ftorafur with uracil), S-1 (a combination of ftorafur, gimeracil, and oteracil), and/or FOLFOX (a combination of folinic acid, 5-fluorouracil, and oxaliplatin). In some embodiments, the individual progressed while on therapy or following therapy with an anti-HER2 antibody and a fluoropyrimidine-based therapy. In some embodiments, the anti-HER2 antibody and the fluoropyrimidine-based therapy were administered in combination (e.g., wherein both agents were part of a single treatment regimen). In some embodiments the anti-HER2 antibody and the fluoropyrimidine-based therapy were each administered in separate treatment regimens (e.g., in two separate prior therapies or two separate prior lines of therapy).

In some embodiments, the individual is considered to have progressed based on the prior anti-HER2 antibody therapy and/or the prior fluoropyrimidine-based therapy for gastric/GEJ cancer (e.g., HER2-positive gastric/GEJ cancer) if the individual demonstrated progressive disease (PD), e.g., as assessed by Response Evaluation In Solid Tumor (RECIST) criteria (e.g., version 1.0 or 1.1) or modified RECIST criteria (see, e.g., Therasse et al. (2000) *J Nat Cancer Inst.* 92: 205-216; Eisenhauer et al. (2009) *Eur J. Cancer.* 45: 229-247; and Jang et al. (2013) *Chin J. Cancer Res.* 25(6): 689-694), World Health Organization (WHO) criteria (see, e.g., WHO. Handbook for Reporting Results of Cancer Treatment. Geneva: World Health Organization Offset Publication; 1979. p. 48; and Miller et al. (1981) *Cancer.* 47: 207-214), or any set of response criteria described in Kurokawa et al. (2013) *Ann Surg Oncol.* 20(9): 3009-3014; Yanagawa et al. (2012) *J Nucl Med.* 53(6): 872-880; Lordick et al. (2016) *Ann Oncol.* 27(suppl 5): v50-v57; or Kim et al. (2015) *Oncology.* 88:69-75. In some embodiments, the individual is resistant to standard therapy (e.g., curative therapy) for gastric/GEJ cancer (e.g., HER2-positive gastric/HER2-positive GEJ cancer). In some embodiments, there is no standard therapy (e.g., curative therapy) available to treat the gastric/GEJ cancer (e.g., HER2-positive gastric/HER2-positive GEJ cancer).

Lymphomas (i) Aggressive Non-Hodgkin Lymphoma

In some embodiments, provided is a method of treating aggressive non-Hodgkin lymphoma or "NHL" (e.g., diffuse large B-cell lymphoma ("DLBCL", e.g., de novo DLBCL or transformed DLBCL or mantle cell lymphoma (MCL)) in an individual (e.g., a human individual) that comprises administering to the individual an effective amount of (a) a polypeptide (e.g., fusion polypeptide) comprising a SIRPα D1 domain variant (e.g., a SIRPα D1 domain variant described herein) and an Fc domain variant (e.g., an Fc domain variant described herein) and (b) a therapeutic anti-CD20 antibody, wherein the aggressive NHL is relapsed and/or refractory aggressive NHL (e.g., wherein the individual has relapsed during or following a prior treatment for aggressive NHL and/or has been refractory to a prior treatment for aggressive NHL) and wherein there is no available therapy (e.g., curative therapy) for the aggressive NHL (e.g., DLBCL, such as de novo DLBCL, transformed DLBCL, or mantle cell lymphoma). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises a SIRPα D1 domain variant that comprises the amino acid sequence of SEQ ID NO: 81 or SEQ ID NO: 85. In some embodiments the polypeptide (e.g., fusion polypeptide) administered to the individual comprises an Fc domain variant that is a human IgG1 Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the polypeptide (e.g., fusion polypeptide) administered to the individual comprises the amino acid sequence of SEQ ID NO: 136 or SEQ ID NO: 135. In some embodiments the polypeptide (e.g., fusion polypeptide) forms a homodimer. In some embodiments, the therapeutic anti-CD20 antibody is rituximab. In some embodiments, the aggressive NHL is diffuse large B-cell lymphoma (DLBCL), e.g., de novo DLBCL or transformed DLBCL. In some embodiments, the aggressive NHL is mantle cell lymphoma (MCL).

In some embodiments, the rituximab is administered subcutaneously. In some embodiments, the rituximab is administered via intravenous infusion. In some embodiments, the rituximab is administered according to its label instructions. In some embodiments, the rituximab is administered to the individual (e.g., via intravenous infusion) at a dose of about 375 mg/m$^2$. In some embodiments, the first four doses (i.e. doses 1-4) of rituximab are administered to the individual (e.g., at a dose of about 375 mg/m$^2$) once a week (e.g., once every 7 days or "qw") for the first four weeks (e.g., 28 days) of treatment, and the next eight doses (i.e., doses 5-12) are administered to the individual once every four weeks (e.g., every 28 days or "q4w"). In some embodiments, the first four doses (i.e. doses 1-4) of rituximab are administered to the individual (e.g., at a dose of about 375 mg/m$^2$) once a week (e.g., once every 7 days or "qw") for the first four weeks (e.g., 28 days) of treatment, and the next four doses (i.e., doses 5-8) are administered to the individual once every four weeks (e.g., every 28 days or "q4w"). In some embodiments, dose modifications of rituximab are made according to the local package insert. Complete information about rituximab preparation, dispensing, dosage, and administration schedule can be found in the local package insert (for the United States, see, e.g., www(dot)accessdata(dot)fda(dot)gov/drugsatfda_docs/label/2012/103705s5367s53881bl(dot)pdf, for Europe, see, e.g., www(dot)ema(dot)europa(dot)eu/en/documents/product-information/mabthera-epar-product-information_en(dot)pdf). In some embodiments, the polypeptide (e.g., fusion polypeptide) is administered (e.g., via intravenous infusion) to the individual weekly (i.e., once every 7 days or "qw"), e.g., at a dose of 10.0 mg/kg or 15.0 mg/kg.

In some embodiments, the individual is diagnosed as having de novo DLBCL (e.g., de novo relapsed and/or refractory DLBCL) if the individual had no prior history of lymphoma. In some embodiments, the individual is diagnosed as having transformed DLBCL if the individual has a history of lymphoma, e.g., indolent lymphoma, such as marginal zone lymphoma, lymphoplasmacytic lymphoma, small lymphocytic lymphoma/chronic lymphocytic leukemia, follicular lymphoma, or lymphocyte predominant Hodgkin lymphoma. In some embodiments, the individual is diagnosed as having mantle cell lymphoma (MCL) if the individual is found to have one or more of the following chromosomal abnormalities: t(11;14), t(14;18). In some embodiments, the individual is diagnosed with mantle cell lymphoma (MCL) if SOX11 overexpression is detected in a sample of leukemic cells from the individual. Other criteria for diagnosing de novo DLBCL, transformed DLBCL, and MCL are known in the art and routinely used by skilled artisans. See, e.g., Balsas et al. (2017) Blood. 130(4):501-513; National Guideline Alliance (UK). Non-Hodgkin's Lymphoma: Diagnosis and Management. London: National Institute for Health and Care Excellence (UK); 2016 Jul. (NICE Guideline, No. 52.) 3, Staging; Dreyling et al. Am Soc Clin Oncol Educ Book. 2014:191-8; and others.

In some embodiments, the individual is considered to have relapsed following a prior therapy for aggressive NHL (e.g., de novo DLBCL, transformed DLBCL, or MCL) if the individual achieved a therapeutic response of least stable disease (SD) to the prior therapy, but stopped responding (e.g., demonstrated disease progression) within about any one of, e.g., 1, 2, 3, 4, 5, 6, 7, 8, 9, 10, 11, or 12 months following the cessation of the prior therapy. In some embodiments, the individual is considered to be refractory to a prior therapy for aggressive NHL if the individual was unresponsive to the prior therapy (e.g., failed to achieve a therapeutic response of at least stable disease (SD) during or following the prior therapy). In some embodiments, the therapeutic response to a therapy for aggressive NHL is assessed according to the criteria described in Cheson et al. (2014) "Recommendations for Initial Evaluation, Staging and Response Assessment of Hodgkin and Non-Hodgkin Lymphoma: The Lugano Classification." *J. Clin Oncol.* 32: 3059-3067.

In some embodiments, the individual was refractory to or had relapsed following treatment with at least one prior therapy (e.g., at least one prior standard approved therapy, at least two prior standard approved therapies, at least three standard approved therapies etc.) for aggressive NHL. Standard therapies for DLBCL (e.g., de novo or transformed DLBCL) and MCL include, but are not limited to, e.g., rituximab, RCHP (i.e., rituximab, cyclophosphamide, doxorubicin, and prednisone); R-CHOP (i.e., rituximab, cyclophosphamide, doxorubicin, vincristine, and prednisone); R-CHOEP (i.e., rituximab, cyclophosphamide, doxorubicin, vincristine, etoposide, and prednisone that is typically administered in 21-day cycles for 6 cycles); EPOCH-R (i.e., rituximab, cyclophosphamide, doxorubicin, vincristine, etoposide, and prednisone that is typically administered as a continuous infusion over 4 days); R-GCVP (i.e., rituximab, gemciabine, cyclopiosphamide, vMcristine, and prednisolone); R-CEPP (i.e., rituximab, cyclphospharnide, etoposide, procarbazine, and prednisone-RCEOP (i.e., rituximab, cyclophosphamide, epirubicin, vincristine, and prednisone): R-CVP (i.e., rjiximab, cyclophosphammid, vincristine, and prednisone); rituximab and bendanustine; rituximab and lenalidomide; DIHAP i.e., dexamethasone, high-dose cytarabine and cisplatin); RDHAP (i.e., DHAP in combination with rituximab); ICE (i.e., ifosfamide, carboplatin, and etoposide); RICE (i.e., ICE in combination with rituximab); DICE (i.e., ICE in combination with dexamethasone); DICE and mesna; BEAM (i.e., carmustine, etoposide, cytarabine, and melphalan); R-BEAM (i.e., BEAM in combination with rituximab); ESHAP (i.e., etoposide, solumedrol, high-dose cytarabine, and cisplatin); R-ESHAP (i.e., ESHAP in combination with rituximab); MIME (i.e., methyl-glyoxal-bis (guanylhydrazone), ifosfamide, methotrexate, and etoposide); parsaclisib (also known as INCB050465); MATRIX (i.e., methotrexate, cytarabine, thiotepa, and rituximab); hyper-CVAD or HCVAD (i.e., hyper-fractionated cyclophosphamide, vincristine, doxorubicin, and dexamethasone) RHCVAD (i.e., HCVAD in combination with rituximab); RHCVAD/MA (i.e., RHCVAD alternating with methotrexate and cytarabine); DHAP (i.e., dexamethasone, cisplatin, and cytarabine); R-DHAP (i.e., DHAP in combination with rituximab); ibrutinib; rituximab, obinituzomab, CVAD (i.e., cyclophosphamide, doxorubicin, vincristine, and prednisolone); RCVAD (i.e., CVAD in combination with rituximab); GemOx (i.e., gemcitabine and oxaliplatin); R-GemOx (i.e., GemOx in combination with rituximab); DHAX (i.e., dexamethasone, cytarabine, and oxaliplatin); R-DHAX (i.e., DHAX in combination with rituximab); GIFOX (i.e., gemcitabine, ifosfamide, and oxaliplatin); RGIFOX (i.e., GIFOX in combination with rituximab); bortezomib and GIFOX; ASCT (i.e., autologous stem cell transplantation) HD-ASCT (i.e., ASCT in combination with high dose therapy, e.g., high-dose chemotherapy); CAR T-cell therapy (e.g., tisagenlecleucel or axicabtagene); brentuximab vedotin, and lenalidomide. In some embodiments, the prior therapy for aggressive NHL comprised any two or more of the preceding treatments (given together in a single treatment regimen, or given in separate treatment regimens). In some embodiments, there are no available treatment options (e.g., curative treatment options) for the individual with aggressive NHL (e.g., relapsed/refractory aggressive NHL). In some embodiments, the individual has DLBCL (e.g., de novo DLBCL or transformed DLBCL) or MCL for which no curative therapy is available. In some embodiments, the individual has DLBCL (e.g., de novo DLBCL or transformed DLBCL) or MCL that has relapsed following or has been refractory to standard approved therapies (e.g., curative therapies).

(ii) Indolent Lymphoma

In some embodiments, provided is a method of treating indolent lymphoma in an individual (e.g., a human individual) that comprises administering to the individual an effective amount of (a) a polypeptide (e.g., fusion polypeptide) comprising a SIRPα D1 domain variant (e.g., a SIRPα D1 domain variant described herein) and an Fc domain variant (e.g., an Fc domain variant described herein) and (b) a therapeutic anti-CD20 antibody, wherein the indolent lymphoma is relapsed and/or refractory indolent lymphoma (e.g., wherein the individual has relapsed during or following at least one prior treatment, e.g., a standard approved therapy, for indolent lymphoma and/or or has been refractory to at least one prior treatment, e.g., a standard approved therapy, for indolent lymphoma. In some embodiments, the individual has relapsed during or after more than one standard approved therapy (e.g., 2, 3, or more standard therapies) for indolent lymphoma and/or is refractory to more than one standard therapy (e.g., 2, 3, or more standard therapies, e.g., curative therapies) for indolent lymphoma In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat. In some embodiments, the polypeptide (e.g., fusion polypeptide) administered to the individual comprises a SIRPα D1 domain variant that comprises the amino acid sequence of SEQ ID NO: 81 or SEQ ID NO: 85. In some embodiments the polypeptide (e.g., fusion polypeptide) administered to the individual comprises an Fc domain variant that is a human IgG1 Fc region comprising L234A, L235A, G237A, and N297A mutations, wherein numbering is according to the EU index of Kabat. In some embodiments, the Fe domain variant comprises the amino acid sequence of SEQ ID NO: 91. In some embodiments, the polypeptide (e.g., fusion polypeptide) administered to the individual comprises the amino acid sequence of SEQ ID NO: 136 or SEQ ID NO: 135. In some embodiments the polypeptide (e.g., fusion polypeptide) forms a homodimer. In some embodiments, the therapeutic anti-CD20 antibody is rituximab.

In some embodiments, the rituximab is administered subcutaneously. In some embodiments, the rituximab is administered via intravenous infusion. In some embodiments, the rituximab is administered according to its label instructions. In some embodiments, the rituximab is administered to the individual (e.g., via intravenous infusion) at a dose of about 375 mg/m$^2$. In some embodiments, the first four doses (i.e. doses 1-4) of rituximab are administered to the individual (e.g., at a dose of about 375 mg/m$^2$) once a week (e.g., once every 7 days or "qw") for the first four weeks (e.g., 28 days) of treatment, and the next eight doses (i.e., doses 5-12) are administered to the individual once every four weeks (e.g., every 28 days or "q4w"). In some embodiments, the first four doses (i.e. doses 1-4) of rituximab are administered to the individual (e.g., at a dose of about 375 mg/m$^2$) once a week (e.g., once every 7 days or "qw") for the first four weeks (e.g., 28 days) of treatment, and the next four doses (i.e., doses 5-8) are administered to the individual once every four weeks (e.g., every 28 days or "q4w"). In some embodiments, dose modifications of rituximab are made according to the local package insert. Complete information about rituximab preparation, dispensing, dosage, and administration schedule can be found in the local package insert (for the United States, see, e.g., www (dot)accessdata(dot)fda(dot)gov/drugsatfda_docs/label/ 2012/103705s5367s53881bl(dot)pdf, for Europe, see, e.g., www(dot)ema(dot)europa(dot)eu/en/documents/product-information/mabthera-epar-product-information_en(dot)pdf). In some embodiments, the polypeptide (e.g., fusion polypeptide) is administered (e.g., via intravenous infusion) to the individual weekly (i.e., once every 7 days or "qw"), e.g., at a dose of 10.0 mg/kg or 15.0 mg/kg.

In some embodiments, the indolent lymphoma is an indolent non-Hodgkin lymphoma (NHL). In some embodiments, the indolent NHL is marginal zone lymphoma (MZL). In some embodiments, the indolent NHL is follicular lymphoma (FL). Details regarding the diagnosis and classification of marginal zone lymphoma and follicular lymphoma (as well as DLBCL, and mantle cell lymphoma) are provided in, e.g., Ayyappan et al. (2018) *Curr Oncol Rep*. 20(4): 33; Dreyling et al. (2013) ESMO Consensus Guidelines: Marginal Cell Lymphoma, Mantle Cell Lymphoma, Peripheral T-cell Lymphoma." *Ann Oncol*. 24(4): 857-877; Vose, J M (2017) "Mantle cell lymphoma: 2017 update on diagnosis, risk-stratification, and clinical management." *Am J Hematol*. 92(8): 806-813; Ciobanu et al. (2013) "Indolent Lymphoma: Diagnosis and Prognosis in Medical Practice." Maedica (Buchar) 8(4) 338-342, and others.

In some embodiments, the individual is considered to have relapsed following a prior therapy for indolent lymphoma (e.g., indolent NHL) if the individual achieved a therapeutic response of least stable disease (SD) to the prior therapy, but stopped responding (e.g., demonstrated disease progression) within about any one of, e.g., 1, 2, 3, 4, 5, 6, 7, 8, 9, 10, 11, or 12 months following the cessation of the prior therapy. In some embodiments, the individual is considered to be refractory to a prior therapy for indolent lymphoma (e.g., indolent NHL) if the individual was unresponsive to the prior therapy (e.g., failed to achieve a therapeutic response of at least stable disease (SD) during or following the prior therapy). In some embodiments, the therapeutic response to therapy for indolent lymphoma (e.g., indolent NHL) is assessed according to the criteria described in Cheson et al. (2014) "Recommendations for Initial Evaluation, Staging and Response Assessment of Hodgkin and Non-Hodgkin Lymphoma: The Lugano Classification." *J. Clin Oncol*. 32: 3059-3067.

In some embodiments, the individual was refractory to or had relapsed following treatment with at least one prior therapy (e.g., at least one prior standard approved therapy, at least two prior standard approved therapies, at least three standard approved therapies etc.) for indolent lymphoma (e.g., indolent NHL). Standard therapies for indolent lymphoma (e.g., indolent NHL, such as marginal zone lymphoma or follicular lymphoma) include, but are not limited to, e.g., the standard therapies for aggressive NHL (e.g., DLBCL or mantle cell lymphoma), which are described in detail elsewhere herein. Other standard therapies for indolent lymphoma (e.g., indolent NHL) include, but are not limited to, e.g., fludarabine, FR (i.e., fludarabine and rituximab); FCR (i.e., FR in combination with cyclophosphamide); FCM (i.e., fludarabine, cyclophosphamide, mitoxantrone); FCMR (i.e., FCM in combination with rituximab); ibritumomab tiuxetan; tositumomab; vorinostat; everolimus; bortezomib; navitoclax (also known as ABT-263); high dose therapy (HDT); autologous stem cell transplantation; and allogenic stem cell transplantation. In some embodiments, the prior therapy for indolent lymphoma (e.g., indolent NHL) comprised any two or more of the preceding standard therapies (including therapies for aggressive NHL, which are described elsewhere herein). In some embodiments, the two or more standard therapies for indolent lymphoma (e.g., indolent NHL) (including standard treatments for aggressive NHL) were given together in a single treatment regimen. In some embodiments, the two or more standard therapies for indolent NHL (including standard treatment for aggressive NHL) were given in separate treatment regimens. In some embodiments, there are no available treatment options (e.g., curative treatment options) for the individual with indolent lymphoma (e.g., indolent NHL) (e.g., relapsed/refractory indolent NHL).

In some embodiments of any of the methods of treatment provided herein, the fusion polypeptide is supplied for use (e.g., intravenous administration) in a 100 mg/5 ml Type I clear glass vial sealed with a 20 mm Teflon coated rubber septum stopper and aluminum seal. In some embodiments, the fusion polypeptide is supplied for use (e.g., intravenous administration) in a 400 mg/20 ml Type I clear glass vial sealed with a 20 mm Teflon coated rubber septum stopper and aluminum seal. In some embodiments, the fusion polypeptide is stored in its original container at 2-8° C. (36-46° F.) until use (e.g., intravenous administration).

In some embodiments of any of the methods of treatment described herein, the polypeptide (e.g., fusion polypeptide comprising a SIRPα D1 domain variant and an Fc domain variant) is administered subcutaneously. In some embodiments, the polypeptide (e.g., fusion polypeptide) is administered via intravenous infusion. In some embodiments, the polypeptide (e.g., fusion polypeptide) is administered (e.g., via intravenous infusion) to the individual (e.g., human individual) at a dose of 0.3 mg/kg, 1.0 mg/kg, 3.0 mg/kg, 10.0 mg/kg, 15.0 mg/kg, or 30.0 mg/kg, including any range in between these values. In some embodiments, the polypeptide (e.g., fusion polypeptide) is administered (e.g., via intravenous infusion) to the individual weekly (i.e., once every 7 days or "qw"), e.g., at a dose of 0.3 mg/kg, 1.0 mg/kg, 3.0 mg/kg, 10.0 mg/kg, 15.0 mg/kg, or 30.0 mg/kg, including any range in between these values. In some embodiments, the polypeptide (e.g., fusion polypeptide) is administered to the individual (e.g., via intravenous infusion) every other week (i.e., once every 14 days or "q2w" or "QoW"), e.g., at a dose of 0.3 mg/kg, 1.0 mg/kg, 3.0 mg/kg, 10.0 mg/kg, 15.0 mg/kg, or 30.0 mg/kg, including any range in between these values. In some embodiments, on the days when the dosing schedules of the polypeptide (e.g., fusion polypeptide) and the therapeutic antibody (e.g., the anti-PD1 antibody (pembrolizumab), the anti-HER2 antibody (trastuzumab), or the anti-CD20 antibody (rituximab)) coincide, the polypeptide and the therapeutic antibody are administered sequentially. In some embodiments, the polypeptide (e.g., fusion polypeptide) is administered prior (e.g., about 30 minutes prior) to the therapeutic antibody. In some embodiments, in the event of a missed dose of the polypeptide, the therapeutic antibody is administered about 24 hours after the missed dose.

In some embodiments, the therapeutic response of an individual having NSCLC, HNSCC, gastric cancer or GEJ cancer to a method of treatment provided herein is assessed according to the RECIST version 1.1 criteria, e.g., as described in Therasse et al. (2000) *J Natl Cancer Inst.* 92: 205-216; Eisenhauer et al. (2009) *Eur J. Cancer.* 45: 229-247, the immune-related response criteria derived from RECIST 1.1 (irRECIST), e.g., as adapted from Nishino, et al. (2013) "Developing a Common Language for Tumor Response to Immunotherapy: Immune-Related Response Criteria Using Unidimensional Measurements." *Clinical Cancer Research* 19(14):3936-43. In some embodiments, the therapeutic response of an individual having aggressive lymphoma (e.g., aggressive NHL such as DLBCL or MCL) to a method of treatment provided herein is assessed according to the Lugano criteria, e.g., as described in Cheson et al. (2014) "Recommendations for Initial Evaluation, Staging and Response Assessment of Hodgkin and Non-Hodgkin Lymphoma: The Lugano Classification." *J. Clin Oncol.* 32: 3059-3067. In some embodiments, the therapeutic response of an individual having indolent lymphoma (e.g., indolent NHL such as FL or MZL) to a method of treatment provided herein is assessed according to the Lugano criteria (see Cheson et al 2014).

In some embodiments, the individual receiving treatment for HNSCC, NSCLC, gastric cancer, or GEJ cancer has at least one measurable lesion as defined by RECIST version 1.1 criteria, e.g., as described in Therasse et al. (2000) *J Natl Cancer Inst.* 92: 205-216; Eisenhauer et al. (2009) *Eur J Cancer.* 45: 229-247. In some embodiments, the individual receiving treatment for lymphoma (e.g., aggressive lymphoma (such as DLBCL or MCL) or indolent lymphoma (such as FL or MZL) has at least one measurable lesion as defined by Lugano criteria e.g., as described in Cheson et al. (2014) "Recommendations for Initial Evaluation, Staging and Response Assessment of Hodgkin and Non-Hodgkin Lymphoma: The Lugano Classification." *J. Clin Oncol.* 32: 3059-3067.

In some embodiments, the individual receiving treatment according to a method herein has adequate bone marrow function, renal function, liver function, and cardiac function. In some embodiments, the individual has an Eastern Cooperative Oncology Group (ECOG) Performance Status (PS) score of 0 or 1 (see, e.g., www(dot)npcrc(dot)org/files/news/ECOG)_performance_status(dot)pdf). In some embodiments, the individual does not have symptomatic central nervous system (CNS) metastases or leptomeningeal disease requiring steroids. In some embodiments, the individual receiving treatment for lung cancer according to a method herein (e.g., NSCLC) does not have ALK or EGFR genomic tumor aberrations. In some embodiments, an individual receiving treatment according to a method herein does not have a history of (non-infectious) pneumonitis that required steroids or has current pneumonitis. In some embodiments, the individual receiving treatment according to a method herein does not have high grade lymphoma (e.g., Burkitts lymphoma, lymphoblastic lymphoma, or Richter's transformation), chronic lymphocytic leukemia, or plasma cell leukemia. In some embodiments, the individual has not undergone high-dose chemotherapy requiring allogeneic stem cell rescue. In some embodiments, the individual receiving treatment for lung cancer (e.g., NSCLC), head and neck cancer (e.g., HNSCC), or gastric/GEJ cancer (e.g., HER2-positive gastric/GEJ adenocarcinoma) according to a method herein has not undergone prior irradiation to >25% of the bone marrow. In some embodiments, the individual has not received radiotherapy within 2 weeks of start of treatment. In some embodiments, the individual has not received prior treatment with any anti-CD47 or anti-SIRPα agent. In some embodiments, the individual has not received systemic anti-cancer therapy within 4 weeks of starting treatment (6 weeks for mitomycin C or nitrosoureas). In some embodiments, the individual does not have an intolerance to or has not had a severe allergic or anaphylactic reaction to antibodies or infused therapeutic protein(s) or any excipients in the formulation(s) comprising the therapeutic protein. In some embodiments, the individual has not discontinued treatment due to a Grade 3 or higher immune-related adverse event (AE) from prior therapy with an anti-PD-1, anti-PD-L1, or anti PD-L2 agent or with an agent aiming to modulate another immune cell target (e.g. CTLA-1, OX40, 41BB, etc.). In some embodiments, the individual has not received experimental antibodies or live vaccines (e.g., including, but not limited to vaccines for measles, mumps, rubella, varicella/zoster, yellow fever, rabies, *Bacillus* Calmette-Guérin (BCG), typhoid, and intranasal influenza vaccines). In some embodiments, the individual is not undergoing current active therapy for the primary diagnosis (e.g., lung cancer (NSCLC), head and neck cancer (HNSCC), gastric/GEJ cancer (HER2-positive gastric/GEJ adenocarcinoma), aggressive lymphoma (de novo DLBCL or transformed DLBCL or mantle cell lymphoma), or indolent lymphoma (e.g., indolent NHL, such as marginal zone lymphoma or follicular lymphoma). In some embodiments, the individual has not received a blood product transfusion within 14 days of the start of treatment. In some embodiments, the individual does not have a history of active autoimmune disorders (including but not limited to, e.g., Crohn's Disease, rheumatoid arthritis, scleroderma, systemic lupus erythematosus, Grave's disease, autoimmune hemolytic anemia, autoimmune thrombocytopenia) and other conditions that compromise or impair the immune system (other than hypogammaglobulinemia). In some embodiments, the individual does not have an active, uncontrolled, clinically significant bacterial, fungal, or viral infection, including hepatitis B (HBV), hepatitis C (HCV), known human immunodeficiency virus (HIV) or acquired immunodeficiency syndrome (AIDS)-related illness. In some embodiments, the individual does not have active graft versus host disease (GVHD) or is not undergoing immunosuppression therapy for GVHD. In some embodiments, the individual has not had any of the following in the previous 12 months: myocardial infarction, severe/unstable angina, coronary/peripheral artery bypass graft, symptomatic congestive heart failure, cerebrovascular accident, transient ischemic attack, deep venous thrombosis, or symptomatic pulmonary embolism. In some embodiments, the individual has not been diagnosed with any other malignancy within the last 3 years prior to the start of treatment, except for, e.g., adequately treated non-melanomatous skin cancer, or carcinoma in situ (e.g., breast carcinoma, cervical cancer in situ) that have undergone potentially curative therapy.

Kits and Articles of Manufacture

In another embodiment of the invention, an article of manufacture or a kit is provided comprising a polypeptide (e.g., a fusion polypeptide described herein) comprising a SIRPα D1 domain variant and an Fc domain variant. In some embodiments, the SIRPα D1 domain variant comprises the amino acid sequence selected from the group consisting of: SEQ ID NO: 81, SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, deG236, and N297A mutations, wherein numbering is according to the EU index of Kabat. In some embodiments, the Fc domain variant comprises the amino acid sequence of SEQ ID NO: 91. In some embodiments the polypeptide comprises the amino acid sequence of SEQ ID NO: 135 or SEQ ID NO: 136. In some embodiments, the polypeptide forms a homodimer. In some embodiments, the kit or article of manufacture is for use according to a method of treatment provided herein.

In some embodiments, the kit or article of manufacture further comprises an anti-PD1 antibody. In some embodiments, the anti-PD1 antibody is pembrolizumab. In some embodiments, the kit comprises a package insert or label with instructions for using the polypeptide (e.g., fusion polypeptide) in conjunction with the anti-PD1 antibody (e.g., pembrolizumab) to treat or delay progression of lung cancer (e.g., NSCLC, including metastatic NSCLC) in an individual according to a method herein. In some embodiments, the kit comprises a package insert or label with instructions for using the polypeptide (e.g., fusion polypeptide) in conjunction with the anti-PD1 antibody (e.g., pembrolizumab) to treat or delay progression of lung cancer (e.g., NSCLC, including metastatic NSCLC) in an individual has received prior therapy for NSCLC. In some embodiments, the individual has progressed (e.g., demonstrated disease progression) during (or following) a prior therapy (e.g., prior immune checkpoint inhibitor therapy) for lung cancer. In some embodiments, the individual has a PD-L1 tumor proportion score (TPS) of less than 50%. In some embodiments, the kit comprises a package insert or label with instructions for using the polypeptide (e.g., fusion polypeptide) in conjunction with the anti-PD1 antibody (e.g., pembrolizumab) to treat or delay progression of HNSCC in an individual according to a method herein. In some embodiments, the kit comprises a package insert or label with instructions for using the polypeptide (e.g., fusion polypeptide) in conjunction with the anti-PD1 antibody (e.g., pembrolizumab) to treat or delay progression of HNSCC in an individual who has received prior immune checkpoint inhibitor therapy (e.g., for HNSCC). In some embodiments, the kit comprises a package insert or label with instructions for using the polypeptide (e.g., fusion polypeptide) in conjunction with the anti-PD1 antibody (e.g., pembrolizumab) to treat or delay progression of HNSCC in an individual who has not received prior immune checkpoint inhibitor therapy (e.g., for HNSCC). In some embodiments, the kit comprises a package insert or label with instructions for using the polypeptide (e.g., fusion polypeptide) in conjunction with the anti-PD1 antibody (e.g., pembrolizumab) to treat or delay progression of head and neck cancer (e.g., HNSCC, including metastatic HNSCC) in an individual who has progressed (e.g., demonstrated disease progression) on (or following) a prior platinum therapy (e.g., a platinum-containing therapy). In some embodiments, the kit or article of manufacture further comprises instructions for administering the pembrolizumab at a dose of 200 mg every 3 weeks (Q3W) by IV infusion. In some embodiments, the kit or article of manufacture further comprises instructions for administering the polypeptide (e.g., fusion polypeptide) at a dose of 10 mg/kg every week (QW) by IV infusion.

In some embodiments, the kit or article of manufacture further comprises an anti-HER2 antibody. In some embodiments, the anti-HER2 antibody is trastuzumab. In some embodiments, the kit comprises a package insert or label with instructions for using the polypeptide (e.g., fusion polypeptide) in conjunction with the anti-HER2 antibody (e.g., trastuzumab) to treat or delay progression of HER2-positive gastric or HER2-positive GEJ cancer (e.g., HER2-positive gastric adenocarcinoma or HER2-positive GEJ adenocarcinoma) in an individual according to a method provided herein. In some embodiments, the kit comprises a package insert or label with instructions for using the polypeptide (e.g., fusion polypeptide) in conjunction with the anti-HER2 antibody (e.g., trastuzumab) to treat or delay progression of HER2-positive gastric or HER2-positive GEJ cancer (e.g., HER2-positive gastric adenocarcinoma or HER2-positive GEJ adenocarcinoma) in an individual who has progressed (e.g., demonstrated disease progression) while on (or following) a prior therapy for gastric or GEJ cancer. In some embodiments the prior therapy comprised anti-HER2 antibody and/or a prior fluoropyrimidine-based therapy. In some embodiments, the kit or article of manufacture further comprises instructions for administering the trastuzumab via intravenous infusion once every three weeks (q3W), wherein the initial dose of trastuzumab is 8 mg/kg and each subsequent dose of trastuzumab (i.e., following the initial dose) is 6 mg/kg. In some embodiments, the kit or article of manufacture further comprises instructions for administering the polypeptide (e.g., fusion polypeptide) at a dose of 10 mg/kg every week (QW) by IV infusion.

In some embodiments, the kit or article of manufacture further comprises an anti-CD20 antibody. In some embodiments, the anti-CD20 antibody is rituximab. In some embodiments, the kit comprises a package insert or label with instructions for using the polypeptide (e.g., fusion polypeptide) in conjunction with the anti-CD20 antibody (e.g., rituximab) to treat or delay progression of aggressive non-Hodgkin lymphoma or "NHL" (e.g., de novo DLBCL or transformed DLBCL, or mantle cell lymphoma) in an individual according to a method herein. In some embodiments, the kit comprises a package insert or label with instructions for using the polypeptide (e.g., fusion polypeptide) in conjunction with the anti-CD20 antibody (e.g., rituximab) to treat or delay progression of aggressive non-Hodgkin lymphoma or "NHL" (e.g., de novo DLBCL or transformed DLBCL, or mantle cell lymphoma) in an individual who has relapsed or was refractory to prior therapy (e.g., prior standard therapy/curative therapy) for aggressive NHL, or in an individual for whom there is no available therapy (e.g., curative therapy) for aggressive NHL. In some embodiments, the kit comprises a package insert or label with instructions for using the polypeptide (e.g., fusion polypeptide) in conjunction with the anti-CD20 antibody (e.g., rituximab) to treat or delay progression of indolent lymphoma (e.g., indolent NHL, such as marginal zone lymphoma or follicular lymphoma) in an individual according to a method herein. In some embodiments, the kit comprises a package insert or label with instructions for using the polypeptide (e.g., fusion polypeptide) in conjunction with the anti-CD20 antibody (e.g., rituximab) to treat or delay progression of indolent lymphoma (e.g., indolent NHL, such as marginal zone lymphoma or follicular lymphoma) in an individual who has relapsed or was refractory to prior therapy (e.g., prior standard therapy, e.g., curative therapy) for indolent lymphoma (e.g., indolent NHL), or in an individual for whom there is no available therapy (e.g., curative therapy) for indolent lymphoma (e.g., indolent NHL). In some embodiments, the kit or article of manufacture further comprises instructions for administering the rituximab to the individual at a dose of 375 mg/m$^2$ once a week (e.g., once every 7 days or "qw") for the first four weeks (e.g., 28 days) of treatment, and then administering the rituximab to the individual at a dose of 375 mg/m$^2$ once every four weeks (e.g., every 28 days or "q4w") for up to four additional doses following the first four doses, or for up to 8 additional doses following the first four doses. In some embodiments, the kit or article of manufacture further comprises instructions for administering the polypeptide (e.g., fusion polypeptide) at a dose of 10 mg/kg or 15 mg/kg every week (QW) by IV infusion.

In some embodiments of any of the kits or articles of manufacture provided herein, the polypeptide (e.g., fusion polypeptide) and the therapeutic antibody (e.g., pembrolizumab, trastuzumab, or rituximab) are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agents include, for example, bottles, vials, bags and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

Example 1: A Phase 1 Study of Drug A in Combination with Established Anticancer Antibodies in Patients with Advanced Malignancies This Example describes a Phase 1 clinical study that evaluated the safety, efficacy, pharmacodynamics (PD) and pharmacokinetics (PK) of Drug A in combination with pembrolizumab, trastuzumab, or rituximab for patients with advanced malignancies. Drug A is a fusion protein consisting of a high affinity CD47-binding SIRPα D1 domain variant fused to a human immunoglobulin Fc domain variant that is modified to eliminate binding to Fc gamma receptors (FIG. 1).

Study Objectives

Primary Objective

The primary objective of this study was to evaluate the safety and tolerability of Drug A administered once every week and/or every 2 weeks in combination with pembrolizumab, trastuzumab, or rituximab in patients with advanced malignancies including non-small cell lung cancer (NSCLC), head and neck squamous cell carcinoma (HN-SCC), HER2-overexpressing gastric cancer, and non-Hodgkin lymphoma (NHL).

Secondary Objectives

The secondary objectives of this study were:
To evaluate the anti-tumor effect of Drug A in combination with anti-cancer therapeutics in patients with advanced malignancies.
To evaluate the overall safety profile of Drug A in combination with other anti-cancer therapeutics.
To characterize the maximum tolerated dose (MTD)/optimal biological dose (OBD) of Drug A in combination with anti-cancer therapeutic agents.
To characterize the single and multiple dose pharmacokinetics of Drug A in combination with the anti-cancer therapeutics pembrolizumab, trastuzumab or rituximab.
To evaluate the immunogenicity of Drug A.

Exploratory Objectives

The exploratory objective of this study was to explore the pharmacodynamic effect of Drug A in combination with anti-cancer therapeutics in patients with advanced malignancies.

Patients

Inclusion Criteria

All patients met the following criteria for the dose escalation phase of the study:
Histological or cytological diagnosis of advanced/metastatic solid tumor malignancy or relapsed/refractory CD20$^+$ B Cell non Hodgkin lymphoma that:
Was resistant to standard therapy or for which no curative therapy was available; or
Met any criteria (a-d) for dose expansion described below
Lesions could be measurable or non-measurable.
All patients met the following criteria for the dose expansion phase of the study:
a) Locally advanced or metastatic NSCLC (TPS ≥1%) which had progressed on prior checkpoint therapy, OR Locally advanced or metastatic NSCLC (TPS <50%) that had progressed following systemic therapy for their metastatic disease; patients were suitable for treatment with pembrolizumab; Or
b) Recurrent or metastatic HNSCC with disease progression on or after platinum-containing chemotherapy and were suitable for treatment with pembrolizumab; Or
c) HER2 overexpressing metastatic gastric or gastroesophageal junction (GEJ) adenocarcinoma that had progressed following systemic therapy with a fluoropyrimidine-containing regimen and/or therapy with an anti-HER2 antibody for their metastatic disease and were suitable for treatment with trastuzumab;
d) Relapsed or refractory, de novo or transformed diffuse large B-cell lymphoma (DLBCL), or mantle cell lymphoma for which no curative therapy was available; OR indolent lymphoma (Marginal zone, follicular,) that was relapsed or refractory to standard approved therapies.
Patients had at least one measurable lesion as defined by RECIST version 1.1 or Lugano criteria (2014).
In addition, all patients met the following criteria:
Adequate Bone Marrow Function, including:
Absolute Neutrophil Count (ANC) ≥1,500/mm$^3$ (≥1.5× 10$^9$/L); Non Hodgkin lymphoma, only, ANC ≥1,000/mm$^3$ (≥1.0×10$^9$L);
Platelets ≥75,000/mm$^3$ (≥75×10$^9$/L); Non Hodgkin lymphoma only: Platelets ≥50,000/mm$^3$ (≥50×10$^9$);
Hemoglobin ≥9 g/dL (≥90 g/L); Non Hodgkin lymphoma only: Hemoglobin ≥8 g/dL (≥80 g/L).
Adequate Renal Function, including:
Serum creatinine ≤1.5× upper limit of normal (ULN) or estimated creatinine clearance ≥60 mL/min as calculated using the method standard for the institution.
Adequate Liver Function, including:
Total serum bilirubin ≤1.5×ULN (≤3.0×ULN if the patient had documented Gilbert syndrome);
Aspartate and Alanine transaminase (AST and ALT) ≤3.0×ULN; ≤5.0×ULN if there was liver involvement secondary to tumor;
Alkaline phosphatase ≤2.5×ULN (≤5.0×ULN if bone or liver metastasis).
QT interval corrected for heart rate Fridericia's (QTcF) interval of ≤480 msec (based upon mean value from triplicate ECGs).
Age ≥18 years.
Eastern Cooperative Oncology Group (ECOG) Performance Status (PS) was 0 or 1.
Resolved acute effects of any prior therapy to baseline severity or Grade ≤1 (NCI CTCAE v.4.03) except for AEs not constituting a safety risk by Investigator judgment.
Available archival (or fresh) metastatic biopsy sample prior to study entry (expansion phase only).
Serum pregnancy test (for females of childbearing potential) negative at screening.

Exclusion Criteria

Patients with any of the following characteristics were not included in this study:
Patients with known symptomatic CNS metastases or leptomeningeal disease requiring steroids. Patients with previously diagnosed brain metastases were eligible if they completed their treatment and recovered from the acute effects of radiation therapy or surgery prior to study entry, discontinued corticosteroid treatment for these metastases and were clinically stable off anticonvulsants for at least 4 weeks and were neurologically stable before enrollment.
Patients with ALK or EGFR genomic tumor aberrations (NSCLC, Part 2 expansion only), or any patient with a history of (non-infectious) pneumonitis that required steroids or had current pneumonitis.
Patients with high grade lymphoma (including Burkitts lymphoma, lymphoblastic lymphoma, Richter's transformation), CLL or plasma cell leukemia
Previous high-dose chemotherapy requiring allogeneic stem cell rescue.
Prior irradiation to >25% of the bone marrow (non-lymphoma patients only), or any patient who received prior radiotherapy within 2 weeks of start of study treatment. Note: Participants must have recovered from all radiation-related toxicities, did not require corticosteroids, and not have had radiation pneumonitis. A 1-week washout was permitted for palliative radiation (≤2 weeks of radiotherapy) to non-CNS disease.

Prior treatment with any anti-CD47 or anti-SIRPα agent.

Systemic anti-cancer therapy within 4 weeks of starting study treatment (6 weeks for mitomycin C or nitrosoureas). If systemic anti-cancer therapy was given within 4 weeks, patient was included if 4-5 times elimination half-life of the drug had passed.

Prior treatment with (Expansion phase only):
  A PD-1 or PD-L1 inhibitor (NSCLC; HNSCC) for metastatic disease with disease progression within 8 weeks of initiation.
  Trastuzumab (Gastric/GEJ Cancer) for metastatic disease with disease progression as the best response.

Patients with intolerance to or who had a severe allergic or anaphylactic reaction to antibodies or infused therapeutic proteins, or patients who had a severe allergic or anaphylactic reaction to any of the substances included in the study drug (including excipients); or who discontinued treatment due to a Grade 3 or higher immune related AE from prior therapy with an anti-PD-1, anti-PD-L1, or anti PD-L2 agent or with an agent aiming to modulate another immune cell target (e.g., CTLA-1, OX40, 41BB, etc.).

Any experimental antibodies or live vaccines in the last 28 days prior to the first dose of study drug. Live attenuated vaccines were not allowed.

Current active therapy for the primary diagnosis.

Blood product transfusions within 14 days of Cycle 1 Day 1.

History of (or active) autoimmune disorders (including but not limited to: Crohn's Disease, rheumatoid arthritis, scleroderma, systemic lupus erythematosus, Grave's disease) and other conditions that compromise or impair the immune system (with the exception of hypogammaglobulinemia).

History of autoimmune hemolytic anemia or autoimmune thrombocytopenia.

Patients with active, uncontrolled, clinically significant bacterial, fungal, or viral infection, including hepatitis B (HBV), hepatitis C (HCV), known human immunodeficiency virus (HV) or acquired immunodeficiency syndrome (AIDS)-related illness.

Patients with active graft versus host disease (GVHD) or ongoing immunosuppression for GVHD.

Any of the following in the previous 12 months: myocardial infarction, severe/unstable angina, coronary/peripheral artery bypass graft, symptomatic congestive heart failure, cerebrovascular accident, transient ischemic attack, deep venous thrombosis, or symptomatic pulmonary embolism.

Current active treatment in another interventional therapeutic clinical study.

Diagnosis of any other malignancy within the last 3 years prior to enrollment except for adequately treated non-melanomatous skin cancer, or carcinoma in situ (e.g., breast carcinoma, cervical cancer in situ) that underwent potentially curative therapy.

Other severe acute or chronic medical or psychiatric condition, including recent (within the past year) or active suicidal ideation or behavior, or laboratory abnormality that increased the risk associated with study participation or investigational product administration or interfered with the interpretation of study results and, in the judgment of the Investigator, made the patient inappropriate for entry into this study.

Males and females of childbearing potential not using highly effective contraception or not having agreed to continue highly effective contraception for at least 90 days after last dose of investigational product.

Patients who were pregnant or breastfeeding.

Study Treatment

Figure 2:
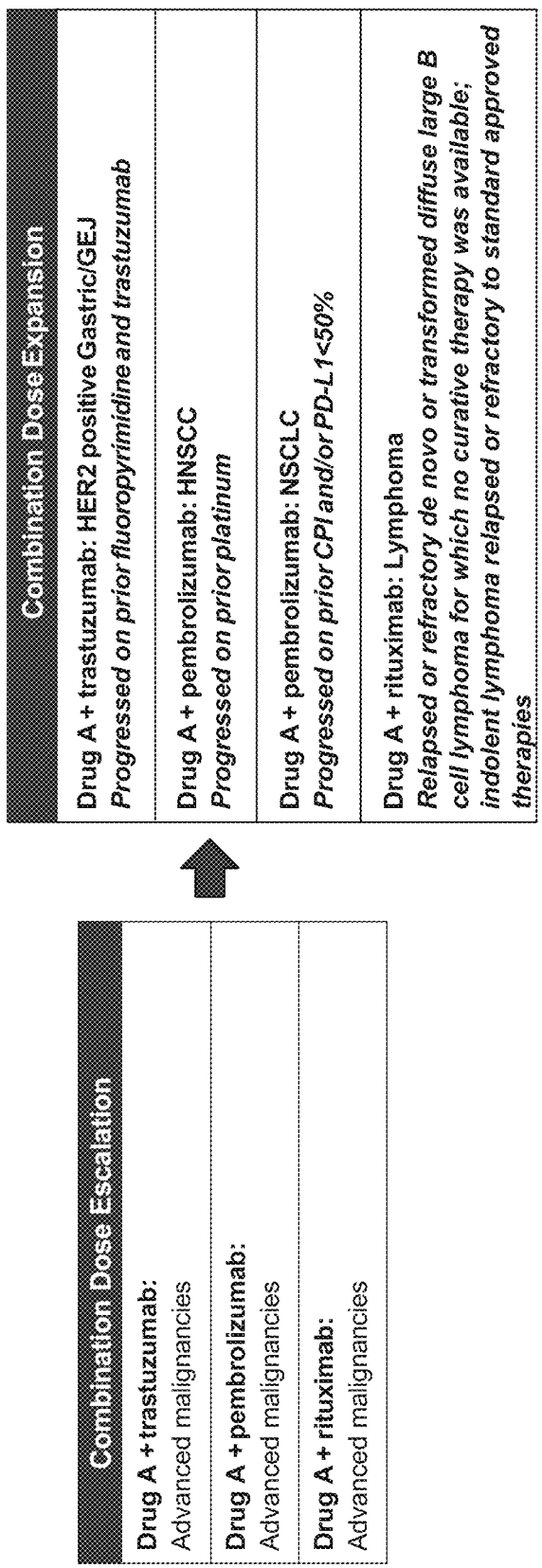
FIG. 2 provides a schematic of the clinical study described in Example 1.

As shown in FIG. 2, this study had three treatment arms (DrugA+pembrolizumab; Drug A+trastuzumab; DrugA+rituximab). The study included an initial dose escalation portion followed by a dose expansion portion. Each dose escalation group had approximately 12 advanced malignancy patients. Each expansion group had approximately 20-40 patients at multiple sites.

Drug A was administered weekly (or every 2 weeks) as an IV infusion over approximately 60 minutes on an outpatient basis. The use of an infusion pump was the preferred method of administration to ensure accurate delivery of the investigational product, but gravity drips were allowed.

Drug A was supplied in either a 100 mg/5 mL or 400 mg/20 mL Type 1 clear glass vial, sealed with a 20 mm Teflon coated rubber serum stopper and a tamper-evident aluminum seal. Each single use vial delivers 100 mg Drug A (5 mL) or 400 mg Drug A (20 mL) and is intended for intravenous (IV) administration.

A cycle was defined as the time from the Day 1 dose to the next Day 1 dose. If there were no treatment delays, a cycle was 21 days for the weekly dosing and 28 days for the dosing every 2 weeks.

All trial treatments were administered on an outpatient basis. Patients were observed in the clinic for at least 2 hours after infusion of Drug A on day 1 of cycle 1(C1D1) and as clinically indicated thereafter.

No premedication for Drug A was required. Guidelines in the pembrolizumab, trastuzumab and rituximab combination therapy package inserts were followed.

In the dose escalation and expansion phases, the combination partner therapy was administered according to its label instructions:
  Trastuzumab: Initial dose of 8 mg/kg administered as an intravenous infusion over 90 minutes, followed by 6 mg/kg intravenous infusion (IV) administered over 30 to 90 minutes every 3 weeks.
  Pembrolizumab: 200 mg IV administered as an intravenous infusion over 30 minutes every 3 weeks for up to 24 months.
  Rituximab: 375 mg/m$^2$ administered as an intravenous infusion once weekly for 4 doses followed by once monthly for 8 doses (initiated at a rate of 50 mg/hr and increased by 50 mg/hr increments every 30 minutes, to a maximum of 400 mg/hr in the absence of infusion toxicity). If the first infusion of rituximab was tolerated, subsequent infusions were started at a rate of 100 mg/hr and increased by 100 mg/hr increments at 30-minute intervals, to a maximum of 400 mg/hr in the absence of toxicity.

On administration days when dosing schedules coincided, the combination partner commenced approximately 30 minutes after Drug A therapy finished. On such days, in the event of a missed dose of the Drug A drug due to toxicity, the partner drug was administered 24 hours after the missed dose. In the event the Drug A was permanently discontinued, the patient was discontinued from the treatment phase of the study. In the event that the partner drug was permanently discontinued, the patient continued single agent Drug A for up to 24 months if in the investigator's opinion, the patient was deriving clinical benefit from Drug A.

Dose Escalation Component

For Drug A, the initial dose escalation component began one dose level below the single agent maximum tolerated dose (MTD) or maximum administered dose (MAD) (3-6 patients in each dose level) taking into account the observed Drug A single agent dose limiting toxicity (DLT) profile and known safety profile of the proposed combination agent (Table A). If the Drug A dose was safe and well tolerated in combination, then the dose level of Drug A was increased to the MTD or MAD with the combination agent.

No MTD for Drug A as a single agent has been reached. The MAD for Drug A as a single agent was 30 mg/kg administered IV every other week (QOW or Q2W)

TABLE A

Dose escalation for Drug A.

| Cohort | Dosage mg/kg | Route of Administration | Frequency of Dosing |
|---|---|---|---|
| 1 | 0.3 | IV | Once a week |
| 2 | 1.0 | IV | Once a week |
| 3 | 3.0 | IV | Once a week |
| 4 | 10.0 | IV | Once a week |
| 5 | 30.0 | IV | Once every 2 weeks |

Expansion Phase

Drug A was administered once per week (QW) at a dose of 10 mg/kg as an intravenous (IV) infusion over approximately 60 minutes on an outpatient basis.

In the expansion phase, the combination partner therapy was administered according to its label instructions, as described above.

The DrugA+pembrolizumab expansion group included up to 20 patients with metastatic NSCLC and up to 20 patients with recurrent or metastatic head and neck squamous cell carcinoma.

The DrugA+trastuzumab expansion group included up to 20 patients with HER2-overexpressing (HER2 positive) gastric carcinoma.

The DrugA+rituximab expansion group included approximately 10 patients with relapsed or refractory, diffuse large B cell lymphoma, and approximately 10 patients with indolent lymphoma.

Each patient received Drug A until disease progression, unacceptable toxicity, withdrawal of consent, or study termination. Patients received study therapy on study after radiographic progression if, in the estimation of the Investigator, the patient was deriving clinical benefit from the study treatment.

Efficacy Analyses

Overall response rate (ORR), disease control rate (DCR), duration of response (DoR), progression free survival (PFS), and overall survival (OS) were analyzed in the ITT population and Evaluable Population.

The objective tumor response was evaluated using the using the Response Evaluation Criteria in Solid Tumors (RECIST) version 1.1 for solid tumors. Tumor assessments included all known or suspected disease sites. Imaging included chest, abdomen and pelvis CT or MRI scans; brain CT or MRI scan for patients with known or suspected brain metastases; bone scan and/or bone x-rays for patients with known or suspected bone metastases. In addition, for lymphoma patients, tests included PET scans and bone marrow evaluation. The same imaging technique used to characterize each identified and reported lesion at baseline was employed in the following tumor assessments.

Antitumor activity was assessed through radiological tumor assessments conducted at baseline, during treatment, whenever disease progression was suspected (e.g., symptomatic deterioration), and at the time of withdrawal from the study (if not done in the previous 6 weeks).

Assessment of response was made using RECIST version 1.1 or, where relevant, the Lugano Criteria (Cheson et al., J. Clin. Oncol (2014) 32:27: 3059-3068.).

Changes in tumor size were categorized as complete response (CR), partial response (PR), stable disease (SD), or progressive disease (PD), the latter incorporating the appearance of new lesions. In the expansion cohorts, a secondary analysis was carried out using the Immune-Related RECIST 1.1. To facilitate this secondary analysis, in expansion cohorts, only, the diameters (longest for non-nodal lesions, shortest for nodal lesions) of all target and new measurable lesions were collected. Additionally, in the expansion cohorts, confirmation of both progression and response by imaging at least 4 weeks from the date first documented was required.

PK/PD and Biomarker Analyses

Drug concentrations of Drug A were measured using validated methods. Drug A serum concentrations were analyzed using a validated ligand binding ELISA. PK parameters were determined from the respective concentration-time data using standard noncompartmental methods. Actual sample collection times were used for the parameter calculations. For Drug A, PK parameters including maximum concentration ($C_{max}$), time to maximum concentration ($T_{max}$), area under the concentration-time curve ($AUC_{last}$, $AUC_{inf}$ and/or $AUC_t$) were calculated. As appropriate, additional PK parameters including clearance (CL), volume of distribution (Vz), terminal elimination half-life ($t_{1/2}$), and accumulation ratio ($R_{ac}$) were calculated.

PK/PD analyses were conducted to explore the exposure-response relationship using appropriate model-based methods to assist OBD determination. Pharmacodynamic data (receptor occupancy and immunophenotyping) were summarized graphically and with descriptive statistics by time and dose.

PK/PD analysis using appropriate model-based methods were explored to better understand the exposure-response relationship. Pre- and post-dose levels of CD47 target occupancy were analyzed and immunophenotyping of circulating leukocyte population was performed. CD47 target occupancy in peripheral blood T lymphocytes and erythrocytes was measured by flow cytometry. Infiltrating leukocyte populations and immune-modulatory molecules in tumor biopsy tissue before and after treatment, and specific cytokines and chemokines in serum before and after treatment were analyzed. Exploratory molecular analysis (including but not limited to additional immune markers) in peripheral blood and tumor biopsy samples was performed before and after treatment.

CD8, CD68, CD163, and PD-L1 on tumor tissue were measured by immunohistochemistry (IHC) assays. Percent positive values for CD8, CD68, and CD163 were obtained by image analysis. PD-L1 (Clone 22C3) tumor proportion score (TPS) and combined positive score (CPS) were obtained by pathologist review. HER2 levels were determined using HERCEPTEST™. RNA expression from paired tumor biopsies were assessed using NANOSTRING IO360™ expression panel. Cell type abundance and pathway profiling analyses using pre-defined gene signatures were performed using NANOSTRING nSOLVER™ analysis software.

Blood samples were collected at the Baseline visit and retained for pharmacogenomic analyses related to drug response. For example, SIRPα gene polymorphisms, putative safety biomarkers, drug metabolizing enzyme genes, drug transport protein genes, or genes thought to be related to the mechanism of drug action are examined.

Results

Patient Characteristics

Eighty-two patients with advanced solid tumor malignancies were enrolled in this study. The patient baseline characteristics are provided in Table B.

TABLE B

Patient baseline characteristics

| | | Trastuzumab n = 30 | Pembrolizumab N = 52 |
|---|---|---|---|
| Primary Disease, n | Gastric/GEJ/Esophageal | 25 | — |
| | HNSCC | — | 20 |
| | NSCLC | — | 26 |
| | Breast | 2 | — |
| | Colorectal | — | 2 |
| | Ovarian | 1 | 2 |
| | Pancreatic | 1 | — |
| | Peritoneal | — | 1 |
| | Appendiceal | — | 1 |
| | Urothelial | 1 | — |
| Median age, years (range) | | 58 (45-79) | 61 (32-81) |
| Sex, n | F | 9 | 23 |
| | M | 21 | 29 |
| Race, n | White | 13 | 34 |
| | Asian | 14 | 11 |
| | Other | 3 | 7 |
| ECOG PS, n | 0 | 8 | 16 |
| | 1 | 22 | 36 |

Safety

Drug A in combination with trastuzumab or pembrolizumab was well tolerated, and most treatment-related adverse events (TRAE) were of low grade and frequency. Treatment-related adverse events occurring in two or more patients are provided in Table C for the Drug A+trastuzumab combination, and in Table D for the DrugA+pembrolizumab combination. The most frequent TRAEF in the DrugA+trastuzumab combination was fatigue (26.70%). The most frequent TRAEF the DrugA+pembrolizumab combination was AST increased (154).

TABLE C

Treatment-related adverse events that occurred in two or more patients treated with the Drug A + trastuzumab combination.
Treatment Related Adverse Events
Drug A + Trastuzumab (N = 30)

| Adverse Event | Total n (%) | ≥Grade 3 |
|---|---|---|
| Fatigue | 8 (26.7) | |
| Platelets decreased | 4 (13.3) | 2 (6.7) |
| Decreased appetite | 3 (10) | |
| Pyrexia | 3 (10) | |
| Anemia | 2 (6.7) | |
| Nausea | 2 (6.7) | |
| Neutropenia | 2 (6.7) | 2 (6.7) |

TABLE D

Treatment-related adverse events that occurred in two or more patients treated with the Drug A + pembrolizumab combination.
Treatment Related Adverse Events
Drug A + Pembrolizumab (N = 52)

| Adverse Event | Total n (%) | ≥Grade 3 |
|---|---|---|
| AST Increased | 8 (15.4) | |
| ALT Increased | 7 (13.5) | 1 (1.9) |
| Fatigue | 6 (11.5) | |
| Pruritus | 5 (9.6) | |
| Anemia | 4 (7.7) | 1 (1.9) |
| Infusion reaction | 4 (7.7) | |
| Platelets decreased | 4 (7.7) | 2 (3.8) |
| Alkaline phosphatase increased | 3 (5.7) | |
| Arthralgia | 3 (5.8) | |
| Pyrexia | 3 (5.8) | |
| WBC decreased | 3 (5.8) | |
| Decreased appetite | 2 (3.8) | |
| Myalgia | 2 (3.8) | |
| Nausea | 2 (3.8) | |
| Neutropenia | 2 (3.8) | 1 (1.9) |
| Rash | 2 (3.8) | |

TRAEs of Grade 3 severity were of low frequency. In the DrugA+trastuzumab combination, one treatment-related serious adverse event of febrile neutropenia was reported. In the DrugA+pembrolizumab combination, three treatment-related serious adverse events were reported: one autoimmune hemolytic anemia, one febrile neutropenia, and one neutropenia.

Efficacy

Dose Escalation

The dose escalation component had a total of 22 patients. In the DrugA+trastuzumab combination cohort (n=10), of the 8 evaluable patients, 3 exhibited stable disease (SD) (2 patients had breast cancer, 1 patient had GEJ). In the DrugA+pembrolizumab combination cohort (n=12), of the 10 evaluable patients, 1 exhibited a partial response (PR) (NSCLC that was CPI refractory) and 3 exhibited stable disease (1 patient had appendiceal cancer, 2 patients had NSCLC).

Dose Expansion

The dose expansion phase had a total of 60 patients.

Figure 3A:
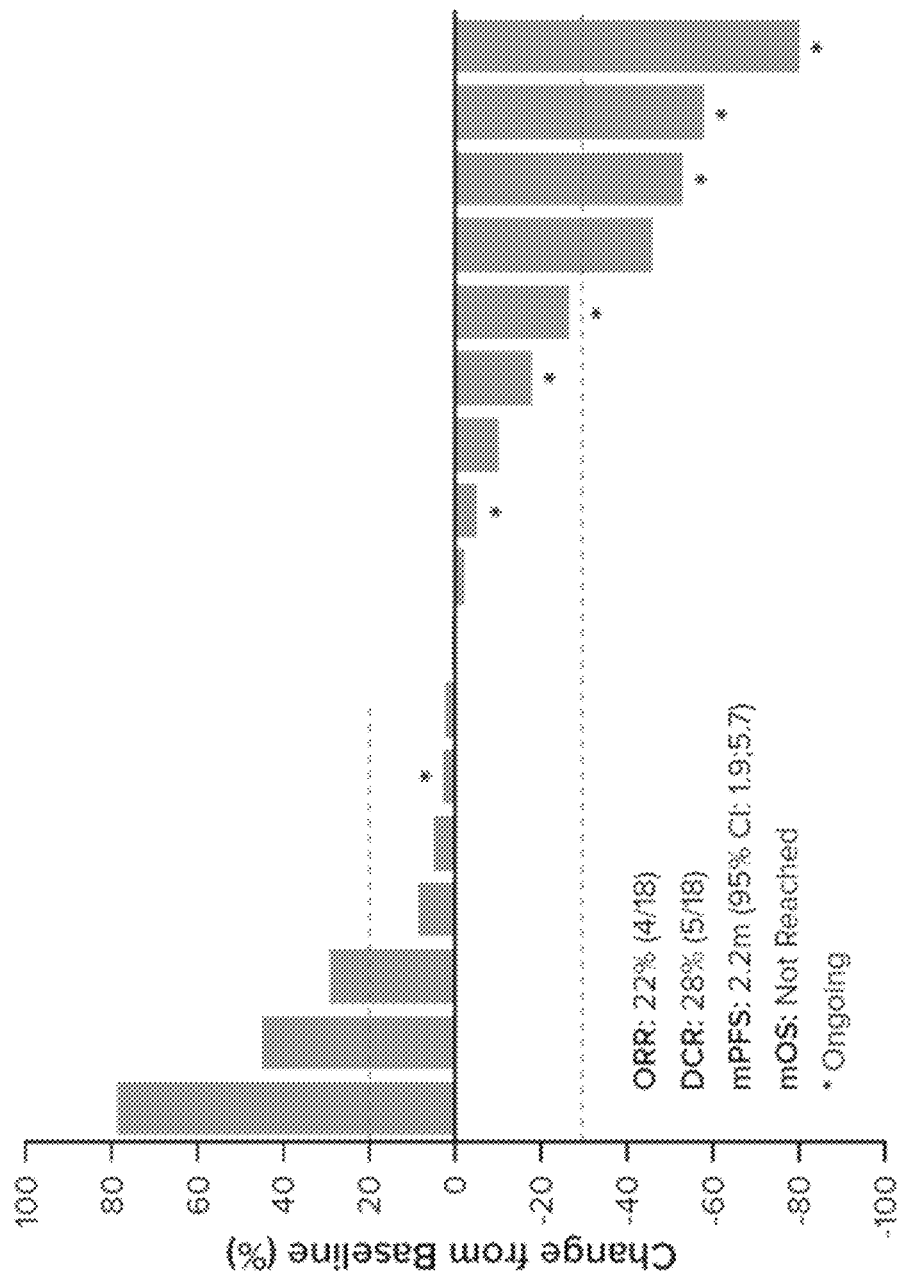
FIGS. 3A-3C show the clinical activity of Drug A+trastuzumab in the HER2 positive gastric/GEJ cancer expansion cohort.
Figure 3B:
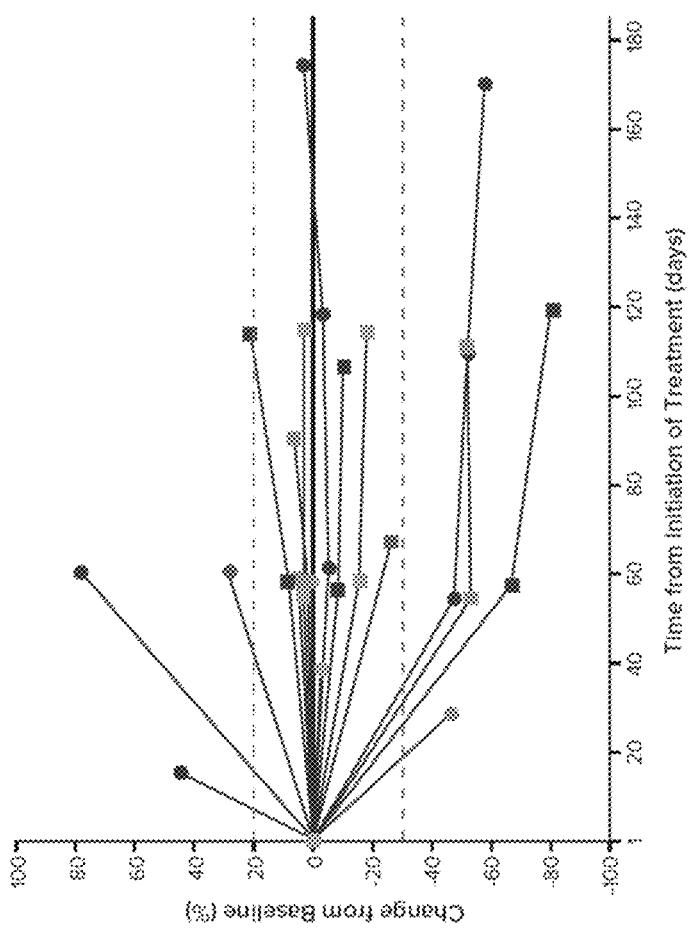
Figure 3C:
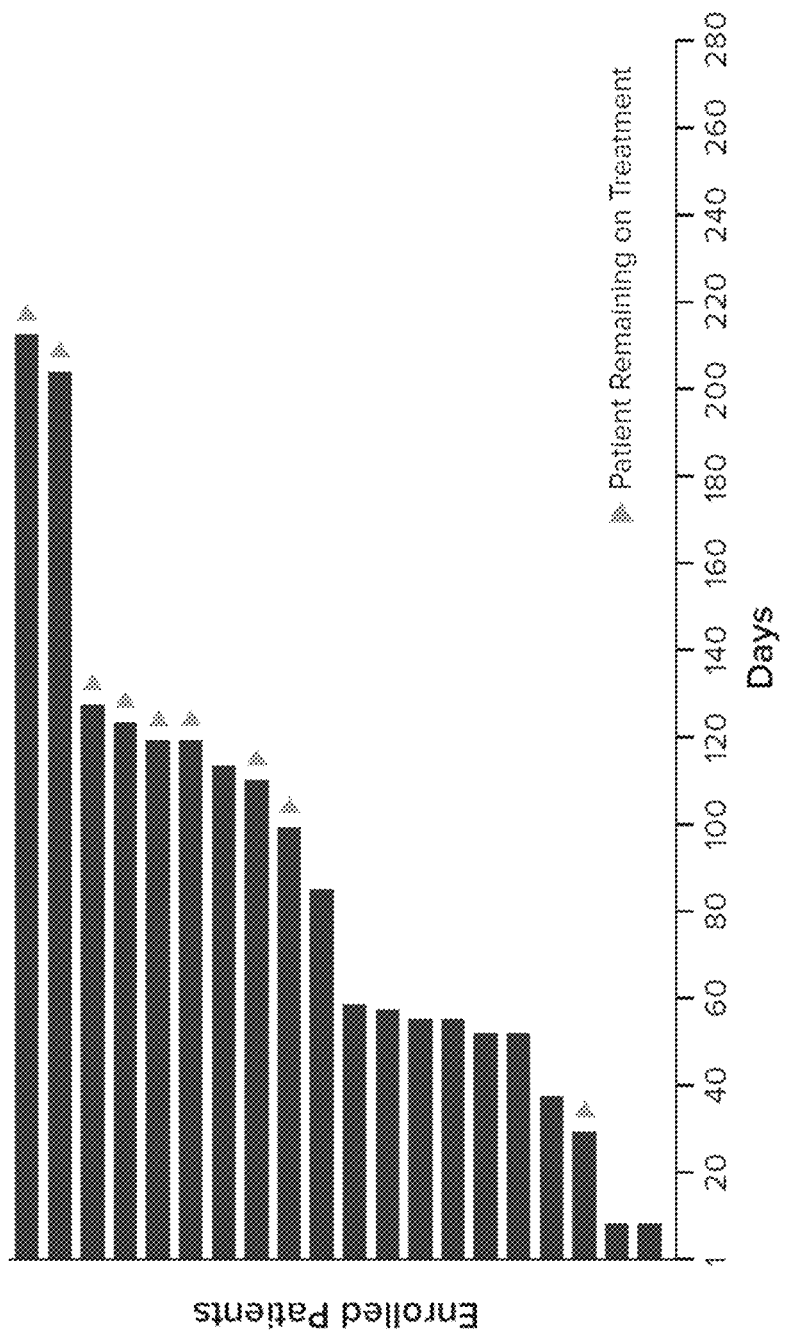

DrugA+trastuzumab combination cohort with HER2 positive gastric GEJ cancer (n=20): Of the 18 evaluable patients, 4 exhibited partial response (confirmed) and 5 exhibited stable disease. FIG. 3A provides the percent change of disease assessment from baseline. The ORR was 22%, the DCR was 28% and the mPFS was 2.2 months. FIG. 3B provides the percent change of disease assessment from baseline for each patient over the study period. FIG. 3C provides the duration of treatment for enrolled patients in this cohort. Tumors were assessed according to the Response Evaluation Criteria in Solid Tumors (RECIST) version 1.1 (E. A. Eisenhauer, et al., European Journal of Cancer 45 (2009) 228-247.)

Figure 4A:
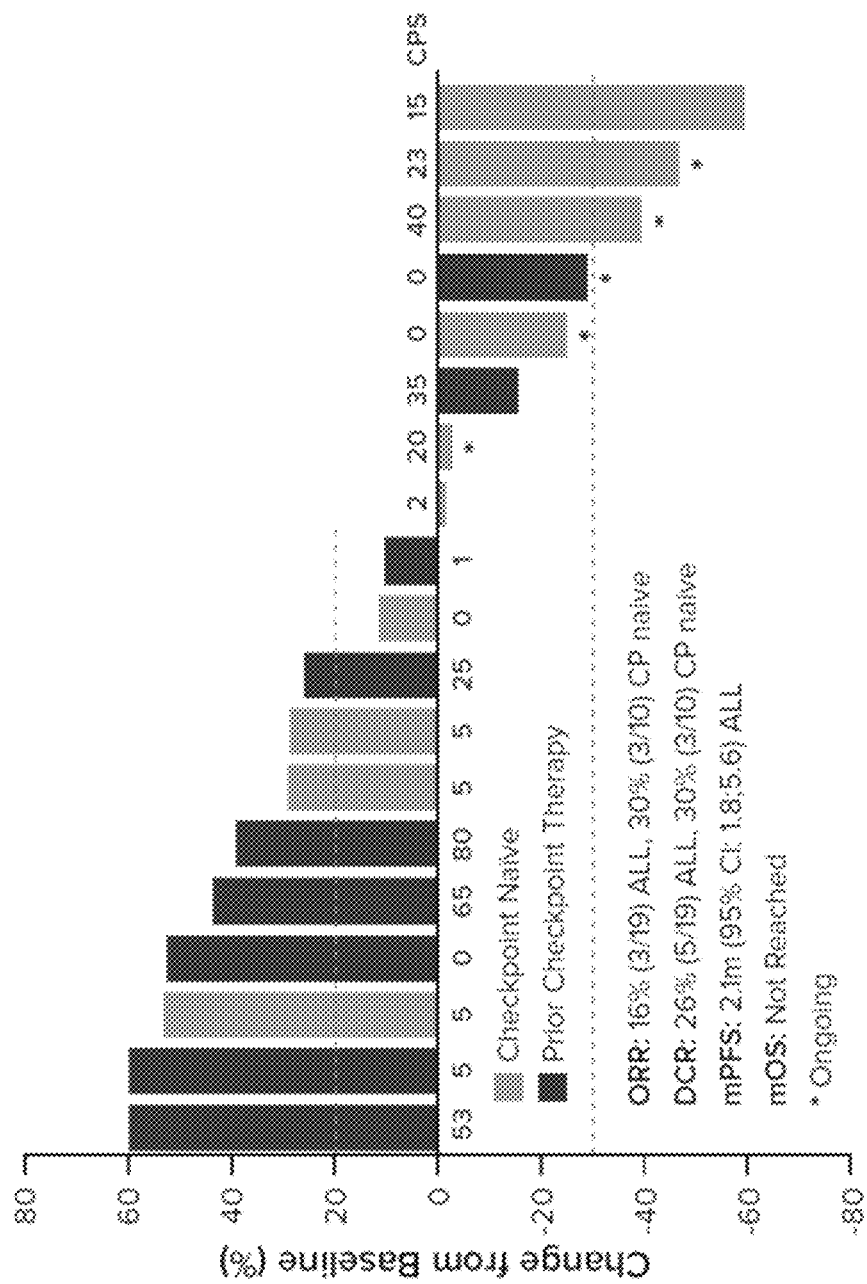
FIGS. 4A-4C show the clinical activity of Drug A+pembrolizumab in the HNSCC expansion cohort.
Figure 4B:
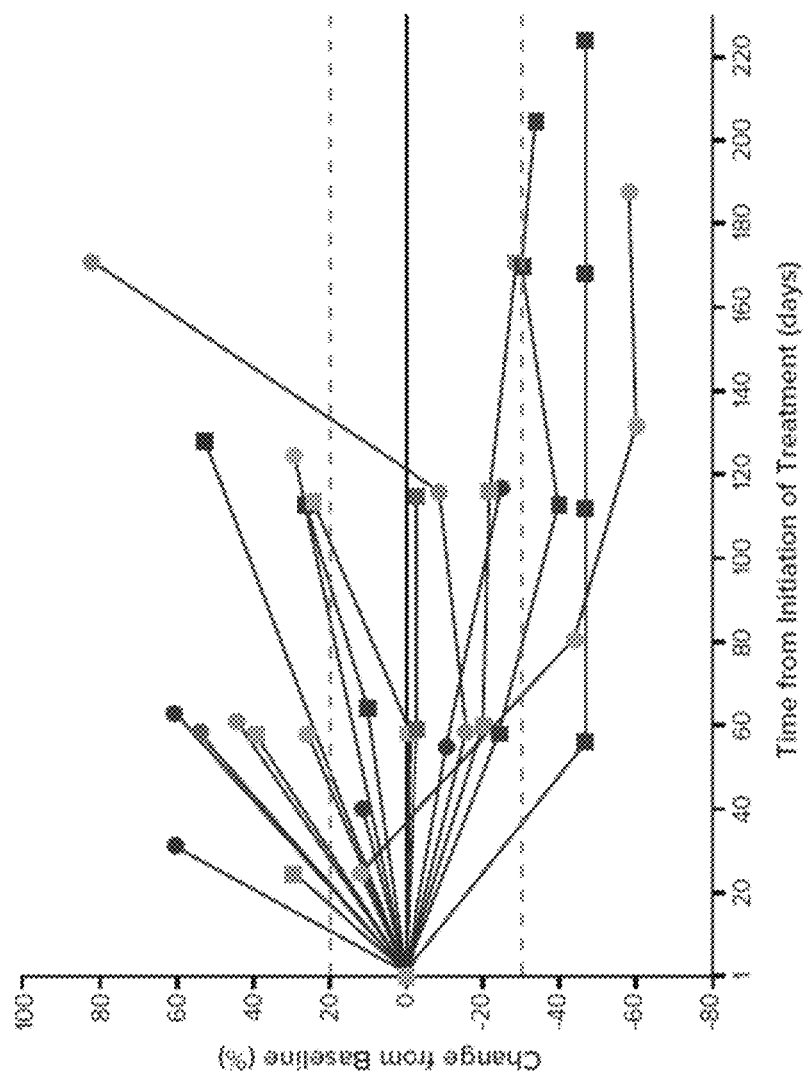
Figure 4C:
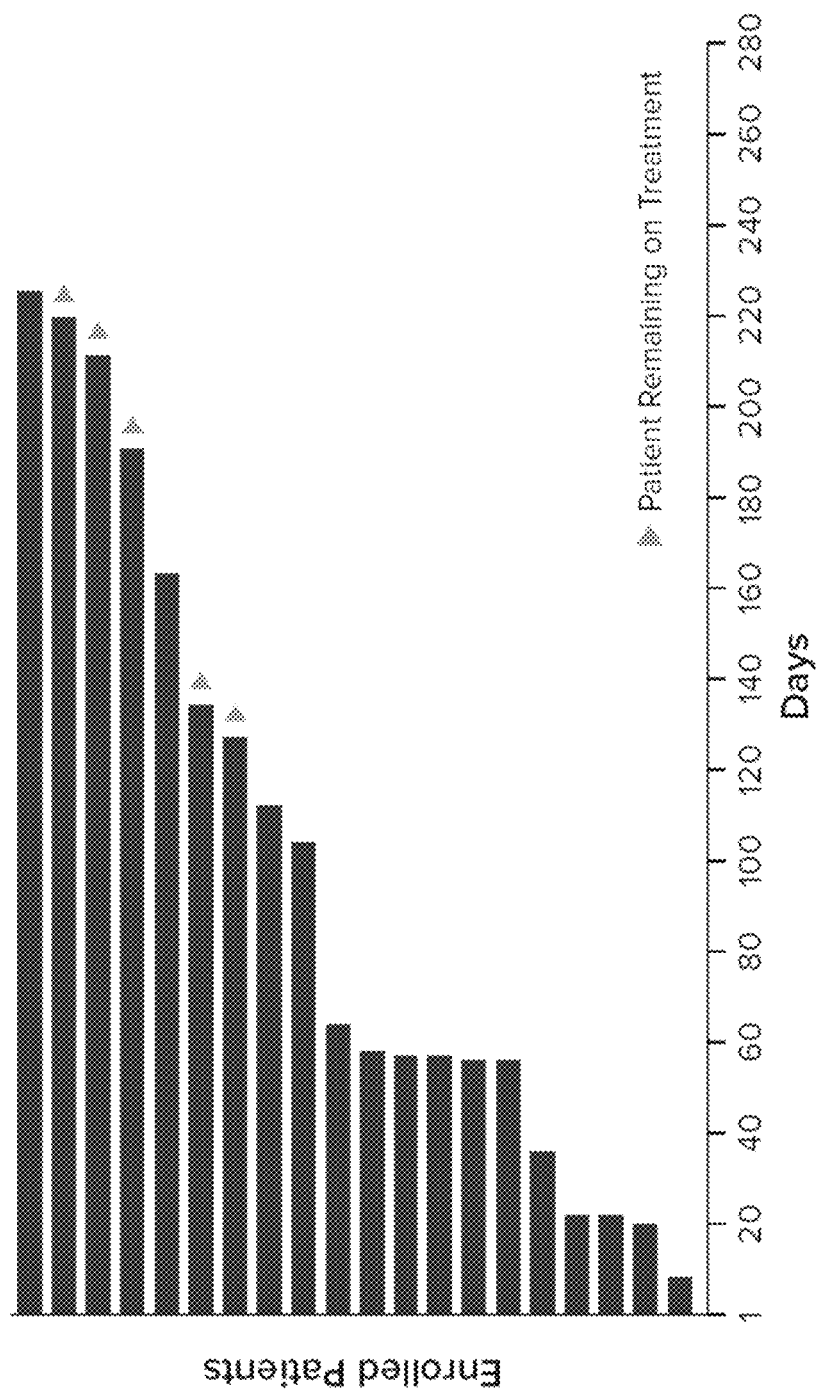

DrugA+pembrolizumab combination cohort with HNSCC (n=20): Of the 19 evaluable patients, 3 exhibited a partial response (2 confirmed, 1 unconfirmed), and 6 exhibited stable disease. FIG. 4A provides the percent change of disease assessment from baseline. The ORR was 16% for all patients, and 30% for checkpoint therapy naïve patients; the DCR was 26% for all patients, and 30% for checkpoint therapy naïve patients; and the mPFS was 2.1 months for all patients. In addition, the combined positive score (CPS) for PD-L1 staining is reported for each patient. FIG. 4B provides the percent change of disease assessment from baseline for each patient over the study period. FIG. 4C provides the duration of treatment for enrolled patients in this cohort. Tumors were assessed according to the Response Evaluation Criteria in Solid Tumors (RECIST) version 1.1 (E. A. Eisenhauer, et al., European Journal of Cancer 45 (2009) 228-247.)

Figure 5A:
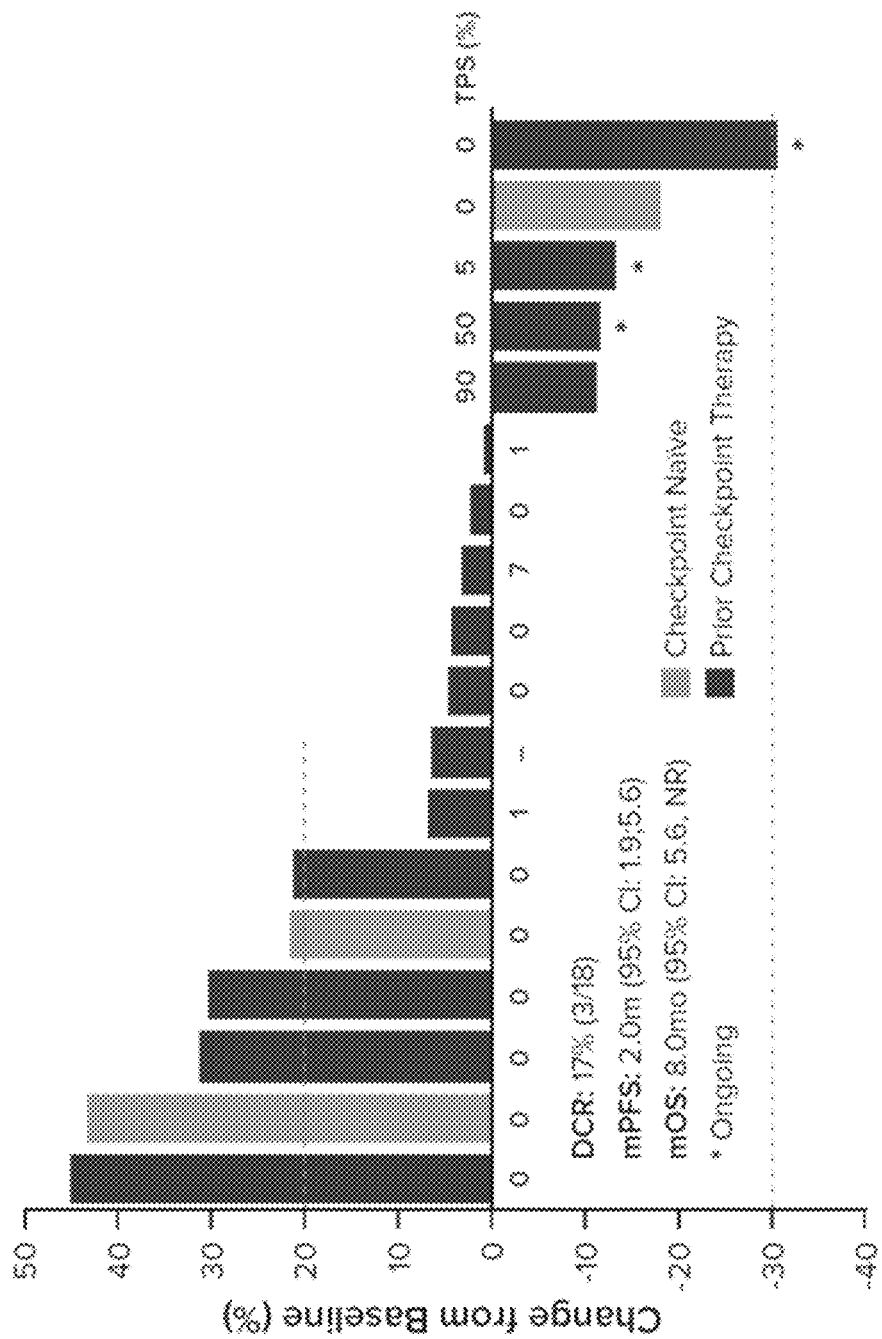
FIGS. 5A-5C show the clinical activity of Drug A+pembrolizumab in the NSCLC expansion cohort.
Figure 5B:
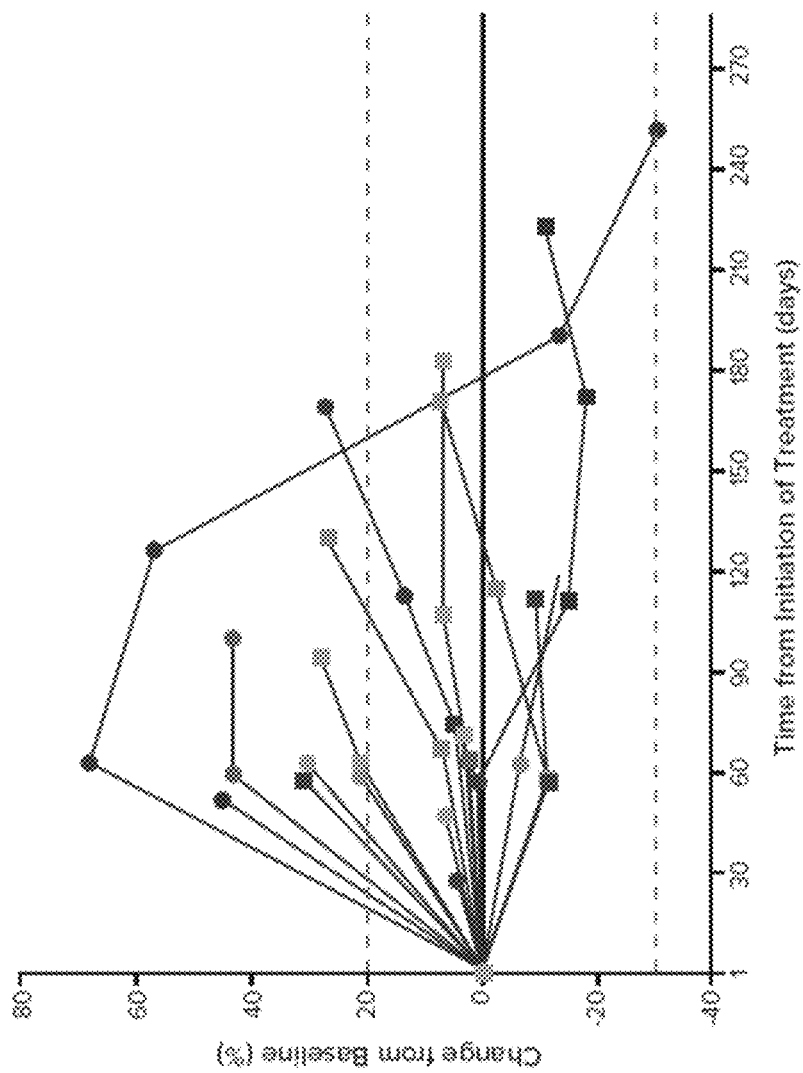
Figure 5C:
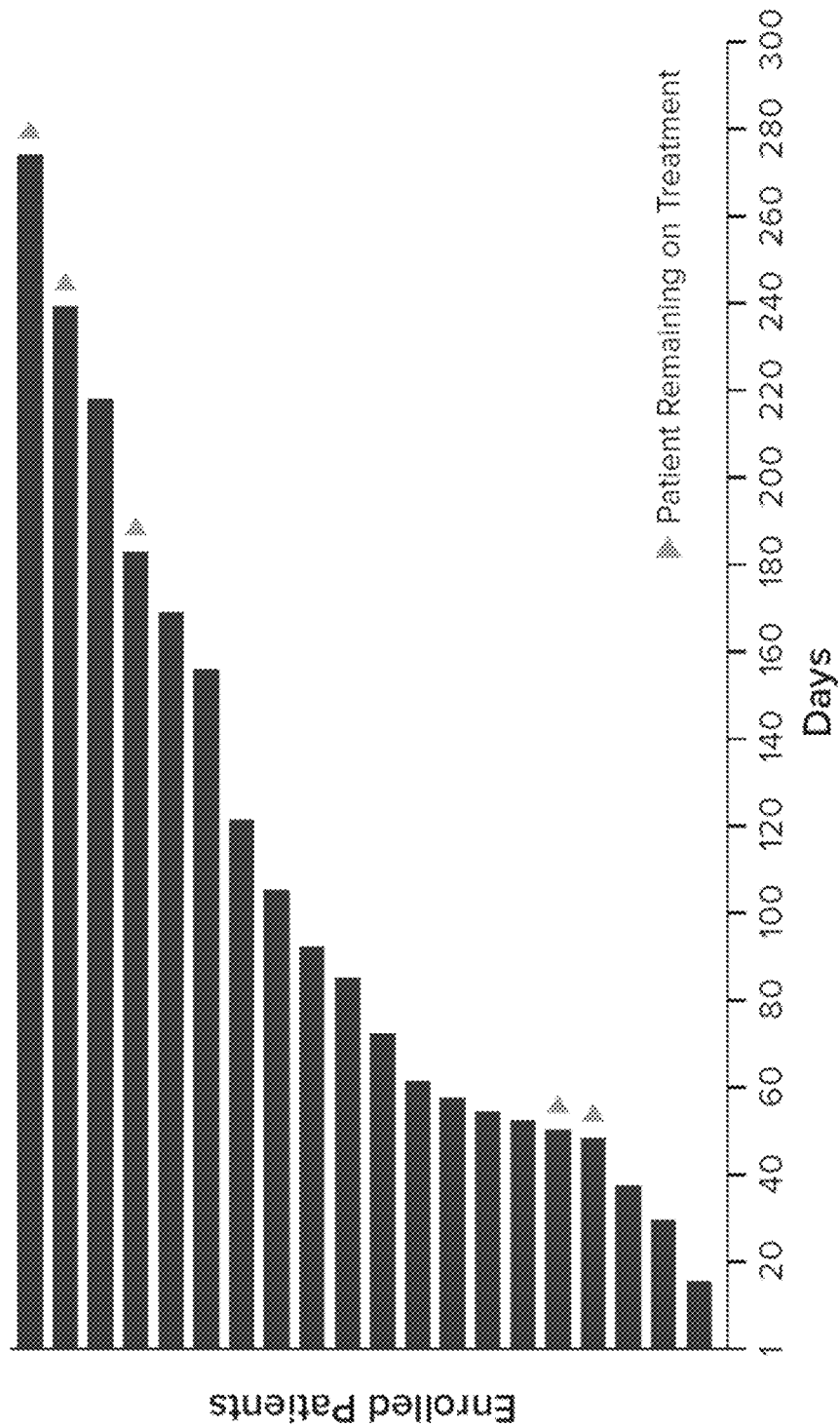

DrugA+pembrolizumab combination cohort with NSCLC (n=20): Of the 18 evaluable patients, 8 exhibited stable disease. FIG. 5A provides the percent change of disease assessment from baseline. The disease control rate (DCR) was 17% and the mPFS was 2 months. In addition, the tumor proportion score (TPS) for PD-L1 staining is reported for each patient. FIG. 5B provides the percent change of disease assessment from baseline for each patient over the study period. FIG. 5C provides the duration of treatment for enrolled patients in this cohort. Tumors were assessed according to the Response Evaluation Criteria in Solid Tumors (RECIST) version 1.1 (E. A. Eisenhauer, et al., European Journal of Cancer 45 (2009) 228-247.)

Pharmacokinetics

Figure 6A:
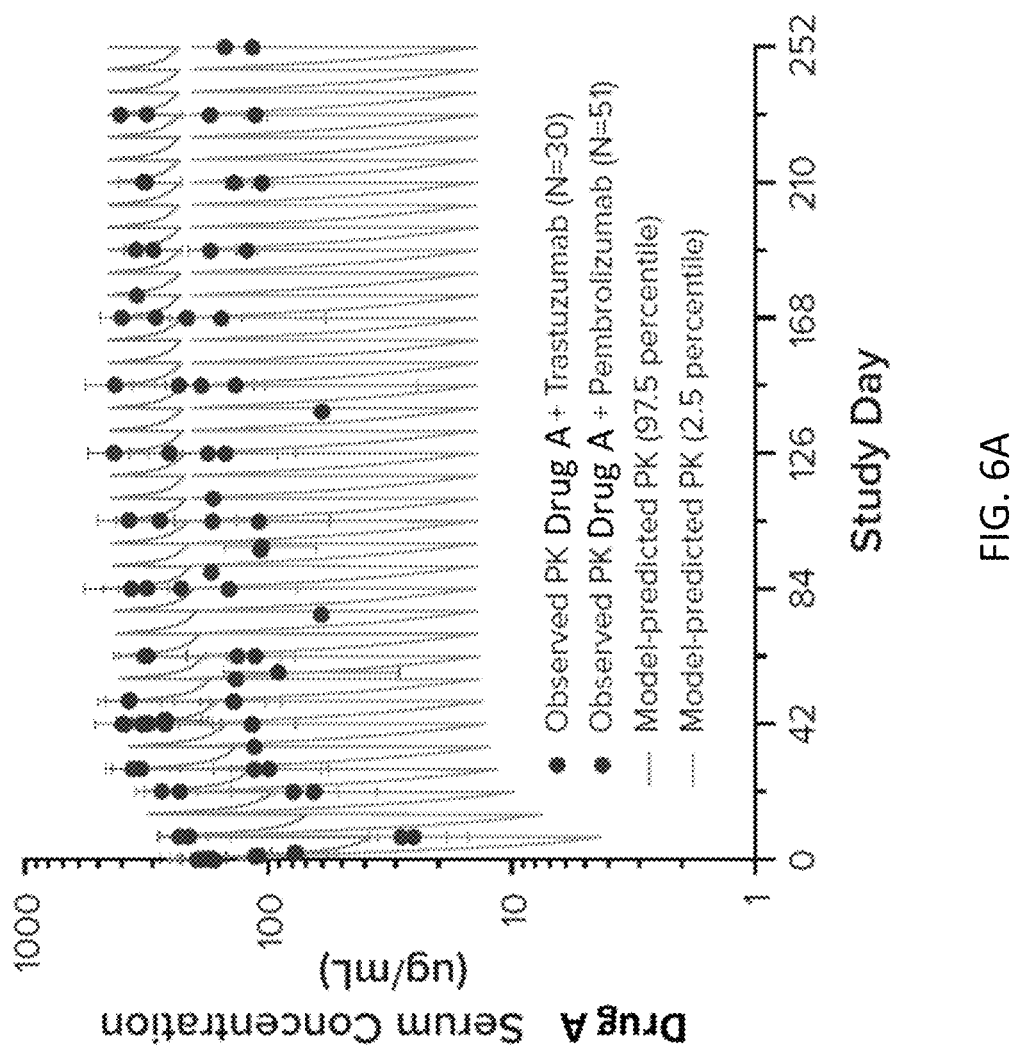
FIGS. 6A-6B provide pharmacokinetic and CD47 target occupancy parameters of Drug A administered in combination with pembrolizumab or trastuzumab over the course of the study.
Figure 6B:
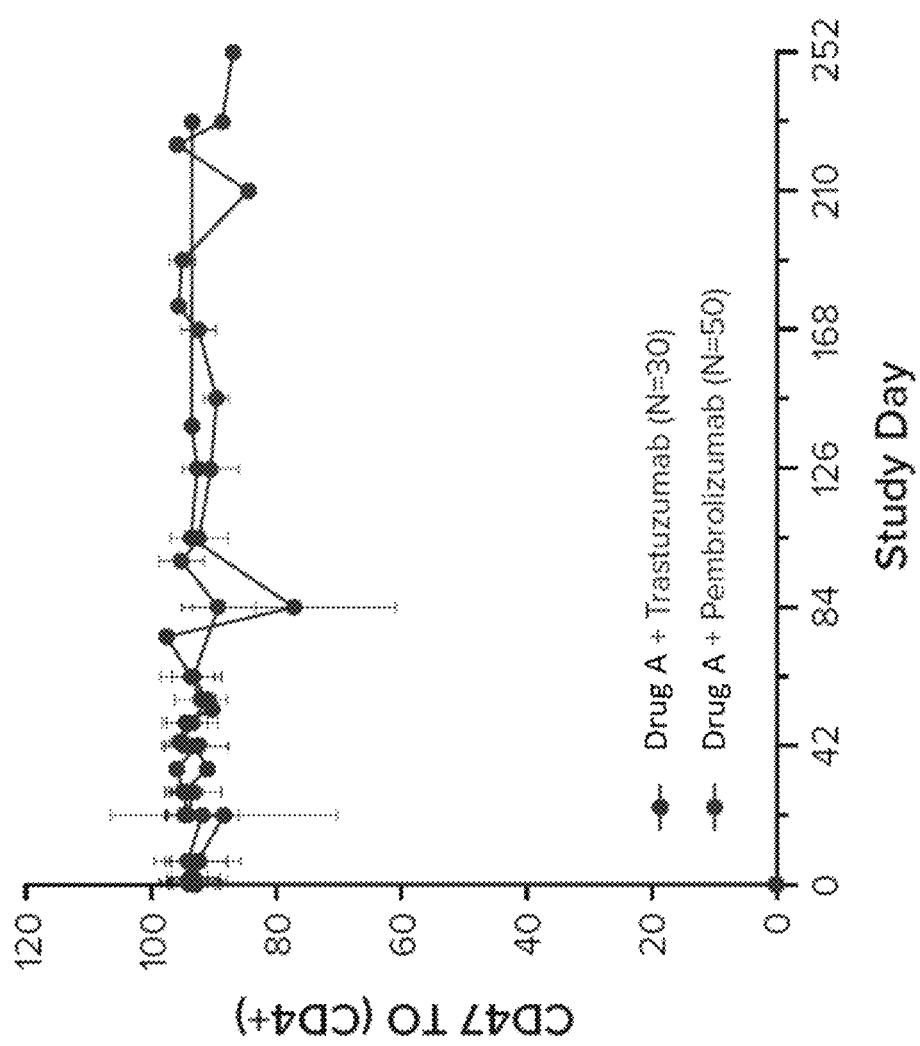

Drug A PK observations from combination cohorts DrugA+trastuzumab and DrugA+pembrolizumab were within predicted 95% intervals based on an established population PK model (Jin F. et al., (2018) Soc Immunotherpay of Cancer Conference, #P340) (FIG. 6A). The steady-state half-life of Drug A (10 mg/kg QW) was predicted to be approximately 16 days. As shown in FIG. 6B, near complete CD47 target occupancy on CD4+ T cells that express CD47 was maintained throughout the Drug A dosing interval in both combinations cohorts.

Anti-Tumor Response

Figure 7A:
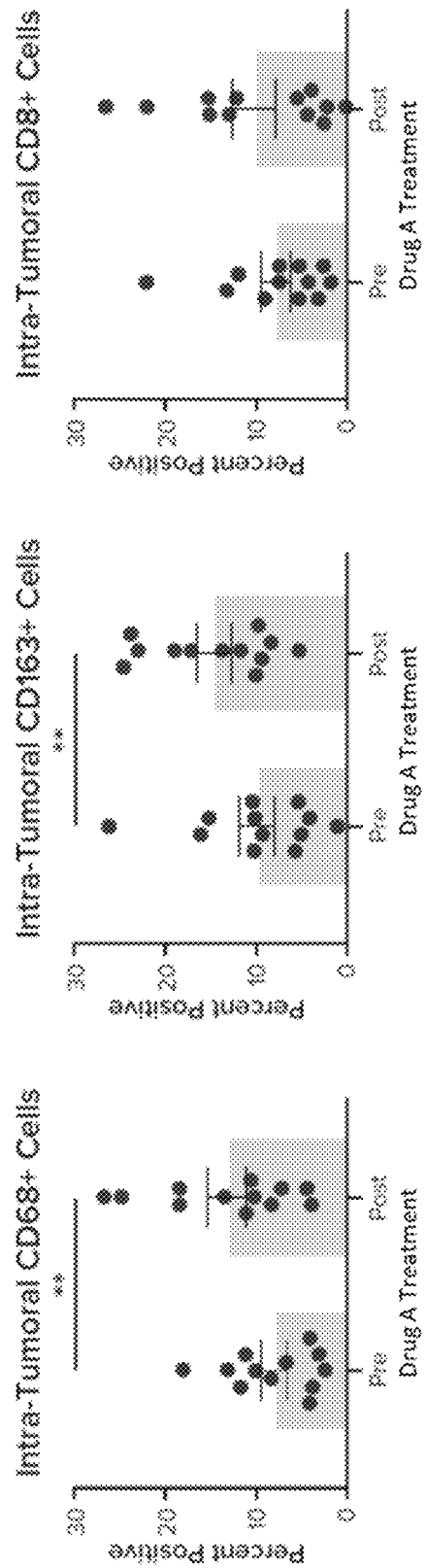
FIGS. 7A-7C show the anti-tumor response in patients treated with Drug A in combination with pembrolizumab or trastuzumab. The percent positive intra-tumoral CD68+ (left), CD163+ (middle), and CD8+ (right) cells in paired biopsies before and after treatment from 5 NSCLC patients treated with Drug A+pembrolizumab, 6 HNSCC patients treated with Drug A+pembrolizumab and 1 gastric cancer patient treated with Drug A+trastuzumab are provided in FIG. 7A. Tumor-associated macrophages and infiltrating lymphocytes were increased after treatment. Images from a biopsy of an NSCLC PD-L1(−) patient treated with Drug A+pembrolizumab showing staining for CD68 and CD8 before and during treatment (C3=Cycle 3) are provided in FIG. 7B. Images from a biopsy of an HNSCC PD-L1(+) patient treated with Drug A+pembrolizumab showing staining for CD68 and CD8 before and during treatment (Cycle 3) are provided in FIG. 7C.
Figure 7B:
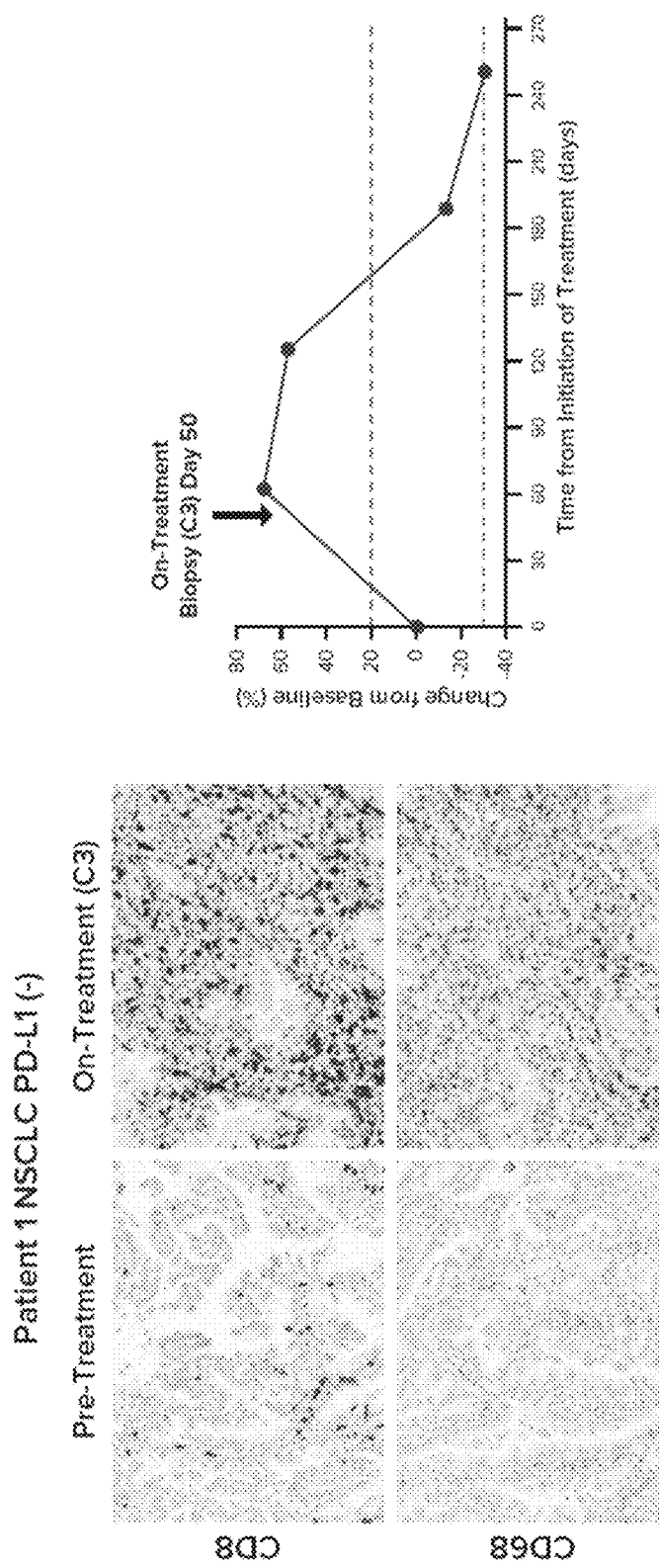
Figure 7C:
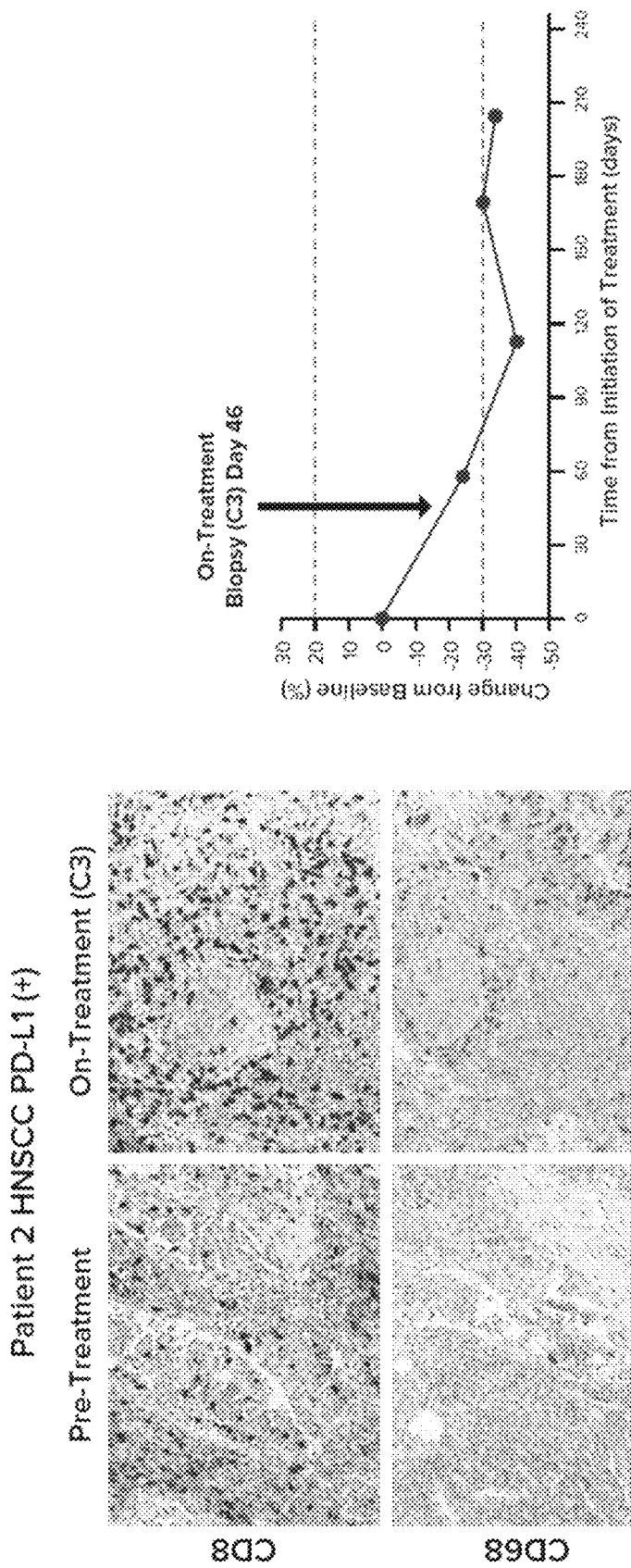

As shown in FIG. 7A, paired biopsies from 5 NSCLC patients treated with DrugA+pembrolizumab, 6 HNSCC patients treated with DrugA+pembrolizumab, and 1 gastric cancer patient treated with DrugA+trastuzumab revealed an increase in tumor-associated macrophages and infiltrating lymphocytes after treatment. Images from individual patients showing staining for CD68 and CD8 before and during treatment are provided in FIG. 7B (NSCLC PD-L1 (−) patient treated with DrugA+pembrolizumab) and FIG. 7C (HNSCC PD-L1(+) patient treated with DrugA+pembrolizumab). CD68 and CD163 markers indicate macrophages; the CD8 marker indicates T lymphocytes.

Conclusions

Drug A in combination with pembrolizumab or trastuzumab demonstrates excellent tolerability with favorable PK/PD characteristics. Objective responses were observed in patients with late line NSCLC, HNSCC, and Gastric/GEJ, including disease relapsed/refractory to prior CPI and HER2-targeted therapies.

Drug A (10 mg/kg QW; molar equivalent to 20 mg/kg of an antibody) in combination with standard regimens of trastuzumab or pembrolizumab was well tolerated with a favorable hematologic safety profile.

Drug A demonstrates anti-cancer activity in combination with trastuzumab in HER2 positive patients that have progressed on prior HER2 targeted therapies (e.g., HER2-positive Gastric/GEJ tumors that have progressed on prior HER2 targeted therapies).

Drug A demonstrates anti-cancer activity in combination with pembrolizumab in patients with:
  ≥2L HNSCC that compares favorably to the pembrolizumab single agent experience.
  NSCLC, including tumors resistant/refractory to prior checkpoint inhibitor therapy.

Drug A demonstrates antibody-like PK and complete CD47 target occupancy in combination with trastuzumab or pembrolizumab.

Preliminary data from paired tumor biopsies suggests increased intra-tumoral macrophages and CD8+ T cells following Drug A treatment.

Figure 8:
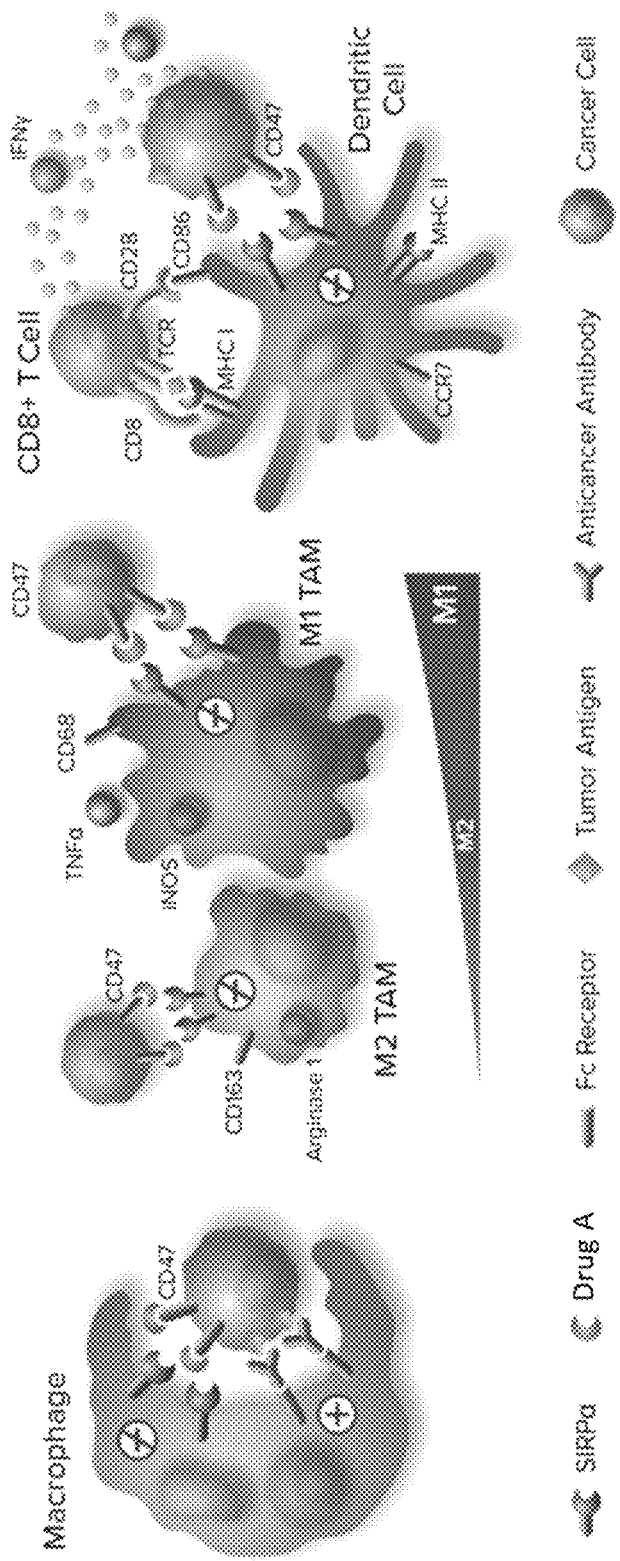
FIG. 8 provides a schematic depiction of a proposed mechanism for the anti-tumor activity of Drug A when administered in combination with anti-cancer therapeutic antibodies such as pembrolizumab, trastuzumab, or rituximab.

Taken together, the data presented in this Example demonstrate the efficacy and safety of Drug A administered in combination with pembrolizumab, trastuzumab or rituximab, in patients with advanced malignancies including non-small cell lung cancer (NSCLC), head and neck squamous cell carcinoma (HNSCC), HER2-overexpressing gastric cancer, and non-Hodgkin lymphoma (NHL). Without wishing to be bound by theory, as shown in FIG. 8, it is believed that Drug A, when administered in combination with anti-cancer therapeutic antibodies such as pembrolizumab, trastuzumab or rituximab, maximizes the innate and adaptive immune response to cancer. In particular, it is believed that Drug A: 1) Enhances macrophage phagocytosis of cancer cells by blocking CD47; 2) Increases the ratio of inflammatory M tumor-associated macrophages (TAMs) to suppressive M2 TAMs; and 3) Activates dendritic cells (DCs) and enhances cross-priming of T cells. Furthermore, it is believed that Drug A in combination with anti-cancer antibodies avoids dose-limiting toxicities associated with other CD47-target approaches while maximizing the innate and adaptive immune response.

Example 2A: Further Safety Results from a Phase 1 Study of Drug A in Combination with Pembrolizumab or Trastuzumab As described in Example 1, 52 patients with solid tumor received Drug A in combination with pembrolizumab, and 30 patients with solid tumor received Drug A in combination with trastuzumab. Treatment-related adverse effects (TRAEs) (including fatigue, AST increase, platelet decrease, ALT increase, anemia, and/or pruritus) were of low grade and low frequency.

35 (67.3%) of patients who received DrugA+pembrolizumab and 22 (73.3%) of patients who received DrugA+trastuzumab experienced any TRAE. The most frequent TRAE experienced by patients who received DrugA+pembrolizumab was low-grade aspartate transaminase (AST) increase (17.3%), and the most frequent TRAE experienced by patients who received DrugA+trastuzumab was low grade fatigue (30%). TRAEs of ≥Grade 3 severity were of low frequency. See Tables E and F below.

TABLE E

| TRAE in Patients Receiving Drug A + Trastuzumab | | |
|---|---|---|
| Adverse Event | Total N (%) | ≥Grade 3 |
| Fatigue | 9 (30) | — |
| PLATELETS DECREASED | 5 (16.7) | 2 (6.7) |
| Decreased Appetite | 3 (10) | — |
| PRURITUS | 3 (10) | — |
| Pyrexia | 3 (10) | — |
| Anemia | 2 (6.7) | — |
| Nausea | 2 (6.7) | — |
| Neutropenia | 2 (6.7) | 2 (6.7) |

TABLE F

TRAE in Patients Receiving Drug A + Pembrolizumab

| Adverse Event | Total N (%) | ≥Grade 3 |
|---|---|---|
| AST Increased | 9 (17.3) | — |
| ALT Increased | 7 (13.5) | 1 (1.9) |
| Fatigue | 6 (11.5) | — |
| Anemia | 5 (9.6) | 1 (1.9) |
| Pruritus | 5 (9.6) | — |
| RASH | 5 (9.6) | — |
| Infusion Reaction | 4 (7.7) | — |
| PLATELETS DECREASED | 4 (7.7) | 2 (3.8) |
| Alkaline Phosphatase Increased | 3 (5.8) | — |
| Arthralgia | 3 (5.8) | — |
| Pyrexia | 3 (5.8) | — |
| WBC Decreased | 3 (5.8) | — |
| Decreased Appetite | 2 (3.8) | — |
| Myalgia | 2 (3.8) | — |
| Nausea | 2 (3.8) | — |
| Neutropenia | 2 (3.8) | 1 (1.9) |

For Tables E and F, RASH: rash, rash papulo-macular, rash vesicular, rash pruritic dermatitis; PLATELETS DECREASED: platelets decrease, thrombocytopenia; PRURITUS: pruritus, pruritus generalized.

Four treatment-related serious adverse events (TRSAEs) were reported in patients receiving DrugA+pembrolizumab: 1 patient experienced autoimmune hemolytic anemia/pancytopenia; 1 patient experienced febrile neutropenia; 1 patient experienced neutropenia; and 1 patient experienced peripheral neuropathy. One TRSAE was reported in patients receiving DrugA+trastuzumab. The patient experienced febrile neutropenia.

Drug A displays a favorable exposure-safety relationship across the exposure ranges administered in the clinic (i.e., 10 mg/kg qw-30 mg/kg qow) with no exposure-dependent cytopenias observed.

Example 2B: Further Results from a Phase 1 Study of Drug a in Combination with Pembrolizumab in Patients with ≥2L Head and Neck Squamous Cell Carcinoma As described in Example 1, 20 patients with ≥2L HNSCC received Drug A in combination with pembrolizumab. Baseline characteristics of all patients receiving DrugA+pembrolizumab (including patients with ≥2L NSCLC, as described in further detail in Example 2C below) are shown in Table G.

TABLE G

Baseline Characteristic of All Patients*
Receiving Drug A + Pembrolizumab

| | Drug A + Pembrolizumab N = 52 |
|---|---|
| Primary Disease, n | |
| Lung | 25 |
| HNSCC | 20 |
| Gastric/GEJ Esophageal | — |
| Breast | — |
| Colorectal | 2 |
| Ovarian | 2 |
| Pancreatic | — |
| Appendiceal | 1 |
| Sarcoma | 1 |
| Urothelial | — |
| Unknown | 1 |
| Median Age | |
| Years (range) | 61 (32-81) |
| Sex, n | |
| M | 29 |
| F | 23 |
| Race, n | |
| White | 34 |
| Asian | 11 |
| Black | 3 |
| Other | 4 |
| ECOG PS, n | |
| 0 | 18 |
| 1 | 34 |

*patients included those with ≥2 L HNSCC and ≥2 L NSCLC (see Example 2C).

Figure 9A:
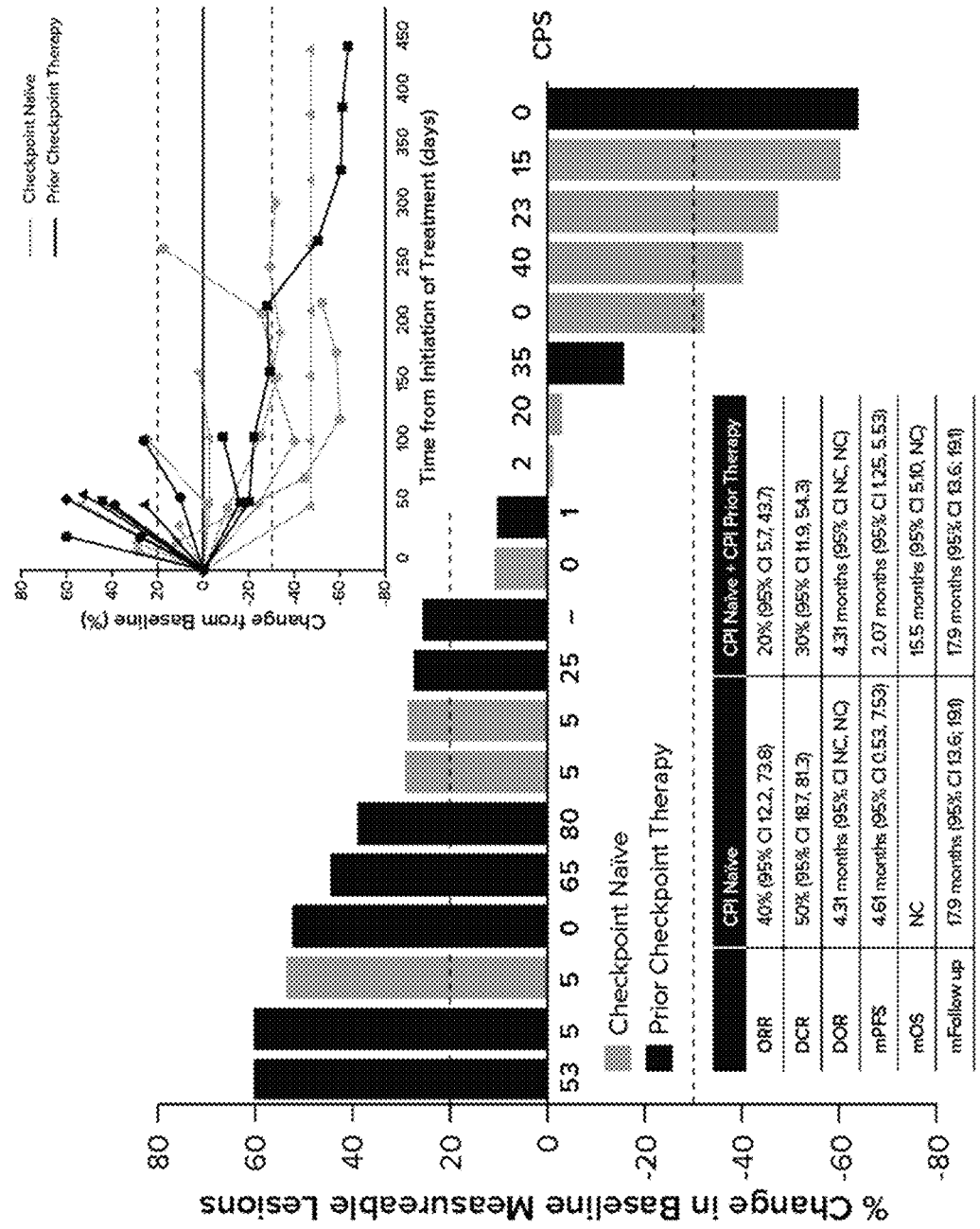
FIG. 9A provides a schematic showing the clinical activity of Drug A in combination with pembrolizumab in response-evaluable ≥2L HNSCC patients (including both checkpoint inhibitor-naïve patients in checkpoint inhibitor-experienced patients). CPS=combined positive score (i.e., the number of PD-L1 positive staining cells (tumor cells, lymphocytes, and macrophages) divided by the total number of viable tumor cells, multiplied by 100).
Figure 9B:
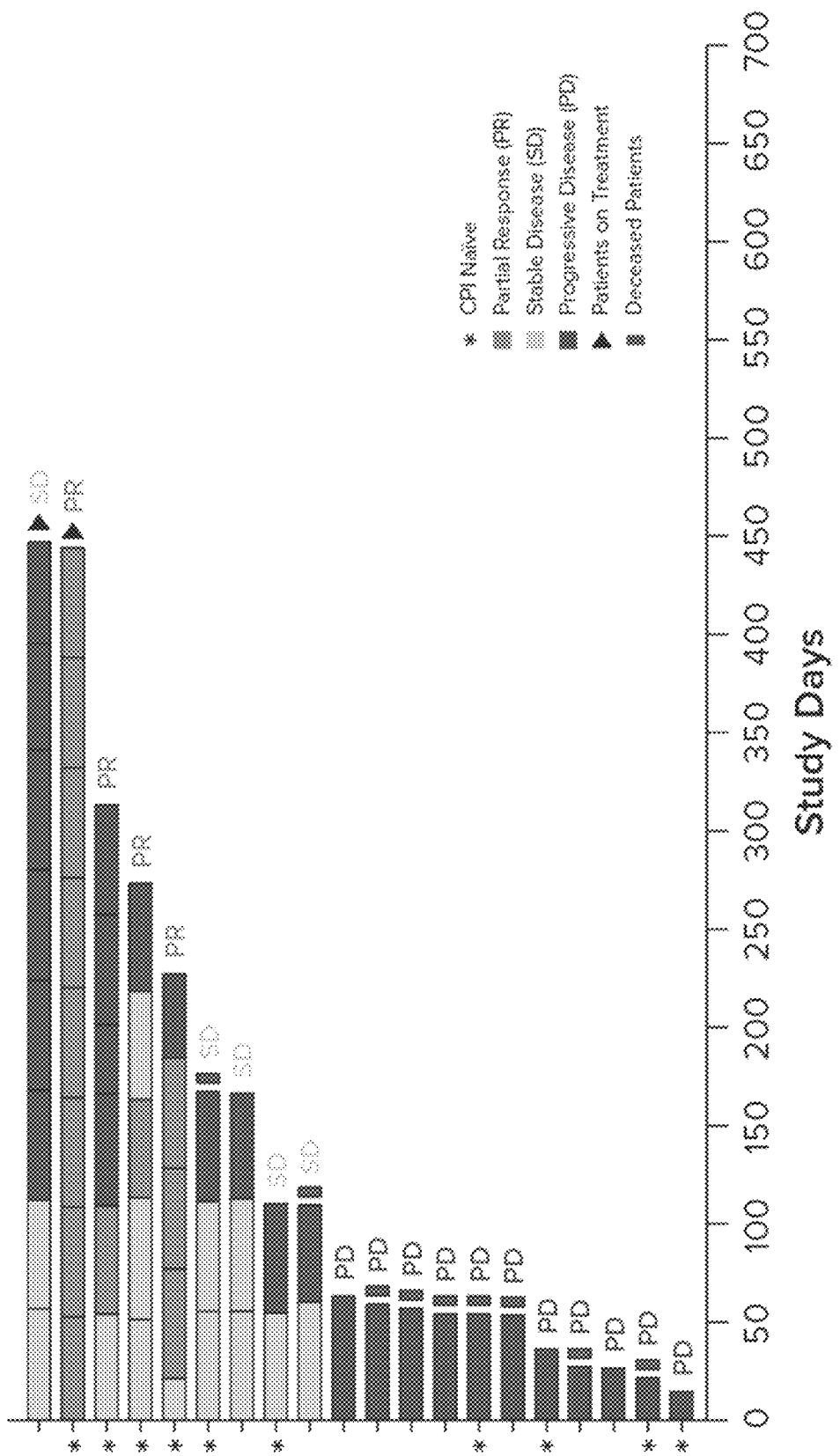
FIG. 9B provides a schematic showing the best overall response and duration of response in ≥2L HNSCC patients treated with Drug A and pembrolizumab.

Anticancer efficacy in HNSCC patients was observed in response-evaluable patients. Clinical activity was based on investigator assessed response using RECIST 1.1 criteria (E. A. Eisenhauer, et al., European Journal of Cancer 45 (2009) 228-247). Among the 10 patients who were checkpoint inhibitor-naïve (i.e., who had not received prior treatment with an immune checkpoint inhibitor), the overall response rate (ORR) was 40% (95% CI:12.2, 73.8); the median PFS (mPFS) was 4.61 months (95% CI:0.53; 7.53), and the median overall survival (mOS) had not been reached with a 14.4 month median follow-up or a 17.9 month follow-up. The disease control rate (DCR) was 50% (95% CI: 18.7: 81.3): 4/10 of the checkpoint-inhibitor naïve patients achieved partial response ("PR") (2 confirmed); 2/10 achieved stable disease ("SD"); and 4 demonstrated progressive disease ("PD"). The duration of response (DOR) was 4.31 months. Among the 10 patients who were checkpoint inhibitor-experienced (i.e., who had received prior treatment with an immune checkpoint inhibitor), the ORR was 0%; the mPFS was 2.0 months [95% CI:0.9; 3.6], and the mOS as 7.4 months (95% CI: 3.1; NC). 3 patients in the checkpoint inhibitor-experienced subgroup achieved SD, and 7 demonstrated PD. See FIG. 9A, which shows the clinical activity of the Drug A+pembrolizumab combination in response-evaluable patients, and FIG. 9B, which shows the best overall response and duration of response in ≥2L HNSCC patients treated with Drug A and pembrolizumab. Additional details regarding ORR, DCR, DOR, mPFS, and mOS for all patients (i.e., both checkpoint inhibitor experienced and checkpoint inhibitor naïve) are provided in FIG. 9A.

Full peripheral CD47 target occupancy and increased infiltrating immune cells in tumor biopsies were seen. These data confirm clinical activity of the DrugA+pembrolizumab combination treatment in patients with advanced checkpoint inhibitor-naïve HNSCC (including PD-L1 negative patients). The clinical activity compares favorably with historic controls, namely, the pembrolizumab single-agent experience. Preliminary biomarker analyses suggested that baseline levels of CD47 and SIRPα gene expression and tumor-infiltrating $CD8^+$ cells $CD68^+$ cells, and $CD163^+$ cells are not associated with tumor response as measured by % change of target lesion size from baseline.

Example 2C: Further Results from a Phase 1 Study of Drug a in Combination with Pembrolizumab in Patients with ≥2L NSCLC Who Progressed on Prior Checkpoint Inhibitor Therapy As described in Example 1, 20 patients with ≥2L NSCLC received Drug A in combination with pembrolizumab. 17 had progressed on prior checkpoint inhibitor therapy, and 3 of the patients were checkpoint-inhibitor naïve.) Baseline characteristics of all patients receiving Drug A+pembrolizumab (including those being treated for HNSCC) are shown in Table G above. Clinical activity in NSCLC patients was based on investigator assessed response using RECIST 1.1 criteria. The overall response rate (ORR) was 5% (95% CI: 0.1, 24.9), with 1 patient achieving partial response (PR), 9 patients achieving stable disease (SD), and 10 patients demonstrating progressive disease (PD). The patient who achieved PR initially exhibited progressive disease, followed by stable disease and subsequent partial response. The patient who achieved PR had a tumor proportion score of 0%. The disease control rate (DCR) was 35% (95% CI:15.4, 59.2). The median progression-free survival was 2.01 months (95% CI: 1.88, 5.56), and the median overall survival was 9.11 months (95% CI: 7.17, NC). See FIG. A, which shows the clinical activity of the Drug A+pembrolizumab combination in response-evaluable ≥2L NSCLC patients, and FIG. 10B, which shows the best overall response and duration of response in ≥2L NSCLC patients treated with Drug A and pembrolizumab.

These data confirm clinical activity of the DrugA+pembrolizumab combination treatment in patients with ≥2L NSCLC, including those who are resistant/refractory to prior checkpoint inhibitor therapy. Preliminary biomarker analyses suggested that baseline levels of CD47 and SIRPα gene expression and tumor-infiltrating CD8$^+$ cells CD68$^+$ cells, and CD163$^+$ cells are not associated with tumor response as measured by % change of target lesion size from baseline.

Example 2D: Further Results from a Phase 1 Study of Drug A in Combination with Trastuzumab in Patients with ≥2L HER2-Positive Gastric/GEJ cancer As described in Example 1, 25 patients with ≥2L HER2$^+$ gastric cancer or HER2+ gastroesophageal cancer received Drug A in combination with trastuzumab. Baseline characteristics of all patients receiving DrugA+trastuzumab are shown in Table H below:

TABLE H

| Baseline Characteristics | |
|---|---|
| | Drug A + Trastuzumab N = 30 |
| Primary Disease, n | |
| Lung | — |
| HNSCC | — |
| Gastric/GEJ Esophageal | 25 |
| Breast | 2 |
| Colorectal | — |
| Ovarian | 1 |
| Pancreatic | 1 |
| Appendiceal | — |
| Sarcoma | — |
| Urothelial | 1 |
| Unknown | — |

TABLE H-continued

| Baseline Characteristics | |
|---|---|
| | Drug A + Trastuzumab N = 30 |
| Median Age | |
| Years (range) | 60 (45-79) |
| Sex, n | |
| M | 21 |
| F | 9 |
| Race, n | |
| White | 13 |
| Asian | 14 |
| Black | 1 |
| Other | 2 |
| ECOG PS, n | |
| 0 | 11 |
| 1 | 19 |

Figure 11A:
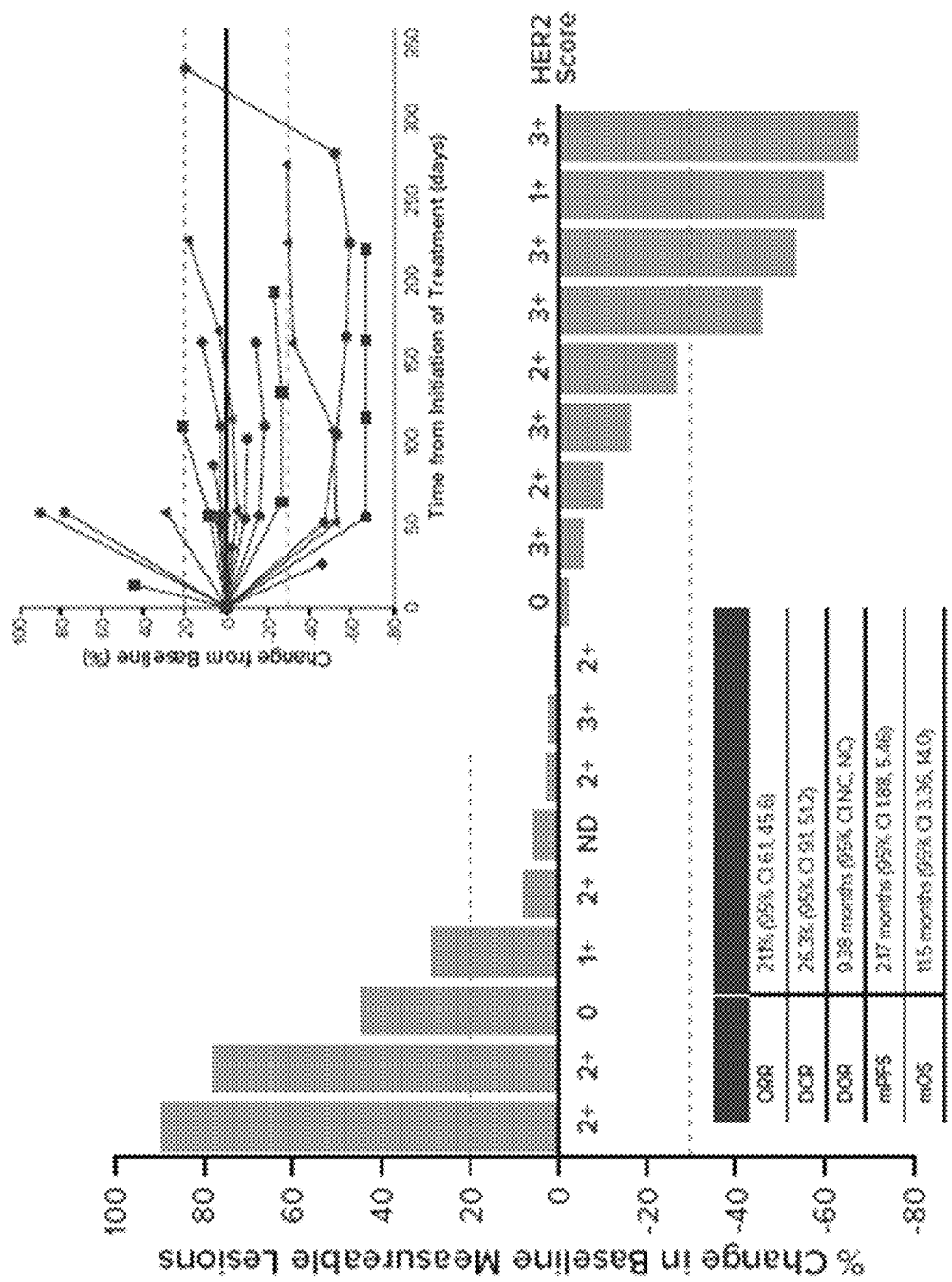
FIG. 11A provides a schematic showing the clinical activity of Drug A in combination with trastuzumab in response-evaluable ≥2L HER2+ gastric or HER2+ GEJ cancer patients. One patient with clinical progression not shown. HER2 score reflects the HER2 expression level of tumor cells.
Figure 11B:
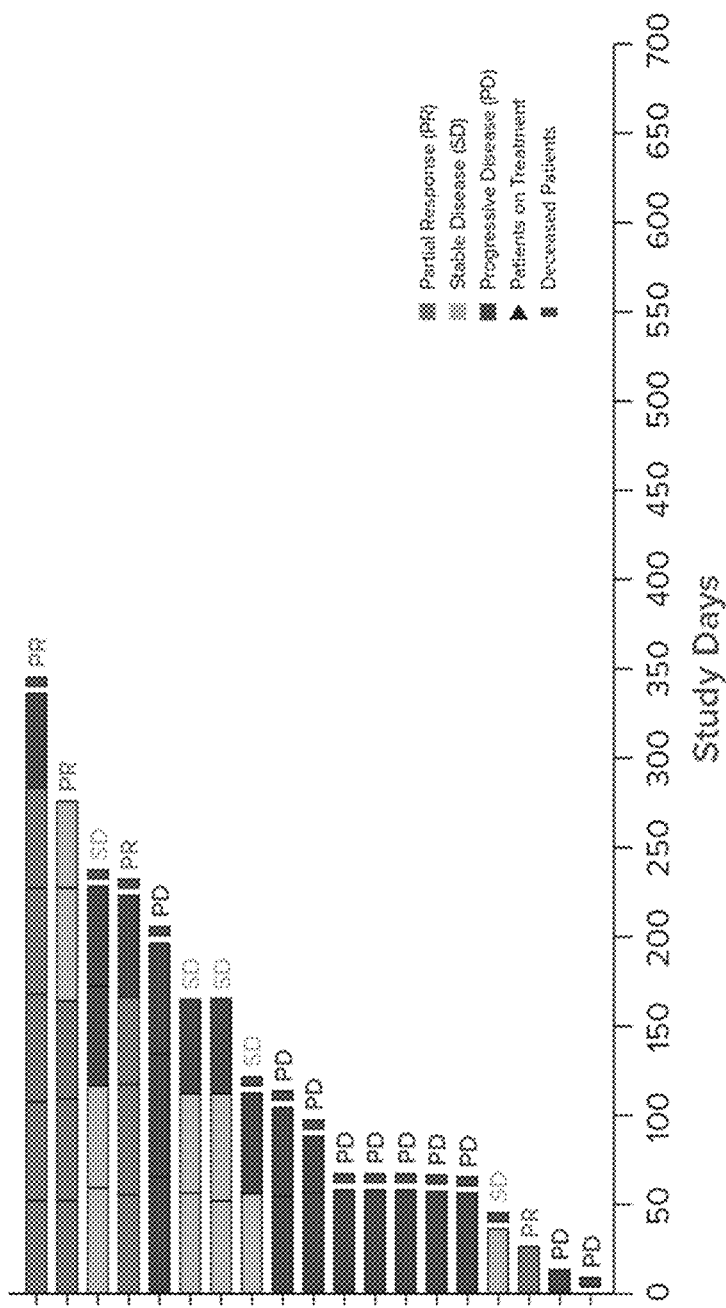
FIG. 11B provides a schematic showing the best overall response and duration of response in ≥2L HER2+ gastric or HER2+ GEJ cancer patients treated with Drug A and trastuzumab.

Clinical activity in patients with gastric cancer/GEJ cancer was based on investigator assessed response using RECIST 1.1 criteria. Anticancer efficacy was observed in response-evaluable patients. The ORR was 21.1% (95% CI: 6.1, 45.6), the mPFS was 2.2 months (95% CI: 1.9; 5.4), the mOS was 11.5 months (95% CI: 3.36; 14.0). Among the 19 response-evaluable patients, 4 achieved partial response (3 confirmed); 5 achieved stable disease; and 10 demonstrated progressive disease. The disease control rate (DCR) was 26.3% (95% CI: 9.1, 51.2), and the duration of response was 9.38 months. See FIG. 11A, which shows the clinical activity of the Drug A+trastuzumab combination in response-evaluable ≥2L HER2$^+$ gastric cancer or ≥2L HER2$^+$ GEJ cancer patients, and FIG. 9B, which shows the best overall response and duration of response in ≥2L HER2$^+$ gastric cancer or ≥2L HER2$^+$ GEJ cancer patients treated with Drug A and trastuzumab.

Full peripheral CD47 target occupancy and increased infiltrating immune cells in tumor biopsies were seen. These data confirm clinical activity of the DrugA+trastuzumab combination treatment in patients with HER2$^+$ gastric or gastroesophageal cancer that have progressed on prior HER2-targeted therapies. The clinical activity compares favorably with historic controls. Preliminary biomarker analyses suggested that baseline levels of CD47 and SIRPα gene expression and tumor-infiltrating CD8$^+$ cells CD68$^+$ cells, and CD163$^+$ cells are not associated with tumor response as measured by % change of target lesion size from baseline.

Example 2E: Further Results from a Phase 1 Study of Drug a in Combination with Rituximab in Patients with Non-Hodgkin Lymphoma This example provides further results from the clinical study of Drug A's safety profile and antitumor activity in combination with rituximab with both aggressive and indolent histologies of non-Hodgkin Lymphoma (NHL), as described in Example 1.

Patients enrolled in the study were ≥18 years of age and had relapsed or refractory CD20-positive B-cell NIL for which no curative therapy was available or were relapsed or refractory to standard approved therapies. Patients were required to have adequate organ function and hemoglobin ≥8 g/dL; absolute neutrophil count ≥1,000/mm$^3$, and platelets ≥50,000/mm$^3$. Patients who had received prior treatment with any anti-CD47 or anti-SIRPα agent were excluded.

Patients received Drug A (10 mg/kg QW or 15 mg/kg QW) in combination with rituximab (375 mg/m² weekly for 4 doses followed by once monthly for 8 doses). The primary endpoint for the safety confirmation population was first cycle dose limiting toxicity (DLT). Tumor response (using Lugano Working Group 2014 response criteria in NHL), adverse events (characterized using NCI CTCAE v 4.03), pharmacokinetic (PK), and pharmacodynamic (PD) markers were assessed in all patients.

33 NHL patients (23 male, 10 female; median prior lines of therapy=3) were administered with Drug A in combination with rituximab. 22 patients (11 with diffuse large B-cell lymphoma (DLBCL); 4 with mantle cell lymphoma (MCL); 5 with follicular lymphoma (FL); and 2 with marginal zone lymphoma (MZL)) were given Drug A 10 mg/kg QW+rituximab, and 11 patients (6 with DLBCL; 1 with MCL; 3 with FL; and 1 with MZL) were given Drug A15 mg/kg QW+rituximab. The baseline characteristics of the patients are shown in Table I, and patient drug exposure and disposition are shown in Table J.

TABLE I

Baseline Characteristics of Patients Receiving Drug A + Rituximab for NHL

|  | Drug A (10 mg/kg QW) + Rituximab (N = 22) | Drug A (15 mg/kg QW) + Rituximab (N = 11) |
| --- | --- | --- |
| Primary Disease, n | | |
| Follicular | 5 | 3 |
| Marginal Zone | 2 | 1 |
| DLBCL | 11 | 6 |
| Mantle Cell | 4 | 1 |
| Median Age | | |
| Years (range) | 66 (32-80) | 64 (53-78) |
| Sex, n | | |
| M | 17 | 6 |
| F | 5 | 5 |
| Race, n | | |
| Asian | 18 | 9 |
| White | 4 | 2 |
| ECOG PS, n | | |
| 0 | 7 | 2 |
| 1 | 15 | 8 |

TABLE J

Patient Drug Exposure and Disposition

|  | Drug A + Rituximab | |
| --- | --- | --- |
|  | Drug A 10 mg/kg (N = 22) | Drug A 15 mg/kg (N = 11) |
| Dose Reductions, n | 0 | 0 |
| Discontinuation Due to TRAE | 1^ | 0 |
| Discontinuation Due to PD | 12 | 4 |
| Discontinuation Due to Death | 2* | 0 |
| Discontinuation Due to Other | 1 | 1 |
| Ongoing Treatment | 6 | 6 |

^Discontinuation due to rituximab infusion reaction;
*Death due to disease progression.

No patient required a dose reduction, and the most common reason for discontinuation of treatment was disease progression.

Drug A in combination with rituximab was well tolerated, and most treatment related adverse events (TRAEs) were of low grade and low frequency. Twenty-six (78.8%) patients experienced any adverse event. Fifteen (45.5%) patients experienced any TRAE. The most common TRAE of Drug A in combination with rituximab was Grade 1-2 rash (18%), fatigue (9%, n=3), anemia (6%, n=2), nausea (6%, n=2), and neutropenia (6%, n=2). TRAEs ≥Grade 3 severity were of low frequency (see Table K). No treatment related serious adverse events were reported. There were 2 deaths on study, both due to disease progression.

TABLE K

Treatment-Related Adverse Events

| Adverse Event | Total N (%) | ≥Grade 3 |
| --- | --- | --- |
| Rash | 6 (18%) | — |
| Fatigue | 3 (9%) | — |
| Nausea | 2 (6%) | — |
| Neutrophil Count Decreased | 2 (6%) | 2 (6%) |
| Anemia | 2 (6%) | 1 (3%) |

No Drug A dose limiting toxicities were reported. The maximum tolerated dose (MTD) of Drug A in combination with rituximab was not reached. The maximum administered dose of Drug A (i.e., administered in combination with rituximab) was 15 mg/kg QW. No significant exposure-cytopenia relationship was observed across the Drug A exposure range evaluated (10 mg/kg QW-15 mg/kg QW).

Anti-tumor activity was observed across all histologies in response-evaluable patients with relapsed/refractory aggressive histologies (i.e., DLBCL and MCL) and relapsed/refractory indolent histologies (i.e., FL and MZL). Responses were evaluated according to Lugano 2014 response criteria (see Cheson et al. (2014) "Recommendations for Initial Evaluation, Staging and Response Assessment of Hodgkin and Non-Hodgkin Lymphoma: The Lugano Classification." J. Clin Oncol. 32: 3059-3067). As shown in Table L and FIG. 12, the overall response rate (ORR) among patients treated with 10 mg/kg QW DrugA+rituximab was 40.9%. 3 Patients (i.e., one with Mantle Cell Lymphoma (MCL), one with Follicular Lymphoma (FL), and one with MZL) achieved complete response (CR), 6 patients (two with Diffuse Large B-Cell Lymphoma (DLBCL), two with MCL, and two with FL) achieved partial response (PR). 6 patients (two with DLBCL, one with MCL, two with FL, and one with MZL) demonstrated stable disease (SD). The ORR among patients treated with 15 mg/kg QW DrugA+rituximab was 54.6% ORR. 2 patients (both with FL) achieved CR. 4 patients (one with MZL, two with DLBCL, and one with MCL) achieved PR. 1 patient (with FL) demonstrated SD. See Table L below and FIG. 12. Further details regarding the duration of treatment for patients administered with 10 mg/kg DrugA+rituximab are provided in FIG. 13A, and further details regarding the duration of treatment for patients administered with 15 mg/kg DrugA+rituximab are provide in FIG. 13B.

TABLE L

Drug A + Rituximab Combination - Clinical Activity in Response-Evaluable Patients

| Population Drug A Dose | N | ORR (95% CI) | Median DOR (95% CI) | Median PFS (95% CI) | Median OS (95% CI) | Median Follow-Up (95% CI) |
|---|---|---|---|---|---|---|
| NHL (10 mg/kg ALL) | 22 | 40.9% (23.3; 61.3) | NC | 7.4 (1.9; 13.2) | NC | 11.3 (10.2; 15.2) |
| NHL (10 mg/kg aggressive) | 15 | 33.3% (15.2; 58.3) | 5.6 (1.8; NC) | 2.5 (1.0; 7.4) | 8.9 (2.5; NC) | 10.4 (9.5; 15.2) |
| NHL (10 mg/kg indolent) | 7 | 57.1% (25.1; 84.2) | NC | NC | NC | 11.3 (7.8; 20.4) |
| NHL (15 mg/kg ALL) | 11 | 54.6% (28.0; 78.7) | NC | NC | NC | 5.1 (4.0; 5.6) |
| NHL (15 mg/kg aggressive) | 7 | 42.9% (15.8; 75.0) | NC | 1.9 (1.1; NC) | NC | 4.7 (4.0; 5.4) |
| NHL (15 mg/kg indolent) | 4 | 75% (30.1; 95.4) | NC | NC | NC | 5.9 (3.5; 7.4) |

Aggressive = relapsed refractory DLBCL or relapsed refractory mantle cell lymphoma; Indolent = relapsed refractory follicular lymphoma or relapsed refractory marginal zone lymphoma; ORR = objective response rate (complete response + partial response); mDOR = median duration of response (months); mPFS = median progression free survival (months); mFollow-Up = median follow up (months); NC = could not be calculated.

Across the exposure range evaluated (10 mg/kg QW-15 mg/kg QW), increased Drug A exposure was observed in subjects with a best response of CR and PR compared to subjects with a best response of SD and PD. Favorable Drug A pharmacokinetics and CD47 receptor occupancy were seen across the dosing interval.

Drug A in combination with standard regimens of rituximab was well tolerated with a favorable hematologic safety profile and no maximum tolerated dose reached. The maximum administered dose was 15 mg/kg QW (molar equivalent to 30 mg/kg QW of an antibody) with no exposure dependent anemia, thrombocytopenia or neutropenia observed across the exposure range evaluated. Drug A demonstrates emerging anti-cancer activity with durable responses in combination with rituximab in patients with relapsed/refractory NHL whose tumors have progressed on prior CD20 targeted therapies that compares favorably to historic controls. Preliminary data suggests Drug A is well tolerated and that higher exposure of Drug A is observed in responders vs non-responders.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

The invention claimed is:

1. A method of treating head and neck squamous cell carcinoma (HNSCC) in an individual, comprising administering to the individual an effective amount of (a) a polypeptide comprising a SIRPα D1 domain variant and an Fc domain variant, and (b) pembrolizumab,
   wherein the SIRPα D1 domain variant comprises the amino acid sequence of SEQ ID NO: 85;
   wherein the Fc domain variant is a human IgG1 Fc region comprising L234A, L235A, G237A, and N297A mutations, wherein numbering is according to the EU index of Kabat;
   and
   wherein the HNSCC in the individual has progressed during a prior platinum therapy or after the prior platinum therapy;
   wherein the individual has not received prior therapy with an immune checkpoint inhibitor; and
   wherein the individual is a human.

2. The method of claim 1, wherein the prior platinum therapy comprised one or more therapeutic agents selected from the group consisting of: cisplatin, carboplatin, and oxaliplatin.

3. The method of claim 1, wherein the pembrolizumab is administered to the individual at a dose of 200 mg every 3 weeks (Q3W) by intravenous (IV) infusion.

4. The method of claim 1, wherein the Fc domain variant comprises the amino acid sequence of SEQ ID NO: 91.

5. The method of claim 1, wherein the polypeptide comprising a SIRPα D1 domain variant and an Fc domain variant comprises the amino acid sequence of SEQ ID NO: 136.

6. The method of claim 1, wherein the polypeptide comprising a SIRPα D1 domain variant and an Fc domain variant forms a homodimer.

7. The method of claim 1, wherein the polypeptide comprising a SIRPα D1 domain variant and an Fc domain variant is administered to the individual at a dose of 10 mg/kg once per week (QW).

* * * * *

UNITED STATES PATENT AND TRADEMARK OFFICE
CERTIFICATE OF CORRECTION

PATENT NO. : 11,613,564 B2
APPLICATION NO. : 16/886559
DATED : March 28, 2023
INVENTOR(S) : Jaume Pons et al.

Page 1 of 10

It is certified that error appears in the above-identified patent and that said Letters Patent is hereby corrected as shown below:

On the Title Page

Item (56), Other Publication, on page 3, second Column, Line 53 please replace "Protein a" with --Protein α--;

Item (56), Other Publication, on page 4, first Column, Line 9 please replace "Immunotherpay" with --Immunotherapy--;

Item (56), Other Publication, on page 4, first Column, Line 52 please replace "Tymphoma" with --Lymphoma--;

Item (56), Other Publication, on page 4, first Column, Line 52 please replace "Health" with --Health:--;

Item (56), Other Publication, on page 4, second Column, Line 25 please replace "Tevels,"" with --levels,"--;

Item (56), Other Publication, on page 4, second Column, Line 71 please replace "NCT028903687V" with --NCT02890368?V--;

Item (56), Other Publication, on page 5, first Column, Line 10 please replace "NCT035306837V" with --NCT03530683?V--;

Item (56), Other Publication, on page 5, second Column, Line 22 please replace "37(3)" with --37(3):--;

In the Drawings

In Sheet 4 of 26, FIG. 3B, in the x-axis, please replace "Inltiation" with --Initiation--;

Signed and Sealed this
Twenty-second Day of August, 2023

Katherine Kelly Vidal
*Director of the United States Patent and Trademark Office*

Figure 12:
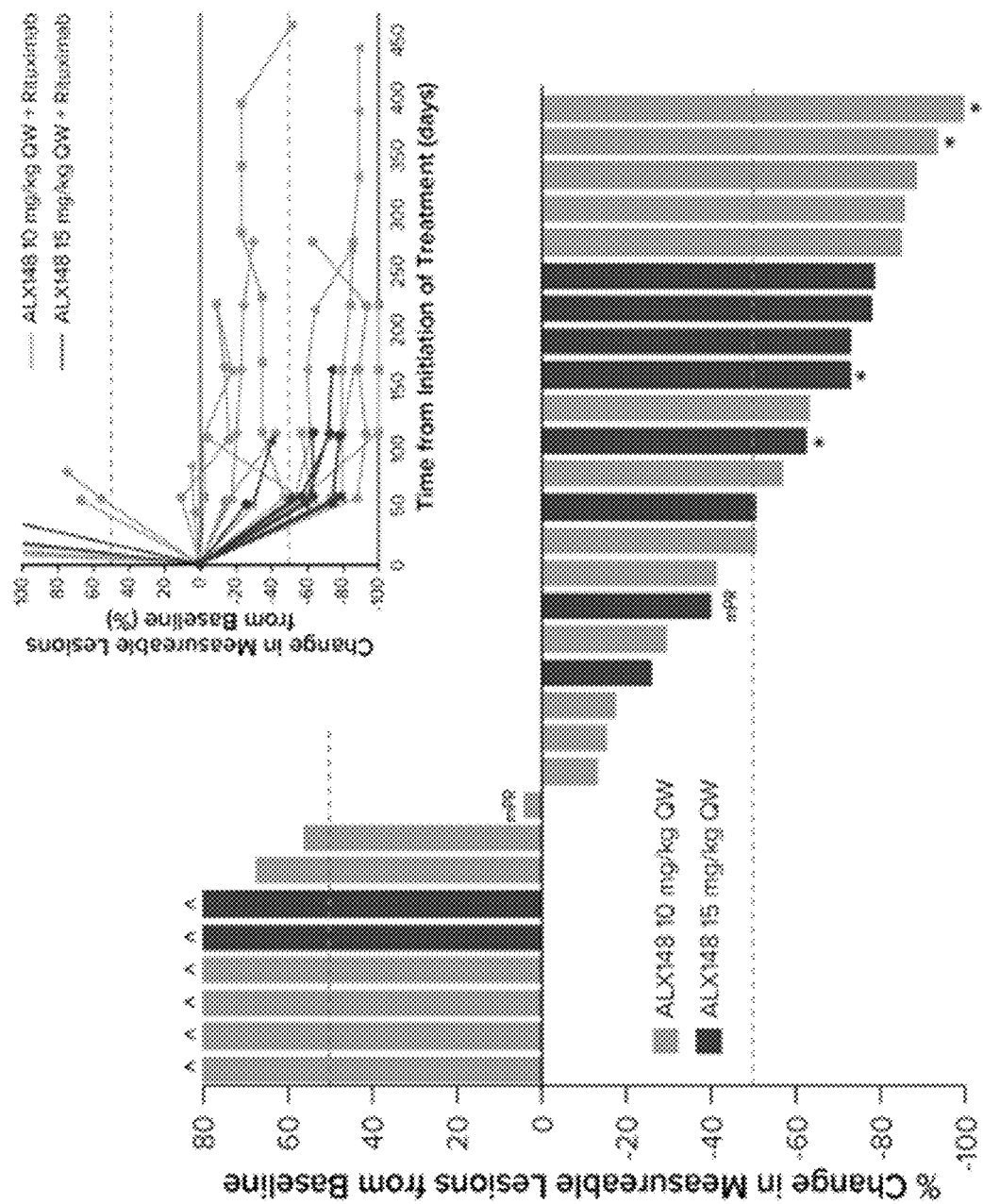
FIG. 12 provides a schematic showing the clinical activity of Drug A in combination with rituximab in response-evaluable patients with relapsed/refractory non-Hodgkin lymphoma. Patients denoted with "\/" demonstrated a more than 80% increase in measurable lesion compared to baseline. Patients denoted with "*" achieved complete response or metabolic complete response. Patients denoted with "mPR" achieved metabolic partial response. Two patients (1 each at 10 mg/kg and 15 mg/kg Drug A) with clinical progression are not shown. One patient (10 mg/kg Drug A) with metabolic CR is not represented in the plots.
Figure 13A:
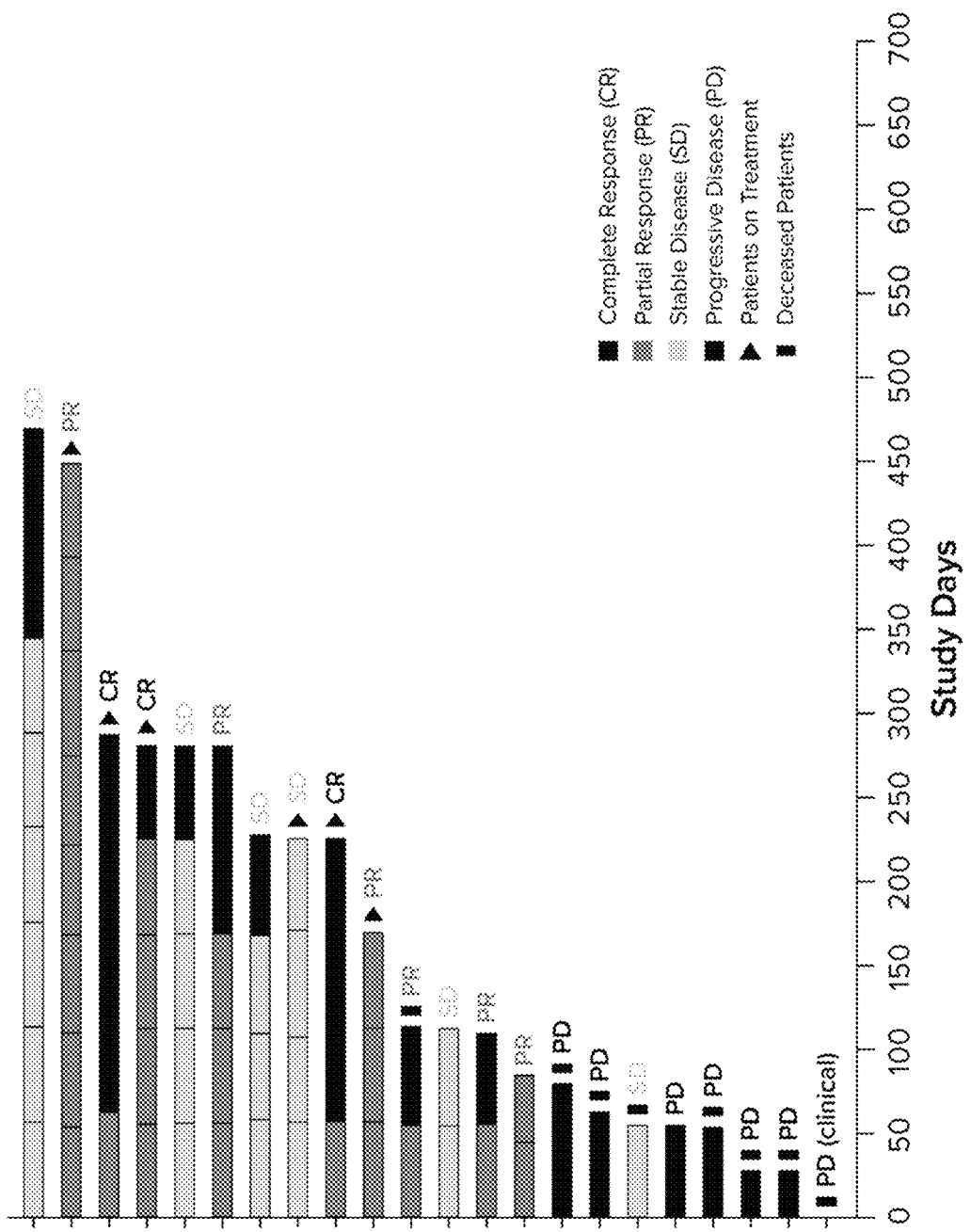
FIG. 13A provides a schematic showing the best overall response and duration of response in patients relapsed/refractory non-Hodgkin lymphoma treated with 10 mg/kg Drug A and rituximab.
Figure 13B:
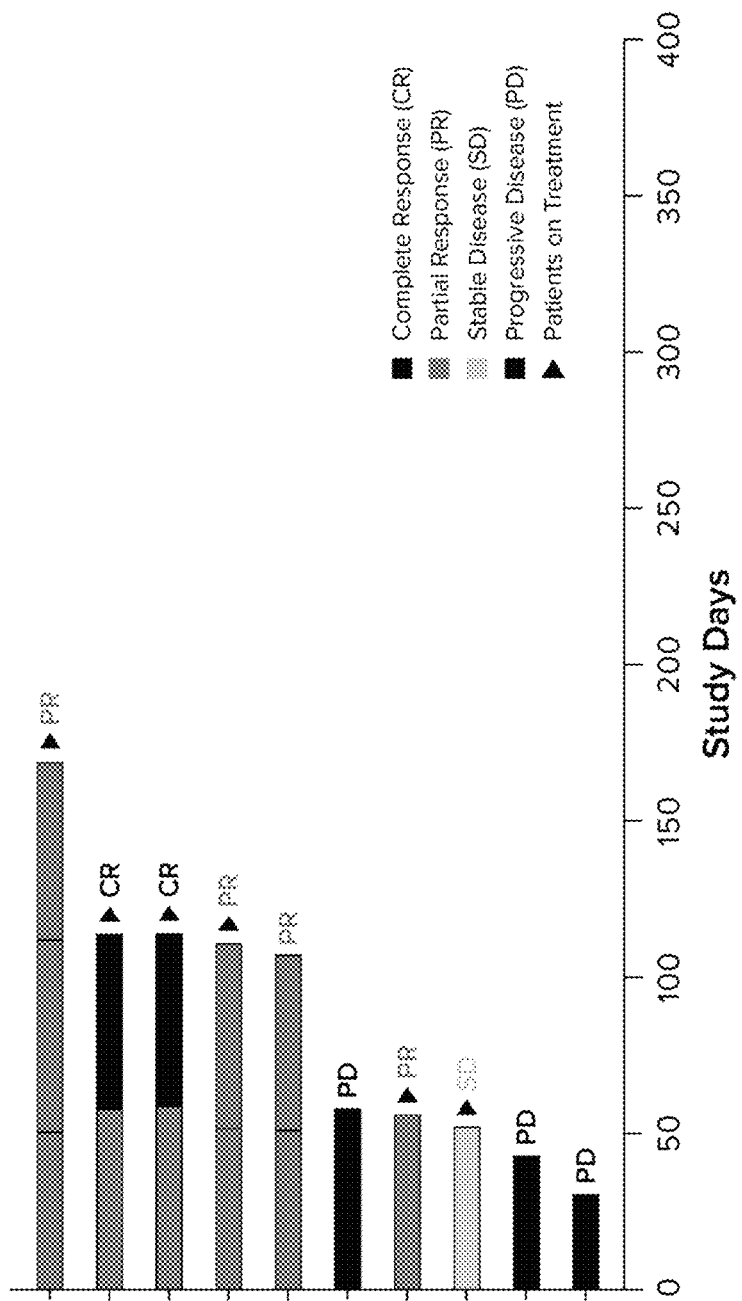
FIG. 13B provides a schematic showing the best overall response and duration of response in patients relapsed/refractory non-Hodgkin lymphoma treated with 15 mg/kg Drug A and rituximab. One patient with clinical progression Study Day 8 as best response not shown.

In Sheet 24 of 26, FIG. 12, in both instances of the y-axis, please replace "Measureable" with --Measurable--;

In the Specification

In Column 2, Line 33 please replace "IgG" with --IgG1--;

In Column 2, Line 47 please replace "50%," with --50%.--;

In Column 2, Line 55 please replace "IgG" with --IgG1--;

In Column 2, Line 64 please replace "deG236," with --delG236,--;

In Column 3, Line 43 please replace "IgG" with --IgG1--;

In Column 3, Line 52 please replace "deG236," with --delG236,--;

In Column 3, Line 64 please replace "IgG" with --IgG1--;

In Column 4, Line 6 please replace "deG236," with --delG236,--;

In Column 4, Line 58 please replace "IgG" with --IgG1--;

In Column 6, Line 8 please replace "IgG" with --IgG1--;

In Column 6, Line 17 please replace "deG236," with --delG236,--;

In Column 6, Line 36 please replace "deG236" with --delG236--;

In Column 6, Line 53 please replace "IgG" with --IgG1--;

In Column 6, Line 59 please replace "deG236" with --delG236--;

In Column 7, Line 8 please replace "ifosfaide," with --ifosfamide,--;

In Column 7, Lines 8-9 please replace "carmustine nielphalan," with --carmustine, melphalan,--;

In Column 7, Line 11 please replace "obinituzumab," with --obinutuzumab,--;

In Column 7, Line 22 please replace "Fe" with --Fc--;

In Column 7, Line 26 please replace "IgG" with --IgG1--;

In Column 7, Line 48 please replace "IgG" with --IgG1--;

In Column 7, Line 57 please replace "deG236," with --delG236,--;

In Column 8, Line 3 please replace "IgG" with --IgG1--;

In Column 8, Lines 27-28 please replace "obinituzumab," with --obinutuzumab,--;

In Column 8, Line 57 please replace "D" with --D1--;

In Column 8, Line 63 please replace "Fe" with --Fc--;

In Column 9, Line 18 please replace "IgG" with --IgG1--;

In Column 9, Line 24 please replace "deG236" with --delG236--;

In Column 9, Line 48 please replace "IgG" with --IgG1--;

In Column 10, Line 12 please replace "IgG" with --IgG1--;

In Column 10, Line 21 please replace "deG236," with --delG236,--;

In Column 10, Line 35 please replace "Fe" with --Fc--;

In Column 10, Line 42 please replace "IgG" with --IgG1--;

In Column 10, Line 49 please replace "deG236" with --delG236--;

In Column 11, Line 15 please replace "deG236" with --delG236--;

In Column 11, Line 38 please replace "IgG" with --IgG1--;

In Column 14, Line 7 please replace ""V"" with --"Λ"--;

In Column 16, Line 29 please replace "IgG" with --IgG1--;

In Column 16, Line 65 please replace "deG236," with --delG236,--;

In Column 17, Line 54 please replace ""PD-L"" with --"PD-L1"--;

In Column 18, Line 29 please replace "deG236" with --delG236--;

In Column 18, Line 40 please replace "the a" with --the--;

In Column 18, Line 49 please replace "IgG" with --IgG1--;

In Column 19, Line 5 please replace "SIRP" with --SIRPα--;

In Column 19, Line 17 please replace "of" with --of:--;

In Column 22, Line 38 please replace "D" with --D1--;

In Column 29, Line 30 please replace "$1\times10^{-8}$M, less than $5\times10^{-9}$M," with --$1\times10^{-8}$ M, less than $5\times10^{-9}$ M,--;

In Column 29, Line 31 please replace "$1\times10^{-9}$M," with --$1\times10^{-9}$ M,--;

In Column 29, Line 32 please replace "$1\times10^{-11}$M." with --$1\times10^{-11}$ M.--;

In Column 30, Line 17 please replace "$1\times10^{-8}$M," with --$1\times10^{-8}$ M,--;

In Column 30, Line 17 please replace "$1\times10^{-9}$M," with --$1\times10^{-9}$ M,--;

In Column 30, Line 18 please replace "$1\times10^{-10}$M" with --$1\times10^{-10}$ M--;

In Column 30, Line 59 please replace "$X_5$" with --$X_{15}$--;

In Column 31, Line 5 please replace "$X_2s$" with --$X_{28}$--;

In Column 42, Line 67 please replace "D" with --D1--;

In Column 43, Line 14 please replace "D" with --D1--;

In Column 43, Line 49 please replace "$X_{18}$" with --$X_{15}$--;

In Column 44, Line 5 please replace "$1\times10^{-8}$M, less than $5\times10^{-9}$M," with --$1\times10^{-8}$ M, less than $5\times10^{-9}$ M,--;

In Column 44, Line 28 please replace "D" with --D1--;

In Column 44, Line 47 please replace "$X_{18}$" with --$X_{15}$--;

In Column 45, Line 1 please replace "$1\times10^{-8}$M," with --$1\times10^{-8}$ M,--;

In Column 45, Line 1 please replace "$1\times10^{-9}$M," with --$1\times10^{-9}$ M,--;

In Column 45, Line 2 please replace "$1\times10^{10}$M" with --$1\times10^{-10}$ M--;

In Column 45, Line 51 please replace "$X_2$" with --$X_{20}$--;

In Column 46, Line 52 please replace "D" with --D1--;

In Column 47, Line 25 please replace "$5\times10^{-1}$" with --$5\times10^{-10}$--;

In Column 48, Line 16 please replace "$5\times10^{-1}$" with --$5\times10^{-10}$--;

In Column 50, Line 61 please replace "5×10$^{-9}$M," with --5×10$^{-9}$ M,--;

In Column 52, Line 24 please replace "5×10$^{-9}$M," with --5×10$^{-9}$ M,--;

In Column 52, Line 25 please replace "5×10$^{-10}$M," with --5×10$^{-10}$ M,--;

In Column 53, Line 8 please replace "SIRPαD1" with --SIRPα D1--;

In Column 54, Line 5 please replace "1×10$^{-8}$M," with --1×10$^{-8}$ M,--;

In Column 54, Line 5 please replace "1×10$^{-9}$M," with --1×10$^{-9}$ M,--;

In Column 54, Line 6 please replace "1×10$^{-11}$M." with --1×10$^{-11}$ M.--;

In Column 60, Line 26 please replace "IgG," with --IgG1,--;

In Column 62, Line 49 please replace "Fe" with --Fc--;

In Column 64, Line 19 please replace "deG236," with --delG236,--;

In Column 66, Line 49 please replace "Fe domain variant or Fe domain" with --Fc domain variant or Fc domain--;

In Column 67, Line 30 please replace "Fe" with --Fc--;

In Column 67, Line 31 please replace "Fe" with --Fc--;

In Column 69, Line 47 please replace "of" with --of:--;

In Column 70, Line 42 please replace "Fe" with --Fc--;

In Column 81, Line 21 please replace "D" with --D1--;

In Column 87, Line 10 please replace "deG236" with --delG236--;

In Column 87, Line 12 please replace "deG236," with --delG236,--;

In Column 87, Line 35 please replace "Fe" with --Fc--;

In Column 87, Line 37 please replace "Fe" with --Fc--;

In Column 87, Line 38 please replace "Fe" with --Fc--;

In Column 87, Line 39 please replace "Fe" with --Fc--;

In Column 87, Line 41 please replace "Fe" with --Fc--;

CERTIFICATE OF CORRECTION (continued)
U.S. Pat. No. 11,613,564 B2

In Column 87, Line 49 please replace "of" with --of:--;

In Column 87, Line 53 please replace "Fe variant, wherein the Fe" with --Fc variant, wherein the Fc--;

In Column 87, Line 54 please replace "Fe domain dimer comprising two Fe" with --Fc domain dimer comprising two Fc--;

In Column 87, Line 55 please replace "Fe" with --Fc--;

In Column 87, Line 65 please replace "Fe" with --Fc--;

In Column 88, Line 1 please replace "Fe" with --Fc--;

In Column 89, TABLE 12, Line 17 please replace "AminoAcidSequence" with --Amino Acid Sequence--;

In Column 90, TABLE 12-continued, Line 4 please replace "AminoAcidSequence" with --Amino Acid Sequence--;

In Column 90, Line 19 please replace "(SRP-α)" with --(SIRP-α)--;

In Column 90, Line 24 please replace "of" with --of:--;

In Column 92, Line 3 please replace "CRL7030," with --CRL7O3O,--;

In Column 94, Line 34 please replace "IgG" with --IgG1--;

In Column 94, Line 40 please replace "deG236" with --delG236--;

In Column 94, Line 50 please replace "IgG" with --IgG1--;

In Column 95, Line 13 please replace "pdf," with --pdf;--;

In Column 95, Line 47 please replace "*J*" with --*J.*--;

In Column 95, Line 48 please replace "*J*" with --*J.*--;

In Column 95, Line 49 please replace "*J*" with --*J.*--;

In Column 96, Line 26 please replace ""Pembrolizurnab" with --"Pembrolizumab--;

In Column 96, Line 47 please replace "IgG" with --IgG1--;

In Column 96, Line 56 please replace "deG236" with --delG236--;

In Column 96, Line 63 please replace "Fe" with --Fc--;

CERTIFICATE OF CORRECTION (continued)
U.S. Pat. No. 11,613,564 B2

Figure 10A:
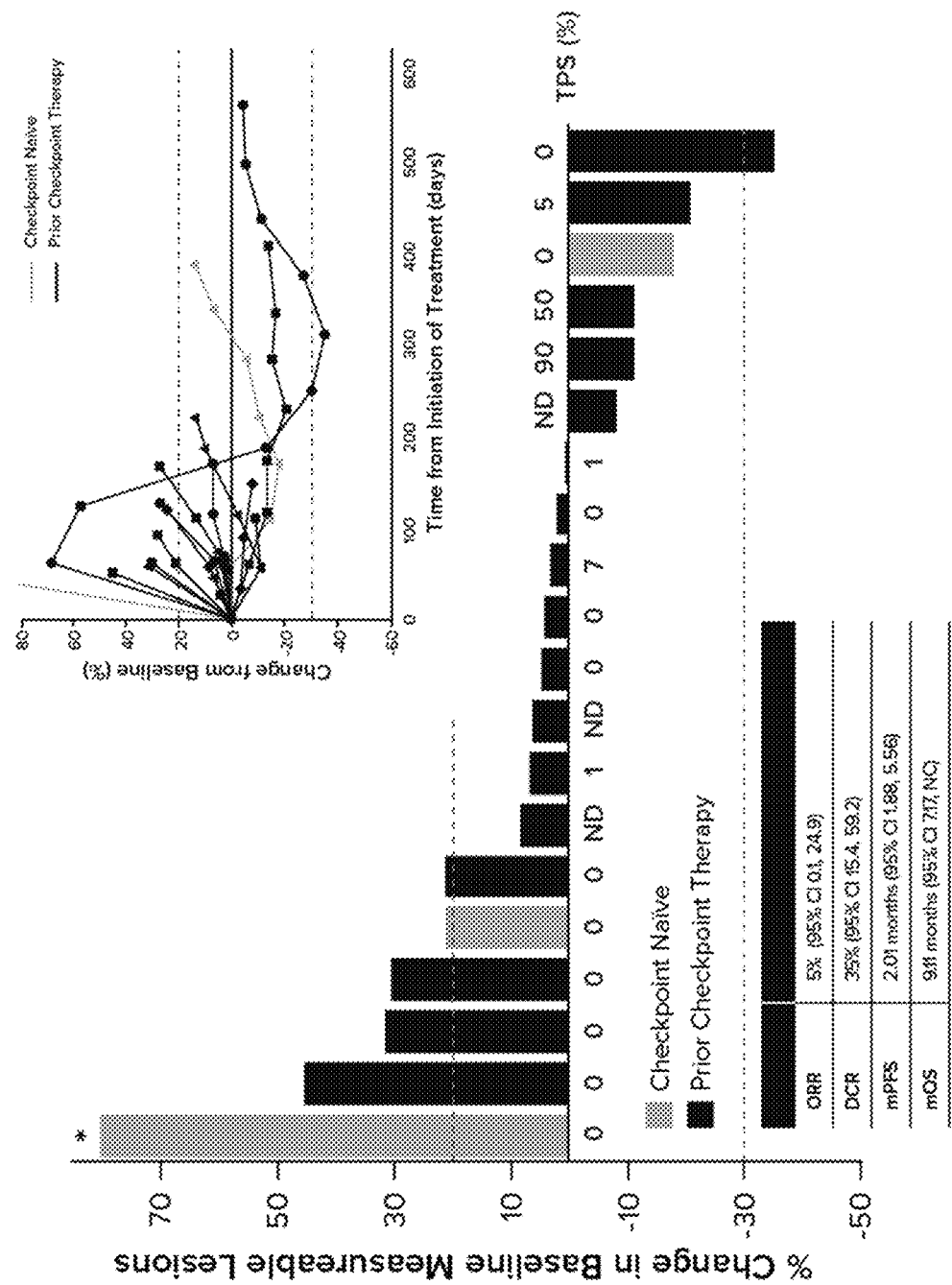
FIG. 10A provides a schematic showing the clinical activity of Drug A in combination with pembrolizumab in response-evaluable ≥2L NSCLC patients. Patient indicated with* demonstrated change greater than 80%. TPS=tumor proportion score.
Figure 10B:
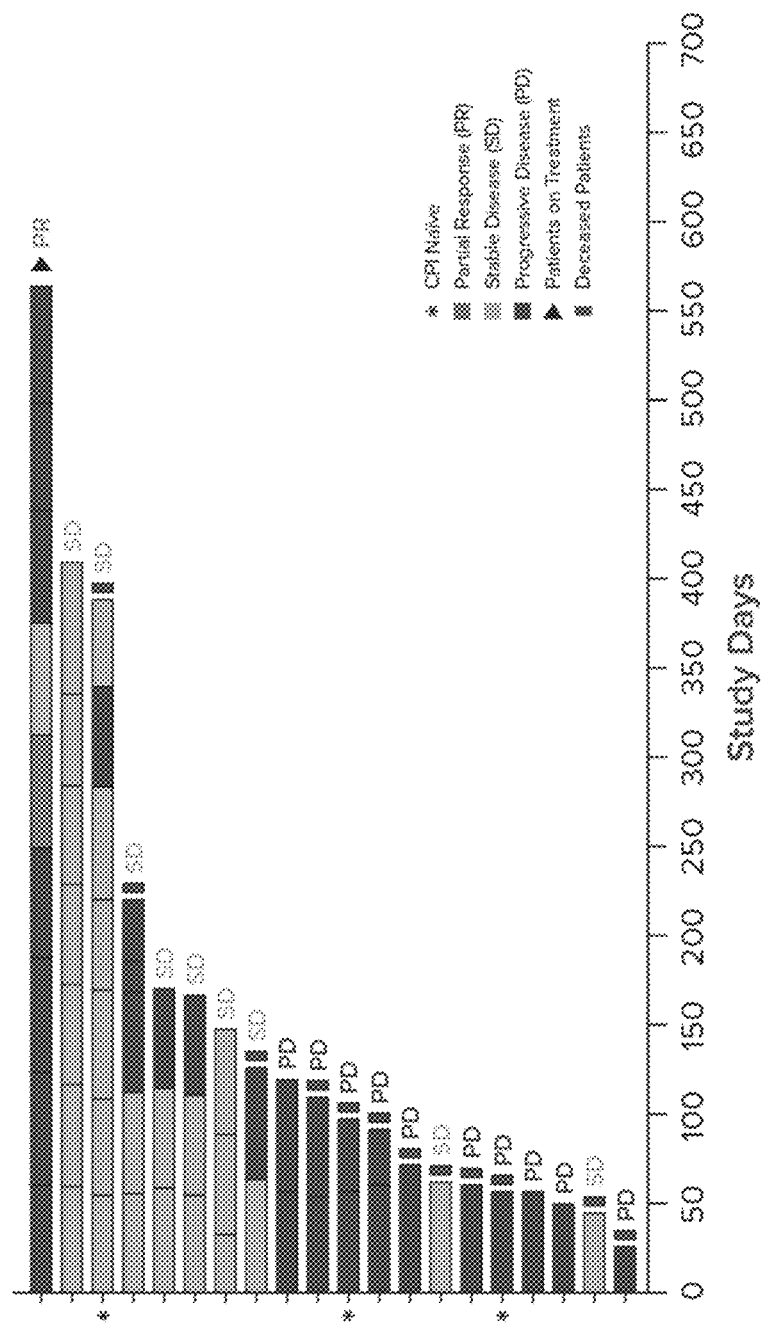
FIG. 10B provides a schematic showing the best overall response and duration of response in ≥2L NSCLC patients treated with Drug A and pembrolizumab.

In Column 96, Line 64 please replace "IgG" with --IgG1--;

In Column 97, Line 12 please replace "herein" with --herein.--;

In Column 97, Line 30 please replace "pdf," with --pdf;--;

In Column 97, Line 66 please replace "*J*" with --*J*.--;

In Column 97, Line 67 please replace "*J*" with --*J*.--;

In Column 98, Line 1 please replace "*J*" with --*J*.--;

In Column 100, Line 2 please replace "*J*" with --*J*.--;

In Column 101, Line 32 please replace "pdf," with --pdf;--;

In Column 102, Line 31 please replace "gemciabine, cyclopiosphamide, vMcristine," with --gemcitabine, cyclophosphamide, vincristine,--;

In Column 102, Line 32 please replace "cyclphospharnide," with --cyclophosphamide,--;

In Column 102, Line 33 please replace "prednisone-RCEOP" with --prednisone); R-CEOP--;

In Column 102, Line 34 please replace "prednisone):" with --prednisone);--;

In Column 102, Line 35 please replace "rjiximab, cyclophosphammid," with --rituximab, cyclophosphamide,--;

In Column 102, Line 36 please replace "bendanustine;" with --bendamustine;--;

In Column 102, Line 37 please replace "DIHAP" with --DHAP--;

In Column 102, Line 56 please replace "obinituzumab," with --obinutuzumab,--;

In Column 103, Line 50 please replace "deG236," with --delG236,--;

In Column 103, Line 60 please replace "Fe" with --Fc--;

In Column 104, Line 26 please replace "pdf," with --pdf;--;

In Column 104, Line 46 please replace "*J*" with --*J*.--;

In Column 106, Line 16 please replace "*J*" with --*J*.--;

In Column 106, Line 39 please replace "*J*" with --*J*.--;

In Column 106, Line 40 please replace ".*J*" with --*J*.--;

In Column 108, Line 17 please replace "deG236," with --delG236,--;

In Column 112, Line 10 please replace "($\geq 1.0 \times 10^9$L);" with --($\geq 1.0 \times 10^9$/L);--;

In Column 112, Line 12 please replace "($\geq 50 \times 10^9$);" with --($\geq 50 \times 10^9$/L);--;

In Column 113, Line 43 please replace "(HV)" with --(HIV)--;

In Column 114, Line 8 please replace "(DrugA+pembrolizumab; Drug A+trastuzumab; DrugA+" with --(Drug A + pembrolizumab; Drug A + trastuzumab; Drug A +--;

In Column 115, Line 14 please replace "Q2W)" with --Q2W).--;

In Column 115, Line 34 please replace "DrugA+pembrolizumab" with --Drug A + pembrolizumab--;

In Column 115, Line 38 please replace "DrugA+trastuzumab" with --Drug A + trastuzumab--;

In Column 115, Line 41 please replace "DrugA+rituximab" with --Drug A + rituximab--;

In Column 116, Line 32 please replace "$AUC_t$)" with --$AUC\tau$)--;

In Column 117, Line 47 please replace "DrugA+pembrolizumab" with --Drug A + pembrolizumab--;

In Column 117, Line 48 please replace "TRAEF in the DrugA+" with --TRAE in the Drug A +--;

In Column 117, Line 49 please replace "(26.70%)." with --(26.7%).--;

In Column 117, Line 50 please replace "TRAEF in the DrugA+" with --TRAE in the Drug A +--;

In Column 117, Line 51 please replace "(154)." with --(15.4%).--;

In Column 118, Line 25 please replace "DrugA+trastuzumab" with --Drug A + trastuzumab--;

In Column 118, Line 27 please replace "DrugA+pembrolizumab" with --Drug A + pembrolizumab--;

In Column 118, Line 34 please replace "DrugA+trastuzumab" with --Drug A + trastuzumab--;

In Column 118, Line 37 please replace "DrugA+pembrolizumab" with --Drug A + pembrolizumab--;

In Column 118, Line 44 please replace "DrugA+trastuzumab" with --Drug A + trastuzumab--;

In Column 118, Line 45 please replace "gastric GEJ" with --gastric/GEJ--;

In Column 118, Line 57 please replace "DrugA+pembrolizumab" with --Drug A + pembrolizumab--;

In Column 119, Line 7 please replace "DrugA+pembrolizumab" with --Drug A + pembrolizumab--;

In Column 119, Line 23 please replace "DrugA+trastuzumab and DrugA+pembrolizumab" with --Drug A + trastuzumab and Drug A + pembrolizumab--;

In Column 119, Lines 25-26 please replace "Immunotherpay" with --Immunotherapy--;

In Column 119, Line 34 please replace "DrugA+pembrolizumab" with --Drug A + pembrolizumab--;

In Column 119, Line 35 please replace "DrugA+pembrolizumab" with --Drug A + pembrolizumab--;

In Column 119, Line 36 please replace "DrugA+trastuzumab" with --Drug A + trastuzumab--;

In Column 119, Line 42 please replace "DrugA+pembrolizumab" with --Drug A + pembrolizumab--;

In Column 119, Lines 43-44 please replace "DrugA+pembrolizumab" with --Drug A + pembrolizumab--;

In Column 120, Line 23 please replace "M" with --M1--;

In Column 120, Lines 43-44 please replace "DrugA+pembrolizumab" with --Drug A + pembrolizumab--;

In Column 120, Lines 44-45 please replace "DrugA+trastuzumab" with --Drug A + trastuzumab--;

In Column 120, Lines 47-48 please replace "DrugA+pembrolizumab" with --Drug A + pembrolizumab--;

In Column 120, Line 50 please replace "DrugA+trastuzumab" with --Drug A + trastuzumab--;

In Column 121, Line 26 please replace "DrugA+pembrolizumab" with --Drug A + pembrolizumab--;

In Column 121, Line 31 please replace "DrugA+trastuzumab" with --Drug A + trastuzumab--;

In Column 121, Line 39 please replace "a" with --A--;

In Column 121, Lines 45-46 please replace "DrugA+pembrolizumab" with --Drug A + pembrolizumab--;

In Column 122, Line 22 please replace "$\geq$2 L HNSCC and $\geq$ 2L" with --$\geq$2L HNSCC and $\geq$2L--;

In Column 122, Line 58 please replace "DrugA+pembrolizumab" with --Drug A + pembrolizumab--;

In Column 123, Line 2 please replace "a" with --A--;

In Column 123, Line 26 please replace "FIG. A," with --FIG. 10A,--;

In Column 123, Lines 31-32 please replace "DrugA+pembrolizumab" with --Drug A + pembrolizumab--;

In Column 123, Line 48 please replace "DrugA+trastuzumab" with --Drug A + trastuzumab--;

In Column 124, Line 40 please replace "DrugA+trastuzumab" with --Drug A + trastuzumab--;

In Column 124, Line 52 please replace "a" with --A--;

In Column 124, Line 61 please replace "NIL" with --NHL--;

In Column 125, Line 18 please replace "A15" with --A 15--;

In Column 126, Lines 47-48 please replace "DrugA+rituximab" with --Drug A + rituximab--;

In Column 126, Line 58 please replace "DrugA+rituximab" with --Drug A + rituximab--;

In Column 126, Line 64 please replace "DrugA+rituximab" with --Drug A + rituximab--; and In Column 126, Line 67 please replace "DrugA+rituximab" with --Drug A + rituximab--.

SEQUENCE LISTING

```
<160> NUMBER OF SEQ ID NOS: 224

<210> SEQ ID NO 1
<211> LENGTH: 119
<212> TYPE: PRT
<213> ORGANISM: Artificial Sequence
<220> FEATURE:
<223> OTHER INFORMATION: Synthetic Construct

<400> SEQUENCE: 1

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110
```

Ser Val Arg Ala Lys Pro Ser
         115

<210> SEQ ID NO 2
<211> LENGTH: 118
<212> TYPE: PRT
<213> ORGANISM: Artificial Sequence
<220> FEATURE:
<223> OTHER INFORMATION: Synthetic Construct

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
         115

<210> SEQ ID NO 3
<211> LENGTH: 118
<212> TYPE: PRT
<213> ORGANISM: Artificial Sequence
<220> FEATURE:
<223> OTHER INFORMATION: Synthetic Construct

<400> SEQUENCE: 3

Glu Glu Glu Leu Gln Val Ile Gln Pro Asp Lys Ser Val Ser Val Ala
1               5                   10                  15

Ala Gly Glu Ser Ala Ile Leu Leu Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
         115

<210> SEQ ID NO 4
<211> LENGTH: 119
<212> TYPE: PRT
<213> ORGANISM: Artificial Sequence
<220> FEATURE:
<223> OTHER INFORMATION: Synthetic Construct

<400> SEQUENCE: 4

Glu Glu Gly Leu Gln Val Ile Gln Pro Asp Lys Ser Val Ser Val Ala
1               5                   10                  15

Ala Gly Glu Ser Ala Ile Leu His Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 5
<211> LENGTH: 119
<212> TYPE: PRT
<213> ORGANISM: Artificial Sequence
<220> FEATURE:
<223> OTHER INFORMATION: Synthetic Construct

<400> SEQUENCE: 5

Glu Glu Glu Leu Gln Val Ile Gln Pro Asp Lys Phe Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 6
<211> LENGTH: 119
<212> TYPE: PRT
<213> ORGANISM: Artificial Sequence
<220> FEATURE:
<223> OTHER INFORMATION: Synthetic Construct

<400> SEQUENCE: 6

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
            50                  55                  60

Asp Leu Thr Lys Arg Asn Asn Met Asp Phe Pro Ile Arg Ile Gly Asn
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 7
<211> LENGTH: 118
<212> TYPE: PRT
<213> ORGANISM: Artificial Sequence
<220> FEATURE:
<223> OTHER INFORMATION: Synthetic Construct

<400> SEQUENCE: 7

Glu Glu Glu Leu Gln Val Ile Gln Pro Asp Lys Ser Val Ser Val Ala
 1               5                  10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Gly Lys Pro Ser
        115

<210> SEQ ID NO 8
<211> LENGTH: 118
<212> TYPE: PRT
<213> ORGANISM: Artificial Sequence
<220> FEATURE:
<223> OTHER INFORMATION: Synthetic Construct

<400> SEQUENCE: 8

Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser

Val Arg Ala Lys Pro Ser
        115

<210> SEQ ID NO 9
<211> LENGTH: 119
<212> TYPE: PRT
<213> ORGANISM: Artificial Sequence
<220> FEATURE:
<223> OTHER INFORMATION: Synthetic Construct

<400> SEQUENCE: 9

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 10
<211> LENGTH: 118
<212> TYPE: PRT
<213> ORGANISM: Artificial Sequence
<220> FEATURE:
<223> OTHER INFORMATION: Synthetic Construct

<400> SEQUENCE: 10

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 11
<211> LENGTH: 119
<212> TYPE: PRT
<213> ORGANISM: Artificial Sequence
<220> FEATURE:

```
<223> OTHER INFORMATION: Synthetic Construct
<220> FEATURE:
<221> NAME/KEY: VARIANT
<222> LOCATION: 3
<223> OTHER INFORMATION: Xaa = E or G
<220> FEATURE:
<221> NAME/KEY: VARIANT
<222> LOCATION: 12
<223> OTHER INFORMATION: Xaa = S or F
<220> FEATURE:
<221> NAME/KEY: VARIANT
<222> LOCATION: 14
<223> OTHER INFORMATION: Xaa = L or S
<220> FEATURE:
<221> NAME/KEY: VARIANT
<222> LOCATION: 20
<223> OTHER INFORMATION: Xaa = T or S
<220> FEATURE:
<221> NAME/KEY: VARIANT
<222> LOCATION: 22
<223> OTHER INFORMATION: Xaa = T or I
<220> FEATURE:
<221> NAME/KEY: VARIANT
<222> LOCATION: 24
<223> OTHER INFORMATION: Xaa = R, H, or L
<220> FEATURE:
<221> NAME/KEY: VARIANT
<222> LOCATION: 27
<223> OTHER INFORMATION: Xaa = A or V
<220> FEATURE:
<221> NAME/KEY: VARIANT
<222> LOCATION: 45
<223> OTHER INFORMATION: Xaa = G or A
<220> FEATURE:
<221> NAME/KEY: VARIANT
<222> LOCATION: 65
<223> OTHER INFORMATION: Xaa = D or E
<220> FEATURE:
<221> NAME/KEY: VARIANT
<222> LOCATION: 66
<223> OTHER INFORMATION: Xaa = L or S
<220> FEATURE:
<221> NAME/KEY: VARIANT
<222> LOCATION: 70
<223> OTHER INFORMATION: Xaa = N, E or D
<220> FEATURE:
<221> NAME/KEY: VARIANT
<222> LOCATION: 75
<223> OTHER INFORMATION: Xaa = S or P
<220> FEATURE:
<221> NAME/KEY: VARIANT
<222> LOCATION: 77
<223> OTHER INFORMATION: Xaa = R or S
<220> FEATURE:
<221> NAME/KEY: VARIANT
<222> LOCATION: 79
<223> OTHER INFORMATION: Xaa = G or S
<220> FEATURE:
<221> NAME/KEY: VARIANT
<222> LOCATION: 99
<223> OTHER INFORMATION: Xaa = P or absent
<220> FEATURE:
<221> NAME/KEY: VARIANT
<222> LOCATION: 100
<223> OTHER INFORMATION: Xaa = D or P
<220> FEATURE:
<221> NAME/KEY: VARIANT
<222> LOCATION: 102
<223> OTHER INFORMATION: Xaa = V or T
<220> FEATURE:
<221> NAME/KEY: VARIANT
<222> LOCATION: 116
<223> OTHER INFORMATION: Xaa = A or G

<400> SEQUENCE: 11

Glu Glu Xaa Leu Gln Val Ile Gln Pro Asp Lys Xaa Val Xaa Val Ala
1               5                   10                  15
```

```
Ala Gly Glu Xaa Ala Xaa Leu Xaa Cys Thr Xaa Thr Ser Leu Ile Pro
            20              25                  30

Val Gly Pro Ile Gln Trp Phe Arg Gly Ala Gly Pro Xaa Arg Glu Leu
        35              40                  45

Ile Tyr Asn Gln Lys Glu Gly His Phe Pro Arg Val Thr Thr Val Ser
    50                  55                  60

Xaa Xaa Thr Lys Arg Xaa Asn Met Asp Phe Xaa Ile Xaa Ile Xaa Asn
65                  70                  75                  80

Ile Thr Pro Ala Asp Ala Gly Thr Tyr Tyr Cys Val Lys Phe Arg Lys
                85                  90                  95

Gly Ser Xaa Xaa Asp Xaa Glu Phe Lys Ser Gly Ala Gly Thr Glu Leu
            100                 105                 110

Ser Val Arg Xaa Lys Pro Ser
            115

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 3, 5, 7, 9
<223> OTHER INFORMATION: Xaa = Any Amino Acid
<220> FEATURE:
<221> NAME/KEY: VARIANT
<222> LOCATION: (3)..(4)
<223> OTHER INFORMATION: Can be present or absent
<220> FEATURE:
<221> NAME/KEY: VARIANT
<222> LOCATION: (5)..(6)
<223> OTHER INFORMATION: Can be present or absent
<220> FEATURE:
<221> NAME/KEY: VARIANT
<222> LOCATION: (7)..(8)
<223> OTHER INFORMATION: Can be present or absent
<220> FEATURE:
<221> NAME/KEY: VARIANT
<222> LOCATION: (9)..(10)
<223> OTHER INFORMATION: Can be present or absent

<400> SEQUENCE: 12

Xaa Pro Xaa Pro Xaa Pro Xaa Pro Xaa Pro
1               5                   10

<210> SEQ ID NO 13
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
```

```
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 13

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Asn
65                  70                  75                  80

Ile Thr Pro Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 14
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
```

```
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 14

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
            115

<210> SEQ ID NO 15
<211> LENGTH: 118
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 15

Glu Glu Glu Xaa Gln Xaa Ile Gln Pro Asp Lys Ser Val Ser Val Ala
1               5                   10                  15

Ala Gly Glu Ser Xaa Ile Leu Leu Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
```

```
                    85                  90                  95
Gly Ser Pro Asp Thr Glu Xaa Lys Ser Gly Ala Gly Thr Glu Leu Ser
                100                 105                 110

Val Arg Ala Lys Pro Ser
            115

<210> SEQ ID NO 16
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 16

Glu Glu Gly Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30
```

```
Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
        50                  55                  60

Asp Xaa Thr Xaa Arg Asn Asn Met Asp Phe Ser Ile Arg Ile Gly Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 17
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
```

```
<221> NAME/KEY: VARIANT
<222> LOCATION: 104
<223> OTHER INFORMATION: Xaa = F, V

<400> SEQUENCE: 17

Glu Glu Glu Xaa Gln Xaa Ile Gln Pro Asp Lys Phe Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Asn
65          70                  75                      80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 18
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
```

```
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 18

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Pro Ile Arg Ile Gly Asn
65              70                  75                  80

Ile Thr Pro Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 19
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
```

```
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 19

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Asn
65              70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Gly Lys Pro Ser
            115

<210> SEQ ID NO 20
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
```

```
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 20

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 21
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
```

```
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 21

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 22
<211> LENGTH: 118
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 22

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
            85                  90                  95
```

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 23
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E, G
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 12
<223> OTHER INFORMATION: Xaa = S, F
<220> FEATURE:
<221> NAME/KEY: VARIANT
<222> LOCATION: 14
<223> OTHER INFORMATION: Xaa = L, S
<220> FEATURE:
<221> NAME/KEY: VARIANT
<222> LOCATION: 20
<223> OTHER INFORMATION: Xaa = S, T
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 22
<223> OTHER INFORMATION: Xaa = I, T
<220> FEATURE:
<221> NAME/KEY: VARIANT
<222> LOCATION: 24
<223> OTHER INFORMATION: Xaa = H, R
<220> FEATURE:
<221> NAME/KEY: VARIANT
<222> LOCATION: 27
<223> OTHER INFORMATION: Xaa = A, V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 45
<223> OTHER INFORMATION: Xaa = A, G
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT

```
<222> LOCATION: 65
<223> OTHER INFORMATION: Xaa = D, E
<220> FEATURE:
<221> NAME/KEY: VARIANT
<222> LOCATION: 66
<223> OTHER INFORMATION: Xaa = S, L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 70
<223> OTHER INFORMATION: Xaa = E, D
<220> FEATURE:
<221> NAME/KEY: VARIANT
<222> LOCATION: 75
<223> OTHER INFORMATION: Xaa = S, P
<220> FEATURE:
<221> NAME/KEY: VARIANT
<222> LOCATION: 77
<223> OTHER INFORMATION: Xaa = S, R
<220> FEATURE:
<221> NAME/KEY: VARIANT
<222> LOCATION: 79
<223> OTHER INFORMATION: Xaa = S, G
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 101
<223> OTHER INFORMATION: Xaa = D or absent
<220> FEATURE:
<221> NAME/KEY: VARIANT
<222> LOCATION: 102
<223> OTHER INFORMATION: Xaa = T, V
<220> FEATURE:
<221> NAME/KEY: VARIANT
<222> LOCATION: 104
<223> OTHER INFORMATION: Xaa = F, V
<220> FEATURE:
<221> NAME/KEY: VARIANT
<222> LOCATION: 116
<223> OTHER INFORMATION: Xaa = A, G

<400> SEQUENCE: 23

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60

Xaa Xaa Thr Xaa Arg Xaa Asn Met Asp Phe Xaa Ile Xaa Ile Xaa Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Xaa Xaa Glu Xaa Lys Ser Gly Ala Gly Thr Glu Leu
            100                 105                 110

Ser Val Arg Xaa Lys Pro Ser
        115

<210> SEQ ID NO 24
```

<211> LENGTH: 102
<212> TYPE: PRT
<213> ORGANISM: Artificial Sequence
<220> FEATURE:
<223> OTHER INFORMATION: Synthetic Construct

<400> SEQUENCE: 24

```
Ala Pro Val Val Ser Gly Pro Ala Ala Arg Ala Thr Pro Gln His Thr
1               5                   10                  15

Val Ser Phe Thr Cys Glu Ser His Gly Phe Ser Pro Arg Asp Ile Thr
            20                  25                  30

Leu Lys Trp Phe Lys Asn Gly Asn Glu Leu Ser Asp Phe Gln Thr Asn
        35                  40                  45

Val Asp Pro Val Gly Glu Ser Val Ser Tyr Ser Ile His Ser Thr Ala
    50                  55                  60

Lys Val Val Leu Thr Arg Glu Asp Val His Ser Gln Val Ile Cys Glu
65                  70                  75                  80

Val Ala His Val Thr Leu Gln Gly Asp Pro Leu Arg Gly Thr Ala Asn
                85                  90                  95

Leu Ser Glu Thr Ile Arg
            100
```

<210> SEQ ID NO 25
<211> LENGTH: 99
<212> TYPE: PRT
<213> ORGANISM: Artificial Sequence
<220> FEATURE:
<223> OTHER INFORMATION: Synthetic Construct

<400> SEQUENCE: 25

```
Val Pro Pro Thr Leu Glu Val Thr Gln Gln Pro Val Arg Ala Glu Asn
1               5                   10                  15

Gln Val Asn Val Thr Cys Gln Val Arg Lys Phe Tyr Pro Gln Arg Leu
            20                  25                  30

Gln Leu Thr Trp Leu Glu Asn Gly Asn Val Ser Arg Thr Glu Thr Ala
        35                  40                  45

Ser Thr Val Thr Glu Asn Lys Asp Gly Thr Tyr Asn Trp Met Ser Trp
    50                  55                  60

Leu Leu Val Asn Val Ser Ala His Arg Asp Asp Val Lys Leu Thr Cys
65                  70                  75                  80

Gln Val Glu His Asp Gly Gln Pro Ala Val Ser Lys Ser His Asp Leu
                85                  90                  95

Lys Val Ser
```

<210> SEQ ID NO 26
<211> LENGTH: 118
<212> TYPE: PRT
<213> ORGANISM: Artificial Sequence
<220> FEATURE:
<223> OTHER INFORMATION: Synthetic Construct

<400> SEQUENCE: 26

```
Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly His Phe Pro Arg Val Thr Thr Val Ser
```

```
                50                  55                  60
Glu Thr Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Val Lys Ser Gly Ala Gly Thr Glu Leu Ser
                100                 105                 110

Val Arg Ala Lys Pro Ser
            115

<210> SEQ ID NO 27
<211> LENGTH: 118
<212> TYPE: PRT
<213> ORGANISM: Artificial Sequence
<220> FEATURE:
<223> OTHER INFORMATION: Synthetic Construct

<400> SEQUENCE: 27

Glu Glu Glu Val Gln Val Ile Gln Pro Asp Lys Ser Val Ser Val Ala
  1               5                  10                  15

Ala Gly Glu Ser Ala Ile Leu His Cys Thr Leu Thr Ser Leu Ile Pro
                 20                  25                  30

Val Gly Pro Ile Gln Trp Phe Arg Gly Ala Gly Pro Ala Arg Val Leu
             35                  40                  45

Ile Tyr Asn Gln Arg Gln Gly His Phe Pro Arg Val Thr Thr Val Ser
         50                  55                  60

Glu Gly Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 28
<211> LENGTH: 118
<212> TYPE: PRT
<213> ORGANISM: Artificial Sequence
<220> FEATURE:
<223> OTHER INFORMATION: Synthetic Construct

<400> SEQUENCE: 28

Glu Glu Glu Val Gln Ile Ile Gln Pro Asp Lys Ser Val Ser Val Ala
  1               5                  10                  15

Ala Gly Glu Ser Val Ile Leu His Cys Thr Ile Thr Ser Leu Thr Pro
                 20                  25                  30

Val Gly Pro Ile Gln Trp Phe Arg Gly Ala Gly Pro Ala Arg Leu Leu
             35                  40                  45

Ile Tyr Asn Gln Arg Glu Gly Pro Phe Pro Arg Val Thr Thr Val Ser
         50                  55                  60

Glu Thr Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Val Lys Leu Arg Lys
                 85                  90                  95

Gly Ser Pro Asp Thr Glu Phe Lys Ser Gly Ala Gly Thr Glu Leu Ser
                100                 105                 110
```

Val Arg Ala Lys Pro Ser
        115

<210> SEQ ID NO 29
<211> LENGTH: 118
<212> TYPE: PRT
<213> ORGANISM: Artificial Sequence
<220> FEATURE:
<223> OTHER INFORMATION: Synthetic Construct

<400> SEQUENCE: 29

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 30
<211> LENGTH: 118
<212> TYPE: PRT
<213> ORGANISM: Artificial Sequence
<220> FEATURE:
<223> OTHER INFORMATION: Synthetic Construct

<400> SEQUENCE: 30

Glu Glu Glu Ile Gln Val Ile Gln Pro Asp Lys Ser Val Ser Val Ala
1               5                   10                  15

Ala Gly Glu Ser Val Ile Ile His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Arg Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Val Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 31
<211> LENGTH: 118
<212> TYPE: PRT
<213> ORGANISM: Artificial Sequence
<220> FEATURE:
<223> OTHER INFORMATION: Synthetic Construct -continued

```
<400> SEQUENCE: 31

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 32
<211> LENGTH: 118
<212> TYPE: PRT
<213> ORGANISM: Artificial Sequence
<220> FEATURE:
<223> OTHER INFORMATION: Synthetic Construct

<400> SEQUENCE: 32

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 33
<211> LENGTH: 119
<212> TYPE: PRT
<213> ORGANISM: Artificial Sequence
<220> FEATURE:
<223> OTHER INFORMATION: Synthetic Construct

<400> SEQUENCE: 33

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45
```

-continued

```
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
 65                  70                  75                  80
Ile Thr Pro Ala Asp Ala Gly Thr Tyr Tyr Cys Ile Lys Phe Arg Lys
                 85                  90                  95
Gly Ser Pro Asp Asp Val Glu Phe Lys Ser Gly Ala Gly Thr Glu Leu
             100                 105                 110
Ser Val Arg Ala Lys Pro Ser
        115
```

<210> SEQ ID NO 34
<211> LENGTH: 118
<212> TYPE: PRT
<213> ORGANISM: Artificial Sequence
<220> FEATURE:
<223> OTHER INFORMATION: Synthetic Construct

<400> SEQUENCE: 34

```
Glu Glu Glu Leu Gln Ile Ile Gln Pro Asp Lys Ser Val Ser Val Ala
  1               5                  10                  15
Ala Gly Glu Ser Ala Ile Leu His Cys Thr Ile Thr Ser Leu Phe Pro
             20                  25                  30
Val Gly Pro Ile Gln Trp Phe Arg Gly Ala Gly Pro Ala Arg Leu Leu
         35                  40                  45
Ile Tyr Asn Gln Arg Gln Gly Pro Phe Pro Arg Val Thr Thr Val Ser
    50                  55                  60
Glu Thr Thr Lys Arg Glu Asn Met Asp Phe Ser Ile Ser Ile Ser Asn
 65                  70                  75                  80
Ile Thr Pro Ala Asp Ala Gly Thr Tyr Tyr Cys Val Lys Phe Arg Lys
                 85                  90                  95
Gly Ser Pro Asp Thr Glu Phe Lys Ser Gly Ala Gly Thr Glu Leu Ser
             100                 105                 110
Val Arg Ala Lys Pro Ser
        115
```

<210> SEQ ID NO 35
<211> LENGTH: 118
<212> TYPE: PRT
<213> ORGANISM: Artificial Sequence
<220> FEATURE:
<223> OTHER INFORMATION: Synthetic Construct

<400> SEQUENCE: 35

```
Glu Glu Glu Val Gln Ile Ile Gln Pro Asp Lys Ser Val Ser Val Ala
  1               5                  10                  15
Ala Gly Glu Ser Ala Ile Leu His Cys Thr Ile Thr Ser Leu Phe Pro
             20                  25                  30
Val Gly Pro Ile Gln Trp Phe Arg Gly Ala Gly Pro Ala Arg Val Leu
         35                  40                  45
Ile Tyr Asn Gln Lys Gln Gly Pro Phe Pro Arg Val Thr Thr Ile Ser
    50                  55                  60
Glu Thr Thr Arg Arg Glu Asn Met Asp Phe Ser Ile Ser Ile Ser Asn
 65                  70                  75                  80
Ile Thr Pro Ala Asp Ala Gly Thr Tyr Tyr Cys Ile Lys Phe Arg Lys
                 85                  90                  95
Gly Ser Pro Asp Thr Glu Phe Lys Ser Gly Ala Gly Thr Glu Leu Ser
             100                 105                 110
```

Val Arg Ala Lys Pro Ser
        115

<210> SEQ ID NO 36
<211> LENGTH: 118
<212> TYPE: PRT
<213> ORGANISM: Artificial Sequence
<220> FEATURE:
<223> OTHER INFORMATION: Synthetic Construct

<400> SEQUENCE: 36

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 37
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT

```
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
      R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 37

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 38
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
```

```
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
     R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
     R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 38

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
            115
```

```
<210> SEQ ID NO 39
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
     R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
     R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 39

Glu Glu Glu Xaa Gln Xaa Ile Gln Pro Asp Lys Ser Val Ser Val Ala
1               5                   10                  15
```

```
Ala Gly Glu Ser Xaa Ile Leu Leu Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 40
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
     R, S, T, V, W, Y
<220> FEATURE:
```

```
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 40

Glu Glu Gly Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Gly Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 41
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
```

-continued

```
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
      R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 41

Glu Glu Glu Xaa Gln Xaa Ile Gln Pro Asp Lys Phe Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 42
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
```

-continued

```
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
     R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
     R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 42

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Pro Ile Arg Ile Gly Xaa
65                  70                  75                  80

Ile Thr Xaa Ala Asp Ala Gly Thr Tyr Tyr Cys Xaa Lys Xaa Arg Lys
                85                  90                  95
```

```
Gly Ser Pro Asp Asp Val Glu Xaa Lys Ser Gly Ala Gly Thr Glu Leu
            100                 105                 110

Ser Val Arg Ala Lys Pro Ser
        115
```

```
<210> SEQ ID NO 43
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
      R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V
```

-continued

<400> SEQUENCE: 43

```
Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Gly Lys Pro Ser
            115
```

<210> SEQ ID NO 44
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:

```
<221> NAME/KEY: VARIANT
<222> LOCATION: 80
<223> OTHER INFORMATION: Xaa = N, A, C, D, E, F, G, H, I, K, L, M, P, Q,
      R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 44

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 45
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
```

```
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
      R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 45

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Ser Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 46
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
```

-continued

```
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
      R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 46

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
```

```
                65                  70                  75                  80
Ile Thr Xaa Ala Asp Ala Gly Thr Tyr Tyr Cys Xaa Lys Xaa Arg Lys
                    85                  90                  95

Gly Ser Pro Asp Thr Glu Xaa Lys Ser Gly Ala Gly Thr Glu Leu Ser
                100                 105                 110

Val Arg Ala Lys Pro Ser
        115
```

```
<210> SEQ ID NO 47
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E, G
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 12
<223> OTHER INFORMATION: Xaa = S, F
<220> FEATURE:
<221> NAME/KEY: VARIANT
<222> LOCATION: 14
<223> OTHER INFORMATION: Xaa = L, S
<220> FEATURE:
<221> NAME/KEY: VARIANT
<222> LOCATION: 20
<223> OTHER INFORMATION: Xaa = S, T
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 22
<223> OTHER INFORMATION: Xaa = I, T
<220> FEATURE:
<221> NAME/KEY: VARIANT
<222> LOCATION: 24
<223> OTHER INFORMATION: Xaa = H, R, L
<220> FEATURE:
<221> NAME/KEY: VARIANT
<222> LOCATION: 27
<223> OTHER INFORMATION: Xaa = A, V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 45
<223> OTHER INFORMATION: Xaa = A, G
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
```

```
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 65
<223> OTHER INFORMATION: Xaa = D, E
<220> FEATURE:
<221> NAME/KEY: VARIANT
<222> LOCATION: 66
<223> OTHER INFORMATION: Xaa = S, L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 70
<223> OTHER INFORMATION: Xaa = E, N
<220> FEATURE:
<221> NAME/KEY: VARIANT
<222> LOCATION: 75
<223> OTHER INFORMATION: Xaa = S, P
<220> FEATURE:
<221> NAME/KEY: VARIANT
<222> LOCATION: 77
<223> OTHER INFORMATION: Xaa = S, R
<220> FEATURE:
<221> NAME/KEY: VARIANT
<222> LOCATION: 79
<223> OTHER INFORMATION: Xaa = S, G
<220> FEATURE:
<221> NAME/KEY: VARIANT
<222> LOCATION: 80
<223> OTHER INFORMATION: Xaa = Any Amino Acid
<220> FEATURE:
<221> NAME/KEY: VARIANT
<222> LOCATION: 83
<223> OTHER INFORMATION: Xaa = Any Amino Acid
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 101
<223> OTHER INFORMATION: Xaa = D or absent
<220> FEATURE:
<221> NAME/KEY: VARIANT
<222> LOCATION: 102
<223> OTHER INFORMATION: Xaa = T, V
<220> FEATURE:
<221> NAME/KEY: VARIANT
<222> LOCATION: 104
<223> OTHER INFORMATION: Xaa = F, V
<220> FEATURE:
<221> NAME/KEY: VARIANT
<222> LOCATION: 116
<223> OTHER INFORMATION: Xaa = A, G

<400> SEQUENCE: 47

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Val Thr Thr Val Ser
    50                  55                  60

Xaa Xaa Thr Xaa Arg Xaa Asn Met Asp Phe Xaa Ile Xaa Ile Xaa Xaa
```

```
                65                  70                  75                  80
Ile Thr Xaa Ala Asp Ala Gly Thr Tyr Tyr Cys Xaa Lys Xaa Arg Lys
                    85                  90                  95
Gly Ser Pro Asp Xaa Xaa Glu Xaa Lys Ser Gly Ala Gly Thr Glu Leu
                    100                 105                 110
Ser Val Arg Xaa Lys Pro Ser
            115

<210> SEQ ID NO 48
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I
<220> FEATURE:
<221> NAME/KEY: VARIANT
<222> LOCATION: 14
<223> OTHER INFORMATION: Xaa =  L, S
<220> FEATURE:
<221> NAME/KEY: VARIANT
<222> LOCATION: 20
<223> OTHER INFORMATION: Xaa =  T, S
<220> FEATURE:
<221> NAME/KEY: VARIANT
<222> LOCATION: 22
<223> OTHER INFORMATION: Xaa =  T, I
<220> FEATURE:
<221> NAME/KEY: VARIANT
<222> LOCATION: 24
<223> OTHER INFORMATION: Xaa =  R, H
<220> FEATURE:
<221> NAME/KEY: VARIANT
<222> LOCATION: 27
<223> OTHER INFORMATION: Xaa =  A, V, I
<220> FEATURE:
<221> NAME/KEY: VARIANT
<222> LOCATION: 31
<223> OTHER INFORMATION: Xaa =  I, R, Y, K, F
<220> FEATURE:
<221> NAME/KEY: VARIANT
<222> LOCATION: 45
<223> OTHER INFORMATION: Xaa =  G, A
<220> FEATURE:
<221> NAME/KEY: VARIANT
<222> LOCATION: 47
<223> OTHER INFORMATION: Xaa =  E, V
<220> FEATURE:
<221> NAME/KEY: VARIANT
<222> LOCATION: 53
<223> OTHER INFORMATION: Xaa =  K, R
<220> FEATURE:
<221> NAME/KEY: VARIANT
<222> LOCATION: 54
<223> OTHER INFORMATION: Xaa =  E, D, Q
<220> FEATURE:
<221> NAME/KEY: VARIANT
<222> LOCATION: 56
<223> OTHER INFORMATION: Xaa =  H, P
<220> FEATURE:
<221> NAME/KEY: VARIANT
<222> LOCATION: 65
<223> OTHER INFORMATION: Xaa =  D, E
<220> FEATURE:
<221> NAME/KEY: VARIANT
<222> LOCATION: 66
<223> OTHER INFORMATION: Xaa =  S, L, T
<220> FEATURE:
<221> NAME/KEY: VARIANT
<222> LOCATION: 70
<223> OTHER INFORMATION: Xaa =  N, E
<220> FEATURE:
```

-continued

```
<221> NAME/KEY: VARIANT
<222> LOCATION: 77
<223> OTHER INFORMATION: Xaa =  R, S
<220> FEATURE:
<221> NAME/KEY: VARIANT
<222> LOCATION: 79
<223> OTHER INFORMATION: Xaa =  G, S
<220> FEATURE:
<221> NAME/KEY: VARIANT
<222> LOCATION: 80
<223> OTHER INFORMATION: Xaa =  N, A
<220> FEATURE:
<221> NAME/KEY: VARIANT
<222> LOCATION: 92
<223> OTHER INFORMATION: Xaa =  V, I
<220> FEATURE:
<221> NAME/KEY: VARIANT
<222> LOCATION: 98
<223> OTHER INFORMATION: Xaa =  S, I, M
<220> FEATURE:
<221> NAME/KEY: VARIANT
<222> LOCATION: 99
<223> OTHER INFORMATION: Xaa =  P or absent
<220> FEATURE:
<221> NAME/KEY: VARIANT
<222> LOCATION: 100
<223> OTHER INFORMATION: Xaa =  D, P
<220> FEATURE:
<221> NAME/KEY: VARIANT
<222> LOCATION: 102
<223> OTHER INFORMATION: Xaa =  V, T

<400> SEQUENCE: 48

Glu Glu Glu Leu Gln Xaa Ile Gln Pro Asp Lys Ser Val Xaa Val Ala
1               5                   10                  15

Ala Gly Glu Xaa Ala Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60

Xaa Xaa Thr Lys Arg Xaa Asn Met Asp Phe Ser Ile Xaa Ile Xaa Xaa
65                  70                  75                  80

Ile Thr Pro Ala Asp Ala Gly Thr Tyr Tyr Cys Xaa Lys Phe Arg Lys
                85                  90                  95

Gly Xaa Xaa Xaa Asp Xaa Glu Phe Lys Ser Gly Ala Gly Thr Glu Leu
            100                 105                 110

Ser Val Arg Ala Lys Pro Ser
            115

<210> SEQ ID NO 49
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I, L
<220> FEATURE:
<221> NAME/KEY: VARIANT
<222> LOCATION: 27
<223> OTHER INFORMATION: Xaa = A, I, V, L
<220> FEATURE:
<221> NAME/KEY: VARIANT
<222> LOCATION: 31
<223> OTHER INFORMATION: Xaa = I, F, S, T
<220> FEATURE:
<221> NAME/KEY: VARIANT
```

```
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, S, G
<220> FEATURE:
<221> NAME/KEY: VARIANT
<222> LOCATION: 80
<223> OTHER INFORMATION: Xaa =  A
<220> FEATURE:
<221> NAME/KEY: VARIANT
<222> LOCATION: 92
<223> OTHER INFORMATION: Xaa = V, I

<400> SEQUENCE: 49

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 50
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I
<220> FEATURE:
<221> NAME/KEY: VARIANT
<222> LOCATION: 27
<223> OTHER INFORMATION: Xaa = V, I
<220> FEATURE:
<221> NAME/KEY: VARIANT
<222> LOCATION: 31
<223> OTHER INFORMATION: Xaa = I, F
<220> FEATURE:
<221> NAME/KEY: VARIANT
<222> LOCATION: 47
<223> OTHER INFORMATION: Xaa = E, V
<220> FEATURE:
<221> NAME/KEY: VARIANT
<222> LOCATION: 53
```

```
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P
<220> FEATURE:
<221> NAME/KEY: VARIANT
<222> LOCATION: 66
<223> OTHER INFORMATION: Xaa = S, T
<220> FEATURE:
<221> NAME/KEY: VARIANT
<222> LOCATION: 80
<223> OTHER INFORMATION: Xaa = N, A
<220> FEATURE:
<221> NAME/KEY: VARIANT
<222> LOCATION: 92
<223> OTHER INFORMATION: Xaa = V, I

<400> SEQUENCE: 50

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Lys Arg Glu Asn Met Asp Phe Ser Ile Ser Ile Ser Xaa
65                  70                  75                  80

Ile Thr Pro Ala Asp Ala Gly Thr Tyr Tyr Cys Xaa Lys Phe Arg Lys
            85                  90                  95

Gly Ser Pro Asp Thr Glu Phe Lys Ser Gly Ala Gly Thr Glu Leu Ser
        100                 105                 110

Val Arg Ala Lys Pro Ser
        115

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I
<220> FEATURE:
<221> NAME/KEY: VARIANT
<222> LOCATION: 27
<223> OTHER INFORMATION: Xaa = A, I
<220> FEATURE:
<221> NAME/KEY: VARIANT
<222> LOCATION: 31
<223> OTHER INFORMATION: Xaa = I, F
<220> FEATURE:
<221> NAME/KEY: VARIANT
<222> LOCATION: 47
<223> OTHER INFORMATION: Xaa = E, V
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 56
<223> OTHER INFORMATION: Xaa = H, P
```

```
<220> FEATURE:
<221> NAME/KEY: VARIANT
<222> LOCATION: 66
<223> OTHER INFORMATION: Xaa = L, T
<220> FEATURE:
<221> NAME/KEY: VARIANT
<222> LOCATION: 80
<223> OTHER INFORMATION: Xaa = N, A
<220> FEATURE:
<221> NAME/KEY: VARIANT
<222> LOCATION: 92
<223> OTHER INFORMATION: Xaa = V, I

<400> SEQUENCE: 51

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Glu Gly Xaa Phe Pro Arg Val Thr Thr Val Ser
50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 80
<223> OTHER INFORMATION: Xaa = N, A

<400> SEQUENCE: 52

Glu Glu Glu Leu Gln Xaa Ile Gln Pro Asp Lys Ser Val Leu Val Ala
1               5                   10                  15
```

-continued

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Glu Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 53
<211> LENGTH: 118
<212> TYPE: PRT
<213> ORGANISM: Artificial Sequence
<220> FEATURE:
<223> OTHER INFORMATION: Synthetic Construct

<400> SEQUENCE: 53

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 54
<211> LENGTH: 118
<212> TYPE: PRT
<213> ORGANISM: Artificial Sequence
<220> FEATURE:
<223> OTHER INFORMATION: Synthetic Construct

<400> SEQUENCE: 54

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn

```
                65                  70                  75                  80
Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 55
<211> LENGTH: 118
<212> TYPE: PRT
<213> ORGANISM: Artificial Sequence
<220> FEATURE:
<223> OTHER INFORMATION: Synthetic Construct

<400> SEQUENCE: 55

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 56
<211> LENGTH: 118
<212> TYPE: PRT
<213> ORGANISM: Artificial Sequence
<220> FEATURE:
<223> OTHER INFORMATION: Synthetic Construct

<400> SEQUENCE: 56

Glu Glu Glu Leu Gln Ile Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

```
<210> SEQ ID NO 57
<211> LENGTH: 118
<212> TYPE: PRT
<213> ORGANISM: Artificial Sequence
<220> FEATURE:
<223> OTHER INFORMATION: Synthetic Construct

<400> SEQUENCE: 57

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 58
<211> LENGTH: 118
<212> TYPE: PRT
<213> ORGANISM: Artificial Sequence
<220> FEATURE:
<223> OTHER INFORMATION: Synthetic Construct

<400> SEQUENCE: 58

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 59
<211> LENGTH: 118
<212> TYPE: PRT
<213> ORGANISM: Artificial Sequence
<220> FEATURE:
<223> OTHER INFORMATION: Synthetic Construct

<400> SEQUENCE: 59

Glu Glu Glu Leu Gln Ile Ile Gln Pro Asp Lys Ser Val Ser Val Ala
```

```
                1               5                   10                  15
Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
            35                  40                  45

Ile Tyr Asn Gln Lys Gln Gly Pro Phe Pro Arg Val Thr Thr Val Ser
            50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
            85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 60
<211> LENGTH: 118
<212> TYPE: PRT
<213> ORGANISM: Artificial Sequence
<220> FEATURE:
<223> OTHER INFORMATION: Synthetic Construct

<400> SEQUENCE: 60

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
            35                  40                  45

Ile Tyr Asn Gln Arg Glu Gly Pro Phe Pro Arg Val Thr Thr Val Ser
            50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
            85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 61
<211> LENGTH: 118
<212> TYPE: PRT
<213> ORGANISM: Artificial Sequence
<220> FEATURE:
<223> OTHER INFORMATION: Synthetic Construct

<400> SEQUENCE: 61

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
            35                  40                  45

Ile Tyr Asn Gln Arg Gln Gly His Phe Pro Arg Val Thr Thr Val Ser
            50                  55                  60
```

```
Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 62
<211> LENGTH: 118
<212> TYPE: PRT
<213> ORGANISM: Artificial Sequence
<220> FEATURE:
<223> OTHER INFORMATION: Synthetic Construct

<400> SEQUENCE: 62

```
Glu Glu Glu Leu Gln Ile Ile Gln Pro Asp Lys Ser Val Ser Val Ala
  1               5                  10                  15

Ala Gly Glu Ser Ala Ile Leu His Cys Thr Ile Thr Ser Leu Phe Pro
                 20                  25                  30

Val Gly Pro Ile Gln Trp Phe Arg Gly Ala Gly Pro Ala Arg Val Leu
             35                  40                  45

Ile Tyr Asn Gln Arg Gln Gly Pro Phe Pro Arg Val Thr Thr Val Ser
 50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 63
<211> LENGTH: 118
<212> TYPE: PRT
<213> ORGANISM: Artificial Sequence
<220> FEATURE:
<223> OTHER INFORMATION: Synthetic Construct

<400> SEQUENCE: 63

```
Glu Glu Glu Leu Gln Ile Ile Gln Pro Asp Lys Ser Val Ser Val Ala
  1               5                  10                  15

Ala Gly Glu Ser Ala Ile Leu His Cys Thr Ile Thr Ser Leu Phe Pro
                 20                  25                  30

Val Gly Pro Ile Gln Trp Phe Arg Gly Ala Gly Pro Ala Arg Val Leu
             35                  40                  45

Ile Tyr Asn Gln Arg Gln Gly Pro Phe Pro Arg Val Thr Thr Val Ser
 50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 64
<211> LENGTH: 118
<212> TYPE: PRT
<213> ORGANISM: Artificial Sequence
<220> FEATURE:
<223> OTHER INFORMATION: Synthetic Construct

<400> SEQUENCE: 64

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 65
<211> LENGTH: 118
<212> TYPE: PRT
<213> ORGANISM: Artificial Sequence
<220> FEATURE:
<223> OTHER INFORMATION: Synthetic Construct

<400> SEQUENCE: 65

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 66
<211> LENGTH: 118
<212> TYPE: PRT
<213> ORGANISM: Artificial Sequence
<220> FEATURE:
<223> OTHER INFORMATION: Synthetic Construct

<400> SEQUENCE: 66

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 67
<211> LENGTH: 118
<212> TYPE: PRT
<213> ORGANISM: Artificial Sequence
<220> FEATURE:
<223> OTHER INFORMATION: Synthetic Construct

<400> SEQUENCE: 67

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 68
<211> LENGTH: 118
<212> TYPE: PRT
<213> ORGANISM: Artificial Sequence
<220> FEATURE:
<223> OTHER INFORMATION: Synthetic Construct

<400> SEQUENCE: 68

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

```
Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 69
<211> LENGTH: 118
<212> TYPE: PRT
<213> ORGANISM: Artificial Sequence
<220> FEATURE:
<223> OTHER INFORMATION: Synthetic Construct

<400> SEQUENCE: 69

Glu Glu Glu Leu Gln Val Ile Gln Pro Asp Lys Ser Val Ser Val Ala
 1               5                  10                  15

Ala Gly Glu Ser Ala Ile Leu His Cys Thr Ile Thr Ser Leu Ile Pro
             20                  25                  30

Val Gly Pro Ile Gln Trp Phe Arg Gly Ala Gly Pro Ala Arg Glu Leu
         35                  40                  45

Ile Tyr Asn Gln Arg Glu Gly Pro Phe Pro Arg Val Thr Thr Val Ser
     50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 70
<211> LENGTH: 118
<212> TYPE: PRT
<213> ORGANISM: Artificial Sequence
<220> FEATURE:
<223> OTHER INFORMATION: Synthetic Construct

<400> SEQUENCE: 70

Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Phe Pro
             20                  25                  30

Val Gly Pro Ile Gln Trp Phe Arg Gly Ala Gly Pro Ala Arg Glu Leu
         35                  40                  45

Ile Tyr Asn Gln Arg Glu Gly Pro Phe Pro Arg Val Thr Thr Val Ser
     50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
```

<210> SEQ ID NO 71
<211> LENGTH: 119
<212> TYPE: PRT
<213> ORGANISM: Artificial Sequence
<220> FEATURE:
<223> OTHER INFORMATION: Synthetic Construct

<400> SEQUENCE: 71

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 72
<211> LENGTH: 119
<212> TYPE: PRT
<213> ORGANISM: Artificial Sequence
<220> FEATURE:
<223> OTHER INFORMATION: Synthetic Construct

<400> SEQUENCE: 72

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 73
<211> LENGTH: 119
<212> TYPE: PRT
<213> ORGANISM: Artificial Sequence
<220> FEATURE:
<223> OTHER INFORMATION: Synthetic Construct

<400> SEQUENCE: 73

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 74
<211> LENGTH: 119
<212> TYPE: PRT
<213> ORGANISM: Artificial Sequence
<220> FEATURE:
<223> OTHER INFORMATION: Synthetic Construct

<400> SEQUENCE: 74

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 75
<211> LENGTH: 119
<212> TYPE: PRT
<213> ORGANISM: Artificial Sequence
<220> FEATURE:
<223> OTHER INFORMATION: Synthetic Construct

<400> SEQUENCE: 75

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser

```
                    50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                     85                  90                  95

Gly Ser Pro Asp Asp Val Glu Phe Lys Ser Gly Ala Gly Thr Glu Leu
                    100                 105                 110

Ser Val Arg Ala Lys Pro Ser
                115

<210> SEQ ID NO 76
<211> LENGTH: 119
<212> TYPE: PRT
<213> ORGANISM: Artificial Sequence
<220> FEATURE:
<223> OTHER INFORMATION: Synthetic Construct

<400> SEQUENCE: 76

Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Phe Pro
                 20                  25                  30

Val Gly Pro Ile Gln Trp Phe Arg Gly Ala Gly Pro Gly Arg Glu Leu
             35                  40                  45

Ile Tyr Asn Gln Arg Glu Gly Pro Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                     85                  90                  95

Gly Ser Pro Asp Asp Val Glu Phe Lys Ser Gly Ala Gly Thr Glu Leu
                    100                 105                 110

Ser Val Arg Ala Lys Pro Ser
                115

<210> SEQ ID NO 77
<211> LENGTH: 119
<212> TYPE: PRT
<213> ORGANISM: Artificial Sequence
<220> FEATURE:
<223> OTHER INFORMATION: Synthetic Construct

<400> SEQUENCE: 77

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Val Leu
             35                  40                  45

Ile Tyr Asn Gln Arg Gln Gly Pro Phe Pro Arg Val Thr Thr Val Ser
 50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Ile Lys Phe Arg Lys
                     85                  90                  95

Gly Ser Pro Asp Asp Val Glu Phe Lys Ser Gly Ala Gly Thr Glu Leu
                    100                 105                 110
```

-continued

```
Ser Val Arg Ala Lys Pro Ser
        115

<210> SEQ ID NO 78
<211> LENGTH: 119
<212> TYPE: PRT
<213> ORGANISM: Artificial Sequence
<220> FEATURE:
<223> OTHER INFORMATION: Synthetic Construct

<400> SEQUENCE: 78

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 79
<211> LENGTH: 119
<212> TYPE: PRT
<213> ORGANISM: Artificial Sequence
<220> FEATURE:
<223> OTHER INFORMATION: Synthetic Construct

<400> SEQUENCE: 79

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
        50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 80
<211> LENGTH: 119
<212> TYPE: PRT
<213> ORGANISM: Artificial Sequence
<220> FEATURE:
<223> OTHER INFORMATION: Synthetic Construct
```

<400> SEQUENCE: 80

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115
```

<210> SEQ ID NO 81
<211> LENGTH: 119
<212> TYPE: PRT
<213> ORGANISM: Artificial Sequence
<220> FEATURE:
<223> OTHER INFORMATION: Synthetic Construct

<400> SEQUENCE: 81

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115
```

<210> SEQ ID NO 82
<211> LENGTH: 119
<212> TYPE: PRT
<213> ORGANISM: Artificial Sequence
<220> FEATURE:
<223> OTHER INFORMATION: Synthetic Construct

<400> SEQUENCE: 82

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45
```

Ile Tyr Asn Gln Arg Glu Gly Pro Phe Pro Arg Val Thr Val Ser
 50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 83
<211> LENGTH: 119
<212> TYPE: PRT
<213> ORGANISM: Artificial Sequence
<220> FEATURE:
<223> OTHER INFORMATION: Synthetic Construct

<400> SEQUENCE: 83

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Glu Leu
             35                  40                  45

Ile Tyr Asn Gln Arg Glu Gly Pro Phe Pro Arg Val Thr Val Ser
 50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 84
<211> LENGTH: 119
<212> TYPE: PRT
<213> ORGANISM: Artificial Sequence
<220> FEATURE:
<223> OTHER INFORMATION: Synthetic Construct

<400> SEQUENCE: 84

Glu Glu Glu Leu Gln Val Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Glu Leu
             35                  40                  45

Ile Tyr Asn Gln Arg Glu Gly Pro Phe Pro Arg Val Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 85
<211> LENGTH: 119
<212> TYPE: PRT
<213> ORGANISM: Artificial Sequence
<220> FEATURE:
<223> OTHER INFORMATION: Synthetic Construct

<400> SEQUENCE: 85

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 86
<211> LENGTH: 119
<212> TYPE: PRT
<213> ORGANISM: Artificial Sequence
<220> FEATURE:
<223> OTHER INFORMATION: Synthetic Construct

<400> SEQUENCE: 86

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 87
<211> LENGTH: 119
<212> TYPE: PRT
<213> ORGANISM: Artificial Sequence
<220> FEATURE:
<223> OTHER INFORMATION: Synthetic Construct

<400> SEQUENCE: 87

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 88
<211> LENGTH: 232
<212> TYPE: PRT
<213> ORGANISM: Artificial Sequence
<220> FEATURE:
<223> OTHER INFORMATION: Synthetic Construct

<400> SEQUENCE: 88

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

Ser Leu Ser Leu Ser Pro Gly Lys
225                 230

<210> SEQ ID NO 89
<211> LENGTH: 325
<212> TYPE: PRT
<213> ORGANISM: Artificial Sequence
<220> FEATURE:
<223> OTHER INFORMATION: Synthetic Construct

<400> SEQUENCE: 89

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 90
<211> LENGTH: 227

<212> TYPE: PRT
<213> ORGANISM: Artificial Sequence
<220> FEATURE:
<223> OTHER INFORMATION: Synthetic Construct

<400> SEQUENCE: 90

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 91
<211> LENGTH: 226
<212> TYPE: PRT
<213> ORGANISM: Artificial Sequence
<220> FEATURE:
<223> OTHER INFORMATION: Synthetic Construct

<400> SEQUENCE: 91

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly
225

<210> SEQ ID NO 92
<211> LENGTH: 223
<212> TYPE: PRT
<213> ORGANISM: Artificial Sequence
<220> FEATURE:
<223> OTHER INFORMATION: Synthetic Construct

<400> SEQUENCE: 92

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Ala Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220
```

<210> SEQ ID NO 93
<211> LENGTH: 222
<212> TYPE: PRT
<213> ORGANISM: Artificial Sequence
<220> FEATURE:
<223> OTHER INFORMATION: Synthetic Construct

<400> SEQUENCE: 93

```
Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Ala Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220
```

<210> SEQ ID NO 94
<211> LENGTH: 228
<212> TYPE: PRT
<213> ORGANISM: Artificial Sequence
<220> FEATURE:
<223> OTHER INFORMATION: Synthetic Construct

<400> SEQUENCE: 94

```
Glu Arg Lys Ser Ser Val Glu Cys Pro Pro Cys Pro Ala Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Ala Ser Thr
65                  70                  75                  80

Phe Arg Val Val Ser Val Leu Thr Val Val His Gln Asp Trp Leu Asn
```

```
               85                  90                  95
Gly Lys Glu Tyr Lys Cys Lys Val Ser Asn Lys Gly Leu Pro Ser Ser
            100                 105                 110
Ile Glu Lys Thr Ile Ser Lys Thr Lys Gly Gln Pro Arg Glu Pro Gln
            115                 120                 125
Val Tyr Thr Leu Pro Pro Ser Arg Glu Glu Met Thr Lys Asn Gln Val
            130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
                180                 185                 190
Val Asp Lys Ser Arg Trp Gln Gln Gly Asn Val Phe Ser Cys Ser Val
                195                 200                 205
Met His Glu Ala Leu His Asn His Tyr Thr Gln Lys Ser Leu Ser Leu
            210                 215                 220
Ser Pro Gly Lys
225

<210> SEQ ID NO 95
<211> LENGTH: 227
<212> TYPE: PRT
<213> ORGANISM: Artificial Sequence
<220> FEATURE:
<223> OTHER INFORMATION: Synthetic Construct

<400> SEQUENCE: 95

Glu Arg Lys Ser Ser Val Glu Cys Pro Pro Cys Pro Ala Pro Pro Val
1               5                  10                  15
Ala Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
            35                  40                  45
His Glu Asp Pro Glu Val Gln Phe Asn Trp Tyr Val Asp Gly Val Glu
50                  55                  60
Val His Asn Ala Lys Thr Lys Pro Arg Glu Glu Gln Phe Ala Ser Thr
65                  70                  75                  80
Phe Arg Val Val Ser Val Leu Thr Val His Gln Asp Trp Leu Asn
                85                  90                  95
Gly Lys Glu Tyr Lys Cys Lys Val Ser Asn Lys Gly Leu Pro Ser Ser
            100                 105                 110
Ile Glu Lys Thr Ile Ser Lys Thr Lys Gly Gln Pro Arg Glu Pro Gln
            115                 120                 125
Val Tyr Thr Leu Pro Pro Ser Arg Glu Glu Met Thr Lys Asn Gln Val
            130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
                180                 185                 190
Val Asp Lys Ser Arg Trp Gln Gln Gly Asn Val Phe Ser Cys Ser Val
                195                 200                 205
Met His Glu Ala Leu His Asn His Tyr Thr Gln Lys Ser Leu Ser Leu
```

Ser Pro Gly
225

<210> SEQ ID NO 96
<211> LENGTH: 346
<212> TYPE: PRT
<213> ORGANISM: Artificial Sequence
<220> FEATURE:
<223> OTHER INFORMATION: Synthetic Construct

<400> SEQUENCE: 96

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys

<210> SEQ ID NO 97
<211> LENGTH: 346
<212> TYPE: PRT
<213> ORGANISM: Artificial Sequence
<220> FEATURE:
<223> OTHER INFORMATION: Synthetic Construct

<400> SEQUENCE: 97

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

```
<210> SEQ ID NO 98
<211> LENGTH: 346
<212> TYPE: PRT
<213> ORGANISM: Artificial Sequence
<220> FEATURE:
<223> OTHER INFORMATION: Synthetic Construct

<400> SEQUENCE: 98

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 99
<211> LENGTH: 346
<212> TYPE: PRT
```

<213> ORGANISM: Artificial Sequence
<220> FEATURE:
<223> OTHER INFORMATION: Synthetic Construct

<400> SEQUENCE: 99

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 100
<211> LENGTH: 346
<212> TYPE: PRT
<213> ORGANISM: Artificial Sequence
<220> FEATURE:
<223> OTHER INFORMATION: Synthetic Construct

<400> SEQUENCE: 100

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 101
<211> LENGTH: 346
<212> TYPE: PRT
<213> ORGANISM: Artificial Sequence
<220> FEATURE:
<223> OTHER INFORMATION: Synthetic Construct

<400> SEQUENCE: 101

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 102
<211> LENGTH: 346
<212> TYPE: PRT
<213> ORGANISM: Artificial Sequence
<220> FEATURE:
<223> OTHER INFORMATION: Synthetic Construct

<400> SEQUENCE: 102

```
Glu Glu Glu Leu Gln Ile Ile Gln Pro Asp Lys Ser Val Leu Val Ala
1               5                   10                  15
```

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
 50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 103
<211> LENGTH: 346
<212> TYPE: PRT
<213> ORGANISM: Artificial Sequence
<220> FEATURE:
<223> OTHER INFORMATION: Synthetic Construct

<400> SEQUENCE: 103

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
         35                  40                  45

Ile Tyr Asn Gln Arg Glu Gly Pro Phe Pro Arg Val Thr Thr Val Ser
 50                  55                  60

Asp Thr Thr Lys Arg Asn Asn Met Asp Phe Ser Ile Arg Ile Gly Ala
65                   70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
                115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
            210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 104
<211> LENGTH: 346
<212> TYPE: PRT
<213> ORGANISM: Artificial Sequence
<220> FEATURE:
<223> OTHER INFORMATION: Synthetic Construct

<400> SEQUENCE: 104

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

```
Ile Tyr Asn Gln Arg Glu Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 105
<211> LENGTH: 342
<212> TYPE: PRT
<213> ORGANISM: Artificial Sequence
<220> FEATURE:
<223> OTHER INFORMATION: Synthetic Construct

<400> SEQUENCE: 105

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
 50                  55                  60
```

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 106
<211> LENGTH: 342
<212> TYPE: PRT
<213> ORGANISM: Artificial Sequence
<220> FEATURE:
<223> OTHER INFORMATION: Synthetic Construct

<400> SEQUENCE: 106

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
            115                 120                 125

Pro Val Ala Gly Pro Ser Val Phe Leu Phe Pro Pro Lys Pro Lys Asp
            130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
            165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
            195                 200                 205

Leu Asn Gly Lys Glu Tyr Lys Cys Lys Val Ser Asn Lys Gly Leu Pro
            210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
            245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
            275                 280                 285

Thr Pro Pro Met Leu Asp Ser Asp Gly Ser Phe Phe Leu Tyr Ser Lys
            290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
            325                 330                 335

Ser Leu Ser Pro Gly Lys
            340

<210> SEQ ID NO 107
<211> LENGTH: 342
<212> TYPE: PRT
<213> ORGANISM: Artificial Sequence
<220> FEATURE:
<223> OTHER INFORMATION: Synthetic Construct

<400> SEQUENCE: 107

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
            50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
            85                  90                  95

Gly Ser Pro Asp Asp Val Glu Phe Lys Ser Gly Ala Gly Thr Glu Leu
              100                 105                 110

Ser Val Arg Ala Lys Pro Ser Val Glu Cys Pro Pro Cys Pro Ala Pro
          115                 120                 125

Pro Val Ala Gly Pro Ser Val Phe Leu Phe Pro Pro Lys Pro Lys Asp
      130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
              165                 170                 175

Val Glu Val His Asn Ala Lys Thr Lys Pro Arg Glu Glu Gln Phe Ala
          180                 185                 190

Ser Thr Phe Arg Val Val Ser Val Leu Thr Val Val His Gln Asp Trp
      195                 200                 205

Leu Asn Gly Lys Glu Tyr Lys Cys Lys Val Ser Asn Lys Gly Leu Pro
      210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
              245                 250                 255

Gln Val Ser Leu Thr Cys Leu Val Lys Gly Phe Tyr Pro Ser Asp Ile
          260                 265                 270

Ala Val Glu Trp Glu Ser Asn Gly Gln Pro Glu Asn Asn Tyr Lys Thr
      275                 280                 285

Thr Pro Pro Met Leu Asp Ser Asp Gly Ser Phe Phe Leu Tyr Ser Lys
      290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
              325                 330                 335

Ser Leu Ser Pro Gly Lys
              340

<210> SEQ ID NO 108
<211> LENGTH: 342
<212> TYPE: PRT
<213> ORGANISM: Artificial Sequence
<220> FEATURE:
<223> OTHER INFORMATION: Synthetic Construct

<400> SEQUENCE: 108

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
              20                  25                  30

Val Gly Pro Ile Gln Trp Phe Arg Gly Ala Gly Pro Gly Arg Glu Leu
          35                  40                  45

Ile Tyr Asn Gln Arg Gln Gly Pro Phe Pro Arg Val Thr Thr Val Ser
      50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
              85                  90                  95

Gly Ser Pro Asp Asp Val Glu Phe Lys Ser Gly Ala Gly Thr Glu Leu
              100                 105                 110

```
Ser Val Arg Ala Lys Pro Ser Val Glu Cys Pro Pro Cys Pro Ala Pro
            115                 120                 125

Pro Val Ala Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 109
<211> LENGTH: 342
<212> TYPE: PRT
<213> ORGANISM: Artificial Sequence
<220> FEATURE:
<223> OTHER INFORMATION: Synthetic Construct

<400> SEQUENCE: 109

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125
```

```
Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 110
<211> LENGTH: 342
<212> TYPE: PRT
<213> ORGANISM: Artificial Sequence
<220> FEATURE:
<223> OTHER INFORMATION: Synthetic Construct

<400> SEQUENCE: 110

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140
```

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
            165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
            195                 200                 205

Leu Asn Gly Lys Glu Tyr Lys Cys Lys Val Ser Asn Lys Gly Leu Pro
            210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
                260                 265                 270

Ala Val Glu Trp Glu Ser Asn Gly Gln Pro Glu Asn Asn Tyr Lys Thr
            275                 280                 285

Thr Pro Pro Met Leu Asp Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 111
<211> LENGTH: 342
<212> TYPE: PRT
<213> ORGANISM: Artificial Sequence
<220> FEATURE:
<223> OTHER INFORMATION: Synthetic Construct

<400> SEQUENCE: 111

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
            115                 120                 125

Pro Val Ala Gly Pro Ser Val Phe Leu Phe Pro Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
            165                 170                 175

Val Glu Val His Asn Ala Lys Thr Lys Pro Arg Glu Glu Gln Phe Ala
        180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
        210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
            245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
            275                 280                 285

Thr Pro Pro Met Leu Asp Ser Asp Gly Ser Phe Phe Leu Tyr Ser Lys
            290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
            325                 330                 335

Ser Leu Ser Pro Gly Lys
            340

<210> SEQ ID NO 112
<211> LENGTH: 342
<212> TYPE: PRT
<213> ORGANISM: Artificial Sequence
<220> FEATURE:
<223> OTHER INFORMATION: Synthetic Construct

<400> SEQUENCE: 112

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser Val Phe Leu Phe Pro Pro Lys Pro Lys Asp
            115                 120                 125

Pro Val Ala Gly Pro Ser Val Phe Leu Phe Pro Pro Lys Pro Lys Asp
            130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
            165                 170                 175

```
Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 113
<211> LENGTH: 342
<212> TYPE: PRT
<213> ORGANISM: Artificial Sequence
<220> FEATURE:
<223> OTHER INFORMATION: Synthetic Construct

<400> SEQUENCE: 113

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190
```

```
Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
                260                 265                 270

Ala Val Glu Trp Glu Ser Asn Gly Gln Pro Glu Asn Asn Tyr Lys Thr
                275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
                340

<210> SEQ ID NO 114
<211> LENGTH: 347
<212> TYPE: PRT
<213> ORGANISM: Artificial Sequence
<220> FEATURE:
<223> OTHER INFORMATION: Synthetic Construct

<400> SEQUENCE: 114

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Ser Ser Val Glu Cys Pro
            115                 120                 125

Pro Cys Pro Ala Pro Pro Val Ala Gly Pro Ser Val Phe Leu Phe Pro
        130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205
```

```
Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
                340                 345

<210> SEQ ID NO 115
<211> LENGTH: 347
<212> TYPE: PRT
<213> ORGANISM: Artificial Sequence
<220> FEATURE:
<223> OTHER INFORMATION: Synthetic Construct

<400> SEQUENCE: 115

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Ser Ser Val Glu Cys Pro
            115                 120                 125

Pro Cys Pro Ala Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
                195                 200                 205

Val His Gln Asp Trp Leu Asn Gly Lys Glu Tyr Lys Cys Lys Val Ser
    210                 215                 220
```

```
Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
            245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
            290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345
```

<210> SEQ ID NO 116
<211> LENGTH: 347
<212> TYPE: PRT
<213> ORGANISM: Artificial Sequence
<220> FEATURE:
<223> OTHER INFORMATION: Synthetic Construct

<400> SEQUENCE: 116

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Thr Lys
225                 230                 235                 240
```

```
Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 117
<211> LENGTH: 347
<212> TYPE: PRT
<213> ORGANISM: Artificial Sequence
<220> FEATURE:
<223> OTHER INFORMATION: Synthetic Construct

<400> SEQUENCE: 117

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255
```

```
Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
            290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 118
<211> LENGTH: 347
<212> TYPE: PRT
<213> ORGANISM: Artificial Sequence
<220> FEATURE:
<223> OTHER INFORMATION: Synthetic Construct

<400> SEQUENCE: 118

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270
```

```
Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 119
<211> LENGTH: 347
<212> TYPE: PRT
<213> ORGANISM: Artificial Sequence
<220> FEATURE:
<223> OTHER INFORMATION: Synthetic Construct

<400> SEQUENCE: 119

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285
```

```
Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
                340                 345

<210> SEQ ID NO 120
<211> LENGTH: 347
<212> TYPE: PRT
<213> ORGANISM: Artificial Sequence
<220> FEATURE:
<223> OTHER INFORMATION: Synthetic Construct

<400> SEQUENCE: 120

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300
```

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
            325                 330                 335

Thr Gln Lys Ser Leu Ser Leu Ser Pro Gly Lys
            340                 345

<210> SEQ ID NO 121
<211> LENGTH: 347
<212> TYPE: PRT
<213> ORGANISM: Artificial Sequence
<220> FEATURE:
<223> OTHER INFORMATION: Synthetic Construct

<400> SEQUENCE: 121

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
            325                 330                 335

Thr Gln Lys Ser Leu Ser Leu Ser Pro Gly Lys
        340                 345

<210> SEQ ID NO 122
<211> LENGTH: 347
<212> TYPE: PRT
<213> ORGANISM: Artificial Sequence
<220> FEATURE:
<223> OTHER INFORMATION: Synthetic Construct

<400> SEQUENCE: 122

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 123
<211> LENGTH: 346
<212> TYPE: PRT
<213> ORGANISM: Artificial Sequence
<220> FEATURE:
<223> OTHER INFORMATION: Synthetic Construct

<400> SEQUENCE: 123

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 124
<211> LENGTH: 346
<212> TYPE: PRT
<213> ORGANISM: Artificial Sequence
<220> FEATURE:
<223> OTHER INFORMATION: Synthetic Construct

<400> SEQUENCE: 124

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 125
<211> LENGTH: 346

<212> TYPE: PRT
<213> ORGANISM: Artificial Sequence
<220> FEATURE:
<223> OTHER INFORMATION: Synthetic Construct

<400> SEQUENCE: 125

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Asp Lys Thr His Thr Cys Pro Pro Cys
        115                 120                 125
Pro Ala Pro Glu Leu Leu Gly Gly Pro Ser Val Phe Leu Phe Pro Pro
130                 135                 140
Lys Pro Lys Asp Thr Leu Met Ile Ser Arg Thr Pro Glu Val Thr Cys
145                 150                 155                 160
Val Val Val Asp Val Ser His Glu Asp Pro Glu Val Lys Phe Asn Trp
                165                 170                 175
Tyr Val Asp Gly Val Glu Val His Asn Ala Lys Thr Lys Pro Arg Glu
            180                 185                 190
Glu Gln Tyr Ala Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345
```

<210> SEQ ID NO 126
<211> LENGTH: 347
<212> TYPE: PRT
<213> ORGANISM: Artificial Sequence
<220> FEATURE:

<223> OTHER INFORMATION: Synthetic Construct

<400> SEQUENCE: 126

| | | | | | | | | | | | | | | | |
|---|---|---|---|---|---|---|---|---|---|---|---|---|---|---|---|
| Glu | Glu | Glu | Leu | Gln | Ile | Ile | Gln | Pro | Asp | Lys | Ser | Val | Leu | Val | Ala |
| 1 | | | | 5 | | | | | 10 | | | | | 15 | |
| Ala | Gly | Glu | Thr | Ala | Thr | Leu | Arg | Cys | Thr | Ile | Thr | Ser | Leu | Phe | Pro |
| | | | 20 | | | | | 25 | | | | | 30 | | |
| Val | Gly | Pro | Ile | Gln | Trp | Phe | Arg | Gly | Ala | Gly | Pro | Gly | Arg | Val | Leu |
| | | | 35 | | | | | 40 | | | | | 45 | | |
| Ile | Tyr | Asn | Gln | Arg | Gln | Gly | Pro | Phe | Pro | Arg | Val | Thr | Thr | Val | Ser |
| | | | 50 | | | | | 55 | | | | | 60 | | |
| Asp | Thr | Thr | Lys | Arg | Asn | Asn | Met | Asp | Phe | Ser | Ile | Arg | Ile | Gly | Asn |
| 65 | | | | | 70 | | | | | 75 | | | | | 80 |
| Ile | Thr | Pro | Ala | Asp | Ala | Gly | Thr | Tyr | Tyr | Cys | Ile | Lys | Phe | Arg | Lys |
| | | | | 85 | | | | | 90 | | | | | 95 | |
| Gly | Ser | Pro | Asp | Asp | Val | Glu | Phe | Lys | Ser | Gly | Ala | Gly | Thr | Glu | Leu |
| | | | | 100 | | | | | 105 | | | | | 110 | |
| Ser | Val | Arg | Ala | Lys | Pro | Ser | Glu | Arg | Lys | Cys | Cys | Val | Glu | Cys | Pro |
| | | | 115 | | | | | 120 | | | | | 125 | | |
| Pro | Cys | Pro | Ala | Pro | Pro | Val | Ala | Gly | Pro | Ser | Val | Phe | Leu | Phe | Pro |
| | | | 130 | | | | | 135 | | | | | 140 | | |
| Pro | Lys | Pro | Lys | Asp | Thr | Leu | Met | Ile | Ser | Arg | Thr | Pro | Glu | Val | Thr |
| 145 | | | | | 150 | | | | | 155 | | | | | 160 |
| Cys | Val | Val | Val | Asp | Val | Ser | His | Glu | Asp | Pro | Glu | Val | Gln | Phe | Asn |
| | | | | 165 | | | | | 170 | | | | | 175 | |
| Trp | Tyr | Val | Asp | Gly | Val | Glu | Val | His | Asn | Ala | Lys | Thr | Lys | Pro | Arg |
| | | | | 180 | | | | | 185 | | | | | 190 | |
| Glu | Glu | Gln | Phe | Asn | Ser | Thr | Phe | Arg | Val | Val | Ser | Val | Leu | Thr | Val |
| | | | 195 | | | | | 200 | | | | | 205 | | |
| Val | His | Gln | Asp | Trp | Leu | Asn | Gly | Lys | Glu | Tyr | Lys | Cys | Lys | Val | Ser |
| | | | 210 | | | | | 215 | | | | | 220 | | |
| Asn | Lys | Gly | Leu | Pro | Ala | Pro | Ile | Glu | Lys | Thr | Ile | Ser | Lys | Thr | Lys |
| 225 | | | | | 230 | | | | | 235 | | | | | 240 |
| Gly | Gln | Pro | Arg | Glu | Pro | Gln | Val | Tyr | Thr | Leu | Pro | Pro | Ser | Arg | Glu |
| | | | | 245 | | | | | 250 | | | | | 255 | |
| Glu | Met | Thr | Lys | Asn | Gln | Val | Ser | Leu | Thr | Cys | Leu | Val | Lys | Gly | Phe |
| | | | | 260 | | | | | 265 | | | | | 270 | |
| Tyr | Pro | Ser | Asp | Ile | Ala | Val | Glu | Trp | Glu | Ser | Asn | Gly | Gln | Pro | Glu |
| | | | 275 | | | | | 280 | | | | | 285 | | |
| Asn | Asn | Tyr | Lys | Thr | Thr | Pro | Pro | Met | Leu | Asp | Ser | Asp | Gly | Ser | Phe |
| | | | 290 | | | | | 295 | | | | | 300 | | |
| Phe | Leu | Tyr | Ser | Lys | Leu | Thr | Val | Asp | Lys | Ser | Arg | Trp | Gln | Gln | Gly |
| 305 | | | | | 310 | | | | | 315 | | | | | 320 |
| Asn | Val | Phe | Ser | Cys | Ser | Val | Met | His | Glu | Ala | Leu | His | Asn | His | Tyr |
| | | | | 325 | | | | | 330 | | | | | 335 | |
| Thr | Gln | Lys | Ser | Leu | Ser | Leu | Ser | Pro | Gly | Lys | | | | | |
| | | | 340 | | | | | 345 | | | | | | | |

<210> SEQ ID NO 127
<211> LENGTH: 347
<212> TYPE: PRT
<213> ORGANISM: Artificial Sequence
<220> FEATURE:
<223> OTHER INFORMATION: Synthetic Construct

<400> SEQUENCE: 127

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Cys Cys Val Glu Cys Pro
            115                 120                 125

Pro Cys Pro Ala Pro Pro Val Ala Gly Pro Ser Val Phe Leu Phe Pro
        130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Asn Ser Thr Phe Arg Val Val Ser Val Leu Thr Val
            195                 200                 205

Val His Gln Asp Trp Leu Asn Gly Lys Glu Tyr Lys Cys Lys Val Ser
        210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 128
<211> LENGTH: 347
<212> TYPE: PRT
<213> ORGANISM: Artificial Sequence
<220> FEATURE:
<223> OTHER INFORMATION: Synthetic Construct

<400> SEQUENCE: 128

Glu Glu Glu Leu Gln Ile Ile Gln Pro Asp Lys Ser Val Leu Val Ala
1               5                   10                  15
```

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Cys Cys Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ala Pro Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 129
<211> LENGTH: 347
<212> TYPE: PRT
<213> ORGANISM: Artificial Sequence
<220> FEATURE:
<223> OTHER INFORMATION: Synthetic Construct

<400> SEQUENCE: 129

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
 50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Cys Cys Val Glu Cys Pro
            115                 120                 125

Pro Cys Pro Ala Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Ala Ser Thr Phe Arg Val Val Ser Val Leu Thr Val
            195                 200                 205

Val His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
            290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 130
<211> LENGTH: 347
<212> TYPE: PRT
<213> ORGANISM: Artificial Sequence
<220> FEATURE:
<223> OTHER INFORMATION: Synthetic Construct

<400> SEQUENCE: 130

Glu Glu Glu Leu Gln Val Ile Gln Pro Asp Lys Ser Val Ser Val Ala
 1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
            35                  40                  45

```
Ile Tyr Asn Gln Lys Glu Gly His Phe Pro Arg Val Thr Val Ser
 50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser Glu Ser Lys Tyr Gly Pro Pro Cys Pro Ser
                115                 120                 125

Cys Pro Ala Pro Glu Phe Leu Gly Gly Pro Ser Val Phe Leu Phe Pro
            130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Asn Ser Thr Tyr Arg Val Val Ser Val Leu Thr Val
            195                 200                 205

Leu His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 131
<211> LENGTH: 348
<212> TYPE: PRT
<213> ORGANISM: Artificial Sequence
<220> FEATURE:
<223> OTHER INFORMATION: Synthetic Construct

<400> SEQUENCE: 131

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Glu Leu
             35                  40                  45

Ile Tyr Asn Gln Arg Glu Gly Pro Phe Pro Arg Val Thr Val Ser
 50                  55                  60
```

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Leu Gly Gly Pro Ser Val Phe Leu Phe
130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 132
<211> LENGTH: 348
<212> TYPE: PRT
<213> ORGANISM: Artificial Sequence
<220> FEATURE:
<223> OTHER INFORMATION: Synthetic Construct

<400> SEQUENCE: 132

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

```
Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
            115                 120                 125

Pro Cys Pro Ala Pro Glu Phe Glu Gly Gly Pro Ser Val Phe Leu Phe
        130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 133
<211> LENGTH: 347
<212> TYPE: PRT
<213> ORGANISM: Artificial Sequence
<220> FEATURE:
<223> OTHER INFORMATION: Synthetic Construct

<400> SEQUENCE: 133

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95
```

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
            115                 120                 125

Pro Cys Pro Ala Pro Pro Val Ala Gly Pro Ser Val Phe Leu Phe Pro
            130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
            195                 200                 205

Leu His Gln Asp Trp Leu Asn Gly Lys Glu Tyr Lys Cys Lys Val Ser
            210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 134
<211> LENGTH: 346
<212> TYPE: PRT
<213> ORGANISM: Artificial Sequence
<220> FEATURE:
<223> OTHER INFORMATION: Synthetic Construct

<400> SEQUENCE: 134

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

```
Ser Val Arg Ala Lys Pro Ser Ala Ala Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
                180                 185                 190

Glu Gln Phe Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
        210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
                340                 345

<210> SEQ ID NO 135
<211> LENGTH: 345
<212> TYPE: PRT
<213> ORGANISM: Artificial Sequence
<220> FEATURE:
<223> OTHER INFORMATION: Synthetic Construct

<400> SEQUENCE: 135

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
        115                 120                 125
```

Pro Ala Pro Glu Ala Ala Gly Ala Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 136
<211> LENGTH: 345
<212> TYPE: PRT
<213> ORGANISM: Artificial Sequence
<220> FEATURE:
<223> OTHER INFORMATION: Synthetic Construct

<400> SEQUENCE: 136

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

```
Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 137
<211> LENGTH: 345
<212> TYPE: PRT
<213> ORGANISM: Artificial Sequence
<220> FEATURE:
<223> OTHER INFORMATION: Synthetic Construct

<400> SEQUENCE: 137

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160
```

```
Val Val Val Asp Val Ser His Glu Asp Pro Glu Val Lys Phe Asn Trp
            165                 170                 175

Tyr Val Asp Gly Val Glu Val His Asn Ala Lys Thr Lys Pro Arg Glu
        180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 138
<211> LENGTH: 346
<212> TYPE: PRT
<213> ORGANISM: Artificial Sequence
<220> FEATURE:
<223> OTHER INFORMATION: Synthetic Construct

<400> SEQUENCE: 138

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175
```

```
Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 139
<211> LENGTH: 227
<212> TYPE: PRT
<213> ORGANISM: Artificial Sequence
<220> FEATURE:
<223> OTHER INFORMATION: Synthetic Construct

<400> SEQUENCE: 139

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190
```

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 140
<211> LENGTH: 346
<212> TYPE: PRT
<213> ORGANISM: Artificial Sequence
<220> FEATURE:
<223> OTHER INFORMATION: Synthetic Construct

<400> SEQUENCE: 140

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

```
Val Phe Ser Cys Ser Val Met His Glu Ala Leu His Asn His Tyr Thr
            325                 330                 335

Gln Lys Ser Leu Ser Leu Ser Pro Gly Lys
        340                 345

<210> SEQ ID NO 141
<211> LENGTH: 227
<212> TYPE: PRT
<213> ORGANISM: Artificial Sequence
<220> FEATURE:
<223> OTHER INFORMATION: Synthetic Construct

<400> SEQUENCE: 141

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 142
<211> LENGTH: 346
<212> TYPE: PRT
<213> ORGANISM: Artificial Sequence
<220> FEATURE:
<223> OTHER INFORMATION: Synthetic Construct

<400> SEQUENCE: 142

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
```

```
                35                  40                  45
Ile Tyr Asn Gln Arg Glu Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 143
<211> LENGTH: 346
<212> TYPE: PRT
<213> ORGANISM: Artificial Sequence
<220> FEATURE:
<223> OTHER INFORMATION: Synthetic Construct

<400> SEQUENCE: 143

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
```

```
            50                  55                  60
Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
                115                 120                 125

Pro Ala Pro Glu Ala Ala Gly Ala Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
            210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 144
<211> LENGTH: 449
<212> TYPE: PRT
<213> ORGANISM: Artificial Sequence
<220> FEATURE:
<223> OTHER INFORMATION: Synthetic Construct

<400> SEQUENCE: 144

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
```

```
            65                  70                  75                  80
Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Arg Lys
    210                 215                 220

Thr His Thr Cys Pro Arg Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 145
<211> LENGTH: 346
<212> TYPE: PRT
<213> ORGANISM: Artificial Sequence
<220> FEATURE:
```

<223> OTHER INFORMATION: Synthetic Construct

<400> SEQUENCE: 145

| | | | | | | | | | | | | | | | |
|---|---|---|---|---|---|---|---|---|---|---|---|---|---|---|---|
|Glu|Glu|Glu|Leu|Gln|Ile|Ile|Gln|Pro|Asp|Lys|Ser|Val|Leu|Val|Ala|
|1| | | |5| | | | |10| | | | |15| |
|Ala|Gly|Glu|Thr|Ala|Thr|Leu|Arg|Cys|Thr|Ile|Thr|Ser|Leu|Phe|Pro|
| | | |20| | | | |25| | | | |30| | |
|Val|Gly|Pro|Ile|Gln|Trp|Phe|Arg|Gly|Ala|Gly|Pro|Gly|Arg|Glu|Leu|
| | | | |35| | | | |40| | | | |45| |
|Ile|Tyr|Asn|Gln|Arg|Glu|Gly|Pro|Phe|Pro|Arg|Val|Thr|Thr|Val|Ser|
| | |50| | | | |55| | | | |60| | | |
|Asp|Thr|Thr|Lys|Arg|Asn|Asn|Met|Asp|Phe|Ser|Ile|Arg|Ile|Gly|Ala|
|65| | | | |70| | | | |75| | | | |80|
|Ile|Thr|Pro|Ala|Asp|Ala|Gly|Thr|Tyr|Tyr|Cys|Val|Lys|Phe|Arg|Lys|
| | | | |85| | | | |90| | | | |95| |
|Gly|Ser|Pro|Asp|Asp|Val|Glu|Phe|Lys|Ser|Gly|Ala|Gly|Thr|Glu|Leu|
| | | |100| | | | |105| | | | |110| | |
|Ser|Val|Arg|Ala|Lys|Pro|Ser|Glu|Lys|Thr|His|Thr|Cys|Pro|Glu|Cys|
| | | |115| | | | |120| | | | |125| | |
|Pro|Ala|Pro|Glu|Ala|Ala|Gly|Ala|Pro|Ser|Val|Phe|Leu|Phe|Pro|Pro|
| | |130| | | | |135| | | | |140| | | |
|Lys|Pro|Lys|Asp|Thr|Leu|Met|Ile|Ser|Arg|Thr|Pro|Glu|Val|Thr|Cys|
|145| | | | |150| | | | |155| | | | |160|
|Val|Val|Val|Asp|Val|Ser|His|Glu|Asp|Pro|Glu|Val|Lys|Phe|Asn|Trp|
| | | | |165| | | | |170| | | | |175| |
|Tyr|Val|Asp|Gly|Val|Glu|Val|His|Asn|Ala|Lys|Thr|Lys|Pro|Arg|Glu|
| | | |180| | | | |185| | | | |190| | |
|Glu|Gln|Tyr|Ala|Ser|Thr|Tyr|Arg|Val|Val|Ser|Val|Leu|Thr|Val|Leu|
| | | |195| | | | |200| | | | |205| | |
|His|Gln|Asp|Trp|Leu|Asn|Gly|Lys|Glu|Tyr|Lys|Cys|Lys|Val|Ser|Asn|
|210| | | | |215| | | | |220| | | | | |
|Lys|Ala|Leu|Pro|Ala|Pro|Ile|Glu|Lys|Thr|Ile|Ser|Lys|Ala|Lys|Gly|
|225| | | | |230| | | | |235| | | | |240|
|Gln|Pro|Arg|Glu|Pro|Gln|Val|Tyr|Thr|Leu|Pro|Pro|Ser|Arg|Glu|Glu|
| | | | |245| | | | |250| | | | |255| |
|Met|Thr|Lys|Asn|Gln|Val|Ser|Leu|Thr|Cys|Glu|Val|Lys|Gly|Phe|Tyr|
| | | |260| | | | |265| | | | |270| | |
|Pro|Ser|Asp|Ile|Ala|Val|Glu|Trp|Glu|Ser|Asn|Gly|Gln|Pro|Glu|Asn|
| | |275| | | | |280| | | | |285| | | |
|Asn|Tyr|Lys|Thr|Thr|Pro|Pro|Val|Leu|Asp|Ser|Asp|Gly|Ser|Phe|Phe|
| |290| | | | |295| | | | |300| | | | |
|Leu|Tyr|Ser|Lys|Leu|Thr|Val|Asp|Lys|Ser|Arg|Trp|Gln|Gln|Gly|Asn|
|305| | | | |310| | | | |315| | | | |320|
|Val|Phe|Ser|Cys|Ser|Val|Met|His|Glu|Ala|Leu|His|Asn|His|Tyr|Thr|
| | | | |325| | | | |330| | | | |335| |
|Gln|Lys|Ser|Leu|Ser|Leu|Ser|Pro|Gly|Lys| | | | | | |
| | | |340| | | | |345| | | | | | | |

<210> SEQ ID NO 146
<211> LENGTH: 346
<212> TYPE: PRT
<213> ORGANISM: Artificial Sequence
<220> FEATURE:
<223> OTHER INFORMATION: Synthetic Construct

<400> SEQUENCE: 146

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 147
<211> LENGTH: 227
<212> TYPE: PRT
<213> ORGANISM: Artificial Sequence
<220> FEATURE:
<223> OTHER INFORMATION: Synthetic Construct

<400> SEQUENCE: 147

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 148
<211> LENGTH: 346
<212> TYPE: PRT
<213> ORGANISM: Artificial Sequence
<220> FEATURE:
<223> OTHER INFORMATION: Synthetic Construct

<400> SEQUENCE: 148

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

```
Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 149
<211> LENGTH: 227
<212> TYPE: PRT
<213> ORGANISM: Artificial Sequence
<220> FEATURE:
<223> OTHER INFORMATION: Synthetic Construct

<400> SEQUENCE: 149

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225
```

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161
<211> LENGTH: 226
<212> TYPE: PRT
<213> ORGANISM: Artificial Sequence
<220> FEATURE:
<223> OTHER INFORMATION: Synthetic Construct

<400> SEQUENCE: 161

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 162
<211> LENGTH: 227
<212> TYPE: PRT
<213> ORGANISM: Homo sapiens

<400> SEQUENCE: 162

```
Glu Arg Lys Cys Cys Val Glu Cys Pro Pro Cys Pro Ala Pro Pro Val
1               5                   10                  15
```

```
Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
    210                 215                 220

Ser Pro Gly
225

<210> SEQ ID NO 163
<211> LENGTH: 5
<212> TYPE: PRT
<213> ORGANISM: Artificial Sequence
<220> FEATURE:
<223> OTHER INFORMATION: Synthetic Construct

<400> SEQUENCE: 163

Gly Gly Gly Gly Ser
1               5

<210> SEQ ID NO 164
<211> LENGTH: 4
<212> TYPE: PRT
<213> ORGANISM: Artificial Sequence
<220> FEATURE:
<223> OTHER INFORMATION: Synthetic Construct

<400> SEQUENCE: 164

Gly Gly Ser Gly
1

<210> SEQ ID NO 165
<211> LENGTH: 4
<212> TYPE: PRT
<213> ORGANISM: Artificial Sequence
<220> FEATURE:
<223> OTHER INFORMATION: Synthetic Construct

<400> SEQUENCE: 165
```

Ser Gly Gly Gly
1

<210> SEQ ID NO 166
<211> LENGTH: 4
<212> TYPE: PRT
<213> ORGANISM: Artificial Sequence
<220> FEATURE:
<223> OTHER INFORMATION: Synthetic Construct

<400> SEQUENCE: 166

Gly Ser Gly Ser
1

<210> SEQ ID NO 167
<211> LENGTH: 6
<212> TYPE: PRT
<213> ORGANISM: Artificial Sequence
<220> FEATURE:
<223> OTHER INFORMATION: Synthetic Construct

<400> SEQUENCE: 167

Gly Ser Gly Ser Gly Ser
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Gly Ser Gly Ser Gly Ser Gly Ser
1               5

<210> SEQ ID NO 169
<211> LENGTH: 10
<212> TYPE: PRT
<213> ORGANISM: Artificial Sequence
<220> FEATURE:
<223> OTHER INFORMATION: Synthetic Construct

<400> SEQUENCE: 169

Gly Ser Gly Ser Gly Ser Gly Ser Gly Ser
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic Construct

<400> SEQUENCE: 170

Gly Ser Gly Ser Gly Ser Gly Ser Gly Ser Gly Ser
1               5                   10

<210> SEQ ID NO 171
<211> LENGTH: 6
<212> TYPE: PRT
<213> ORGANISM: Artificial Sequence
<220> FEATURE:
<223> OTHER INFORMATION: Synthetic Construct

<400> SEQUENCE: 171

Gly Gly Ser Gly Gly Ser

```
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Construct

<400> SEQUENCE: 172

Gly Gly Ser Gly Gly Ser Gly Gly Ser
1               5

<210> SEQ ID NO 173
<211> LENGTH: 12
<212> TYPE: PRT
<213> ORGANISM: Artificial Sequence
<220> FEATURE:
<223> OTHER INFORMATION: Synthetic Construct

<400> SEQUENCE: 173

Gly Gly Ser Gly Gly Ser Gly Gly Ser Gly Gly Ser
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct

<400> SEQUENCE: 174

Gly Gly Ser Gly Gly Gly Ser Gly
1               5

<210> SEQ ID NO 175
<211> LENGTH: 12
<212> TYPE: PRT
<213> ORGANISM: Artificial Sequence
<220> FEATURE:
<223> OTHER INFORMATION: Synthetic Construct

<400> SEQUENCE: 175

Gly Gly Ser Gly Gly Gly Ser Gly Gly Gly Ser Gly
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Synthetic Construct

<400> SEQUENCE: 176

Gly Gly Gly Gly Ser Gly Gly Gly Gly Ser Gly Gly Gly Gly Ser
1               5                   10                  15

<210> SEQ ID NO 177
<211> LENGTH: 3
<212> TYPE: PRT
<213> ORGANISM: Artificial Sequence
<220> FEATURE:
<223> OTHER INFORMATION: Synthetic Construct

<400> SEQUENCE: 177

Ala Ala Ser
1
```

```
<210> SEQ ID NO 178
<211> LENGTH: 4
<212> TYPE: PRT
<213> ORGANISM: Artificial Sequence
<220> FEATURE:
<223> OTHER INFORMATION: Synthetic Construct

<400> SEQUENCE: 178

Ala Ala Ala Leu
1

<210> SEQ ID NO 179
<211> LENGTH: 4
<212> TYPE: PRT
<213> ORGANISM: Artificial Sequence
<220> FEATURE:
<223> OTHER INFORMATION: Synthetic Construct

<400> SEQUENCE: 179

Ala Ala Ala Lys
1

<210> SEQ ID NO 180
<211> LENGTH: 4
<212> TYPE: PRT
<213> ORGANISM: Artificial Sequence
<220> FEATURE:
<223> OTHER INFORMATION: Synthetic Construct

<400> SEQUENCE: 180

Ala Ala Ala Arg
1

<210> SEQ ID NO 181
<211> LENGTH: 14
<212> TYPE: PRT
<213> ORGANISM: Artificial Sequence
<220> FEATURE:
<223> OTHER INFORMATION: Synthetic Construct

<400> SEQUENCE: 181

Glu Gly Lys Ser Ser Gly Ser Gly Ser Glu Ser Lys Ser Thr
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Synthetic Construct

<400> SEQUENCE: 182

Gly Ser Ala Gly Ser Ala Ala Gly Ser Gly Glu Phe
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic Construct

<400> SEQUENCE: 183

Ala Glu Ala Ala Ala Lys Glu Ala Ala Ala Lys Ala
1               5                   10
```

<210> SEQ ID NO 184
<211> LENGTH: 18
<212> TYPE: PRT
<213> ORGANISM: Artificial Sequence
<220> FEATURE:
<223> OTHER INFORMATION: Synthetic Construct

<400> SEQUENCE: 184

Lys Glu Ser Gly Ser Val Ser Ser Glu Gln Leu Ala Gln Phe Arg Ser
1               5                   10                  15

Leu Asp

<210> SEQ ID NO 185
<211> LENGTH: 9
<212> TYPE: PRT
<213> ORGANISM: Artificial Sequence
<220> FEATURE:
<223> OTHER INFORMATION: Synthetic Construct

<400> SEQUENCE: 185

Gly Gly Gly Gly Ala Gly Gly Gly Gly
1               5

<210> SEQ ID NO 186
<211> LENGTH: 10
<212> TYPE: PRT
<213> ORGANISM: Artificial Sequence
<220> FEATURE:
<223> OTHER INFORMATION: Synthetic Construct

<400> SEQUENCE: 186

Gly Glu Asn Leu Tyr Phe Gln Ser Gly Gly
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 187

Ser Ala Cys Tyr Cys Glu Leu Ser
1               5

<210> SEQ ID NO 188
<211> LENGTH: 5
<212> TYPE: PRT
<213> ORGANISM: Artificial Sequence
<220> FEATURE:
<223> OTHER INFORMATION: Synthetic Construct

<400> SEQUENCE: 188

Arg Ser Ile Ala Thr
1               5

<210> SEQ ID NO 189
<211> LENGTH: 17
<212> TYPE: PRT
<213> ORGANISM: Artificial Sequence
<220> FEATURE:
<223> OTHER INFORMATION: Synthetic Construct

<400> SEQUENCE: 189

Arg Pro Ala Cys Lys Ile Pro Asn Asp Leu Lys Gln Lys Val Met Asn
1               5                   10                  15

His

<210> SEQ ID NO 190
<211> LENGTH: 36
<212> TYPE: PRT
<213> ORGANISM: Artificial Sequence
<220> FEATURE:
<223> OTHER INFORMATION: Synthetic Construct

<400> SEQUENCE: 190

Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35

<210> SEQ ID NO 191
<211> LENGTH: 17
<212> TYPE: PRT
<213> ORGANISM: Artificial Sequence
<220> FEATURE:
<223> OTHER INFORMATION: Synthetic Construct

<400> SEQUENCE: 191

Ala Ala Ala Asn Ser Ser Ile Asp Leu Ile Ser Val Pro Val Asp Ser
1               5                   10                  15

Arg

<210> SEQ ID NO 192
<211> LENGTH: 36
<212> TYPE: PRT
<213> ORGANISM: Artificial Sequence
<220> FEATURE:
<223> OTHER INFORMATION: Synthetic Construct

<400> SEQUENCE: 192

Gly Gly Ser Gly Gly Gly Ser Glu Gly Gly Ser Glu Gly Gly
1               5                   10                  15

Ser Glu Gly Gly Gly Ser Glu Gly Gly Gly Ser Glu Gly Gly Gly Ser
            20                  25                  30

Gly Gly Gly Ser
        35

<210> SEQ ID NO 193
<211> LENGTH: 5
<212> TYPE: PRT
<213> ORGANISM: Artificial Sequence
<220> FEATURE:
<223> OTHER INFORMATION: Synthetic Construct

<400> SEQUENCE: 193

Glu Ala Ala Ala Lys
1               5

<210> SEQ ID NO 194
<211> LENGTH: 5
<212> TYPE: PRT
<213> ORGANISM: Artificial Sequence
<220> FEATURE:
<223> OTHER INFORMATION: Synthetic Construct

<400> SEQUENCE: 194

Pro Ala Pro Ala Pro
1               5

<210> SEQ ID NO 195
<211> LENGTH: 119
<212> TYPE: PRT
<213> ORGANISM: Artificial Sequence
<220> FEATURE:
<223> OTHER INFORMATION: Synthetic Construct

<400> SEQUENCE: 195

Glu Glu Glu Leu Gln Ile Ile Gln Pro Asp Lys Ser Val Leu Val Ala
1               5                   10                  15

Ala Gly Glu Thr Ala Thr Leu Arg Cys Thr Met Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 196
<211> LENGTH: 119
<212> TYPE: PRT
<213> ORGANISM: Artificial Sequence
<220> FEATURE:
<223> OTHER INFORMATION: Synthetic Construct

<400> SEQUENCE: 196

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Lys Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 197
<211> LENGTH: 119
<212> TYPE: PRT
<213> ORGANISM: Artificial Sequence
<220> FEATURE:
<223> OTHER INFORMATION: Synthetic Construct -continued

<400> SEQUENCE: 197

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 198
<211> LENGTH: 119
<212> TYPE: PRT
<213> ORGANISM: Artificial Sequence
<220> FEATURE:
<223> OTHER INFORMATION: Synthetic Construct

<400> SEQUENCE: 198

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 199
<211> LENGTH: 119
<212> TYPE: PRT
<213> ORGANISM: Artificial Sequence
<220> FEATURE:
<223> OTHER INFORMATION: Synthetic Construct

<400> SEQUENCE: 199

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

```
Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115
```

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
                100                 105                 110

Ser Val Arg Ala Lys Pro Ser
            115
```

<210> SEQ ID NO 201
<211> LENGTH: 119
<212> TYPE: PRT
<213> ORGANISM: Artificial Sequence
<220> FEATURE:
<223> OTHER INFORMATION: Synthetic Construct

<400> SEQUENCE: 201

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Met Pro Asp Asp Val Glu Phe Lys Ser Gly Ala Gly Thr Glu Leu
                100                 105                 110
```

Ser Val Arg Ala Lys Pro Ser
        115

<210> SEQ ID NO 202
<211> LENGTH: 118
<212> TYPE: PRT
<213> ORGANISM: Artificial Sequence
<220> FEATURE:
<223> OTHER INFORMATION: Synthetic Construct

<400> SEQUENCE: 202

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Val Glu Phe Lys Ser Gly Ala Gly Thr Glu Leu Ser
            100                 105                 110

Val Arg Ala Lys Pro Ser
        115

<210> SEQ ID NO 203
<211> LENGTH: 120
<212> TYPE: PRT
<213> ORGANISM: Artificial Sequence
<220> FEATURE:
<223> OTHER INFORMATION: Synthetic Construct

<400> SEQUENCE: 203

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Ser Glu Pro Asp Val Glu Phe Lys Ser Gly Ala Gly Thr Glu
            100                 105                 110

Leu Ser Val Arg Ala Lys Pro Ser
        115                 120

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct

<400> SEQUENCE: 204

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 205
<211> LENGTH: 119
<212> TYPE: PRT
<213> ORGANISM: Artificial Sequence
<220> FEATURE:
<223> OTHER INFORMATION: Synthetic Construct

<400> SEQUENCE: 205

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 206
<211> LENGTH: 119
<212> TYPE: PRT
<213> ORGANISM: Artificial Sequence
<220> FEATURE:
<223> OTHER INFORMATION: Synthetic Construct

<400> SEQUENCE: 206

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
            50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ile Pro Asp Asp Val Glu Phe Lys Ser Gly Ala Gly Thr Glu Leu
            100                 105                 110

Ser Val Arg Ala Lys Pro Ser
            115

<210> SEQ ID NO 207
<211> LENGTH: 119
<212> TYPE: PRT
<213> ORGANISM: Artificial Sequence
<220> FEATURE:
<223> OTHER INFORMATION: Synthetic Construct

<400> SEQUENCE: 207

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
            50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
            50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ile Pro Asp Asp Val Glu Phe Lys Ser Gly Ala Gly Thr Glu Leu

Ser Val Arg Ala Lys Pro Ser
        115

<210> SEQ ID NO 209
<211> LENGTH: 119
<212> TYPE: PRT
<213> ORGANISM: Artificial Sequence
<220> FEATURE:
<223> OTHER INFORMATION: Synthetic Construct

<400> SEQUENCE: 209

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 210
<211> LENGTH: 119
<212> TYPE: PRT
<213> ORGANISM: Artificial Sequence
<220> FEATURE:
<223> OTHER INFORMATION: Synthetic Construct

<400> SEQUENCE: 210

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 211
<211> LENGTH: 345
<212> TYPE: PRT
<213> ORGANISM: Artificial Sequence
<220> FEATURE:

<223> OTHER INFORMATION: Synthetic Construct

<400> SEQUENCE: 211

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345
```

<210> SEQ ID NO 212
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT

```
<222> LOCATION: 6
<223> OTHER INFORMATION: Xaa = V, L, I
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 80
<223> OTHER INFORMATION: Xaa = N, A

<400> SEQUENCE: 212

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Glu Leu
        35                  40                  45

Ile Tyr Asn Gln Xaa Glu Gly Xaa Phe Pro Arg Val Thr Thr Val Ser
50                  55                  60

Glu Xaa Thr Lys Arg Glu Asn Met Asp Phe Ser Ile Ser Ile Ser Xaa
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 213
<211> LENGTH: 119
<212> TYPE: PRT
<213> ORGANISM: Artificial Sequence
<220> FEATURE:
<223> OTHER INFORMATION: Synthetic Construct

<400> SEQUENCE: 213

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Val Ala Asp Ala Gly Thr Tyr Tyr Cys Val Lys Phe Arg Lys
```

```
                    85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 214
<211> LENGTH: 346
<212> TYPE: PRT
<213> ORGANISM: Artificial Sequence
<220> FEATURE:
<223> OTHER INFORMATION: Synthetic Construct

<400> SEQUENCE: 214

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
            115                 120                 125

Pro Cys Pro Ala Pro Pro Val Ala Gly Pro Ser Val Phe Leu Phe Pro
        130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
```

```
                    325                 330                 335

Thr Gln Lys Ser Leu Ser Leu Ser Pro Gly
                340                 345

<210> SEQ ID NO 215

<400> SEQUENCE: 215

000

<210> SEQ ID NO 216
<211> LENGTH: 346
<212> TYPE: PRT
<213> ORGANISM: Artificial Sequence
<220> FEATURE:
<223> OTHER INFORMATION: Synthetic Construct

<400> SEQUENCE: 216

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300
```

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 217
<211> LENGTH: 346
<212> TYPE: PRT
<213> ORGANISM: Artificial Sequence
<220> FEATURE:
<223> OTHER INFORMATION: Synthetic Construct

<400> SEQUENCE: 217

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Lys Thr His Thr Cys Pro Glu Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Glu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

```
Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 218
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = A, V, L, or I
<220> FEATURE:
<221> NAME/KEY: VARIANT
<222> LOCATION: 31
<223> OTHER INFORMATION: Xaa = I, S, T, or F
<220> FEATURE:
<221> NAME/KEY: VARIANT
<222> LOCATION: 47
<223> OTHER INFORMATION: Xaa = E, L, or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, R or P
<220> FEATURE:
<221> NAME/KEY: VARIANT
<222> LOCATION: 66
<223> OTHER INFORMATION: Xaa = S,G, L or  T
<220> FEATURE:
<221> NAME/KEY: VARIANT
<222> LOCATION: 80
<223> OTHER INFORMATION: Xaa = Any Amino Acid
<220> FEATURE:
<221> NAME/KEY: VARIANT
<222> LOCATION: 81
<223> OTHER INFORMATION: Xaa = Any Amino Acid
<220> FEATURE:
<221> NAME/KEY: VARIANT
<222> LOCATION: 82
<223> OTHER INFORMATION: Xaa = Any Amino Acid
<220> FEATURE:
<221> NAME/KEY: VARIANT
<222> LOCATION: 83
<223> OTHER INFORMATION: Xaa = Any Amino Acid
<220> FEATURE:
<221> NAME/KEY: VARIANT
<222> LOCATION: 92
<223> OTHER INFORMATION: Xaa = V or I

<400> SEQUENCE: 218

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60
```

-continued

```
Asp Xaa Thr Lys Arg Asn Asn Met Asp Phe Ser Ile Arg Ile Gly Xaa
 65                  70                  75                  80

Xaa Xaa Xaa Ala Asp Ala Gly Thr Tyr Tyr Cys Xaa Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 219
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L or I
<220> FEATURE:
<221> NAME/KEY: VARIANT
<222> LOCATION: 27
<223> OTHER INFORMATION: Xaa = A, V, L, or I
<220> FEATURE:
<221> NAME/KEY: VARIANT
<222> LOCATION: 31
<223> OTHER INFORMATION: Xaa = I, S, T or F
<220> FEATURE:
<221> NAME/KEY: VARIANT
<222> LOCATION: 47
<223> OTHER INFORMATION: Xaa = E, L, or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, R or P
<220> FEATURE:
<221> NAME/KEY: VARIANT
<222> LOCATION: 66
<223> OTHER INFORMATION: Xaa = S,G, L, or T
<220> FEATURE:
<221> NAME/KEY: VARIANT
<222> LOCATION: 80
<223> OTHER INFORMATION: Xaa = N
<220> FEATURE:
<221> NAME/KEY: VARIANT
<222> LOCATION: 83
<223> OTHER INFORMATION: Xaa = Any Amino Acid other than P
<220> FEATURE:
<221> NAME/KEY: VARIANT
<222> LOCATION: 92
<223> OTHER INFORMATION: Xaa = V or I

<400> SEQUENCE: 219

Glu Glu Glu Leu Gln Xaa Ile Gln Pro Asp Lys Ser Val Leu Val Ala
 1               5                  10                  15

Ala Gly Glu Thr Ala Thr Leu Arg Cys Thr Xaa Thr Ser Leu Xaa Pro
                20                  25                  30

Val Gly Pro Ile Gln Trp Phe Arg Gly Ala Gly Pro Gly Arg Xaa Leu
                35                  40                  45

Ile Tyr Asn Gln Xaa Xaa Gly Xaa Phe Pro Arg Val Thr Thr Val Ser
 50                  55                  60
```

```
Asp Xaa Thr Lys Arg Asn Asn Met Asp Phe Ser Ile Arg Ile Gly Xaa
 65                  70                  75                  80

Ile Thr Xaa Ala Asp Ala Gly Thr Tyr Tyr Cys Xaa Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 220

<400> SEQUENCE: 220

000

<210> SEQ ID NO 221
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = X1 is V or I
<220> FEATURE:
<221> NAME/KEY: VARIANT
<222> LOCATION: 27
<223> OTHER INFORMATION: Xaa = X2 is A or I
<220> FEATURE:
<221> NAME/KEY: VARIANT
<222> LOCATION: 31
<223> OTHER INFORMATION: Xaa = X3 is I or F
<220> FEATURE:
<221> NAME/KEY: VARIANT
<222> LOCATION: 47
<223> OTHER INFORMATION: Xaa = X4 is E or V
<220> FEATURE:
<221> NAME/KEY: VARIANT
<222> LOCATION: 53
<223> OTHER INFORMATION: Xaa = X5 is K or R
<220> FEATURE:
<221> NAME/KEY: VARIANT
<222> LOCATION: 56
<223> OTHER INFORMATION: Xaa = X6 is H or P
<220> FEATURE:
<221> NAME/KEY: VARIANT
<222> LOCATION: 66
<223> OTHER INFORMATION: Xaa = X7 is L or T
<220> FEATURE:
<221> NAME/KEY: VARIANT
<222> LOCATION: 80
<223> OTHER INFORMATION: Xaa = X8 is Any Amino Acid other than N
<220> FEATURE:
<221> NAME/KEY: VARIANT
<222> LOCATION: 92
<223> OTHER INFORMATION: Xaa = and X9 is V or I

<400> SEQUENCE: 221

Glu Glu Glu Leu Gln Xaa Ile Gln Pro Asp Lys Ser Val Leu Val Ala
  1               5                  10                  15

Ala Gly Glu Thr Ala Thr Leu Arg Cys Thr Xaa Thr Ser Leu Xaa Pro
                 20                  25                  30

Val Gly Pro Ile Gln Trp Phe Arg Gly Ala Gly Pro Gly Arg Xaa Leu
             35                  40                  45

Ile Tyr Asn Gln Xaa Glu Gly Xaa Phe Pro Arg Val Thr Thr Val Ser
         50                  55                  60

Asp Xaa Thr Lys Arg Asn Asn Met Asp Phe Ser Ile Arg Ile Gly Xaa
 65                  70                  75                  80
```

```
Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 222
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = X1 is V, L, or I
<220> FEATURE:
<221> NAME/KEY: VARIANT
<222> LOCATION: 27
<223> OTHER INFORMATION: Xaa = X2 is A, I, or L
<220> FEATURE:
<221> NAME/KEY: VARIANT
<222> LOCATION: 31
<223> OTHER INFORMATION: Xaa = X3 is I, T, S, or F
<220> FEATURE:
<221> NAME/KEY: VARIANT
<222> LOCATION: 53
<223> OTHER INFORMATION: Xaa = X4 is K or R
<220> FEATURE:
<221> NAME/KEY: VARIANT
<222> LOCATION: 56
<223> OTHER INFORMATION: Xaa = X5 is H or P
<220> FEATURE:
<221> NAME/KEY: VARIANT
<222> LOCATION: 66
<223> OTHER INFORMATION: Xaa = X6 is L, T, or G
<220> FEATURE:
<221> NAME/KEY: VARIANT
<222> LOCATION: 80
<223> OTHER INFORMATION: Xaa = X7 is N or A

<400> SEQUENCE: 222

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Glu Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 223
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 223

His His His His His His
1               5

<210> SEQ ID NO 224
<211> LENGTH: 10
<212> TYPE: PRT
<213> ORGANISM: Artificial Sequence
<220> FEATURE:
<223> OTHER INFORMATION: Synthetic Construct

<400> SEQUENCE: 224

His His His His His His His His His His
1               5                   10
```